US012653776B2

(12) United States Patent
Narain et al.

(10) Patent No.: US 12,653,776 B2

(45) Date of Patent: *Jun. 16, 2026

(54) METHODS OF TREATMENT OF CANCER BY CONTINUOUS INFUSION OF COENZYME Q10

(71) Applicant: BPGbio, Inc., Framingham, MA (US)

(72) Inventors: Niven Rajin Narain, Cambridge, MA (US); Rangaprasad Sarangarajan, Boylston, MA (US); Thomas Mitchell Gray, Mt. Juliet, TN (US); John Patrick McCook, Frisco, TX (US); Joaquin J. Jimenez, Miami, FL (US)

(73) Assignee: BPGbio, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/962,608

(22) Filed: Oct. 10, 2022

(65) Prior Publication Data

US 2023/0285272 A1 Sep. 14, 2023

Related U.S. Application Data

(63) Continuation of application No. 17/686,569, filed on Mar. 4, 2022, now abandoned, which is a continuation of application No. 15/869,630, filed on Jan. 12, 2018, now Pat. No. 11,298,313, which is a continuation of application No. 14/477,828, filed on Sep. 4, 2014, now Pat. No. 9,901,542.

(60) Provisional application No. 61/912,770, filed on Dec. 6, 2013, provisional application No. 61/901,351, filed on Nov. 7, 2013, provisional application No. 61/873,510, filed on Sep. 4, 2013.

(51) Int. Cl.

| | |
|---|---|
| ***A61K 9/00*** | (2006.01) |
| ***A61K 31/122*** | (2006.01) |
| ***A61K 31/337*** | (2006.01) |
| ***A61K 31/513*** | (2006.01) |
| ***A61K 31/519*** | (2006.01) |
| ***A61K 31/704*** | (2006.01) |
| ***A61K 31/7068*** | (2006.01) |
| ***A61K 31/7076*** | (2006.01) |
| ***A61K 38/43*** | (2006.01) |

(52) U.S. Cl.

CPC .......... *A61K 9/0019* (2013.01); *A61K 31/122* (2013.01); *A61K 31/337* (2013.01); *A61K 31/513* (2013.01); *A61K 31/519* (2013.01); *A61K 31/704* (2013.01); *A61K 31/7068* (2013.01); *A61K 31/7076* (2013.01); *A61K 38/43* (2013.01)

(58) Field of Classification Search

CPC ................ A61K 9/0019; A61K 31/122; A61K 31/337; A61K 31/513; A61K 31/519; A61K 31/704; A61K 31/7068; A61K 31/7076; A61K 38/43; A61K 38/04

See application file for complete search history.

(56) References Cited

U.S. PATENT DOCUMENTS

| | | | |
|---|---|---|---|
| 4,483,873 | A | 11/1984 | Ohashi et al. |
| 4,515,736 | A | 5/1985 | Deamer |
| 4,525,350 | A | 6/1985 | Casey et al. |
| 4,636,381 | A | 1/1987 | Takada et al. |
| 4,654,373 | A | 3/1987 | Bertelli |
| 4,824,669 | A | 4/1989 | Folkers et al. |
| 4,833,128 | A | 5/1989 | Solomon et al. |
| 4,895,727 | A | 1/1990 | Allen |
| 5,015,483 | A | 5/1991 | Haynes et al. |
| 5,045,559 | A | 9/1991 | Scott |
| 5,362,494 | A | 11/1994 | Zysman et al. |
| 5,378,461 | A | 1/1995 | Neigut |
| 5,527,789 | A | 6/1996 | Nyce |
| 5,602,184 | A | 2/1997 | Myers et al. |
| 5,603,958 | A | 2/1997 | Morein et al. |
| 5,605,930 | A | 2/1997 | Samid |
| 5,651,991 | A | 7/1997 | Sugiyama et al. |
| 5,700,482 | A | 12/1997 | Frederiksen et al. |
| 5,719,303 | A | 2/1998 | Yoshida et al. |
| 5,770,222 | A | 6/1998 | Unger et al. |
| 5,876,737 | A | 3/1999 | Schonrock et al. |
| 5,889,062 | A | 3/1999 | Hoppe et al. |
| 5,891,465 | A | 4/1999 | Keller et al. |
| 5,912,272 | A | 6/1999 | Hoppe et al. |
| 5,944,012 | A | 8/1999 | Pera |
| 5,962,243 | A | 10/1999 | Brown et al. |

(Continued)

FOREIGN PATENT DOCUMENTS

| | | | |
|---|---|---|---|
| CA | 2436374 | A1 | 8/2002 |
| CA | 2553690 | A1 | 8/2005 |

(Continued)

OTHER PUBLICATIONS

Definition of continuous infusion in NCI Dictionary retrieved on Feb. 10, 2020, 1 page. (Year: 2020).*

Arthur J. D'Alessandro, Vitamin K and its rôole in blood coagulation, The American Journal of Surgery, vol. 57, Issue 1, 1942, pp. 104-111, ISSN 0002-9610, doi.org/10.1016/S0002-9610(42)90956-5. Abstract Only. (Year: 1942).*

Mousa, Antithrombotic Effects of Naturally Derived Products on Coagulation and Platelet Function. Anticoagulants, Antiplatelets, and Thrombolytics, 2nd Edition. Humana Press, 2010, Chapter 9, pp. 229-240.

(Continued)

*Primary Examiner* — Kade Ariani

(74) *Attorney, Agent, or Firm* — McCarter & English, LLP; Jill Mello

(57) ABSTRACT

The invention provides regimens and methods for the treatment of cancer comprising continuous infusion of coenzyme Q10. The coenzyme Q10 may be administered as a monotherapy, or in combination with an additional agent, such as an anticancer agent, a chemotherapeutic agent, or an anti-angiogenic agent. The coenzyme Q10 may be administered at two or more different rates.

12 Claims, 16 Drawing Sheets

(56) References Cited

U.S. PATENT DOCUMENTS 6,005,086 A 12/1999 Evans et al.
6,048,886 A 4/2000 Neigut
6,063,820 A 5/2000 Cavazza
6,071,495 A 6/2000 Unger et al.
6,093,706 A 7/2000 Zeligs
6,093,743 A 7/2000 Lai et al.
6,184,353 B1 2/2001 Evans et al.
6,228,891 B1 5/2001 Enzmann et al.
6,261,575 B1 7/2001 Hoppe et al.
6,348,506 B2 2/2002 Sneed
6,372,234 B1 4/2002 Deckers et al.
6,403,116 B1 6/2002 Anderson et al.
6,416,957 B1 7/2002 Evans et al.
6,417,233 B1 7/2002 Sears et al.
6,441,050 B1 8/2002 Chopra
6,461,593 B1 10/2002 Hanioka et al.
6,465,517 B1 10/2002 Van Der Zee
6,468,552 B1 10/2002 Stahl et al.
6,469,061 B1 10/2002 Flescher et al.
6,482,943 B1 11/2002 Blokhin et al.
6,503,506 B1 1/2003 Germano
6,503,523 B2 1/2003 Hoppe et al.
6,506,915 B1 1/2003 West
6,511,800 B1 1/2003 Singh
6,531,117 B2 3/2003 Heger et al.
6,569,463 B2 5/2003 Patel et al.
6,573,284 B1 6/2003 Riley et al.
6,576,660 B1 6/2003 Liao et al.
6,576,678 B1 6/2003 Bruening et al.
6,582,710 B2 6/2003 Deckers et al.
6,582,723 B2 6/2003 Gorsek
6,596,287 B2 7/2003 Deckers et al.
6,599,513 B2 7/2003 Deckers et al.
6,623,746 B1 9/2003 Wadle et al.
6,630,160 B1 10/2003 Evans et al.
6,632,443 B2 10/2003 Borowy-Borowski et al.
6,652,891 B2 11/2003 Selzer
6,682,763 B2 1/2004 Kuno et al.
6,686,485 B2 2/2004 West
6,696,484 B2 2/2004 Liao et al.
6,726,924 B2 4/2004 Keller
6,727,234 B2 4/2004 Wiemer et al.
6,733,790 B1 5/2004 Garces Garces
6,753,325 B2 6/2004 Rosenbloom
6,803,193 B1 10/2004 Hopper et al.
6,806,069 B2 10/2004 Chokshi
6,809,176 B2 10/2004 Blokhin et al.
6,866,864 B2 3/2005 Mousa
6,867,024 B2 3/2005 Chokshi
6,906,106 B2 6/2005 Chevalier
6,923,988 B2 8/2005 Patel et al.
7,005,274 B1 2/2006 Terkeltaub et al.
7,060,733 B2 6/2006 Pandol et al.
7,083,572 B2 8/2006 Unger et al.
7,083,780 B2 8/2006 Ansmann et al.
7,091,241 B2 8/2006 Gilloteaux et al.
7,101,536 B2 9/2006 Mongiat et al.
7,132,268 B2 11/2006 Miyake et al.
7,147,841 B2 12/2006 Herzog
7,169,385 B2 1/2007 Fantuzzi et al.
7,169,590 B2 1/2007 Ueda et al.
7,176,171 B2 2/2007 Nieendick et al.
7,179,880 B2 2/2007 Kawa et al.
7,182,938 B2 2/2007 Andre et al.
7,182,950 B2 2/2007 Garti et al.
7,198,801 B2 4/2007 Carrara et al.
7,208,298 B2 4/2007 Miyake et al.
7,247,714 B2 7/2007 Kunsch et al.
7,250,174 B2 7/2007 Lee et al.
7,268,107 B2 9/2007 Nieendick et al.
7,273,606 B2 9/2007 Fantuzzi et al.
7,279,456 B2 10/2007 Dufay et al.
7,311,897 B2 12/2007 Ehlis et al.
7,318,929 B2 1/2008 Schieferstein et al.
7,357,918 B2 4/2008 Comte et al.
7,456,161 B2 11/2008 Nyce
7,635,722 B1 12/2009 Bachynsky et al.
7,776,894 B2 8/2010 Ronai et al.
7,824,673 B2 11/2010 Wegman et al.
7,858,659 B2 12/2010 Hoffman et al.
7,879,823 B2 2/2011 Seiberg et al.
7,906,140 B2 3/2011 Bromley et al.
8,147,825 B2 4/2012 Hsia et al.
8,293,227 B2 10/2012 Hsia et al.
8,562,976 B2 10/2013 Hsia et al.
8,586,030 B2 11/2013 Hsia et al.
8,746,515 B2 6/2014 Fatherazi et al.
8,771,680 B2 7/2014 Hsia et al.
9,205,064 B2 12/2015 Narain et al.
9,220,776 B2 12/2015 Sharma et al.
9,896,731 B2 2/2018 Narain et al.
9,901,542 B2 2/2018 Narain et al.
9,926,580 B2 3/2018 Yajima et al.
10,351,915 B2 7/2019 Narain et al.
10,376,477 B2 8/2019 Jimenez et al.
10,519,504 B2 12/2019 Narain et al.
10,583,098 B2 3/2020 Hsia et al.
10,933,032 B2 3/2021 Narain et al.
11,028,446 B2 6/2021 Narain et al.
11,298,313 B2 4/2022 Narain et al.
11,400,058 B2 8/2022 Narain et al.
11,452,699 B2 9/2022 Jimenez et al.
2001/0022965 A1 9/2001 Heger et al.
2001/0043909 A1 11/2001 SaNogueira et al.
2001/0053356 A1 12/2001 Mousa
2002/0039595 A1 4/2002 Keller
2002/0044913 A1 4/2002 Hamilton
2002/0045230 A1 4/2002 Rosen et al.
2002/0048559 A1 4/2002 Shinoda et al.
2002/0048798 A1 4/2002 Avery et al.
2002/0049176 A1 4/2002 Anderson et al.
2002/0049253 A1 4/2002 Kaddurah-Daouk
2002/0049422 A1 4/2002 Brewitt
2002/0058712 A1 5/2002 Sneed
2002/0071852 A1 6/2002 Deckers et al.
2002/0091288 A1 7/2002 Wilbur et al.
2002/0098169 A1 7/2002 Smith
2002/0106337 A1 8/2002 Deckers et al.
2002/0114820 A1 8/2002 Deckers et al.
2002/0127252 A1 9/2002 Kramer et al.
2002/0136711 A1 9/2002 Cochran
2002/0146463 A1 10/2002 Clayton
2002/0155151 A1 10/2002 Enzmann et al.
2002/0156302 A1 10/2002 West
2002/0164317 A1 11/2002 Gorsek
2002/0182199 A1 12/2002 Hoppe et al.
2002/0198177 A1 12/2002 Horrobin
2003/0012762 A1 1/2003 Zulli et al.
2003/0012779 A1 1/2003 Grieb et al.
2003/0012825 A1 1/2003 Kapper
2003/0031688 A1 2/2003 Ghosh et al.
2003/0044441 A1 3/2003 Schmid et al.
2003/0077297 A1 4/2003 Chen et al.
2003/0077335 A1 4/2003 Richardson et al.
2003/0087331 A1 5/2003 Pettit et al.
2003/0091518 A1 5/2003 Pauly et al.
2003/0103954 A1 6/2003 Rosenbloom
2003/0104048 A1 6/2003 Patel et al.
2003/0104080 A1 6/2003 Singh et al.
2003/0105027 A1 6/2003 Rosenbloom
2003/0105030 A1 6/2003 Liao et al.
2003/0105031 A1 6/2003 Rosenbloom
2003/0108493 A1 6/2003 Henry et al.
2003/0113354 A1 6/2003 Schmid et al.
2003/0118525 A1 6/2003 Grigg
2003/0118536 A1 6/2003 Rosenbloom
2003/0118576 A1 6/2003 Brancato et al.
2003/0124158 A1 7/2003 Heidenfelder et al.
2003/0129150 A1 7/2003 Pauly et al.
2003/0138792 A1 7/2003 Schlegel et al.
2003/0143166 A1 7/2003 Heger et al.
2003/0144346 A1 7/2003 Liao et al.
2003/0152598 A1 8/2003 Heidenfelder et al.
2003/0161849 A1 8/2003 Heidenfelder et al.

(56) References Cited

U.S. PATENT DOCUMENTS

2003/0167556 A1 9/2003 Kelley
2003/0170265 A1 9/2003 Henry et al.
2003/0180231 A1 9/2003 Danoux et al.
2003/0180278 A1 9/2003 Hoppe et al.
2003/0180352 A1 9/2003 Patel et al.
2003/0185865 A1 10/2003 Jentzsch et al.
2003/0207834 A1 11/2003 Dale et al.
2003/0212114 A1 11/2003 Sato
2003/0215406 A1 11/2003 Schreiner et al.
2003/0219472 A1 11/2003 Pauletti et al.
2003/0235812 A1 12/2003 Anderson et al.
2004/0028614 A1 2/2004 Corbella et al.
2004/0028668 A1 2/2004 Gaetani
2004/0034107 A1 2/2004 Enzmann
2004/0043045 A1 3/2004 Seipel et al.
2004/0047896 A1 3/2004 Malnoe et al.
2004/0049022 A1 3/2004 Nyce et al.
2004/0063648 A1 4/2004 Pandol et al.
2004/0063661 A1 4/2004 Linnane
2004/0067260 A1 4/2004 Milley et al.
2004/0082522 A1 4/2004 Nyce
2004/0086538 A1 5/2004 Sauermann et al.
2004/0101874 A1 5/2004 Ghosh et al.
2004/0109880 A1 6/2004 Pauly et al.
2004/0110848 A1 6/2004 Peffley et al.
2004/0115181 A1 6/2004 Fujii et al.
2004/0122109 A1 6/2004 Fujii et al.
2004/0126367 A1 7/2004 Fujii et al.
2004/0133352 A1 7/2004 Bevilacqua et al.
2004/0142006 A1 7/2004 Bleckmann et al.
2004/0142007 A1 7/2004 Moussou et al.
2004/0142009 A1 7/2004 Ansmann et al.
2004/0151710 A1 8/2004 Bozzacco
2004/0151711 A1 8/2004 West
2004/0170560 A1 9/2004 Fossheim et al.
2004/0170581 A1 9/2004 Henry et al.
2004/0185071 A1 9/2004 Hatazaki
2004/0191190 A1 9/2004 Pauly et al.
2004/0191263 A1 9/2004 Hageman et al.
2004/0197279 A1 10/2004 Bleckmann et al.
2004/0197354 A1 10/2004 Doring et al.
2004/0202740 A1 10/2004 Tan
2004/0219114 A1 11/2004 Andersson et al.
2004/0228910 A1 11/2004 Enzmann et al.
2004/0234559 A1 11/2004 Bleckmann et al.
2004/0253323 A1 12/2004 Giles
2004/0258717 A1 12/2004 Sauermann et al.
2005/0000390 A1 1/2005 Nieendick et al.
2005/0008581 A1 1/2005 Parkhideh
2005/0019268 A1 1/2005 Enzmann
2005/0019278 A1 1/2005 Berg-Schultz
2005/0019353 A1 1/2005 Prinz et al.
2005/0025756 A1 2/2005 Erwin
2005/0026848 A1 2/2005 Robinson et al.
2005/0026850 A1 2/2005 Robinson et al.
2005/0036976 A1 2/2005 Rubin et al.
2005/0037036 A1 2/2005 Nielsen et al.
2005/0037102 A1 2/2005 Tan et al.
2005/0042678 A1 2/2005 Epstein et al.
2005/0043336 A1 2/2005 Hennequin et al.
2005/0058610 A1 3/2005 Baschong et al.
2005/0069582 A1 3/2005 Fantuzzi
2005/0070610 A1 3/2005 Fujii et al.
2005/0070611 A1 3/2005 Fantuzzi
2005/0079164 A1 4/2005 Fantuzzi et al.
2005/0100537 A1 5/2005 Evans et al.
2005/0106190 A1 5/2005 Kawa et al.
2005/0106199 A1 5/2005 Schreiber et al.
2005/0112156 A1 5/2005 Busch et al.
2005/0118151 A1 6/2005 Larsen et al.
2005/0118209 A1 6/2005 Jentszch et al.
2005/0136081 A1 6/2005 Kawa et al.
2005/0142123 A1 6/2005 Chen et al.
2005/0142153 A1 6/2005 Schreiber et al.
2005/0147598 A1 7/2005 Ueda et al.
2005/0148603 A1 7/2005 Jimenez et al.
2005/0152856 A2 7/2005 Andersson et al.
2005/0184275 A1 8/2005 Mora-Gutierrez et al.
2005/0202521 A1 9/2005 Crum
2005/0214333 A1 9/2005 Lanzendoerfer et al.
2005/0220726 A1 10/2005 Pauly et al.
2005/0220826 A1 10/2005 Kawa et al.
2005/0226824 A1 10/2005 Kawa et al.
2005/0226858 A1 10/2005 Kitamura et al.
2005/0226947 A1 10/2005 Kern
2005/0238679 A1 10/2005 Biergiesser et al.
2005/0239721 A1 10/2005 Rosenbloom
2005/0255057 A1 11/2005 Andre et al.
2005/0276764 A1 12/2005 Kolbe et al.
2005/0281772 A1 12/2005 Bromley et al.
2005/0287206 A1 12/2005 Fantuzzi et al.
2005/0288333 A1 12/2005 Kem
2005/0288378 A1 12/2005 Yan et al.
2006/0002911 A1 1/2006 Casteilla et al.
2006/0002964 A9 1/2006 Schreiber et al.
2006/0008482 A1 1/2006 Prinz et al.
2006/0010519 A1 1/2006 Kadowaki et al.
2006/0013888 A1 1/2006 Fantuzzi
2006/0035981 A1 2/2006 Mazzio et al.
2006/0039956 A1 2/2006 Hensen et al.
2006/0041017 A1 2/2006 Chopra
2006/0051462 A1 3/2006 Wang
2006/0052438 A1 3/2006 Ho et al.
2006/0057081 A1 3/2006 Boxrud
2006/0062755 A1 3/2006 Woodward
2006/0069068 A1 3/2006 Kajander et al.
2006/0073106 A1 4/2006 Berg-Schultz et al.
2006/0093633 A1 5/2006 Stab et al.
2006/0099158 A1 5/2006 Zander et al.
2006/0099244 A1 5/2006 Guilford
2006/0110415 A1 5/2006 Gupta
2006/0120997 A1 6/2006 Lipton
2006/0121016 A1 6/2006 Lee
2006/0127384 A1 6/2006 Capaccioli et al.
2006/0127928 A1 6/2006 Bacus et al.
2006/0128643 A1 6/2006 Kaddurah-Daouk et al.
2006/0153783 A1 7/2006 Ehlis et al.
2006/0188459 A1 8/2006 Heinrichs et al.
2006/0188492 A1 8/2006 Richardson et al.
2006/0193905 A1 8/2006 Ehringer et al.
2006/0205771 A1 9/2006 Noble et al.
2006/0251690 A1 11/2006 Lipshutz et al.
2006/0251708 A1 11/2006 Chen et al.
2006/0252042 A1 11/2006 Molero
2006/0286046 A1 12/2006 Haber
2006/0292220 A1 12/2006 Giordano et al.
2007/0021360 A1 1/2007 Nyce et al.
2007/0026072 A1 2/2007 Olsen et al.
2007/0053985 A1 3/2007 Ueda et al.
2007/0054282 A1 3/2007 Liew
2007/0071779 A1 3/2007 McKie
2007/0085059 A1 4/2007 Mora-Gutierrez et al.
2007/0092469 A1 4/2007 Jacobs
2007/0104701 A1 5/2007 Ueda et al.
2007/0104810 A1 5/2007 Kern
2007/0110731 A1 5/2007 Riley
2007/0129428 A1 6/2007 Richelle et al.
2007/0149618 A1 6/2007 Cuevas Sanchez et al.
2007/0160685 A1 7/2007 Knox et al.
2007/0172436 A1 7/2007 Zhang
2007/0184041 A1 8/2007 Burja
2007/0184076 A1 8/2007 Unger et al.
2007/0189994 A1 8/2007 Berg et al.
2007/0196349 A1 8/2007 Kitamura et al.
2007/0196914 A1 8/2007 Murray et al.
2007/0202090 A1 8/2007 Prosek et al.
2007/0202496 A1 8/2007 Beretta
2007/0203091 A1 8/2007 Rapaport
2007/0218042 A1 9/2007 Khaled
2007/0225255 A1 9/2007 Frohlich et al.
2007/0243180 A1 10/2007 Tanaka et al.
2007/0248590 A1 10/2007 Milne et al.
2007/0248693 A1 10/2007 Mazzio et al.
2007/0253941 A1 11/2007 Naidu et al.

(56) References Cited

U.S. PATENT DOCUMENTS

| | | | |
|---|---|---|---|
| 2007/0258966 | A1 | 11/2007 | Ueda et al. |
| 2007/0258967 | A1 | 11/2007 | Ueda et al. |
| 2007/0259009 | A1 | 11/2007 | Linder |
| 2007/0275021 | A1 | 11/2007 | Lee et al. |
| 2008/0014187 | A1 | 1/2008 | Villeponteau |
| 2008/0020018 | A1 | 1/2008 | Moodley et al. |
| 2008/0020022 | A1 | 1/2008 | Udell |
| 2008/0025929 | A1 | 1/2008 | Burton et al. |
| 2008/0031862 | A1 | 2/2008 | Ghosal |
| 2008/0038736 | A1 | 2/2008 | Llovet et al. |
| 2008/0057116 | A1 | 3/2008 | Pleva |
| 2008/0063674 | A1 | 3/2008 | Vollhardt et al. |
| 2008/0069779 | A1 | 3/2008 | Tamarkin et al. |
| 2008/0069898 | A1 | 3/2008 | Smith et al. |
| 2008/0075684 | A1 | 3/2008 | Barg et al. |
| 2008/0081034 | A1 | 4/2008 | Zimmerman et al. |
| 2008/0081082 | A1 | 4/2008 | Zimmerman et al. |
| 2008/0089852 | A1 | 4/2008 | Hotz et al. |
| 2008/0089913 | A1 | 4/2008 | Kallmayer et al. |
| 2008/0095719 | A1 | 4/2008 | Herrmann et al. |
| 2008/0102313 | A1 | 5/2008 | Nilsen et al. |
| 2008/0103104 | A1 | 5/2008 | Moore et al. |
| 2008/0138326 | A1 | 6/2008 | Fujii et al. |
| 2008/0233183 | A1 | 9/2008 | McCook et al. |
| 2008/0260878 | A1 | 10/2008 | Harano et al. |
| 2008/0287541 | A1 | 11/2008 | Hoffman et al. |
| 2008/0299100 | A1 | 12/2008 | Hsia et al. |
| 2009/0005398 | A1 | 1/2009 | Dar |
| 2009/0010917 | A1 | 1/2009 | Rosenblum et al. |
| 2009/0036516 | A1 | 2/2009 | Scherrer et al. |
| 2009/0060891 | A1 | 3/2009 | Harris et al. |
| 2009/0068281 | A1 | 3/2009 | Toyomura et al. |
| 2009/0137556 | A1 | 5/2009 | Bonnichsen |
| 2009/0280987 | A1 | 11/2009 | Strobel |
| 2010/0062048 | A1 | 3/2010 | Hsia et al. |
| 2010/0150894 | A1 | 6/2010 | Wakabayashi et al. |
| 2010/0209388 | A1 | 8/2010 | Mazzio et al. |
| 2010/0209497 | A1 | 8/2010 | Thornthwaite |
| 2010/0239652 | A1 | 9/2010 | Rochlitz et al. |
| 2011/0020312 | A1 | 1/2011 | Narain et al. |
| 2011/0027247 | A1 | 2/2011 | Narain et al. |
| 2011/0064747 | A1 | 3/2011 | Sarangarajan et al. |
| 2011/0123550 | A1 | 5/2011 | Shibayama et al. |
| 2011/0123986 | A1 | 5/2011 | Narain et al. |
| 2011/0129503 | A1 | 6/2011 | Strober et al. |
| 2011/0136231 | A1 | 6/2011 | Narain et al. |
| 2011/0142914 | A1 | 6/2011 | Persaud et al. |
| 2012/0164215 | A1 | 6/2012 | Hsia et al. |
| 2012/0183621 | A1 | 7/2012 | Sinko et al. |
| 2012/0201801 | A1 | 8/2012 | Hsia et al. |
| 2012/0269867 | A1 | 10/2012 | Jimenez et al. |
| 2012/0309086 | A1 | 12/2012 | Narain et al. |
| 2013/0203853 | A1 | 8/2013 | Jacobson |
| 2014/0017317 | A1 | 1/2014 | Narain et al. |
| 2014/0255372 | A1 | 9/2014 | Hsia et al. |
| 2015/0023940 | A1 | 1/2015 | Narain et al. |
| 2016/0145693 | A1 | 5/2016 | Narain et al. |
| 2017/0137879 | A1 | 5/2017 | Narain et al. |
| 2017/0189350 | A1 | 7/2017 | Narain et al. |
| 2017/0216223 | A1 | 8/2017 | Narain et al. |
| 2018/0021270 | A1 | 1/2018 | Nastke et al. |
| 2018/0334721 | A1 | 11/2018 | Narain et al. |
| 2019/0010554 | A1 | 1/2019 | Narain et al. |
| 2020/0009377 | A1 | 1/2020 | Chang et al. |
| 2020/0138744 | A1 | 5/2020 | Sarangarajan et al. |
| 2021/0002725 | A1 | 1/2021 | Narain et al. |
| 2021/0128453 | A1 | 5/2021 | Hsia et al. |
| 2021/0322339 | A1 | 10/2021 | Narain et al. |
| 2021/0332439 | A1 | 10/2021 | Narain et al. |
| 2021/0369645 | A1 | 12/2021 | Narain et al. |
| 2022/0081720 | A1 | 3/2022 | Narain et al. |
| 2022/0096399 | A1 | 3/2022 | Narain et al. |
| 2022/0096400 | A1 | 3/2022 | Nastke et al. |
| 2022/0202741 | A1 | 6/2022 | Narain et al. |
| 2023/0149292 | A1 | 5/2023 | Hsia et al. |

FOREIGN PATENT DOCUMENTS

| | | | |
|---|---|---|---|
| CA | 2680825 | A1 | 9/2008 |
| CA | 2772068 | A1 | 3/2011 |
| CA | 2791693 | A1 | 9/2011 |
| CN | 1535605 | A | 10/2004 |
| CN | 1853507 | A | 11/2006 |
| CN | 1928556 | A | 3/2007 |
| CN | 1953743 | A | 4/2007 |
| CN | 101099084 | A | 1/2008 |
| CN | 101102768 | A | 1/2008 |
| CN | 101365806 | A | 2/2009 |
| CN | 102481269 | A | 5/2012 |
| DE | 4327063 | A1 | 2/1995 |
| EA | 201001624 | A1 | 6/2011 |
| EP | 1473043 | A1 | 11/2004 |
| EP | 1493437 | A1 | 1/2005 |
| EP | 1908459 | A1 | 4/2008 |
| EP | 2028492 | A1 | 2/2009 |
| EP | 2371362 | A1 | 10/2011 |
| EP | 2371363 | A1 | 10/2011 |
| EP | 2429512 | A2 | 3/2012 |
| EP | 2854528 | A1 | 4/2015 |
| JP | S57-075916 | A | 5/1982 |
| JP | S62-123113 | A | 6/1987 |
| JP | H01-143826 | A | 6/1989 |
| JP | H02-273619 | A | 11/1990 |
| JP | 2004-345988 | A | 12/2004 |
| JP | 2005-323573 | A | 11/2005 |
| JP | 2007-001922 | A | 1/2007 |
| JP | 2007-176804 | A | 7/2007 |
| JP | 2007-518805 | A | 7/2007 |
| JP | 2009-050168 | A | 3/2009 |
| JP | 2009-096757 | A | 5/2009 |
| JP | 2015-515272 | A | 5/2015 |
| JP | 2015-151900 | A | 8/2015 |
| JP | 2018-109093 | A | 7/2018 |
| JP | 2018-168164 | A | 11/2018 |
| KR | 10-2005-0112942 | A | 12/2005 |
| RU | 2307666 | C2 | 10/2007 |
| RU | 2345367 | | 1/2009 |
| WO | 1988/04173 | A1 | 6/1988 |
| WO | 1993/016704 | A1 | 9/1993 |
| WO | 1994/11547 | A1 | 5/1994 |
| WO | 1995/05164 | A1 | 2/1995 |
| WO | 1995/10271 | A2 | 4/1995 |
| WO | 1996/017626 | A2 | 6/1996 |
| WO | 1998/35660 | A1 | 8/1998 |
| WO | 1999/11242 | A1 | 3/1999 |
| WO | 1999/65469 | A2 | 12/1999 |
| WO | 2000/007607 | A1 | 2/2000 |
| WO | 2002/40012 | A1 | 5/2002 |
| WO | 2002/060484 | A1 | 8/2002 |
| WO | 2002/062329 | A1 | 8/2002 |
| WO | 2002/062338 | A1 | 8/2002 |
| WO | 2002/078727 | A1 | 10/2002 |
| WO | 2002/085297 | A2 | 10/2002 |
| WO | 2003/008405 | A1 | 1/2003 |
| WO | 2003/077895 | A1 | 9/2003 |
| WO | 2003/078456 | A2 | 9/2003 |
| WO | 2004/003564 | A2 | 1/2004 |
| WO | 2004/059293 | A2 | 7/2004 |
| WO | 2004/060316 | A2 | 7/2004 |
| WO | 2005/055738 | A1 | 6/2005 |
| WO | 2005/069916 | A2 | 8/2005 |
| WO | 2006/017494 | A2 | 2/2006 |
| WO | 2006/063402 | A1 | 6/2006 |
| WO | 2007/039184 | A2 | 4/2007 |
| WO | 2007/095186 | A2 | 8/2007 |
| WO | 2007/131047 | A2 | 11/2007 |
| WO | 2008/049330 | A1 | 5/2008 |
| WO | 2008/116135 | A2 | 9/2008 |
| WO | 2008/156654 | A2 | 12/2008 |
| WO | 2009/005215 | A1 | 1/2009 |
| WO | 2009/006366 | A2 | 1/2009 |
| WO | 2009/012718 | A1 | 1/2009 |
| WO | 2009/014639 | A2 | 1/2009 |
| WO | 2009/073843 | A1 | 6/2009 |
| WO | 2009/126764 | A1 | 10/2009 |

(56) References Cited

FOREIGN PATENT DOCUMENTS

| | | | | |
|---|---|---|---|---|
| WO | 2010/065601 | A1 | 6/2010 |
| WO | 2010/132440 | A2 | 11/2010 |
| WO | 2010/132507 | A2 | 11/2010 |
| WO | 2011/031503 | A2 | 3/2011 |
| WO | 2011/112900 | A2 | 9/2011 |
| WO | 2012/012347 | A2 | 1/2012 |
| WO | 2012/138765 | A1 | 10/2012 |
| WO | 2013/181639 | A1 | 12/2013 |
| WO | 2014/168993 | A1 | 10/2014 |
| WO | 2015/035094 | A1 | 3/2015 |
| WO | 2016/054574 | A1 | 4/2016 |
| WO | 2016/062722 | A1 | 4/2016 |
| WO | 2016/094639 | A1 | 6/2016 |
| WO | 2017/087576 | A1 | 5/2017 |

OTHER PUBLICATIONS

Mura et al., Evaluation of transcutol as a clonazepam transdermal permeation enhancer from hydrophilic gel formulations. Eur J Pharm Sci. Feb. 2000;9(4):365-72.
Narain et al., API 31510 as a potential agent in management of CNS leukemia. Cancer Research. 2011;71 (Suppl 8), Abstract 1565. Proceedings: AACR 102nd Annual Meeting 2011.
Narain et al., Effect of pretreatment, dose and route of administration of BPM31510 (Coenxyme Q10 containing proprietry formulation) alone or in combination with gemcitabine improves survival in pancreatic cancer. Cancer Res. 2014;74(19 Suppl.):Abstract 4321.
NatMed Pro, Vitamin K1 vs K2: what you should know. Retrieved online at: https://naturalmedicines.therapeuticresearch.com/news/news-items/2019/may/vitamin-k1-vs-k2-what-you-should-know.aspx. 1 page, May 2019.
Neidle, Cancer Drug Design and Discovery. Elsevier/Academic Press. p. 431, (2008).
NIH, National Cancer Institute, Drugs Approved for Different Types of Cancer. 7 pages, Jan. 16, 2015.
Nissim, A Gentle Cancer Killer. University of Miami Medicine-Online. Retrieved online at: http://www6.miami.edu/ummedicine-magazine/fall2005/fstory4.html. 3 pages. 2005.
O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.
Ohanian et al., Is acute myeloid leukemia a liquid tumor? Int J Cancer. Aug. 1, 2013;133(3):534-43.
Ohira et al., Expression profiling and characterization of 4200 genes cloned from primary neuroblastomas: identification of 305 genes differentially expressed between favorable and unfavorable subsets. Oncogene. Aug. 21, 2003;22(35):5525-36.
Okumura et al., Identification of biomarkers in ductal carcinoma in situ of the breast with microinvasion. BMC Cancer. Oct. 6, 2008;8:287.
Olopade et al., Overexpression of BCL-x protein in primary breast cancer is associated with high tumor grade and nodal metastases. Cancer J Sci Am. Jul.-Aug. 1997;3(4):230-7.
Olson, Karl August Folkers (1906-1997). American Society for Nutritional Sciences, J. Nutr. 2001;131:2227-2230.
Palan et al., Plasma concentrations of coenzyme Q10 and tocopherols in cervical intraepithelial neoplasia and cervical cancer. Eur J Cancer Prev. Aug. 2003;12(4):321-6.
Panwar et al., Preparation, characterization, and in vitro release study of albendazole-encapsulated nanosize liposomes. Int J Nanomedicine. Mar. 9, 2010;5:101-8.
Peddinghaus et al., Evaluation of the Usage Pattern and Safety Profile of a Frozen Plasma Transfusion Protocol. Transfusion. 2009;49:159A, Abstract SP285.
Persaud et al., Apoptotic affect of Ubiquinone precursors in melanoma. Cancer Research. Cellular and Molecular Biology. AACR Annual Meeting. 2 pages. Abstract 3281. May 1, 2009.
Perumal et al., Combined efficacy of tamoxifen and coenzyme Q10 on the status of lipid peroxidation and antioxidants in DMBA induced breast cancer. Mol Cell Biochem. May 2005;273(1-2):151-60.
Perumal et al., Therapeutic effect of tamoxifen and energy-modulating vitamins on carbohydrate-metabolizing enzymes in breast cancer. Cancer Chemother Pharmacol. 2005 ul;56(1):105-14.
Pfaffl et al., Real-time RT-PCR quantification of insulin-like growth factor (IGF)-1, IGF-1 receptor, IGF-2, IGF-2 receptor, insulin receptor, growth hormone receptor, IGF-binding proteins 1, 2 and 3 in the bovine species. Domest Anim Endocrinol. Apr. 2002;22(2):91-102.
Pravst et al., Coenzyme Q10 contents in foods and fortification strategies. Crit Rev Food Sci Nutr. Apr. 2010;50(4):269-80.
Prostate-Specific Antigen (PSA) Test. Retrieved online at: http://www.cancer.gov/cancertopics/factsheet/detection/PSA. Mar. 18, 2009.
Rastogi, Analytical control of preservative labelling on skin creams. Contact Dermatitis. Dec. 2000;43(6):339-43. (Abstract only).
Recht et al., A Phase 1 Study of BPM31510 Plus Vitamin K in Subjects wtih High-grade Glioma that has Recurred on a Bevacizumab-containing Regimen. Neuro-Oncology. Nov. 2019;21(Suppl. 6):vi27, Abstract ACTR-59.
Riethdorf et al., Differential expression of CD66a (BGP), a cell adhesion molecule of the carcinoembryonic antigen family, in benign, premalignant, and malignant lesions of the human mammary gland. J Histochem Cytochem. Jul. 1997;45(7):957-63.
Roffe et al., Efficacy of coenzyme Q10 for improved tolerability of cancer treatments: a systematic review. J Clin Oncol. Nov. 1, 2004;22(21):4418-24.
Rydberg et al., Toll-like receptor agonists induce inflammation and cell death in a model of head and neck squamous cell carcinomas. Immunology. Sep. 2009;128(1 Suppl):e600-11.
Sander et al., Vesicle associated membrane protein (VAMP)-7 and VAMP-8, but not VAMP-2 or VAMP-3, are required for activation-induced degranulation of mature human mast cells. Eur J Immunol. Mar. 2008;38(3):855-63.
Scambia et al., Cathepsin D and epidermal growth factor in human breast cyst fluid. Br J Cancer. Nov. 1991;64(5):965-7.
Scotton et al., Analysis of CC chemokine and chemokine receptor expression in solid ovarian tumours. Br J Cancer. Sep. 14, 2001;85(6):891-7.
Seifried et al., The antioxidant conundrum in cancer. Cancer Res. Aug. 1, 2003;63(15):4295-8.
Shaoqiong et al., Related gene expressions in anti-keratinocyte aging induced by Ganoderma lucidum polysaccharides. J of Medical Colleges of PLA. 2008;23:167-175.
Shekelle et al., Effect of the supplemental use of antioxidants vitamin C, vitamin E, and coenzyme Q10 for the prevention and treatment of cancer. Evid Rep Technol Assess (Summ). Oct. 2003;(75):1-3.
Shen et al., Bioactive Components from the Mycelium of Antrodia salmonea. Journal of the Chinese Chemical Society. 2008;55:854-857.
Sheng et al., The efficacy of combining antiangiogenic agents with chemotherapy for patients with advanced non-small cell lung cancer who failed first-line chemotherapy: a systematic review and meta-analysis. PLoS One. Jun. 2, 2015;10(6):e0127306.
Shimada et al., Effect of high dose of pyridoxine on mammary tumorigenesis. Nutr Cancer. 2005;53(2):202-7.
Shimizu, Paclitaxel Pirarubicin Weekly. Japan J. Cancer and Chemotherapy, Jan. 2003;30:105-109.
Sieben et al., Differential Gene Expressionin Ovarian Tumors Reveals Dusp 4 and Serpina 5 as Key Regulators for Benign Behavior of Serous Borderline Tumors. J Clinical Oncology. Oct. 1, 2005;23(29):7275-7264.
Small Cell Lung Cancer Treatment (PDQ®)—National Cancer Institute. Retrieved online at: http://www.cancer.gov/cancertopics/pdq/treatment/small-cell-lung/healthprofessional. Jan. 20, 2012.
Soule et al., A human cell line from a pleural effusion derived from a breast carcinoma. J Natl Cancer Inst. Nov. 1973;51(5):1409-16.
Stafford et al., Meningioma radiosurgery: tumor control, outcomes, and complications among 190 consecutive patients. Neurosurgery. Nov. 2001;49(5):1029-37.

(56) References Cited

OTHER PUBLICATIONS

Sun et al., BPM31510, a Coenzyme Q10 (CoQ10) containing lipid nanodispersion, enhances radiation effects to prolong survival in a rodent glioblastoma model. Cancer Res. 80(16 Suppl):2968, 2 pages.
Sun et al., BPM31510 exploits differential redox vulnerabilities between normal and glioblastoma cells to mediate its anti-cancer effect. Molecular and Cellular Biology/Genetics. Abstract 3608, Jul. 1, 2019.
The National Cancer Institute, Coenzyme Q10 (PDQ.RTM.) Patient Version. Retrieved online at: http://www.cancer.gov/cancertopics/pdq/cam/coenzymeQ10/patient/allpages. 13 pages, Jul. 10, 2009.
Thibault et al., Phase I Study of Lovastatin, an Inhibitor of the Mevalonate Pathway, in Patients with Cancer. Clinical Cancer Research. Mar. 1996;2:483-491.
Tockman et al., Considerations in bringing a cancer biomarker to clinical application. Cancer Res. May 1, 1992;52(9 Suppl):2711s-2718s.
Todaro et al., Apoptosis resistance in epithelial tumors is mediated by tumor-cell-derived interleukin-4. Cell Death Differ. Apr. 2008;15(4):762-72.
Tsubaki et al., [Investigation of the preventive effect of CoQ10 against the side-effects of anthracycline antineoplastic agents]. Gan To Kagaku Ryoho. Jul. 1984;11(7):1420-7.
Tsuneki et al., Coenzyme Q10 prevents high glucose-induced oxidative stress in human umbilical vein endothelial cells. Eur J Pharmacol. Jul. 2, 2007;566(1-3):1-10.
Abe et al., Effect of coenzyme Q10 in patients with mitochondrial myopathy, encephalopathy, lactic acidosis, and stroke-like episodes (MELAS): evaluation by noninvasive tissue oximetry. J Neurol Sci. Jan. 1, 1999;162(1):65-8.
Abe et al., Marked reduction in CSF lactate and pyruvate levels after CoQ therapy in a patient with mitochondrial myopathy, encephalopathy, lactic acidosis and stroke-like episodes (MELAS). Acta Neurol Scand. Jun. 1991;83(6):356-9.
Adeberg et al., Radiotherapy plus concomitant temozolomide in primary gliosarcoma. J Neurooncol. Jun. 2016;128(2):341-8.
Aizawa, Morphology of polysorbate 80 (Tween 80) micelles in aqueous dimethyl sulfoxide solutions. J Appl Crystallogr. Jun. 1, 2010;43(Pt 3):630-631.
American Cancer Society, Brain and Spinal Cord Tumors in Adults. Retrieved online at: http://www.cancer.org/cancer/braincnstumorsinadults/detailedguide/brain-and-spinal-cord-tumors-in-adults-what-are-brain-spinal-tumors. Nov. 12, 2009. 4 pages.
American Cancer Society, Colorectal Cancer. Retrieved online at: http:www.cancer.org/acs/groups/cid/documents/webcontent/003096-pdf.pdf. 122 pages, (2016).
Anderson et al., The transcriptional response to a peroxisome proliferator-activated receptor alpha agonist includes increased expression of proteome maintenance genes. J Biol Chem. Dec. 10, 2004;279(50):52390-8.
Ansell et al., Brain tumor signs and symptoms: analysis of primary health care records from the UKCCS. Pediatrics. Jan. 2010; 125(1):112-9.
Antoneeva et al., Markers of Apoptosis and Proliferation of Tumor Cells in the Dynamic of Ovarian Cancer Progression. Oncologiya. 2008;10(2):234-237.
Aris et al., Noise filtering and nonparametric analysis of microarray data underscores discriminating markers of oral, prostate, lung, ovarian and breast cancer. BMC Bioinformatics. Nov. 29, 2004;5(185):1-9.
Barbiroli et al., Coenzyme Q10 improves mitochondrial respiration in patients with mitochondrial cytopathies. An in vivo study on brain and skeletal muscle by phosphorous magnetic resonance spectroscopy. Cell Mol Biol (Noisy-le-grand). Jul. 1997;43(5):741-9.
Bjarnason, Chronobiology. Implications for cancer chemotherapy. Acta Oncol. 1995;34(5):615-24.
Bliznakov et al., Coenzymes Q: stimulants of the phagocytic activity in rats and immune response in mice. Experientia. Sep. 26, 1970;26(9):953-4.
Bliznakov, Effect of stimulation of the host defense system by coenzyme Q 0 on dibenzpyrene-induced tumors and infection with Friend leukemia virus in mice. Proc Natl Acad Sci U S A. Feb. 1973;70(2):390-4.
Blom et al., The risk of a venous thrombotic event in lung cancer patients: higher risk for adenocarcinoma than squamous cell carcinoma. J Thromb Haemost. Oct. 2004;2(10):1760-5.
Bresolin et al., Clinical and biochemical correlations in mitochondrial myopathies treated with coenzyme Q10. Neurology. Jun. 1988;38(6):892-9.
Buric et al., Modulation of Antioxidant Potential with Coenzyme Q10 Suppressed Invasion of Temozolomide-Resistant Rat Glioma In Vitro and In Vivo. Oxid Med Cell Longev. Mar. 12, 2019;2019:3061607, 14 pages.
Cabrera et al., Radiation therapy for glioblastoma: Executive summary of an American Society for Radiation Oncology Evidence-Based Clinical Practice Guideline. Pract Radiat Oncol. Jul.-Aug. 2016;6(4):217-225.
Cancer.net, Brain Tumor: Symptoms and Signs. Retrieved online at: https://www.cancer.net/cancer-types/brain-tumor/symptoms-and-signs. 4 pages, (2005).
Cancer.net, Stages of Cancer. Doctor-Approved Patient Information from ASCO. Retrieved online at: https://www.cancer.net/navigating-cancer-care/diagnosing-cancer/stages-cancer. 4 pages, Mar. 2018.
Carmona et al., Coadministration of coenzyme Q prevents rosiglitazone-induced adipogenesis in ob/ob mice. Int J Obes (Lond). Feb. 2009;33(2):204-11.
Chan et al., Metabolic changes in patients with mitochondrial myopathies and effects of coenzyme Q10 therapy. J Neurol. Oct. 1998;245(10):681-5.
Chang et al., Patterns of resistance and incomplete response to docetaxel by gene expression profiling in breast cancer patients. J Clin Oncol. Feb. 20, 2005;23(6):1169-77.
Chen et al., Coenzyme Q10 treatment in mitochondrial encephalomyopathies. Short-term double-blind, crossover study. Eur Neurol. 1997;37(4):212-8.
Cheung et al., Novel markers of subclinical disease for Ewing family tumors from gene expression profiling. Clin Cancer Res. Dec. 1, 2007;13(23):6978-83.
Chew et al., Coenzyme Q10 and diabetic endotheliopathy: oxidative stress and the ‘recoupling hypothesis’. QJM. Aug. 2004;97(8):537-48.
Chop, Pediatric Leukemias. Children’s Hospital of Philadelphia, retrieved online at: https://www.chop.edu/conditions-diseases/pediatric-leukemias. 9 pages, (2021).
ClinicalTrials.gov, BPM31510 Administered Intravenously With Gemcitabine in Advanced Pancreatic Cancer Patients. NCT02650804, 9 pages, Sep. 16, 2020.
ClinicalTrials.gov, NCT01928394, A Study of Nivolumab by Itself or Nivolumab Combined With Ipilimumab in Patients With Advanced or Metastatic Solid Tumors. 9 pages, Oct. 4, 2019.
Colman et al., Hemostasis and Thrombosis. Basic Principles and Clinical Practice, 5th Edition, Lippincott Williams & Wilkins, p. 1161 (2006).
Colon cancer: Tests and diagnosis—MayoClinic.com. Retrieved online at: http://www.mayoclinic.com/health/colon-cancer/ds00035/dsection=tests-and-diagnosis. 3 pages, Aug. 13, 2011.
Conklin, Cancer chemotherapy and antioxidants. J Nutr. Nov. 2004;134(11):3201S-3204S.
Conklin, Coenzyme q10 for prevention of anthracycline-induced cardiotoxicity. Integr Cancer Ther. Jun. 2005;4(2):110-30.
Crane, New Functions for Coenzyme Q. Protoplasma. 2000;213:127-133.
Crawford et al., Multiplex standardized RT-PCR for expression analysis of many genes in small samples. Biochem Biophys Res Commun. Apr. 26, 2002;293(1):509-16.
De Oliveria, A Nutritious Cocktail for the Treatment of Melanoma: A Case Report. The Journal of Orthomolecular Medicine. 1998;13(3)13, 2 pages.

(56) References Cited

OTHER PUBLICATIONS

Deeb et al., Vitamin D signalling pathways in cancer: potential for anticancer therapeutics. Nat Rev Cancer. Sep. 2007;7(9):684-700.
Doi et al., The JAK/STAT pathway is involved in the upregulation of PD-L1 expression in pancreatic cancer cell lines. Oncol Rep. 2017;37(3):1545-1554.
Domae et al., Cardiomyopathy and other chronic toxic effects induced in rabbits by doxorubicin and possible prevention by coenzyme Q10. Cancer Treat Rep. Jan.-Feb. 1981;65(1-2):79-91.
Eisenhauer et al., New response evaluation criteria in solid tumours: Revised RECIST guideline (version 1.1). European Journal of Cancer. 2009;45:228-247.
Family Caregiver Alliance, Fact Sheet: Brain Tumor. Los Angeles Caregiver Resource Center. Retrieved online at: http://lacrc.usc.edu/forms/brain tumor.pdf. 12 pages (2004).
Fang et al., Expression of ectonucleotide pyrophosphatase/phosphodiesterase 1 in human ovary and its relationship with polycystic ovary syndrome. ACTA Anatomica Sinica. 2008;39(4):552-556.
Fernández-Ayala et al., Coenzyme Q protects cells against serum withdrawal-induced apoptosis by inhibition of ceramide release and caspase-3 activation. Antioxid Redox Signal. 2000 Summer;2(2):263-75.
Ferrara et al., Protective role of chronic ubiquinone administration on acute cardiac oxidative stress. J Pharmacol Exp Ther. Aug. 1995;274(2):858-65.
Folkers et al., Survival of cancer patients on therapy with coenzyme Q10. Biochem Biophys Res Commun. Apr. 15, 1993;192(1):241-5.
Folkers, Relevance of the biosynthesis of coenzyme Q10 and of the four bases of DNA as a rationale for the molecular causes of cancer and a therapy. Biochem Biophys Res Commun. Jul. 16, 1996;224(2):358-61.
Foulkes et al., Triple-negative breast cancer. N Engl J Med. Nov. 11, 2010;363(20):1938-48.
Friedman et al., Temozolomide and Treatment of Malignant Glioma. Clinical Cancer Research. Jul. 2000;6:2585-2597, plus supplemental material.
Frontinan-Rubio et al., Regulation of the oxidative balance with coenzyme Q10 sensitizes human glioblastoma cells to radiation and temozolomide. Radiother Oncol. Aug. 2018;128(2):236-244.
Gaby, The Role of Coenzyme Q10 in Clinical Medicine: Part I. Alt Med Rev. 1996;1:11-17.
Galili et al., Clinical response of myelodysplastic syndromes patients to treatment with coenzyme Q10. Leuk Res. Jan. 2007;31(1):19-26.
Gao et al., Effects of coenzyme Q10 on vascular endothelial function in humans: a meta-analysis of randomized controlled trials. Atherosclerosis. Apr. 2012;221(2):311-6.
Garrel et al., The diagnostic accuracy of reverse transcription-PCR quantification of cytokeratin mRNA in the detection of sentinel lymph node invasion in oral and oropharyngeal squamous cell carcinoma: a comparison with immunohistochemistry. Clin Cancer Res. Apr. 15, 2006;12(8):2498-505.
Gersten, Brain Cancer Overview. The New York Times. Retrieved online at: http://health.nytimes.com/health/guides/disease/brain-tumor-adults. 3 pages.
Gesta et al., BPM31510, a clinical stage metabolic modulator demonstrates therapeutic efficacy in an in vivo C6 rat glioma model and synergizes with temozolomide. Cancer Research. Jul. 2017;77(Suppl. 13):Abstract 4067.
Gillet et al., Mechanisms of Multidrug Resistance in Cancer. Multi-Drug Resistance in Cancer, Methods in Molecular Biology, vol. 596, J. Zhou (Ed.). Humana Press. Chapter 4, pp. 47-76, (2010).
Gogvadze et al., Mitochondria as targets for chemotherapy. Apoptosis. Apr. 2009;14(4):624-40.
Golay et al., Link between obesity and type 2 diabetes. Best Pract Res Clin Endocrinol Metab. Dec. 2005;19(4):649-63.
Gorelick et al., Coenzyme Q10 and lipid-related gene induction in Hela cells. Am J Obstet Gynecol. May 2004;190(5):1432-4.
Groneberg et al., Coenzyme Q10 affects expression of genes involved in cell signaling, metabolism and transport in human CaCo-2 cells. The International Journal of Biochemistry and Cell Biology. 2005;37:1208-1218.
Haider et al., Effects of etanercept are distinct from infliximab in modulating proinflammatory genes in activated human leukocytes. J Investig Dermatol Symp Proc. May 2007;12(1):9-15.
Happold et al., Distinct molecular mechanisms of acquired resistance to temozolomide in glioblastoma cells. J Neurochem. Jul. 2012;122(2):444-55.
Hertz et al., Improved survival in patients with end-stage cancer treated with coenzyme Q(10) and other antioxidants: a pilot study. J Int Med Res. Nov.-Dec. 2009;37(6):1961-71.
Higdon et al., Obesity and oxidative stress: a direct link to CVD? Arterioscler Thromb Vasc Biol. Mar. 1, 2003;23(3):365-7.
Hill et al., Pharmacokinetics of drug infusions. Continuing Education in Anaesthesia. 2004. 4(3):76-80.
Hodges et al., CoQ10: could it have a role in cancer management? Biofactors. 1999;9(2-4):365-70.
Hodgson et al., Coenzyme Q10 improves blood pressure and glycaemic control: a controlled trial in subjects with type 2 diabetes. Eur J Clin Nutr. Nov. 2002;56(11):1137-42.
Huang et al., Treatment of refractory recurrent malignant glioma with adoptive cellular immunotherapy: a case report. Critical Reviews in Oncology/Hematology. 2001;57:17-23.
Hudson et al., Characterization of potentially chemopreventive phenols in extracts of brown rice that inhibit the growth of human breast and colon cancer cells. Cancer Epidemiol Biomarkers Prev. Nov. 2000;9(11):1163-70.
Iarussi et al., Protective effect of coenzyme Q10 on anthracyclines cardiotoxicity: control study in children with acute lymphoblastic leukemia and non-Hodgkin lymphoma. Mol Aspects Med. 1994;15 Suppl:s207-12.
Izyumov, Programmed Death of Cells and Oxidative Stress Caused by Inhibitors of Mitochondrial Functions. (synopsis of Ph.D. thesis), Moscow, 2005, pp. 17-20: URL: <http://www.lib.ua.net/diss/cont/151000.html>>.
Johnson et al., Gene expression profiles differentiate between sterile SIRS and early sepsis. Ann Surg. Apr. 2007;245(4):611-21.
Judy et al., Coenzyme Q10 Facts or Fiction. Natural Products Insider. 3 pages. Oct. 22, 2007.
Kawase et al., Enhancing effect of coenzyme, Q10 on immunorestoration with *Mycobacterium bovis* BCG in tumor-bearing mice. Gan. Aug. 1978;69(4):493-7.
Khan et al., Prolongation of Survival of Mice Bearing Leukemia 1210; Treated with Adriamycin and Coenzyme Q10. Proceedings of the American Association for Cancer Research. 1990;31:388, Poster 2303.
Kokawa et al., Coenzyme Q10 in cancer chemotherapy—experimental studies on augmentation of the effects of masked compounds, especially in the combined chemotherapy with immunopotentiators. Gan To Kagaku Ryoho. Mar. 1983;10(3):768-74. (Abstract only).
Kunitomo et al., Beneficial effect of coenzyme Q10 on increased oxidative and nitrative stress and inflammation and individual metabolic components developing in a rat model of metabolic syndrome. J Pharmacol Sci. Jun. 2008;107(2):128-37.
Lamson et al., Antioxidants in cancer therapy; their actions and interactions with oncologic therapies. Altern Med Rev. Oct. 1999;4(5):304-29.
Langer et al., Protein expression profiling in esophageal adenocarcinoma patients indicates association of heat-shock protein 27 expression and chemotherapy response. Clin Cancer Res. Dec. 15, 2008;14(24):8279-87.
Langham et al., Increased renal gene transcription of protein kinase C-beta in human diabetic nephropathy: relationship to long-term glycaemic control. Diabetologia. Apr. 2008;51(4):668-74.
Langsjoen, Alleviating Congestive Heart Failure with Coenzyme Q10. LifeExtension. http://www.lef.org/. Feb. 2008. 7 pages.
Laohapensang et al., An Unusual Complication of EVAR, Spontaneous Rectus Sheath Hematoma: A Case Report. Ann Vasc Dis. 2009;2(2):122-5.

(56) References Cited

OTHER PUBLICATIONS

Larsson, Effects of isoprenoids on growth of normal human mammary epithelial cells and breast cancer cells in vitro. Anticancer Res. Jan.-Feb. 1994;14(1A):123-8.
Lassman, Molecular Biology of Gliomas. Current Neurology and Neuroscience Reports. 2004;4:228-233.
Li et al., Candidate genes responsible for human hepatocellular carcinoma identified from differentially expressed genes in hepatocarcinogenesis of the tree shrew (*Tupaia belangeri chinesis*). Hepatol Res. Jan. 2008;38(1):85-95.
Li et al., Protective Effect of Coenzyme Q10 against the Adverse Reaction of Mytomycin G in Mouse Liver. Acta Histochemica et Cytochemica. 1987;20(4):455-467.
Liao et al., The compounding effects of coenzyme q10 and radiation treatment on glial fibrillary acidic protein network of glioma in vitro. AACR Annual Meeting. Oncodevelopment Biology and Medicine. Abstract 2931, Jul. 2019.
Littman et al., Effect of Cholesterol-Free, Fat-Free Diet and Hypocholesteremic Agents on Growth of Transplantable Animal Tumors. Cancer Chemotherapy Reports. Jan.-Feb. 1996;50(1 and 2):25-45.
Liu et al., The compounding effects of coenzyme q10 and radiation treatment on glial fibrillary acidic protein network of glioma in vitro. Cancer Res. 2019;79(13 Suppl):2931. 4 pages.
Lockwood et al., Apparent partial remission of breast cancer in 'high risk' patients supplemented with nutritional antioxidants, essential fatty acids and coenzyme Q10. Mol Aspects Med. 1994;15 Suppl:s231-40.
Lockwood et al., Partial and complete regression of breast cancer in patients in relation to dosage of coenzyme Q10. Biochem Biophys Res Commun. Mar. 30, 1994;199(3):1504-8.
Lockwood et al., Progress on therapy of breast cancer with vitamin Q10 and the regression of metastases. Biochem Biophys Res Commun. Jul. 6, 1995;212(1):172-7.
Marin et al., Overview of the molecular bases of resistance to chemotherapy in liver and gastrointestinal tumours. Curr Mol Med. Dec. 2009;9(9):1108-29.
Mazoff, Bleeding Disorders & Hepatitis C. HCV Advocate, HCSP Fact Sheet. www.hcvadvocate.org. HCSP, Version 3, 5 pages. Dec. 2014.
Mazzio et al., Effects of enhancing mitochondrial oxidative phosphorylation with reducing equivalents and ubiquinone on 1-methyl-4-phenylpyridinium toxicity and complex I-IV damage in neuroblastoma cells. Biochem Pharmacol. Mar. 15, 2004;67(6):1167-84.
Merck Manual Japanese Edition, 17th ed., pp. 59-63 (2002).
Merlo et al., FOXP3 expression and overall survival in breast cancer. J Clin Oncol. Apr. 10, 2009;27(11):1746-52.
Miles et al., Coenzyme Q10 changes are associated with metabolic syndrome. Clin Chim Acta. Jun. 2004;344 (1-2):173-9.
Modi et al., Effect of coenzyme Q10 on catalase activity and other antioxidant parameters in streptozotocin-induced diabetic rats. Biol Trace Elem Res. Jan. 2006;109(1):25-34.
Mohammed et al., Prognostic significance of vascular endothelial cell growth factors-A, -C and -D in breast cancer and their relationship with angio- and lymphangiogenesis. Br J Cancer. Apr. 10, 2007;96(7):1092-100.
UT Health Cancer Center, Clinical trial to study the safety and efficacy of MBG453 given alone and in combination with PDR001 in adults with advanced cancer. Retrieved online at: http://www.uthscsa.edu/pateint-care/ctrc/clinical-trial/HSC20150730HU. 3 pages, Jul. 30, 2015.
Verhoeff et al., Bevacizumab and dose-intense temozolomide in recurrent high-grade glioma. Ann Oncol. Aug. 2010;21(8):1723-7.
Vermeer, Vitamin K: the effect on health beyond coagulation—an overview. Food & Nutrition Research. 2012;56(5329):1-6.
Women's Health Update: Coenzyme Q10 and Breast Cancer. Retrieved online at: http://www.encognitive.com/node/13574 on Dec. 26, 2012. 4 pages.
Yagasaki et al., Clinical significance of E-cadherin and vimentin co-expression in breast cancer. Int J Oncol. Oct. 1996;9(4):755-61.
Yang et al., Efficiency Observations of 116 cases on Coenzyme Q10 as an Auxiliary Therapy for Treating Diabetes Combined with Coronary Heart Disease. Journal of Chinese Physician. Oct. 2002;4(10):1148-1149.
Yunis et al., Human pancreatic carcinoma (MIA PaCa-2) in continuous culture: sensitivity to asparaginase. Int J Cancer. Jan. 1977;19(1):128-35.
Zhang et al., Preparation and Physico-chemical Property of Coenzyme Q10 Submicroemulsion. China Pharmacy. 2007;18(19):1476-1478.
Zhao et al., The Clinical Application of Coenzyme Q10. Shandong Medical Journal. Jan. 31, 1996;36(1):52.
Zucher et al., Liposome drugs' loading efficiency: a working model based on loading conditions and drug's physicochemical properties. J Control Release. Oct. 1, 2009;139(1):73-80.
European Search Report for Application No. EP10775420, dated Feb. 18, 2013. 7 pages.
International Preliminary Report on Patentability for Application No. PCT/US2014/033402, dated Oct. 13, 2014.
International Search Report for Application No. PCT/US2007/068052, dated Apr. 15, 2008.
International Search Report for Application No. PCT/US2008/057786, dated Oct. 23, 2008.
International Search Report for Application No. PCT/US2010/034376, dated Jan. 28, 2011. 3 pages.
International Search Report for Application No. PCT/US2010/034427, dated Jan. 17, 2011.
International Search Report for Application No. PCT/US2010/034447, dated Feb. 24, 2011, 4 pages.
International Search Report for Application No. PCT/US2010/034453, dated Jan. 31, 2011.
International Search Report for Application No. PCT/US2014/033402, dated Aug. 15, 2014.
Supplementary European Search Report for Application No. EP05711599, dated Apr. 10, 2008.
Zhipeng et al., Toxicity of coenzyme Q(10): a report of 90-day repeated dose toxicity study in rats. J Toxicol Sci. Dec. 2007;32(5):505-14.

* cited by examiner

Coenzyme Q10 (Once/Daily) ± Gemcitabine

- - ◆ - - Control    - ☐ - Coenzyme Q10 - 50 mg/kg    - ◄ - Gemcitabine    - ✕ - Gemcitabine + Coenzyme Q10 - 50 mg/kg Number of Animals

DAYS

Coenzyme Q10 (Twice/Daily) ± Gemcitabine

Coenzyme Q10 (Three/Daily) ± Gemcitabine

TREATMENT OF LUNG CANCER CLONE WITH COENZYME Q10
THREE TIMES DAILY OR CONTINUOUS INFUSION (PUMP)

TREATMENT OF LUNG CANCER WITH COENZYME Q10 CONTINUOUS INFUSION WITH AND WITHOUT CHEMOTHERAPY

METHODS OF TREATMENT OF CANCER BY CONTINUOUS INFUSION OF COENZYME Q10

RELATED APPLICATIONS

This application is a continuation of U.S. patent application Ser. No. 17/686,569 filed Mar. 4, 2022 which, in turn, is a continuation of U.S. patent application Ser. No. 15/869,630 filed on Jan. 12, 2018 which, in turn, is a continuation of U.S. patent application Ser. No. 14/477,828 filed on Sep. 4, 2014 which, in turn, claims priority to U.S. Provisional Patent Application No. 61/873,510 filed on Sep. 4, 2013. U.S. Provisional Patent Application No. 61/901,351 filed on Nov. 7, 2013, and U.S. Provisional Patent Application No. 61/912,770 filed on Dec. 6, 2013, the contents of each of which are incorporated herein in their entirety.

FIELD OF THE INVENTION

The invention generally relates to methods for the treatment of oncological disorders comprising administration of coenzyme Q10 by continuous infusion.

BACKGROUND

Cancer is presently one of the leading causes of death in developed nations. A diagnosis of cancer traditionally involves serious health complications. Cancer can cause disfigurement, chronic or acute pain, lesions, organ failure, or even death. Commonly diagnosed cancers include pancreatic cancer, breast cancer, lung cancer, melanoma, lymphoma, carcinoma, sarcoma non-Hodgkin's lymphoma, leukemia, endometrial cancer, colon and rectal cancer, prostate cancer, and bladder cancer. Traditionally, many cancers (e.g., breast cancer, leukemia, lung cancer, or the like) are treated with surgery, chemotherapy, radiation, or combinations thereof. Chemotherapeutic agents used in the treatment of cancer are known to produce several serious and unpleasant side effects in patients. For example, some chemotherapeutic agents cause neuropathy, nephrotoxicity (e.g., hyperlipidemia, proteinuria, hypoproteinemia, combinations thereof, or the like), stomatitis, mucositisemesis, alopecia, anorexia, esophagitis amenorrhea, decreased immunity, anaemia, high tone hearing loss, cardiotoxicity, fatigue, neuropathy, myelosuppression, or combinations thereof. Oftentimes, chemotherapy is not effective, or loses effectiveness after a period of efficacy, either during treatment, or shortly after the treatment regimen concludes (i.e., the treatment regimen does not result in a cure). Improved methods for the treatment of oncological diseases, including cancer, and compositions capable of delivering bioactive agents to aid in the treatment of diseases and other conditions remain desirable.

SUMMARY OF THE INVENTION

The invention provides methods of treatment of cancer. e.g., a solid tumor or a non-solid tumor (e.g., a leukemia) by continuous, intravenous administration of coenzyme Q10.

The invention provides methods of treating cancer in a subject, comprising administering a composition comprising coenzyme Q10 by continuous intravenous infusion for at least 48 hours.

The invention also provides methods of treating cancer in a subject, comprising administering a composition comprising coenzyme Q10 by continuous intravenous infusion wherein the coenzyme Q10 is administered at two or more different rates.

In certain embodiments, the coenzyme Q10 is administered sequentially at a first rate and a second rate, wherein the first rate is higher than the second rate.

In certain embodiments, the methods further comprise administration of coenzyme Q10 at a third rate after the second rate.

In certain embodiments, the third rate is slower than the first rate and faster than the second rate.

In certain embodiments, the coenzyme Q10 is administered at the first rate for about 0.5 hours to about 3 hours.

In certain embodiments, the coenzyme Q10 is administered at the first rate for about 0.5 hours to about 2 hours.

In certain embodiments, the coenzyme Q10 is administered at the first rate for about 1 hour.

In certain embodiments, the total time of the infusion at the first rate plus the time of the infusion at the second rate is about 24 hours.

In certain embodiments, the total time of the infusion at the first rate plus the time of the infusion at the second rate is about 48 hours.

In certain embodiments, the coenzyme Q10 is administered by continuous intravenous infusion for at least 48 hours.

In certain embodiments, the coenzyme Q10 is administered by continuous intravenous infusion for at least 72 hours.

In certain embodiments, the coenzyme Q10 is administered by continuous intravenous infusion for at least 96 hours.

In certain embodiments, the coenzyme Q10 is administered by continuous intravenous infusion for no more than 120 hours.

In certain embodiments, the continuous intravenous infusion is administered once per week.

In certain embodiments, one or more doses of the continuous intravenous infusion is administered.

In certain embodiments, the continuous intravenous infusion is administered for two or more consecutive weeks, for three or more consecutive weeks, for four or more consecutive weeks, for five or more consecutive weeks, for six or more consecutive weeks, for seven or more consecutive weeks, or for eight or more consecutive weeks.

In certain embodiments, the coenzyme Q10 is administered by continuous intravenous infusion for at least 120 hours, for at least 144 hours, for at least 168 hours, for at least 192 hours, for at least 216 hours, for at least 240 hours, for at least 288 hours, for at least 312 hours, for at least 336 hours, for at least 360 hours, for at least 384 hours, for at least 408 hours, for at least 432 hours, for at least 456 hours, or for at least 480 hours.

In certain embodiments, the coenzyme Q10 is administered by continuous intravenous infusion for no more than 480 hours. In certain embodiments, the coenzyme Q10 is administered by continuous intravenous infusion for no more than 456 hours.

In certain embodiments, the intravenous infusion is administered every two weeks, every three weeks, or every four weeks.

In certain embodiments, the continuous intravenous infusion is administered one or more times, two or more times, or three or more times.

In certain embodiments, the coenzyme Q10 is administered with an additional agent.

In certain embodiments, administration of the additional agent is initiated on the same day as administration of coenzyme Q10 is initiated.

In certain embodiments, administration of the additional agent is initiated one or more weeks after the administration of coenzyme Q10 is initiated, two or more weeks after the administration of coenzyme Q10 is initiated, three or more weeks after the administration of coenzyme Q10 is initiated, four or more weeks after the administration of coenzyme Q10 is initiated, live or more weeks after the administration of coenzyme Q10 is initiated, six or more weeks after the administration of coenzyme Q10 is initiated, seven or more weeks after the administration of coenzyme Q10 is initiated, or eight or more weeks after the administration of coenzyme Q10 is initiated.

In certain embodiments, the additional agent is an anti-cancer agent.

In certain embodiments, the additional agent is a chemotherapeutic agent.

In certain embodiments, the additional agent is selected from the group consisting of gemcitabine, 5-fluorouracil, leucovorin, and docetaxel. In certain embodiments, the additional agent is selected from the group consisting of fludarabine and cytarabine. In certain embodiments, the additional agent is selected from the group consisting of cyclophosphamide, paclitaxel, docetaxel, busulfan, methotrexate, daunorubicin, doxorubicin, melphalan, cladribine, vincristine, vinblastine, chlorambucil, tamoxifen, taxol, camptothecin, actinomycin-D, mitomycin C, combretastatin, cisplatin, etoposide, verapamil, podophyllotoxin, and 5-fluoruracil.

In certain embodiments, the additional agent is an anti-angiogenic agent.

In certain embodiments, the additional agent is administered upon progression of the cancer during treatment with coenzyme Q10. In certain embodiments, the additional agent is administered upon stable disease or regression of the cancer during treatment with coenzyme Q10.

In certain embodiments, adverse effects of the additional agent are limited or decreased in subjects administered coenzyme Q10 by continuous infusion with the additional agent as compared to subjects not administered coenzyme Q10 by continuous infusion with the additional agent.

In certain embodiments, the adverse event is myelosuppression. In certain embodiments, the adverse event is cardiotoxicity.

In certain embodiments, the first rate is no more than 4.2 mg/kg/hour. In certain embodiments, the first rate is no more than 5.5 mg/kg/hour. In certain embodiments, the first rate is no more than 7.4 mg/kg/hour. In certain embodiments, the first rate is no more than 8.3 mg/kg/hour. In certain embodiments, the first rate is no more than 9.2 mg/kg/hour. In certain embodiments, the first rate is no more than 11 mg/kg/hour. In certain embodiments the first rate is no more than 14.5 mg/kg/hour. In certain embodiments, the first rate is no more than 18.4 mg/kg/hour. In certain embodiments, the first rate is no more than 19.6 mg/kg/hour. In certain embodiments, the first rate is no more than 22.9 mg/kg/hour. In certain embodiments, the first rate is no more than 26.0 mg/kg/hour. In certain embodiments, the first rate is no more than 28.7 mg/kg/hour. In certain embodiments, the first rate is no more than 35.8 mg/kg/hour.

The invention provides methods of treating cancer in a subject, comprising (a) administering a composition comprising coenzyme Q10 by continuous intravenous infusion wherein the coenzyme Q10 is administered at two or more different rates:
(b) monitoring the subject for decreased coagulation; and
(c) discontinuing treatment with coenzyme Q10 in a subject identified as having decreased coagulation.

The invention provides methods of treating cancer in a subject, comprising (a) administering a composition comprising coenzyme Q10 by continuous intravenous infusion wherein the coenzyme Q10 is administered at two or more different rates;
(b) monitoring the subject for decreased coagulation;
(c) administering an agent to increase coagulation in a subject identified as having decreased coagulation;
(d) confirming the subject has normal coagulation, and
(e) continuing treatment with coenzyme Q10.

In certain embodiments, the agent to increase coagulation comprises vitamin K.

The invention provides methods of treating cancer in a subject, comprising (a) administering a composition comprising coenzyme Q10 by continuous intravenous infusion wherein the coenzyme Q10 is administered at two or more different rates;
(b) monitoring the subject for decreased coagulation, and
(c) continuing treatment with coenzyme Q10 in a subject identified as having normal coagulation.

The invention provides methods of treating cancer in a subject, comprising (a) administering a composition comprising coenzyme Q10 by continuous intravenous infusion for at least 48 hours;
(b) monitoring the subject for decreased coagulation; and
(c) discontinuing treatment with coenzyme Q10 in a subject identified as having decreased coagulation.

The invention provides methods of treating cancer in a subject, comprising (a) administering a composition comprising coenzyme Q10 by continuous intravenous infusion for at least 48 hours;
(b) monitoring the subject for decreased coagulation;
(c) administering an agent to increase coagulation in a subject identified as having decreased coagulation;
(d) confirming the subject has normal coagulation; and
(e) continuing treatment with coenzyme Q10.

In certain embodiments, the agent to increase coagulation comprises vitamin K.

The invention provides methods of treating cancer in a subject, comprising (a) administering a composition comprising coenzyme Q10 by continuous intravenous infusion for at least 48 hours;
(b) monitoring the subject for decreased coagulation; and
(c) continuing treatment with coenzyme Q10 in a subject identified as having normal coagulation.

In certain embodiments, decreased coagulation comprises an INR of greater than 2 and normal coagulation comprises an INR of 2 or less.

In certain embodiments, decreased coagulation comprises an INR of greater than 3 and normal coagulation comprises an INR of 3 or less.

In certain embodiments, decreased coagulation comprises a platelet threshold less than 50,000/uL.

In certain embodiments, normal coagulation comprises a platelet threshold of at least 50,000/uL.

The invention provides methods of preventing or limiting severity of an adverse event associated with treatment of cancer with intravenously administered coenzyme Q10, comprising administering to a subject having cancer a composition comprising coenzyme Q10 by continuous intravenous infusion for at least 48 hours, wherein the severity of adverse events in the subject is reduced as compared to intravenous administration of the same dose of coenzyme Q10 over a period of 6 hours or less.

In certain embodiments, the coenzyme Q10 is administered by continuous intravenous infusion for at least 72 hours.

In certain embodiments, the coenzyme Q10 is administered by continuous intravenous infusion for at least 96 hours.

In certain embodiments, the coenzyme Q10 is administered by continuous infusion for no more than 120 hours.

In certain embodiments, the continuous intravenous infusion dose is administered twice per week.

In certain embodiments, the continuous intravenous infusion dose is administered once per week.

In certain embodiments, the continuous intravenous infusion dose is administered one or more times.

In certain embodiments, the continuous intravenous infusion dose is administered for two or more consecutive weeks, three or more consecutive weeks four or more consecutive weeks, five or more consecutive weeks, six or more consecutive weeks, seven or more consecutive weeks, or eight or more consecutive weeks.

In certain embodiments, the coenzyme Q10 is administered by continuous intravenous infusion for at least 120 hours, at least 144 hours, at least 168 hours, at least 192 hours, at least 216 hours, at least 240 hours, at least 264 hours, at least 288 hours, at least 312 hours, at least 336 hours, at least 360 hours, at least 384 hours, at least 408 hours, at least 432 hours, at least 456 hours, or at least 480 hours.

In certain embodiments, the coenzyme Q10 is administered by continuous infusion for no more than 456 hours. In certain embodiments, the coenzyme Q10 is administered by continuous infusion for no more than 480 hours.

In certain embodiments, the continuous intravenous infusion is administered once every two weeks, once every three weeks, or once every four weeks.

In certain embodiments, the continuous intravenous infusion is administered one or more times, two or more times, or three or more times.

In certain embodiments, the adverse event comprises a coagulopathy.

In certain embodiments, the coagulopathy comprises a grade 1 coagulopathy.

In certain embodiments, the coagulopathy comprises a grade 2 coagulopathy.

In certain embodiments, the coagulopathy comprises a grade 3 coagulopathy.

In certain embodiments, the coagulopathy comprises a grade 4 coagulopathy.

In certain embodiments, the adverse event comprises a severe adverse event.

In certain embodiments, the adverse event comprises a bleeding event.

In certain embodiments, the adverse event comprises an INR of at least 2.

In certain embodiments, the adverse event comprises an INR of at least 3.

The invention provides method of treating cancer comprising administering a composition comprising coenzyme Q10 by continuous intravenous infusion for about 96 hours wherein the composition is administered sequentially at a first rate, a second rate, and a third rate wherein.

(a) the first rate is a highest rate administered during the first hour of the continuous intravenous infusion;

(b) the second rate is a lowest rate administered during hours 2 to 48 of the continuous intravenous infusion; and (c) the third rate is an intermediate rate between the first rate and the second rate and is administered during hours 49 to 96 of the continuous intravenous infusion.

In preferred embodiments, the amount of coenzyme Q10 administered during hours 1 to 48 of the continuous intravenous infusion is equivalent to the amount of coenzyme Q10 administered during hours 49 to 96 of the continuous intravenous infusion.

In certain embodiments, the first rate is selected from the group consisting of no more than 4.2 mg-kg/hour, no more than 5.5 mg/kg/hour, no more than 7.4 mg/kg/hour, no more than 8.3 mg/kg/hour, no more than 9.2 mg/kg/hour, no more than 11.0 mg/kg/hour, no more than 14.5 mg/kg/hour, no more than 18.4 mg/kg/hour, no more than 19.6 mg/kg/hour, no more than 22.9 mg/kg/hour, no more than 26.0 mg/kg/hour, no more than 28.7 mg/kg/hour, and no more than 35.8 mg/kg/hour.

In certain embodiments, the coenzyme Q10 is administered at a dose of about 50 mg/kg/96 hour infusion and the first rate is about 4.2 mg/kg/hour, the second rate is about 0.98 mg/kg/hour, and the third rate is about 1.05 mg/kg/hour. In certain embodiments, the coenzyme Q10 is administered at a dose of about 66 mg/kg/96 hour infusion and the first rate is about 5.5 mg/kg/hour, the second rate is about 1.29 mg/kg/hour, and the third rate is about 1.38 mg/kg/hour. In certain embodiments, the coenzyme Q10 is administered at a dose of about 88 mg/kg/96 hour infusion and the first rate is about 7.4 mg/kg/hour, the second rate is about 1.71 mg/kg/hour, and the third rate is about 1.83 mg/kg/hour. In certain embodiments, the coenzyme Q10 is administered at a dose of about 110 mg/kg/96 hour infusion and the first rate is about 9.2 mg/kg/hour, the second rate is about 2.14 mg-kg/hour, and the third rate is about 2.29 mg/kg/hour. In certain embodiments, the coenzyme Q10 is administered at a dose of about 137 mg/kg/96 hour infusion and the first rate is about 11 mg/kg/hour, the second rate is about 2.68 mg/kg/hour, and the third rate is about 2.85 mg/kg/hour. In certain embodiments, the coenzyme Q10 is administered at a dose of about 171 mg/kg/96 hour infusion and the first rate is about 14 mg/kg/hour, the second rate is about 3.34 mg/kg/hour, and the third rate is about 3.56 mg/kg/hour. In certain embodiments, the coenzyme Q10 is administered at a dose of about 215 mg/kg/96 hour infusion and the first rate is about 18 mg/kg/hour, the second rate is about 4.19 mg/kg/hour, and the third rate is about 4.48 mg/kg/hour.

In certain embodiments, the coenzyme Q10 is administered at a dose of about 40 mg/kg/96 hour infusion to about 250 mg/kg/96 hour infusion and the first rate is about 3.4 mg/kg/hour to about 21 mg/kg/hour, the second rate is about 0.8 mg/kg/hour to about 4.8 mg/kg/hour, and the third rate is about 0.84 mg/kg/hour to about 5.25.

In certain embodiments, about 3-5% of the total coenzyme Q10 administered over the 96 hours of the continuous intravenous infusion is administered during the first hour of the continuous intravenous infusion.

The invention provides method of treating cancer comprising administering a composition comprising coenzyme Q10 by continuous intravenous infusion for about 18 days wherein the composition is administered sequentially at a first rate, a second rate, and a third rate wherein:

(a) the first rate is a highest rate administered during hour 1 of day 1 of the continuous infusion;

(b) the second rate is a lowest rate administered during hours 2 to 24 of day 1 the continuous infusion; and (c) the third rate comprises an intermediate rate administered between the first rate and the second rate administered during days 2 to 17 of the continuous infusion.

In preferred embodiments, the amount of coenzyme Q10 administered during each 24 hour period of the continuous intravenous infusion is equivalent.

In certain embodiments, the first rate is a rate selected from the group consisting of no more than 4.2 mg/kg/hour, no more than 5.5 mg/kg/hour, no more than 7.4 mg/kg/hour, no more than 8.3 mg/kg/hour, no more than 9.2 mg/kg/hour, no more than 11.0 mg/kg/hour, no more than 14.5 mg/kg/hour, no more than 18.4 mg/kg/hour, no more than 19.6 mg/kg/hour, no more than 22.9 mg/kg/hour, no more than 26.0 mg/kg/hour, no more than 28.7 mg/kg/hour, and no more than 35.8 mg/kg/hour.

In certain embodiments, the coenzyme Q10 is administered at a dose of about 33 mg/kg/24 hours of infusion and the first rate is about 8.3 mg/kg/hour, the second rate is about 1.07 mg/kg/hour, and the third rate is about 1.38 mg/kg/hour. In certain embodiments, the coenzyme Q10 is administered at a dose of about 44 mg/kg/24 hours of infusion and the first rate is about 11 mg/kg/hour, the second rate is about 1.43 mg/kg/hour, and the third rate is about 1.83 mg/kg/hour. In certain embodiments, the coenzyme Q10 is administered at a dose of about 58.7 mg/kg/24 hours of infusion and the first rate is about 14.7 mg/kg/hour, the second rate is about 1.91 mg/kg/hour, and the third rate is about 2.44 mg/kg/hour. In certain embodiments, the coenzyme Q10 is administered at a dose of about 73.4 mg/kg/24 hours of infusion and the first rate is about 18.4 mg/kg/hour, the second rate is about 2.39 mg/kg/hour, and the third rate is about 3.06 mg/kg/hour. In certain embodiments, the coenzyme Q10 is administered at a dose of about 91.7 mg/kg/24 hours of infusion and the first rate is about 22.9 mg/kg/hour, the second rate is about 2.99 mg/kg/hour, and the third rate is about 3.82 mg/kg/hour. In certain embodiments, the coenzyme Q10 is administered at a dose of about 114.6 mg/kg/24 hours of infusion and the first rate is about 28.7 mg/kg/hour, the second rate is about 3.73 mg/kg/hour, and the third rate is about 4.78 mg/kg/hour. In certain embodiments, the coenzyme Q10 is administered at a dose of about 143.3 mg/kg/24 hours of infusion and the first rate is about 35.8 mg/kg/hour, the second rate is about 4.67 mg/kg/hour, and the third rate is about 5.97 mg/kg/hour.

In certain embodiments, the coenzyme Q10 is administered at a dose of about 30 mg/kg/24 hours of infusion to about 170 mg/kg/24 hour infusion and the first rate is about 7.5 mg/kg/hour to about 42.5 mg/kg/hour, the second rate is about 0.98 mg/kg/hour to about 5.54 mg/kg/hour, and the third rate is about 1.25 mg/kg/hour to about 7.08.

In certain embodiments, about 20-30% of the total coenzyme Q10 administered during hours 1 to 48 of the continuous infusion is administered during the first hour of the continuous infusion.

In certain embodiments, the coenzyme Q10 is administered with an additional agent.

In certain embodiments, administration of the additional agent is prior to the administration of coenzyme Q10. In certain embodiments, administration of the additional agent is not prior to the administration of coenzyme Q10.

In certain embodiments, administration of the additional agent is initiated on the same day as administration of coenzyme Q10 is initiated.

In certain embodiments, administration of the additional agent is initiated one or more weeks after the administration of coenzyme Q10 is initiated.

In certain embodiments, administration of the additional agent is initiated two or more weeks after the administration of coenzyme Q10 is initiated.

In certain embodiments, administration of the additional agent is initiated three or more weeks after the administration of coenzyme Q10 is initiated.

In certain embodiments, administration of the additional agent is initiated four or more weeks after the administration of coenzyme Q10 is initiated.

In certain embodiments, administration of the additional agent is initiated five or more weeks after the administration of coenzyme Q10 is initiated.

In certain embodiments, administration of the additional agent is initiated six or more weeks after the administration of coenzyme Q10 is initiated.

In certain embodiments, administration of the additional agent is initiated seven or more weeks after the administration of coenzyme Q0 is initiated.

In certain embodiments, administration of the additional agent is initiated eight or more weeks after the administration of coenzyme Q10 is initiated.

In certain embodiments, the invention further comprises monitoring the subject for myelosuppression.

In certain embodiments, no myelosuppression is observed.

In certain embodiments, the additional agent is an anti-cancer agent.

In certain embodiments, the additional agent is a chemotherapeutic agent.

In certain embodiments, the additional agent is selected from the group consisting of gemcitabine, 5-fluorouracil, leucovorin, and docetaxel.

In certain embodiments, the additional agent is selected from the group consisting of fludarabine and cytarabine.

In certain embodiments, the additional agent is selected from the group consisting of cyclophosphamide, paclitaxel, docetaxel, busulfan, methotrexate, daunorubicin, doxorubicin, melphalan, cladribine, vincristine, vinblastine, chlorambucil, tamoxifen, taxol, camptothecin, actinomycin-D, mitomycin C, combretastatin, cisplatin, etoposide, verapamil, podophyllotoxin, and 5-fluorouracil.

In certain embodiments, the additional agent is administered upon progression of the cancer during treatment with coenzyme Q10.

In certain embodiments, the additional agent is administered without progression of the cancer during treatment with coenzyme Q10.

In certain embodiments, adverse effects of the additional agent are limited or decreased in subjects administered coenzyme Q10 by continuous infusion with the additional agent as compared to subjects not administered coenzyme Q10 by continuous infusion with the additional agent.

In certain embodiments, the adverse event is myelosuppression.

In certain embodiments, the adverse event is cardiotoxicity.

In certain embodiments, the cancer comprises a solid tumor.

In certain embodiments, the solid tumor is selected from the group consisting of carcinoma, melanoma, sarcoma, and lymphoma.

In certain embodiments, the solid tumor is selected from the group consisting of breast cancer, bladder cancer, colon cancer, rectal cancer, endometrial cancer, kidney (renal cell) cancer, lung cancer, melanoma, pancreatic cancer, prostate cancer, thyroid cancer, skin cancer, bone cancer, brain cancer, cervical cancer, liver cancer, stomach cancer, mouth and oral cancers, neuroblastoma, testicular cancer, uterine cancer, thyroid cancer, and vulvar cancer. In preferred embodiments, the Coenzyme Q10 compositions are used for treatment, of various types of solid tumors, for example breast cancer, bladder cancer, colon and rectal cancer, endometrial cancer, kidney (renal cell) cancer, lung cancer, melanoma, pancreatic cancer, prostate cancer, thyroid cancer, skin cancer, bone cancer, brain cancer, cervical cancer, liver cancer, stomach cancer, mouth and oral cancers, neuroblastoma, testicular cancer, uterine cancer, thyroid cancer, and vulvar cancer. In certain embodiments, solid tumors include breast cancer, including triple negative breast cancer. In certain embodiments, skin cancer includes melanoma, squamous cell carcinoma, cutaneous T-cell lymphoma (CTCL).

In certain embodiments, the cancer comprises a leukemia.

In certain embodiments, the leukemia is selected from the group consisting of acute lymphocytic (or lymphoblastic) leukemia (ALL), acute myelogenous (or myeloid or non-lymphatic) leukemia (AML), chronic lymphocytic leukemia (CLL), and chronic myelogenous leukemia (CML). Further types of leukemia include Hairy cell leukemia (HCL), T-cell prolymphocytic leukemia (T-PLL), large granular lymphocytic leukemia, and adult T-cell leukemia.

In certain embodiments, the leukemia is an acute leukemia.

In certain embodiments, the leukemia is selected from the group consisting of ALL and AML.

In certain embodiments, the coenzyme Q10 is administered at a dose of about 12.5 mg/kg/day (24 hours). In certain embodiments, the coenzyme Q10 is administered at a dose of about 16.5 mg/kg/day (24 hours). In certain embodiments, the coenzyme Q10 is administered at a dose of about 22 mg/kg/day (24 hours). In certain embodiments, the coenzyme Q10 is administered at a dose of about 27.5 mg/kg/day (24 hours). In certain embodiments, the coenzyme Q10 is administered at a dose of about 33 mg/kg/day (24 hours). In certain embodiments, the coenzyme Q10 is administered at a dose of about 34.2 mg/kg/day (24 hours). In certain embodiments, the coenzyme Q10 is administered at a dose of about 42.8 mg/kg/day (24 hours). In certain embodiments, the coenzyme Q10 is administered at a dose of about 44 mg/kg/day (24 hours). In certain embodiments, the coenzyme Q10 is administered at a dose of about 53.8 mg/kg/day (24 hours). In certain embodiments, the coenzyme Q10 is administered at a dose of about 58.7 mg/kg/day (24 hours). In certain embodiments, the coenzyme Q10 is administered at a dose of about 73.4 mg/kg/day (24 hours). In certain embodiments, the coenzyme Q10 is administered at a dose of about 91.7 mg/kg/day (24 hours). In certain embodiments, the coenzyme Q10 is administered at a dose of about 114.6 mg/kg/day (24 hours). In certain embodiments, the coenzyme Q10 is administered at a dose of about 143.3 mg/kg/day (24 hours).

In certain embodiments, the coenzyme Q10 is administered at a dose of about 33 mg/kg/day (24 hours) to about 143.3 mg/kg/day (24 hours).

In certain embodiments, the coenzyme Q10 is administered at a dose of about 50 mg/kg/week. In certain embodiments, the coenzyme Q10 is administered at a dose of about 66 mg/kg/week. In certain embodiments, the coenzyme Q10 is administered at a dose of about 88 mg/kg/week. In certain embodiments, the coenzyme Q10 is administered at a dose of about 110 mg/kg/week. In certain embodiments, the coenzyme Q10 is administered at a dose of about 137 mg/kg/week. In certain embodiments, the coenzyme Q10 is administered at a dose of about 171 mg/kg/week. In certain embodiments, the coenzyme Q10 is administered at a dose of about 215 mg/kg/week.

In certain embodiments, the coenzyme Q10 is administered at a dose of about 50 mg/kg/week to about 215 mg/kg/week.

In certain embodiments, the coenzyme Q10 is administered at a dose of about 50 mg/kg/week.

In certain embodiments, the continuous intravenous infusion of coenzyme Q10 is administered at a higher rate for the first hour of the infusion.

In certain embodiments, at least 5% of the total dose of coenzyme Q10 administered over the first 48 hours of the continuous infusion is administered during the first hour of the continuous intravenous infusion. In certain embodiments, at least 6% of the total dose of coenzyme Q10 administered over the first 48 hours of the continuous infusion is administered during the first hour of the continuous intravenous infusion. In certain embodiments, at least 7% of the total dose of coenzyme Q10 administered over the first 48 hours of the continuous infusion is administered during the first hour of the continuous intravenous infusion. In certain embodiments, at least 8% of the total dose of coenzyme Q10 administered over the first 48 hours of the continuous infusion is administered during the first hour of the continuous intravenous infusion. In certain embodiments, at least 9% of the total dose of coenzyme Q10 administered over the first 48 hours of the continuous infusion is administered during the first hour of the continuous intravenous infusion. In certain embodiments, at least 10% of the total dose of coenzyme Q10 administered over the first 48 hours of the continuous infusion is administered during the first hour of the continuous intravenous infusion.

In certain embodiments, no more than 10% of the total dose of coenzyme Q10 administered over the first 48 hours of the continuous infusion is administered during the first hour of the continuous intravenous infusion.

In certain embodiments, at least 20% of the total dose of coenzyme Q10 administered over the first 24 hours of the continuous infusion is administered during the first hour of the continuous intravenous infusion. In certain embodiments, at least 21% of the total dose of coenzyme Q10 administered over the first 24 hours of the continuous infusion is administered during the first hour of the continuous intravenous infusion. In certain embodiments, at least 22% of the total dose of coenzyme Q10 administered over the first 24 hours of the continuous infusion is administered during the first hour of the continuous intravenous infusion. In certain embodiments, at least 23% of the total dose of coenzyme Q10 administered over the first 24 hours of the continuous infusion is administered during the first hour of the continuous intravenous infusion. In certain embodiments, at least 24% of the total dose of coenzyme Q10 administered over the first 24 hours of the continuous infusion is administered during the first hour of the continuous intravenous infusion. In certain embodiments, at least 25% of the total dose of coenzyme Q10 administered over the first 24 hours of the continuous infusion is administered during the first hour of the continuous intravenous infusion. In certain embodiments, at least 26% of the total dose of coenzyme Q10 administered over the first 24 hours of the continuous infusion is administered during the first hour of the continuous intravenous infusion. In certain embodiments, at least 27% of the total dose of coenzyme Q10 administered over the first 24 hours of the continuous infusion is administered during the first hour of the continuous intravenous infusion. In certain embodiments, at least 28% of the total dose of coenzyme Q10 administered over the first 24 hours of the continuous infusion is administered during the first hour of the continuous intravenous infusion.

In certain embodiments, no more than 28% of the total dose of coenzyme Q10 administered over the first 24 hours of the continuous infusion is administered during the first hour of the continuous intravenous infusion.

In certain embodiments, the continuous intravenous infusion of coenzyme Q10 is performed at a constant rate.

In certain embodiments, the composition comprises 0.1% to 10% why coenzyme Q10.

In certain embodiments, comprises 1% to 10% w/v coenzyme Q10.

In certain embodiments, the composition comprises 1% to 5% w/v coenzyme Q10.

In certain embodiments, the composition comprises 2% to 6% w/v coenzyme Q10.

In certain embodiments, the composition comprises 3% to 5% w/v coenzyme Q10.

In certain embodiments, the method further comprises selecting a subject having cancer for treatment with coenzyme Q10, wherein the subject has adequate coagulation.

In certain embodiments, adequate coagulation comprises platelet threshold of 50,000/mcL, prothrombin time (PT), partial thromboplastin time (PTT), and an International Normalized Ratio (INR) within normal limits.

In certain embodiments, the methods further comprise selecting against a subject having cancer for treatment with coenzyme Q10, wherein the subject exhibits at least one condition or characteristic selected from the group consisting of:

(a) subject is taking HMG-CoA reductase inhibitors;
(b) subject is taking digoxin, digitoxin, lanatoside C or any type of digitalis alkaloids
(c) subject has uncontrolled or severe coagulopathies or a history of clinically significant bleeding within the past 6 months,
(d) subject has at least one of hemoptysis, epistaxis, hematochezia, hematuria, or gastrointestinal bleeding;
(e) subject has predisposition for bleeding;
(f) subject has been administered anticoagulant: (g) subject has a ≥grade 3 thrombocytopenia with clinically significant bleeding;
(h) subject has a ≥grade 4 hematologic toxicity;
(i) subject has a grade 2 INR/PTT elevation with clinically significant bleeding; and
(j) subject has a grade 3 INR/PTT abnormality.

In certain embodiments of the aforementioned method, the predisposition for bleeding comprises von Willebrand's disease. In certain embodiments of the aforementioned methods, the ≥grade 4 hematologic toxicity is selected from the group consisting of death, grade 4 anemia, grade 4 thrombocytopenia, grade 4 neutropenia of greater than 5 days duration, and grade 4 neutropenia of any duration with fever or documented infection.

The invention provides methods of increasing therapeutic index of intravenously administered coenzyme Q10, by increasing time of infusion of a dose of coenzyme Q10 from at least 6 hours to a continuous intravenous infusion for at least 48 hours.

In certain embodiments, the subject is assessed for response to the coenzyme Q10 at the end of the four week cycle. In certain embodiments, if no tumor progression is observed by RECIST criteria, the subject is maintained on treatment with coenzyme Q10. In certain embodiments, if no tumor progression is observed by RECIST criteria, the subject is maintained on treatment with coenzyme Q10 alone. In certain embodiments, the dose of coenzyme Q10 is increased as compared to the dose of coenzyme Q10 administered during the first 28 days of treatment. In certain embodiments, the increased dose is administered FIG. 21 days. In certain embodiments, the increased dose is administered weekly in one 96 hour continuous infusion per week. In certain embodiments, the dose is continuously increased until a maximum tolerated dose is identified for the subject.

In certain embodiments, if tumor progression is observed by RECIST criteria, the subject is maintained on treatment with coenzyme Q10 supplemented with standard of care chemotherapy. In certain embodiments, the standard of care chemotherapy is selected from gemcitabine, 5-fluorouracil with leucovorin, and docetaxel. In certain embodiments, gemcitabine is administered IV once weekly at a starting dose of 600 $mg/m^2$. In certain embodiments, 5-Fluorouracil (5-FU) is administered IV once weekly at a starting dose of 350 $mg/m^2$ with leucovorin UN) 100 $mg/m^2$. In certain embodiments, docetaxel is administered IV once weekly at a starting dose of 20 $mg/m^2$.

In certain embodiments, the coenzyme Q10 is administered as an 18 day continuous infusion. In certain embodiments, the cancer is a leukemia. In certain embodiments, if no disease progression is observed by standard criteria, the subject is maintained on treatment with coenzyme Q10. In certain embodiments, if disease progression is observed by standard criteria, the subject is maintained on treatment with coenzyme Q10 alone. In certain embodiments, if tumor progression is observed by standard criteria, the subject is maintained on treatment with coenzyme Q10 supplemented with standard of care chemotherapy. In certain embodiments, the standard of care Preferred coenzyme Q10 compositions and dosages for intravenous administration are provided, for example, in WO2011112900.

In certain embodiments of the invention, the coenzyme Q10 compound is formulated as a nanodispersion.

In certain embodiments of the invention, the coenzyme Q10 compound is provided for intravenous administration in a coenzyme Q10 formulation comprising:

an aqueous solution;

a coenzyme Q10 dispersed into a nano-dispersion of particles; and at least one of a dispersion stabilizing agent and an opsonization reducer;

wherein the nano-dispersion of the coenzyme Q10 is dispersed into nano-particles having a mean particle size of less than 200-nm. In certain embodiments, the dispersion stabilizing agent is selected from the group consisting of pegylated castor oil, Cremophor® EL, Cremophor® RH 40, Pegylated vitamin E, Vitamin E TPGS, and Dimyristoylphosphatidyl choline (DMPC). In certain embodiments, the dispersion stabilizing agent is DMPC. In certain embodiments, the opsonization reducer is selected from the group consisting of poloxamers and poloxamines. In certain embodiments, the opsonization reducer is poloxamer 188. In certain embodiments, the opsonization reducer is poloxamer 188 and the dispersion stabilizing agent is DMPC.

In certain embodiments of the invention, the coenzyme Q10 formulation has a weight-per-volume of the coenzyme Q10, DMPC and poloxamer 188 of 4%, 3% and 1.5%, respectively.

In certain embodiments of the invention, the CoQ10 compound is administered to the subject with an additional agent. In certain embodiments, additional agent is a chemotherapeutic agent.

In preferred embodiments of the invention, the CoQ10 compound is coenzyme Q10.

The invention provides intravenously administered coenzyme Q10 for use in any of the methods provided herein.

The invention provides for the use of intravenously administered coenzyme Q10 for any of the methods provided herein.

The invention provides pharmaceutical compositions comprising coenzyme Q10 for any of the methods provided herein.

The invention provides compositions comprising a CoQ10 compound for practicing any of the methods provided herein.

In certain embodiments of the invention, the CoQ10 compound is administered at least one time per week. In certain embodiments, the CoQ10 compound is administered at least two times per week. In certain embodiments, the CoQ10 compound is administered at least three times per week. In certain embodiments, the CoQ10 compound is administered one time per week. In certain embodiments, the CoQ10 compound is administered two times per week. In certain embodiments, the CoQ10 compound is administered three times per week.

In certain embodiments of the invention, the CoQ10 compound is administered at a 24 hour dose selected from the group consisting of at least 5.6 mg/kg/dose, at least 11.2 mg/kg/dose, at least 22.5 mg/kg/dose, at least 33 mg/kg/dose, at least 44 mg/kg/dose, at least 58.7 mg/kg/dose, at least 73.4 mg/kg/dose, at least 78.2 mg/kg/dose, at least 91.7 mg/kg/dose, at least 104.3 mg/kg/dose, at least 114.6 mg/kg/dose, at least 139 mg/kg/dose, and at least 78.2 mg/kg/dose. In certain embodiments, the CoQ10 compound is administered at a 24 hour dose of at least 50 mg/kg/dose, at least 75 mg/kg/dose, at least 100 mg/kg/dose, at least 125 mg/kg/dose, at least 150 mg/kg/dose, at least 200 mg/kg/dose. In certain embodiments, the dose is administered for four (4) consecutive 24 hour periods (i.e., a 96-hour continuous infusion). In certain embodiments, the dose is administered for eighteen (18) consecutive 24 hour periods (i.e., a 432-hour continuous infusion).

In certain embodiments of the invention, the CoQ10 compound is administered at a 24 hour dose of no more than 500 mg/kg/dose, no more than 400 mg/kg/dose, no more than 300 mg/kg/dose, no more than 250 mg/kg/dose, no more than 200 mg/kg/dose, no more than 150 mg/kg/dose, or no more than 100 mg/kg/dose.

In certain embodiments of the invention, the CoQ10 compound is administered at a 96 hour dose selected from the group consisting of at least 50 mg/kg/dose, at least 66 mg/kg/dose, at least 88 mg/kg/dose, at least 110 mg/kg/dose, at least 137 mg/kg/dose, at least 171 mg/kg/dose, and at least 215 mg/kg/dose. In certain embodiments of the invention, the CoQ10 compound is administered at a 96 hour dose selected from the group consisting of about 50 mg/kg/dose, about 66 mg/kg/dose, about 88 mg/kg/dose, about 110 mg/kg/dose, about 137 mg/kg/dose, about 171 mg/kg/dose, and about 215 mg/kg/dose.

In certain embodiments, the CoQ10 compound is administered at a dose that does not result in a Grade III toxicity in the subject. In certain embodiments, the CoQ10 compound is administered at a dose that does not result in a Grade IV toxicity to the subject.

In certain embodiments of the invention, at least 12 doses of the CoQ10 compound are administered to the subject. That is, in certain embodiments, at least 8, 9, 10, 11, 12, 13, 14, 15, 16, 17, 18, 19, 20, 21, 22, 23, 24, 25, 62, 27, 28, 29, 30, 31, 32, 33, 34, 35, 36, 37, 38, 39, 40, 45, 50, 55, 60, 65, 70, 75, 80, 85, 90, 95, 100, or more doses are administered to the subject.

In certain embodiments, the subject is treated with CoQ10 for at least 4 weeks. In certain embodiments, the subject is treated with CoQ10 for at least 8 weeks. That is, in certain embodiments, the subject is treated with CoQ10 for at least 4, 5, 6, 7, 8, 9, 10, 11, 12, 13, 14, 15, 16, 17, 18, 19, 20, 21, 22, 23, 24, 25, 62, 27, 28, 29, 30, 31, 32, 33, 34, 35, 36, 37, 38, 39, 40, 45, 50, 55, 60, 65, 70, 75, 80, 85, 90, 95, 100, 0, or more weeks.

In a preferred embodiment, the coenzyme Q10 is formulated in a solution of about 3% to about 5% coenzyme Q10 (e.g., about 4%) prior to administration. In certain embodiments, the coenzyme Q10 is formulated in a solution of about 3% to about 5% coenzyme Q10 is diluted prior to administration in an appropriate carrier.

In certain embodiments, treatment of the subject is assayed or monitored by the detection of one or more markers. Markers for use in the method can include protein markers, nucleic acid markers, and lipid markers. Markers can be assayed or monitored in any subject sample including, but not limited to, blood, urine, or tissue. In certain embodiments, one or more markers is at least one cancer marker. In certain embodiments, one or more markers is at least one metabolic marker.

The invention also provides methods of treating cancer in a subject, comprising administering a composition comprising coenzyme Q10 by continuous intravenous infusion for at least 48 hours.

The invention also provides methods of treating cancer in a subject, comprising administering a composition comprising coenzyme Q10 by continuous intravenous infusion wherein the coenzyme Q10 is administered at two or more different rates.

In certain embodiments, the coenzyme Q10 is administered sequentially at a first rate and a second rate, wherein the first rate is higher than the second rate.

In certain embodiments, the methods further comprise administration of coenzyme Q10 at a third rate after the second rate. In certain embodiments, the third rate is lower than the first rate and higher than the second rate.

In certain embodiments, the coenzyme Q10 is administered at the first rate for about 0.5 hours to about 3 hours, or for about 0.5 hours to about 2 hours. In certain embodiments, the coenzyme Q10 is administered at the first rate for about 1 hour.

In certain embodiments, the total time of the infusion at the first rate plus the time of the infusion at the second rate is about 24 hours, about 48 hours, or about 72 hours.

In certain embodiments, the coenzyme Q10 is administered by continuous intravenous infusion for at least 48 hours. In certain embodiments, the coenzyme Q10 is administered by continuous intravenous infusion for at least 72 hours. In certain embodiments, the coenzyme Q10 is administered by continuous intravenous infusion for at least 96 hours. In certain embodiments, the coenzyme Q10 is administered by continuous intravenous infusion for at least 144 hours.

In certain embodiments, the continuous intravenous infusion is administered once per week. In certain embodiments, the continuous infusion is administered twice per week.

In certain embodiments, the coenzyme Q10 is administered by continuous intravenous infusion for at least 120 hours, for at least 144 hours, for at least 168 hours, for at least 192 hours, for at least 216 hours, for at least 240 hours, for at least 288 hours, for at least 312 hours, for at least 336 hours, for at least 360 hours, for at least 384 hours, for at least 408 hours, for at least 432 hours, fir at least 456 hours, or fir at least 480 hours.

In certain embodiments, the continuous intravenous infusion is administered once every two weeks, once every three weeks, or once every four weeks.

In certain embodiments, the first rate is no more than 3.1 mg/kg/hr, 4.2 mg/kg/hour, no more than 5.5 mg/kg/hour, no more than 7.4 mg/kg/hour, no more than 8.3 mg/kg/hour, no more than 9.2 mg/kg/hour, no more than 11.0 mg/kg/hour, no more than 11.2 mg/kg/hour, no more than 14 mg/kg/hour, no more than 14.5 mg/kg/hour, no more than 18.0 mg/kg/hour, no more than 18.4 mg/kg/hour, no more than 19.6 mg/kg/hour, no more than 22.9 mg/kg/hour, no more than 26.0 mg/kg/hour, no more than 28.7 mg/kg/hour, or no more than 35.8 mg/kg/hour.

The invention also provides a method of treating cancer in a subject, comprising: (a) administering a composition comprising coenzyme Q10 by continuous intravenous infusion wherein the coenzyme Q10 is administered at two or more different rates; (b) monitoring the subject for decreased coagulation; and (c) discontinuing treatment with coenzyme Q10 in a subject identified as having decreased coagulation.

The invention also provides a method of treating cancer in a subject, comprising: (a) administering a composition comprising coenzyme Q10 by continuous intravenous infusion wherein the coenzyme Q10 is administered at two or more different rates; (b) monitoring the subject for decreased coagulation; (c) administering an agent to increase coagulation in a subject identified as having decreased coagulation; (d) confirming the subject has normal coagulation; and (e) continuing treatment with coenzyme Q10.

In certain embodiments, the agent to increase coagulation comprises vitamin K.

The invention also provides a method of treating cancer in a subject, comprising: (a) administering a composition comprising coenzyme Q10 by continuous intravenous infusion wherein the coenzyme Q10 is administered at two or more different rates; (b) monitoring the subject for decreased coagulation; and (c) continuing treatment with coenzyme Q10 in a subject identified as having normal coagulation.

The invention also provides a method of treating cancer in a subject, comprising (a) administering a composition comprising coenzyme Q10 by continuous intravenous infusion for at least 48 hours, (b) monitoring the subject for decreased coagulation; and (c) discontinuing treatment with coenzyme Q10 in a subject identified as having decreased coagulation.

The invention also provides a method of treating cancer in a subject, comprising (a) administering a composition comprising coenzyme Q10 by continuous intravenous infusion for at least 48 hours; (b) monitoring the subject for decreased coagulation; (c) administering an agent to increase coagulation in a subject identified as having decreased coagulation; (d) confirming the subject has normal coagulation; and (e) continuing treatment with coenzyme Q10.

In certain embodiments, the agent to increase coagulation comprises vitamin K.

The invention also provides a method of treating cancer in a subject, comprising (a) administering a composition comprising coenzyme Q10 by continuous intravenous infusion for at least 48 hours; (b) monitoring the subject for decreased coagulation; and (c) continuing treatment with coenzyme Q10 in a subject identified as having normal coagulation.

In certain embodiments, the decreased coagulation comprises an INR of greater than 2 and normal coagulation comprises an INR of 2 or less. In certain embodiments, the decreased coagulation comprises an INR of greater than 3 and normal coagulation comprises an INR of 3 or less. In certain embodiments, the decreased coagulation comprises a platelet threshold less than 50,000/uL. In certain embodiments, normal coagulation comprises a platelet threshold of at least 50,000/uL.

The invention also provides a method of preventing or limiting severity of an adverse event associated with treatment of cancer with intravenously administered coenzyme Q10, comprising administering to a subject having cancer a composition comprising coenzyme Q10 by continuous intravenous infusion for at least 48 hours, wherein the severity of adverse event in the subject is reduced as compared to intravenous administration of the same dose of coenzyme Q10 over a period of 6 hours or less.

In certain embodiments, the coenzyme Q10 is administered by continuous intravenous infusion for at least 72 hours. In certain embodiments, the coenzyme Q10 is administered by continuous intravenous infusion for at least 96 hours. In certain embodiments, the coenzyme Q10 is administered by continuous intravenous infusion for at least 144 hours.

In certain embodiments, the continuous intravenous infusion dose is administered twice per week. In certain embodiments, the continuous intravenous infusion dose is administered once per week.

In certain embodiments, the coenzyme Q10 is administered by continuous intravenous infusion for at least 120 hours, at least 144 hours, at least 168 hours, at least 192 hours, at least 216 hours, at least 240 hours, at least 264 hours, at least 288 hours, at least 312 hours, at least 336 hours, at least 360 hours, at least 384 hours, at least 408 hours, at least 432 hours, at least 456 hours, or at least 480 hours.

In certain embodiments, the continuous intravenous infusion is administered once every two weeks, once every three weeks, or once every four weeks.

In certain embodiments, the adverse event comprises a coagulopathy. In certain embodiments, the adverse event comprises a bleeding event. In certain embodiments, the adverse event comprises an INR of at least 2, or an INR of at least 3.

The invention also provides a method of treating cancer comprising administering a composition comprising coenzyme Q10 by continuous intravenous infusion for about 96 hours wherein the composition is administered sequentially at a first rate, a second rate, and a third rate wherein: (a) the first rate is a highest rate administered during the first hour of the continuous intravenous infusion; (b) the second rate is a lowest rate administered during hours 2 to 48 of the continuous intravenous infusion; and (c) the third rate is an intermediate rate between the first rate and the second rate and is administered during hours 49 to 96 of the continuous intravenous infusion.

In certain embodiments, the amount of coenzyme Q10 administered during hours 1 to 48 of the continuous intravenous infusion is equivalent to the amount of coenzyme Q10 administered during hours 49 to 96 of the continuous intravenous infusion.

The invention also provides a method of treating cancer comprising administering a composition comprising coenzyme Q10 by continuous intravenous infusion for about 144 hours wherein the composition is administered sequentially at a first rate, a second rate, and a third rate wherein: (a) the first rate is a highest rate administered during the first hour of the continuous intravenous infusion; (b) the second rate is a lowest rate administered during hours 2 to 72 of the continuous intravenous infusion; and (c) the third rate is an intermediate rate between the first rate and the second rate and is administered during hours 73 to 144 of the continuous intravenous infusion.

In certain embodiments, the amount of coenzyme Q10 administered during hours 1 to 72 of the continuous intravenous infusion is equivalent to the amount of coenzyme Q10 administered during hours 73 to 144 of the continuous intravenous infusion In certain embodiments, the first rate is selected from the group consisting of no more than 3.1 mg/kg/hour, no more than 4.2 mg/kg/hour, no more than 5.5 mg/kg/hour, no more than 7.4 mg/kg/hour, no more than 8.3 mg/kg/hour, no more than 9.2 mg/kg/hour, no more than 11.0 mg/kg/hour, no more than 11.2 mg/kg/hour, no more than 14.0 mg/kg/hour, no more than 14.5 mg/kg/hour, no more than 18.0 mg/kg/hour, no more than 18.4 mg/kg/hour, no more than 19.6 mg/kg/hour, no more than 22.9 mg/kg/hour, no more than 26.0 mg/kg/hour, no more than 28.7 mg/kg/hour, and no more than 35.8 mg/kg/hour.

In certain embodiments, the coenzyme Q10 is administered at a dose selected from the group consisting of about 50 mg/kg/48 hour infusion and the first rate is about 4.2 mg/kg/hour, about 66 mg/kg/48 hour infusion and the first rate is about 5.5 mg/kg/hour, about 88 mg/kg/48 hour infusion and the first rate is about 7.4 mg/kg/hour, about 110 mg/kg/48 hour infusion and the first rate is about 9.2 mg/kg/hour, about 137 mg/kg/48 hour infusion and the first rate is about 11 mg/kg/hour, about 171 mg/kg/48 hour infusion and the first rate is about 14 mg/kg/hour, about 215 mg/kg/48 hour infusion and the first rate is about 18 mg/kg/hour, and about 40 mg/kg/48 hour infusion to about 250 mg/kg/48 hour infusion and the first rate is about 3.4 mg/kg/hour to about 21 mg/kg/hour.

In certain embodiments, the coenzyme Q10 is administered at a dose selected from the group consisting of about 38 mg/kg/72 hour infusion and the first rate is about 3.1 mg/kg, about 50 mg/kg/72 hour infusion and the first rate is about 4.1 mg/kg/hour, about 66 mg/kg/72 hour infusion and the first rate is about 5.4 mg/kg/hour, about 88 mg/kg/72 hour infusion and the first rate is about 7.2 mg-kg/hour, about 110 mg/kg/72 hour infusion and the first rate is about 9.0 mg/kg/hour, about 137 mg/kg/72 hour infusion and the first rate is about 11.2 mg/kg/hour, about 171 mg/kg/72 hour infusion and the first rate is about 14.0 mg/kg/hour, about 215 mg/kg/72 hour infusion and the first rate is about 17.6 mg/kg/hour, and about 38 mg-kg/72 hour infusion to about 250 mg/kg/72 hour infusion and the first rate is about 3.1 mg/kg/hour to about 21 mg/kg/hour.

In certain embodiments, 3-5% of the total coenzyme Q10 administered over the 96 hours of the continuous intravenous infusion is administered during the first hour of the continuous intravenous infusion. In certain embodiments, 3-5% of the total coenzyme Q10 administered over the 144 hours of the continuous intravenous infusion is administered during the first hour of the continuous intravenous infusion.

The invention also provides a method of treating cancer comprising administering a composition comprising coenzyme Q10 by continuous intravenous infusion for about 18 days wherein the composition is administered sequentially at a first rate, a second rate, and a third rate wherein: (a) the first rate is a highest rate administered during hour 1 of day 1 of the continuous infusion; (b) the second rate is a lowest rate administered during hours 2 to 24 of day 1 the continuous infusion; and (c) the third rate comprises an intermediate rate administered between the first rate and the second rate administered during dais 2 to 17 of the continuous infusion.

In certain embodiments, the amount of coenzyme Q10 administered during each 24 hour period of the continuous intravenous infusion is equivalent.

In certain embodiments, the first rate is a rate selected from the group consisting of no more than 4.2 mg/kg/hour, no more than 5.5 mg/kg/hour, no more than 7.4 mg/kg/hour, no more than 8.3 mg/kg/hour, no more than 9.2 mg/kg/hour, no more than 11.0 mg/kg/hour, no more than 14.5 mg/kg/hour, no more than 18.4 mg/kg/hour, no more than 19.6 mg/kg/hour, no more than 22.9 mg/kg/hour, no more than 26.0 mg/kg/hour, no more than 28.7 mg/kg/hour, and no more than 35.8 mg/kg/hour.

In certain embodiments, the coenzyme Q10 is administered at a dose selected from the group consisting of about 33 mg/kg/24 hours of infusion and the first rate is about 8.3 mg/kg/hour, about 44 mg/kg/24 hours of infusion and the first rate is about 11 mg/kg/hour, about 58.7 mg/kg/24 hours of infusion and the first rate is about 14.7 mg/kg/hour, about 73.4 mg/kg/24 hours of infusion and the first rate is about 18.4 mg/kg/hour, about 91.7 mg/kg/24 hours of infusion and the first rate is about 22.9 mg/kg/hour, about 114.6 mg/kg/24 hours of infusion and the first rate is about 28.7 mg/kg/hour, about 143.3 mg/kg/24 hours of infusion and the first rate is about 35.8 mg/kg/hour, and about 30 mg/kg/24 hours of infusion to about 170 mg/kg/24 hour infusion and the first rate is about 7.5 mg/kg/hour to about 42.5 mg/kg/hour.

In certain embodiments, 20-30% of the total coenzyme Q10 administered during hours 1 to 48 of the continuous infusion is administered during the first hour of the continuous infusion.

In certain embodiments, the coenzyme Q10 is administered with an additional agent. In certain embodiments, administration of the additional agent is initiated on the same day as administration of coenzyme Q10 is initiated. In certain embodiments, administration of the additional agent is initiated one or more weeks after the administration of coenzyme Q10 is initiated, two or more weeks after the administration of coenzyme Q10 is initiated, three or more weeks after the administration of coenzyme Q10 is initiated, four or more weeks after the administration of coenzyme Q10 is initiated, five or more weeks after the administration of coenzyme Q10 is initiated, six or more weeks after the administration of coenzyme Q10 is initiated, seven or more weeks after the administration of coenzyme Q10 is initiated, or eight or more weeks after the administration of coenzyme Q10 is initiated.

In certain embodiments, the methods further comprise monitoring the subject for myelosuppression.

In certain embodiments, the additional agent is an anticancer agent. In certain embodiments, the additional agent is a chemotherapeutic agent. In certain embodiments, the additional agent is selected from the group consisting of gemcitabine, 5-fluorouracil, leucovorin, docetaxel, fludarabine, cytarabine, cyclophosphamide, paclitaxel, docetaxel, busulfan, methotrexate, daunorubicin, doxorubicin, melphalan, cladribine, vincristine, vinblastine, chlorambucil, tamoxifen, taxol, camptothecin, actinomycin-D, mitomycin C, combretastatin, cisplatin, etoposide, verapamil, podophyllotoxin, and 5-fluorouracil. In certain embodiments, the additional agent is an anti-angiogenic agent.

In certain embodiments, the additional agent is administered upon progression of the cancer during treatment with coenzyme Q10. In certain embodiments, the additional agent is administered without progression of the cancer during treatment with coenzyme Q10.

In certain embodiments, an adverse effect of the additional agent is limited or decreased in subjects administered coenzyme Q10 by continuous infusion with the additional agent as compared to subjects not administered coenzyme Q10 by continuous infusion with the additional agent.

In certain embodiments, the adverse effect is myelosuppression. In certain embodiments, the adverse effect is cardiotoxicity.

In certain embodiments, the cancer comprises a solid tumor.

In certain embodiments, the solid tumor is selected from the group consisting of carcinoma, melanoma, sarcoma, and lymphoma.

In certain embodiments, the solid tumor is selected from the group consisting of breast cancer, bladder cancer, colon cancer, rectal cancer, endometrial cancer, kidney (renal cell) cancer, lung cancer, melanoma, pancreatic cancer, prostate cancer, thyroid cancer, skin cancer, bone cancer, brain cancer, cervical cancer, liver cancer, stomach cancer, mouth and oral cancers, neuroblastoma, testicular cancer, uterine cancer, thyroid cancer, and vulvar cancer. In certain embodiments, the solid tumor comprises triple negative breast cancer. In certain embodiments, the skin cancer comprises melanoma, squamous cell carcinoma, and cutaneous T-cell lymphoma (CTCL).

In certain embodiments, the cancer comprises a leukemia. In certain embodiments, the leukemia is selected from the group consisting of acute lymphocytic leukemia (ALL), acute myelogenous leukemia (AML), chronic lymphocytic leukemia (CLL), and chronic myelogenous leukemia (CML). Hairy cell leukemia (HCL), T-cell prolymphocytic leukemia (T-PLL), large granular lymphocytic leukemia, and adult T-cell leukemia.

In certain embodiments, the leukemia is an acute leukemia.

In certain embodiments, the coenzyme Q10 is administered at a dose of about 10 mg/kg/day (24 hours) to about 150 mg/kg/day (24 hours). In certain embodiments, the coenzyme Q10 is administered at a dose selected from the group consisting of about 11.8 mg/kg/day (24 hours), about 12.5 mg/kg/day (24 hours), about 14.4 mg/kg/day (24 hours), about 15.6 mg/kg (24 hours), about 16.5 mg/kg/day (24 hours), about 19 mg/kg/day (24 hours), about 20.4 mg/kg/day (24 hours), about 22 mg/kg/day (24 hours), about 25 mg/kg/day (24 hours), about 27.5 mg/kg/day (24 hours), about 29.3 mg/kg/day (24 hours), about 33 mg/kg/day (24 hours), about 34.2 mg/kg/day (24 hours), about 36.7 mg/kg/day (24 hours), about 41.7 mg/kg/day (24 hours), 42.8 mg/kg/day (24 hours), about 44 mg/kg/day (24 hours), about 45.7 mg/kg/day (24 hours), about 51.9 mg/kg/day (24 hours), about 53.8 mg/kg/day (24 hours), about 55 mg/kg/day (24 hours), about 57 mg/kg/day (24 hours), about 58.7 mg/kg/day (24 hours), about 64.8 mg/kg/day (24 hours), about 66.7 mg/kg/day (24 hours), about 68.5 mg/kg/day (24 hours), about 71.7 mg/kg/day (24 hours), about 73.4 mg/kg/day (24 hours), about 81.5 mg/kg/day (24 hours), about 85.5 mg/kg/day (24 hours), about 91.7 mg/kg/day (24 hours), about 107.5 mg/kg/day (24 hours), about 114.6 mg/kg/day (24 hours), and about 143.3 mg/kg/day (24 hours).

In certain embodiments, the coenzyme Q10 is administered at a dose selected from the group consisting of about 38 mg/kg/week, about 50 mg/kg/week, about 66 mg/kg/week, about 76 mg/kg/week, about 88 mg/kg/week, about 100 mg/kg/week, about 110 mg/kg/week, about 132 mg/kg/seek, about 137 mg/kg/week, about 171 mg/kg/week, about 176 mg/kg/week, about 215 mg/kg/week, about 220 mg/kg/week, about 274 mg/kg/week, about 342 mg/kg week, and about 430 mg/kg/week.

In certain embodiments, the continuous intravenous infusion of coenzyme Q10 is administered at a higher rate for the first hour of the infusion.

In certain embodiments, at least 5%, 6%, 7%, 8%, 9% or 10% of the total dose of coenzyme Q10 administered over the first 48 hours of the continuous infusion is administered during the first hour of the continuous intravenous infusion.

In certain embodiments, at least 20%, 21%, 22%, 23%, 24%, 25%, 26%, 27%, or 28% of the total dose of coenzyme Q10 administered over the first 24 hours of the continuous infusion is administered during the first hour of the continuous intravenous infusion.

In certain embodiments, the continuous intravenous infusion of coenzyme Q10 is performed at a constant rate.

In certain embodiments, the composition comprises 0.1% to 20% w/v coenzyme Q10. In certain embodiments, the composition comprises 1% to 10% w/v coenzyme Q10. In certain embodiments, the composition comprises 1% to 5% w/v coenzyme Q10.

In certain embodiments, the methods further comprise selecting a subject having cancer for treatment with coenzyme Q10, wherein the subject has adequate coagulation.

In certain embodiments, adequate coagulation comprises platelet threshold of 50,000/mcL, prothrombin time (PT), partial thromboplastin time (PTT), and an International Normalized Ratio (INR) within normal limits.

In certain embodiments, the methods further comprise selecting against a subject having cancer for treatment with coenzyme Q10, wherein the subject exhibits at least one condition or characteristic selected from the group consisting of: (a) the subject is taking HMG-CoA reductase inhibitors; (b) the subject is taking digoxin, digitoxin, lanatoside C, or any type of digitalis alkaloids; (c) the subject has uncontrolled or severe coagulopathies or a history of clinically significant bleeding within the past 6 months; (d) the subject has at least one of hemoptysis, epistaxis, hematochezia, hematuria, or gastrointestinal bleeding; (e) the subject has a predisposition for bleeding; It) the subject has been administered anticoagulant; (g) the subject has a ≥grade 3 thrombocytopenia with clinically significant bleeding; (h) the subject has a ≥grade 4 hematologic toxicity, (i) the subject has a grade 2 INR/PTT elevation with clinically significant bleeding; and (j) the subject has a glade 3 INR/PTT abnormality.

In certain embodiments, the methods comprise increasing therapeutic index of intravenously administered coenzyme Q10, by increasing time of infusion of a dose of coenzyme Q10 from no more than 6 hours to a continuous intravenous infusion for at least 48 hours.

The invention also provides a method of increasing therapeutic index of intravenously administered coenzyme Q10, by increasing time of infusion of a dose of coenzyme Q10 from no more than 6 hours to a continuous intravenous infusion for at least 48 hours.

In certain embodiments, the coenzyme Q10 is administered for at least two cycles.

The invention also provides intravenously administered coenzyme Q10 for use in any of the aforementioned methods.

The invention also provides uses of intravenously administered coenzyme Q10 for any of the aforementioned methods.

The invention also provides a pharmaceutical composition comprising coenzyme Q10 for any of the aforementioned methods.

Other embodiments are provided infra.

DETAILED DESCRIPTION AND PREFERRED EMBODIMENTS

I. Definitions

Figure 1:
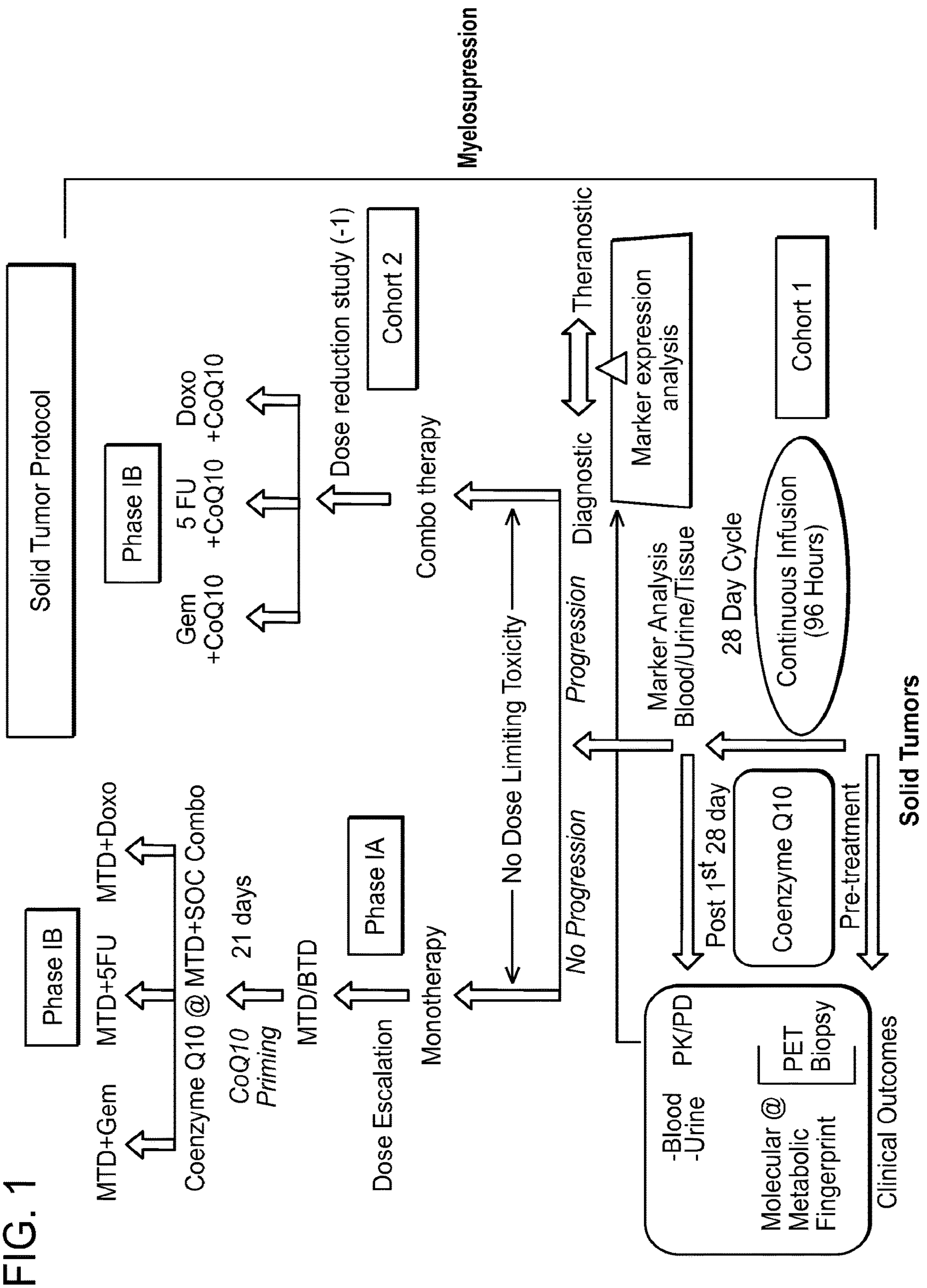
FIG. 1 shows a flow chart of treatment methods for a clinical trial for the treatment of subjects with solid tumors with coenzyme Q10, optionally in combination with other agents.
Figure 2:
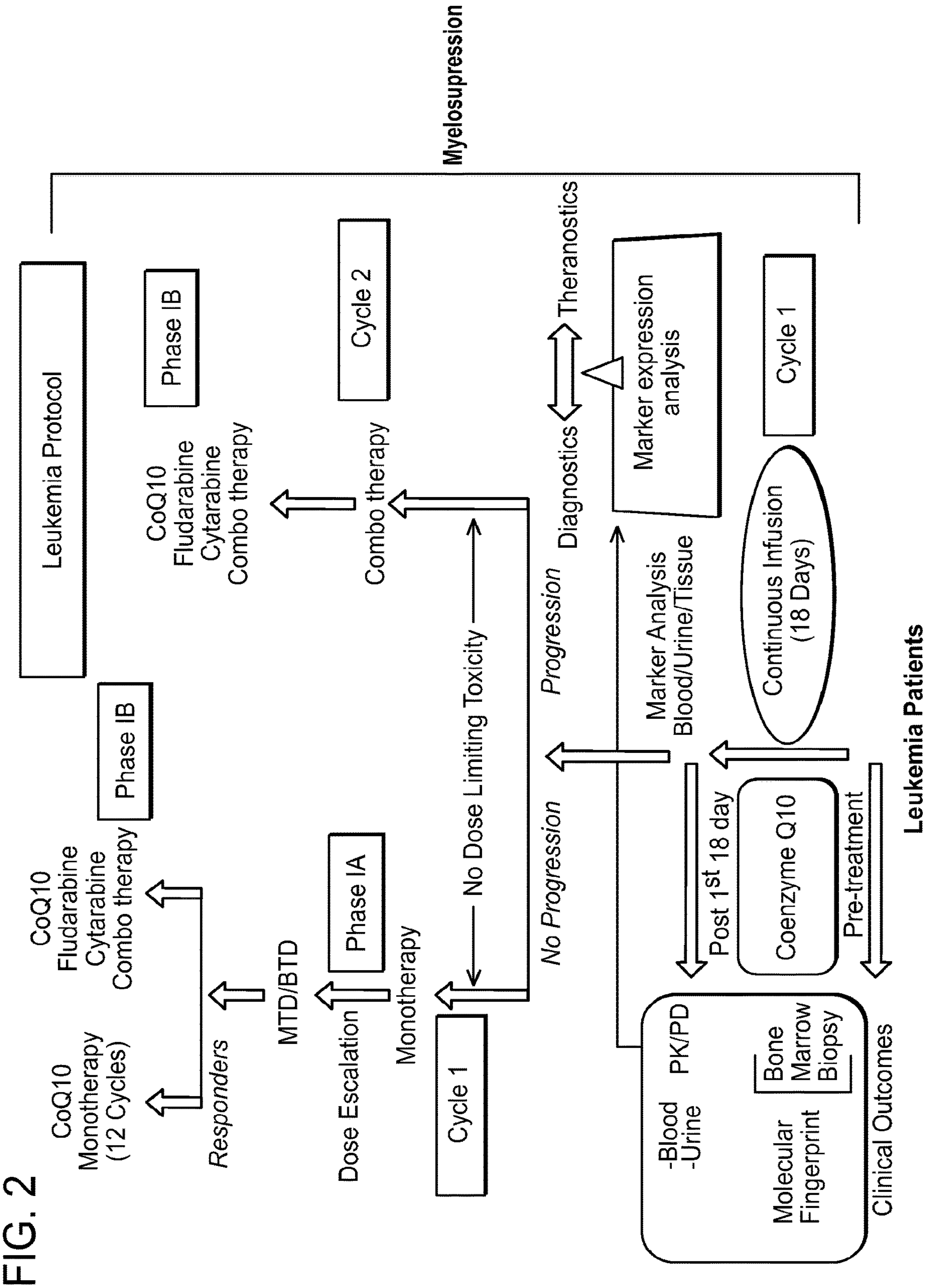
FIG. 2 shows a flow chart of treatment methods for a clinical trial for the treatment of subjects with leukemia with coenzyme Q10, optionally in combination with other agents.
Figure 3:
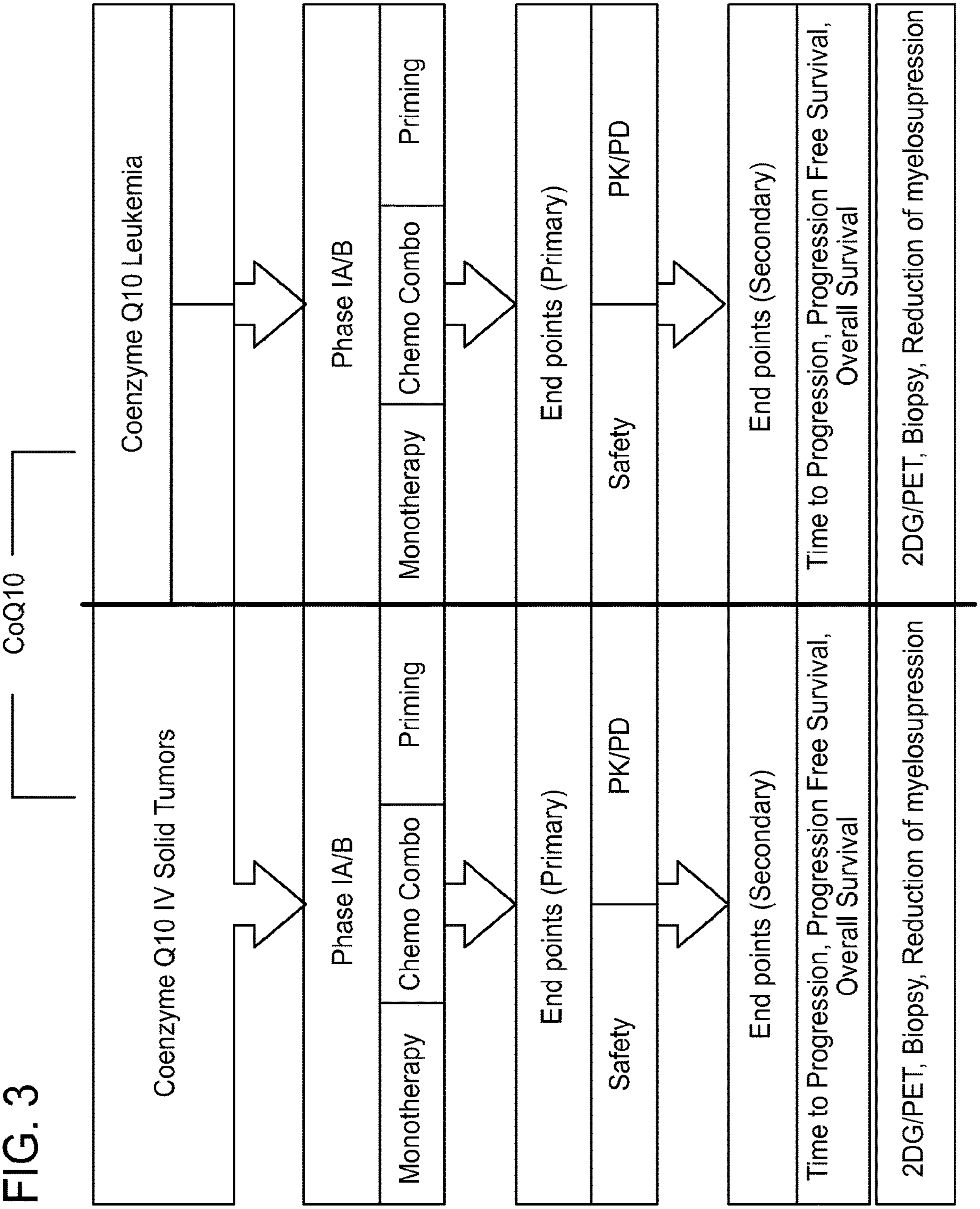
FIG. 3 shows a flow chart of the clinical trial protocols.

The terms 'cancer' or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death (apoptosis, and certain characteristic morphological features.

As used herein, "cancer" refers to all types of cancer or neoplasm or malignant tumors found in humans, including, but not limited to leukemias, lymphomas, melanomas, carcinomas and sarcomas. As used herein, the terms or language "cancer," "neoplasm." and "tumor." are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. In certain embodiments, the cancer is not a central nervous system (CNS) cancer, i.e., not a cancer of a tumor present in at least one of the spinal cord, the brain, and the eye. In certain embodiments, the primary cancer is not a CNS cancer. In certain embodiments, the cancer is a solid tumor. In certain embodiments, the cancer is a blood tumor (i.e., a non-solid tumor).

A "solid tumor" is a tumor that is detectable on the basis of tumor mass; e.g., by procedures such as CAT scan, MR imaging. X-ray, ultrasound or palpation, and/or which is detectable because of the expression of one or more cancer-specific antigens in a sample obtainable from a patient. The tumor does not need to have measurable dimensions.

Specific criteria for the staging of cancer are dependent on the specific cancer type based on tumor size, histological characteristics, tumor markers, and other criteria known by those of skill in the art. Generally, cancer stages can be described as follows.

Stage 0—Carcinoma in situ

Stage I, Stage II, and Stage III—Higher numbers indicate more extensive disease: Larger tumor size and/or spread of the cancer beyond the organ m which it first developed to nearby lymph nodes and/or tissues or organs adjacent to the location of the primary tumor Stage IV—The cancer has spread to distant tissues or organs As used herein, the terms "treat," "treating" or "treatment" refer, preferably, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) of the state of disease, amelioration or palliation of the disease state, diminishing rate of or time to progression, and remission (whether partial or total) "Treatment" of a cancer can also mean prolonging survival as compared to expected survival in the absence of treatment. Treatment need not be curative. In certain embodiments, treatment includes one or more of a decrease in pain or an increase in the quality of life (QOL) as judged by a qualified individual, e.g., a treating physician, e.g., using accepted assessment tools of pain and QOL. In certain embodiments, a decrease in pain or an increase in the quality of life (QOL) as judged by a qualified individual. e.g., a treating physician, e.g., using accepted assessment tools of pain and QOL is not considered to be a "treatment" of the cancer.

RECIST criteria are clinically accepted assessment criteria used to provide a standard approach to solid tumor measurement and provide definitions for objective assessment of change in tumor size for use in clinical trials. Such criteria can also be used to monitor response of an individual undergoing treatment for a solid tumor. The RECIST 1.1 criteria are discussed in detail in Eisenhauer et al. (Neu response evaluation criteria in solid tumors. Revised RECIST guideline (version 1.1) *Eur. J. Cancer.* 45:228-247, 2009), the entire contents of which are incorporated herein by reference. Response criteria for target lesions include:

Complete Response (CR): Disappearance of all target lesions. Any pathological lymph nodes (whether target or non-target) must have a reduction in short axis to <10 mm.

Partial Response (PR): At least a 30% decrease in the sum of diameters of target lesion, taking as a reference the baseline sum diameters.

Progressive Diseases (PD): At least a 20% increase in the sum of diameters of target lesions, taking as a reference the smallest sum on the study (this includes the baseline sum if that is the smallest on the study). In addition to the relative increase of 20%, the sum must also demonstrate an absolute increase of at least 5 mm. (Note: the appearance of one or more new lesions is also considered progression.)

Stable Disease (SD): Neither sufficient shrinkage to qualify for PR, nor sufficient increase to qualify for PD, taking as a reference the smallest sum diameters while on study.

RECIST 1.1 criteria also consider non-target lesions which are defined as lesions that may be measureable, but need not be measured, and should only be assessed qualitatively at the desired time points. Response criteria for non-target lesions include:

Complete Response (CR). Disappearance of all non-target lesions and normalization of tumor marker levels. All lymph nodes must be non-pathological in size (<10 mm short axis).

Non-CR/Non-PD: Persistence of one or more non-target lesion(s) and/or maintenance of tumor marker level above the normal limits.

Progressive Disease (PD): Unequivocal progression (emphasis in original) of existing non-target lesions. The appearance of one or more new lesions is also considered progression. To achieve "unequivocal progression" on the basis of non-target disease, there must be an overall level of substantial worsening of non-target disease such that, even in the presence of SD or PR in target disease, the overall tumor burden has increased sufficiently to merit discontinuation of therapy. A modest "increase" in the size of one or more non-target lesions is usually not sufficient to qualify for unequivocal progression status. The designation of overall progression solely on the basis of change in non-target disease in the face of SD or PR in target disease will therefore be extremely rare.

Clinically acceptable criteria for response to treatment in acute leukemias are as follows:

Complete remission (CR): The patient must be free of all symptoms related to leukemia and have an absolute neutrophil count of $\geq 1.0\times10^9$/L, platelet count $\geq 100\times10^9$/L. and normal bone marrow with <5% blasts and no Auer rods.

Complete remission with incomplete blood count recovery (Cri): As per CE, but with residual thrombocytopenia (platelet count<$100\times10^9$/L) or residual neutropenia (absolute neutrophil count<$1.0\times10^9$/L).

Partial remission (PR): A ≥50% decrease in bone marrow blasts to 5 to 25% abnormal cells in the marrow; or CR with ≤5% blasts if Auer rods are present.

Treatment failure: Treatment has failed to achieve CR, Cri, or PR Recurrence.

Relapse after confirmed CR: Reappearance of leukemic blasts in peripheral blood or ≥5% blasts in the bone marrow not attributable to any other cause (e.g., bone marrow regeneration after consolidated therapy) or appearance of new dysplastic changes.

"Chemotherapeutic agent" refers to a drug used for the treatment of cancer. Chemotherapeutic agents include, but are not limited to, small molecules, hormones and hormone analogs, and biologics (e.g., antibodies, peptide drugs, nucleic acid drugs). In certain embodiments, chemotherapy does not include hormones and hormone analogs.

A "chemotherapeutic regimen" is a clinically accepted dosing protocol for the treatment of cancer that includes administration of one or more chemotherapeutic agents to a subject in specific amounts on a specific schedule. In certain embodiments, the chemotherapeutic agent can be an agent in clinical trials.

Chemotherapeutic regimens can include administration of a drug on a predetermined "cycle" including intervals of dosing and not dosing with one or more agents for the treatment of cancer. For example, an agent can be administered one or more times per week for three consecutive weeks followed by a week of no agent administered to provide a four week cycle. The cycle can be repeated so that the subject would be subjected to three treatment weeks, one no treatment week, three treatment weeks, one no treatment week, etc., for the desired number of cycles. In certain embodiments, treatment of efficacy and laboratory values (e.g., liver enzymes, blood count, kidney function) are assessed at the end of each cycle or every other cycle.

A "subject who has failed a chemotherapeutic regimen" is a subject with cancer that does not respond, or ceases to respond to treatment with a chemotherapeutic regimen per RECIST 1.1 criteria (see, Eisenhauer et al., 2009 and as discussed above), i.e., does not achieve at least stable disease (i.e., stable disease, partial response, or complete response) in the target lesion; or does not achieve at least non-CR/non-PD (i.e., non-CR/non-PD or complete response) of non-target lesions, either during or after completion of the chemotherapeutic regimen, either alone or in conjunction with surgery and/or radiation therapy which, when possible, are often clinically indicated in conjunction with chemotherapy. A failed chemotherapeutic regime results in, e.g., tumor growth, increased tumor burden, and/or tumor metastasis. In some embodiments, failed chemotherapeutic regimen as used herein includes a treatment regimen that was terminated due to a dose limiting toxicity, e.g., a grade III or a grade IV toxicity that cannot be resolved to allow continuation or resumption of treatment with the chemotherapeutic agent or regimen that caused the toxicity. In some embodiments, a "failed chemotherapeutic regimen includes a treatment regimen that does not result in at least stable disease fig all target and non-target lesions for an extended period. e.g., at least 1 month, at least 2 months, at least 3 months, at least 4 months, at least 5 months, at least 6 months, at least 12 months, at least 18 months, or any time period less than a clinically defined cure. In some embodiments, a failed chemotherapeutic regimen includes a treatment regimen that results in progressive disease of at least one target lesion during treatment with the chemotherapeutic agent, or results in progressive disease less than 2 weeks, less than 1 month, less than two months, less than 3 months, less than 4 months, less than 5 months, less than 6 months, less than 12 months, or less than 18 months after the conclusion of the treatment regimen, or less than any time period less than a clinically defined cure.

A failed chemotherapeutic regimen does not include a treatment regimen wherein the subject treated for a cancer achieves a clinically defined cure, e.g., 5 years of complete response after the end of the treatment regimen, and wherein the subject is subsequently diagnosed with a distinct cancer. e.g., more than 5 years, more than 6 years, more than 7 years, more than 8 years, more than 9 years, more than 10 years, more than 11 years, more than 12 years, more than 13 sears, more than 14 years, or more than 15 years after the end of the treatment regimen. For example, a subject who suffered from a pediatric cancer may develop cancer later in life after being cured of the pediatric cancer. In such a subject, the chemotherapeutic regimen to treat the pediatric cancer is considered to have been successful.

A "refractory cancer" is a malignancy for which surgery is ineffective, which is either initially unresponsive to chemo- or radiation therapy, or which becomes unresponsive to chemo- or radiation therapy over time.

A "therapeutically effective amount" is that amount sufficient to treat a disease in a subject. A therapeutically effective amount can be administered in one or more administrations.

The terms "administer", "administering" or "administration" include any method of delivery of a pharmaceutical composition or agent into a subject's system or to a particular region in or on a subject. In certain embodiments, the agent is delivered orally. In certain embodiments, the agent is administered parenterally. In certain embodiments, the agent is delivered topically including transmucosally. In certain embodiments, the agent is delivered by inhalation. In certain embodiments of the invention, an agent is administered by parenteral delivery, including, intravenous, intramuscular, subcutaneous, intramedullary injections, as well as intrathecal, direct intraventricular, intraperitoneal, intranasal, or intraocular injections. In one embodiment, the compositions provided herein may be administered by injecting directly to a tumor. In a preferred embodiment, the agent is delivered by injection or infusion.

In a preferred embodiment, the formulations of the invention may be administered by intravenous injection or intravenous infusion. In still more preferred embodiments, the formulation of the invention can be administered by continuous infusion.

In certain embodiments, administration is not oral. In certain embodiments, administration is systemic. In certain embodiments, administration is local. In some embodiments, administration is not intravenous administration for less than 8, 6, or 4 hours. In some embodiments, one or more routes of administration may be combined, such as, for example, intravenous and intratumoral, or intravenous and peroral, or intravenous and oral, intravenous and topical, or intravenous and transdermal or transmucosal. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery, by a trained professional, e.g., intravenous delivery, intramuscular delivery, intratumoral delivery, etc.

As used herein. "continuous infusion" refers to administration of a dose of the formulation continuously for at least 24 hours. Continuous administration is typically facilitated by use of a pump, either an implantable or external pump. A formulation can be administered by continuous infusion in multiple, separated doses, with a break of one or more days between continuous infusion doses.

It is understood that continuous infusion can include short interruptions of administration, for example, to change the reservoir of coenzyme Q10 being administered. For example, two 48 hour continuous infusions administered sequentially or four 24 hour continuous infusions and the like, administered without a significant pause by design (less than 4 hours, preferably less than 2 hours, preferably less than one hour, preferably about 30 minutes) between the end of one infusion and the start of the next is considered to be the same as one % hour continuous administration. Similarly, two 72 hour continuous infusions administered sequentially without a significant pause (e.g., less than 4 hours, preferably less than 2 hours, preferably less than one hour, preferably about 30 minutes) between the end of one infusion and the start of the next is considered to be the same as one 144 hour (6 day) continuous infusion. In certain embodiments, the subject treated with a 96 hour continuous infusion of coenzyme Q10 or a 144 hour continuous infusion of coenzyme Q10 has a solid tumor. In certain embodiments, the subject treated with a 96 hour continuous infusion of coenzyme Q10 or a 144 hour continuous infusion of coenzyme Q10 has a leukemia.

An 18 day continuous infusion will similarly likely include short interruptions during the dosing and will be considered to be a continuous infusion as long as the dose is administered without significant pause by design (less than 4 hours, preferably less than 2 hours, preferably less than one hour, preferably about 30 minutes) between the end of one infusion and the start of the next. In certain embodiments, the subject treated with an 18 day continuous infusion of coenzyme Q10 has a leukemia. In certain embodiments, the subject treated with an 18 day continuous infusion of coenzyme Q10 has a solid tumor It is understood that one day of a multi-day continuous infusion is one of a series of sequential 24 hour periods during the continuous infusion that does not necessarily, or even typically, correspond to a calendar day. For example, day 1 of a continuous infusion includes hours 1-24 of the continuous infusion, day 2 of a continuous infusion includes hours 25-48 of the continuous infusion, day 3 of a continuous infusion includes hours 49-72 of the continuous infusion, etc.

Continuous administration is typically facilitated by the use of a pump. Continuous administration can include administration at a single rate. Continuous administration can include administration at a more than one rate (e.g., two rates, three rates). Continuous administration can include a loading dose at a higher rate followed by a lower dose rate for the remainder of the dose. Continuous infusion is carried out without including any significant interruptions of dosing by design. As used herein, interruptions to assess vital signs and/or perform laboratory assessments to ensure the safety of the patients and that no unacceptable adverse event have occurred are not considered to be significant interruptions. Interruptions resulting from equipment failure, e.g., pump failure, are not interruptions by design.

As used herein, continuous administration does not include intravenous administration of two or more doses wherein the end of the first dose and the start of the second dose are separated from each other by at least four hours, preferably at least eight, twelve, or twenty four hours by design. When two intravenous administrations are separated by at least four hours by design, they are separate doses.

In certain embodiments, a continuous infusion is designed for administration at a single rate. In certain embodiments, a continuous infusion is designed for administration at a higher rate at the beginning of the infusion to provide a loading dose. For example, the dose for administration during the first 24 hours of the continuous infusion can be administered at two rates such that at least 5% of the dose is administered in the first hour, and the remainder of the dose (95% of the dose) for the first 24 hours is administered in the remaining 23 hours. In certain embodiments, the dose for administration during the first 24 hours of the continuous infusion can be administered at two rates such that at least 6% of the dose is administered in the first hour, and the remainder of the dose (94% of the dose) for the first 24 hours is administered in the remaining 23 hours. For example, the dose for administration during the first 24 hours of the continuous infusion can be administered at two rates such that at least 7% of the dose is administered in the first hour, and the remainder of the dose (95% of the dose) for the first 24 hours is administered in the remaining 23 hours. For example, the dose for administration during the first 24 hours of the continuous infusion can be administered at two rates such that at least a % of the dose is administered in the first hour, and the remainder of the dose (92% of the dose) for the first 24 hours is administered in the remaining 23 hours. For example, the dose for administration during the first 24 hours of the continuous infusion can be administered at two rates such that at least 9% of the dose is administered in the first hour, and the remainder of the dose (91% of the dose) for the first 24 hours is administered in the remaining 23 hours. For example, the dose for administration during the first 24 hours of the continuous infusion can be administered at two rates such that at least 10% of the dose is administered in the first hour, and the remainder of the dose (90% of the dose) for the first 24 hours is administered in the remaining 23 hours. For example, the dose for administration during the first 24 hours of the continuous infusion can be administered at two rates such that at least 11% of the dose is administered in the first hour, and the remainder of the dose (89% of the dose) for the first 24 hours is administered in the remaining 23 hours. For example, the dose for administration during the first 24 hours of the continuous infusion can be administered at two rates such that at least 12% of the dose is administered in the first hour, and the remainder of the dose (88% of the dose) for the first 24 hours is administered in the remaining 23 hours. For example, the dose for administration during the first 24 hours of the continuous infusion can be administered at two rates such that at least 13% of the dose is administered in the first hour, and the remainder of the dose (87% of the dose) for the first 24 hours is administered in the remaining 23 hours. For example, the dose for administration during the first 24 hours of the continuous infusion can be administered at two rates such that at least 14% of the dose is administered in the first hour, and the remainder of the dose (86% of the dose) for the first 24 hours is administered in the remaining 23 hours. For example, the dose for administration during the first 24 hours of the continuous infusion can be administered at two rates such that at least 15% of the dose is administered in the first hour, and the remainder of the dose (85% of the dose) for the first 24 hours is administered in the remaining 23 hours. In certain embodiments, at least 16%, 170, 18%, 19%, 20%, 21%, 22%, 23%, 24% or 25% of the dose is administered in the first hour, with the remainder being administered in the subsequent 23 hours.

In certain embodiments about 5%, about 6%, about 7%, about 8%, about 8.1%, about 8.2%, about 8.3%, about 8.4%, about 8.5%, about 8.6%, about 8.7%, about 8.8%, about 8.9%, about 9%, about 10%, about 11%, about 12%, about 13%, about 14%, about 13%, about 16%, about 17%, about 18%, about 19%, about 20% about 21% about 22%, about 23%, about 24%, or about 25% of the dose is administered in the first hour, and the remainder of the dose for the first 24 hours, for example, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, or about 75% is administered in the subsequent 23 hours. Any of these values may be used to define a range for the percentage of the dose that is administered in the first hour and the percentage of the dose administered in the subsequent 23 hours. For example, the percentage of the dose that is administered in the first hour may range from 5% to 25%, 5% to 20%, 5% to 15%, 5% to 10%, 10% to 25%, 10% to 20%, 10% to 15%, 15% to 25%, 15% to 20%, 20% to 25%, 8% to 25%, 8% to 15%, 6% to 9%, or 7% to 9%. The remaining dose is administered in the subsequent 23 hours. For example, the percentage of the dose that is administered in the subsequent 23 hours may range from 75% to 95%, 75% to 90%, 75% to 85%, 75% to 80%, 80% to 95%, 80% to 90%, 80% to 85%, 85% to 95%, 85% to 90%, 90% to 95%, 91% to 94%, 91% to 93%, from 75% to 92%, or from 85% to 92%.

In certain embodiments, the dose for administration during the first 48 hours of the continuous infusion can be administered at two rates such that at least 5% of the dose is administered in the first hour, and the remainder of the dose (95% of the dose) for the first 48 hours is administered in the remaining 47 hours. In certain embodiments, the dose for administration during the first 48 hours of the continuous infusion can be administered at two rates such that at least 6% of the dose is administered in the first hour, and the remainder of the dose (94% of the dose) for the first 48 hours is administered in the remaining 47 hours. For example, the dose for administration during the first 48 hours of the continuous infusion can be administered at two rates such that at least 7% of the dose is administered in the first hour, and the remainder of the dose (95% of the dose) for the first 48 hours is administered in the remaining 47 hours. For example, the dose for administration during the first 48 hours of the continuous infusion can be administered at two rates such that at least 8% of the dose is administered in the first hour, and the remainder of the dose (92% of the dose) for the first 48 hours is administered in the remaining 23 hours. For example, the dose for administration during the first 48 hours of the continuous infusion can be administered at two rates such that at least 9% of the dose is administered in the first hour, and the remainder of the dose (91% of the dose) for the first 48 hours is administered in the remaining 47 hours. For example, the dose for administration during the first 48 hours of the continuous infusion can be administered at two rates such that at least 10% of the dose is administered in the first hour, and the remainder of the dose (90% of the dose) for the first 48 hours is administered in the remaining 47 hours. For example, the dose for administration during the first 48 hours of the continuous infusion can be administered at two rates such that at least 11% of the dose is administered in the first hour, and the remainder of the dose (89% of the dose) for the first 48 hours is administered in the remaining 47 hours. For example, the dose for administration during the first 48 hours of the continuous infusion can be administered at two rates such that at least 12% of the dose is administered in the first hour, and the remainder of the dose (88% of the dose) for the first 48 hours is administered in the remaining 47 hours. For example, the dose for administration during the first 48 hours of the continuous infusion can be administered at two rates such that at least 13% of the dose is administered in the first hour, and the remainder of the dose (87% of the dose) for the first 48 hours is administered in the remaining 47 hours. For example, the dose for administration during the first 48 hours of the continuous infusion can be administered at two rates such that at least 14% of the dose is administered in the first hour, and the remainder of the dose (86% of the dose) for the first 48 hours is administered in the remaining 47 hours. For example, the dose for administration during the first 48 hours of the continuous infusion can be administered at two rates such that at least 15% of the dose is administered in the first hour, and the remainder of the dose (85% of the dose) for the first 48 hours is administered in the remaining 47 hours. In certain embodiments, at least 16%, 17%, 18%, 19%, 20%, 21%, 22%, 23%, 24% or 25% of the dose is administered in the first hour, with the remainder being administered in the subsequent 47 hours.

In certain embodiments about 5%, about 6%, about 7%, about 8%, about 8.1%, about 8.2%, about 8.3%, about 8.4%, about 8.5%, about 8.6%, about 8.7°βu, about 8.8%, about 8.9% about 9%, about 10%, about 11%, about 12%, about 13%, about 14%, about 15%, about 16%, about 17%, about 18%, about 19%, about 20% about 21% about 22%, about 23%, about 24%, or about 25% of the dose is administered in the first hour, and the remainder of the dose for the first 48 hours, for example, about 95%, about 94%, about 93%, about 92%, about 91%, about 90%, about 89%, about 88%, about 87%, about 86%, about 85%, about 84%, about 83%, about 82%, about 81°βu, about 80%, about 79%, about 78%, about 77%, about 76%, or about 75% is administered in the subsequent 47 hours. Any of these values may be used to define a range for the percentage of the dose that is administered in the first hour and the percentage of the dose administered in the subsequent 47 hours. For example, the percentage of the dose that is administered in the first hour may range from 5% to 25%, 5% to 20%, 5% to 15%, 5% to 10%, 1(1% to 25%, 10% to 20%, 10% to 15%, 15% to 25%, 15% to 20%, 20% to 25%, 8% to 25%, 8% to 15%, 6% to 9%, or 7% to 9%. The remaining dose is administered in the subsequent 47 hours. For example, the percentage of the dose that is administered in the subsequent 47 hours may range from 75% to 95%, 75% to 90%, 75% to 85%, 75% to 80%, 80% to 95%, 80% to 90%, 80% to 83%, 85% to 93%, 85% to 90%, 90% to 95%, 91% to 94%, 91% to 93%, from 75% to 92%, or from 85% to 92%.

In certain embodiments, the dose for administration during the first 72 hours of the continuous infusion can be administered at two rates such that at least 5% of the dose is administered in the first hour, and the remainder of the dose (95% of the dose) for the first 72 hours is administered in the remaining 71 hours. In certain embodiments, the dose for administration during the first 72 hours of the continuous infusion can be administered at two rates such that at least 6% of the dose is administered in the first hour, and the remainder of the dose (94% of the dose) for the first 72 hours is administered in the remaining 71 hours. For example, the dose for administration during the first 72 hours of the continuous infusion can be administered at two rates such that at least 7% of the dose is administered in the first hour, and the remainder of the dose (95% of the dose) for the first 72 hours is administered in the remaining 71 hours. For example, the dose for administration during the first 72 hours of the continuous infusion can be administered at two rates such that at least 8% of the dose is administered in the first hour, and the remainder of the dose (92% of the dose) for the first 72 hours is administered in the remaining 71 hours. For example, the dose for administration during the first 72 hours of the continuous infusion can be administered at two rates such that at least 9% of the dose is administered in the first hour, and the remainder of the dose (91% of the dose) for the first 72 hours is administered in the remaining 71 hours. For example, the dose for administration during the first 72 hours of the continuous infusion can be administered at two rates such that at least 10% of the dose is administered in the first hour, and the remainder of the dose (90% of the dose) for the first 72 hours is administered in the remaining 71 hours. For example, the dose for administration during the first 72 hours of the continuous infusion can be administered at two rates such that at least 11% of the dose is administered in the first hour, and the remainder of the dose (89% of the dose) for the first 72 hours is administered in the remaining 71 hours. For example, the dose for administration during the first 72 hours of the continuous infusion can be administered at two rates such that at least 12% of the dose is administered in the first hour, and the remainder of the dose (88% of the dose) for the first 72 hours is administered in the remaining 71 hours. For example, the dose for administration during the first 72 hours of the continuous infusion can be administered at two rates such that at least 13% of the dose is administered in the first hour, and the remainder of the dose (87% of the dose) for the first 72 hours is administered in the remaining 71 hours. For example, the dose for administration during the first 72 hours of the continuous infusion can be administered at two rates such that at least 14% of the dose is administered in the first hour, and the remainder of the dose (86% of the dose)

for the first 72 hours is administered in the remaining 71 hours. For example, the dose for administration during the first 72 hours of the continuous infusion can be administered at two rates such that at least 15% of the dose is administered in the first hour, and the remainder of the dose (85% of the dose) for the first 72 hours is administered in the remaining 71 hours. In certain embodiments, at least 16%, 17%, 18%, 19%, 20%, 21%, 22%, 23%, 24% or 25% of the dose is administered in the first hour, with the remainder being administered in the subsequent 71 hours.

In certain embodiments about 5%, about 6%, about 7%, about 8%, about 8.1%, about 8.2%, about 8.3%, about 8.4%, about 8.5%, about 8.6%, about 8.7%, about 8.8%, about 8.9% about 9%, about 10%, about 11%, about 12% about 13%, about 14%, about 15%, about 16%, about 17%, about 18%, about 19%, about 20% about 21% about 22%, about 23%, about 24%, or about 25% of the dose is administered in the first hour, and the remainder of the dose for the first 72 hours, for example, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, or about 75% is administered in the subsequent 71 hours. Any of these values may be used to define a range for the percentage of the dose that is administered in the first hour and the percentage of the dose administered in the subsequent 71 hours. For example, the percentage of the dose that is administered in the first hour may range from 5% to 25%, 5% to 20%, 5% to 13%, 5% to 10%, 10% to 25%, 10% to 20%, 10% to 15%, 15% to 25%, 15% to 20%, 20% to 25%, 8% to 25%, 8% to 15%, 6% to 9%, or 7% to 9%. The remaining dose is administered in the subsequent 71 hours. For example, the percentage of the dose that is administered in the subsequent 71 hours may range from 75% to 95%, 75% to 90%, 75% to 85%, 75% to 80%, 80% to 95%, 80% to 90%, 80% to 85%, 85% to 95%, 85% to 90%, 90% to 95%, 91% to 94%, 91% to 93%, from 75% to 92%, or from 85% to 92%.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, a "formulation" is understood as an active ingredient, e.g., CoQ10, a metabolite of CoQ10, a biosynthetic precursor of CoQ10, or a CoQ10 related compound, in combination with any pharmaceutically acceptable carrier. Formulations can include, but are not limited to, aqueous formulations, liposomal formulations, suspensions, emulsions, microemulsions, nanoemulsions, nanosuspensions, formulations for specific routes of administration for injection or infusion.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure. By "therapeutically effective amount" is meant an amount of a compound of the present disclosure effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives. The "therapeutically effective amount" will vary depending on the compound the disease and its seventy and the age, weight, etc., of the patient to be treated.

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment, in certain embodiments, a therapeutically-effective amount of a compound will depend on its therapeutic index, solubility, and the like.

"Adverse events" or "AEs" are characterized by grade depending on the severity. Some AE (e.g., nausea, low blood counts, pain, reduced blood clotting) can be treated so that the specific chemotherapeutic regimen can be continued or resumed. Some adverse events (e.g., loss of cardiac, liver, or kidney function; nausea) may not be treatable, requiring termination of treatment with the drug. Determination of AE grade and appropriate interventions can be determined by those of skill in the art. Common Terminology Criteria for Adverse Events v4.0 (CTCAE) (Publish Date: May 28, 2009) provide a grading scale for adverse events as follows:

Grade 1—Mild: asymptomatic or mild symptoms; clinical or diagnostic observations only; intervention not indicated.

Grade 2—Moderate; minimal, local or noninvasive intervention indicated; limiting age-appropriate instrumental activities of daily life (ADL).

Grade 3—Severe or medically significant but not immediately life-threatening; hospitalization or prolongation of hospitalization indicated; disabling, limiting self care ADL.

Grade 4—Life-threatening consequences: urgent intervention indicated

Grade 5—Death related to adverse event.

Adverse events include "coagulopathy" or "reduced blood clotting." Methods to determine clotting times are well known and typically are based on determination of the "international normalized ratio" or "INR" which is a ratio based on the prothrombin time (in seconds) for a normal individual. The prothrombin time is the time it takes plasma to clot after addition of tissue factor. The INR was devised to standardize clotting time results between individuals and tissue factor used in the assay prepared by different manufacturers. Each manufacturer assigns an ISI value (International Sensitivity Index) for any tissue factor each batch of tissue factor manufactured. The ISI value indicates how a particular batch of tissue factor compares to an international reference tissue factor. The ISI is usually between 1.0 and 2.0. The INR is the ratio of a patient's prothrombin time to a normal (control) sample, raised to the power of the ISI value for the analytical system used. Such methods are routine in the art. The INR is typically used to monitor patients on anticoagulant therapy, e.g., warfarin therapy, or being treated with other agents, e.g., agents for the treatment of cancer including coenzyme Q10. The normal range for a healthy person not using warfarin is 0.8-1.2, and for people on warfarin therapy an INR of 2.0-3.0 usually targeted. Therefore, an elevation of INR over that observed in a healthy person (e.g., up to 1.5, 2.0, 2.5, or 3.0) is not necessarily considered to be an adverse event requiring intervention. Such considerations are understood by those of skill in the art. If the INR is outside the target range, a high INR indicates a higher risk of bleeding, while a low INR suggests a higher risk of developing a clot. Other methods to assess clotting times are known in the art.

As used herein. "co-administration" or "combination therapy" is understood as administration of two or more active agents using separate formulations or a single pharmaceutical formulation, or consecutive administration in any order such that, there is a time period while both (or all) active agents simultaneously exert their biological activities. Co-administration does not require that the agents are administered at the same time, at the same frequency, or by the same route of administration. As used herein, "co-administration" or "combination therapy" includes administration of a CoQ10 compound with one or more additional anti-cancer agents, e.g., chemotherapeutic agents, or administration of two or more CoQ10 compounds. Examples of anticancer agents, including chemotherapeutic agents, are provided herein.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

The articles "a", "an" and "the" are used herein to refer to one or to more than one (i c to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein including, but not limited to, combinations of dosing rates, dosing times, dosing amounts, treatment methods, monitoring methods, selection methods, and use of agents other than coenzyme Q10.

I. Coenzyme Q10 Compounds

It will be understood that the methods provided herein are contemplated to be carried out with a composition comprising one or more Coenzyme Q10 compounds. Coenzyme Q10 compounds are intended to include a class of CoQ10 compounds. Coenzyme Q10 compounds effective for the methods described herein include coenzyme Q10, a metabolite of coenzyme Q10, a biosynthetic precursor of coenzyme Q10, an analog of coenzyme Q10, a derivative of coenzyme Q10, and coenzyme Q10 related compounds. An analog of coenzyme Q10 includes analogs having no or at least one isoprenyl repeats. Coenzyme Q10 has the following structure:

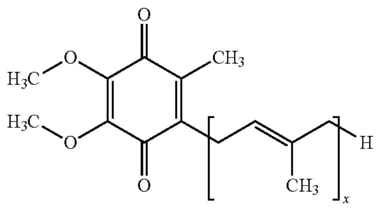

wherein x is 10. In the instant invention, CoQ10 compounds can include derivatives of coenzyme Q10 in which x is any number of isoprenyl units from 4-10, or any number of isoprenyl units from 6-10, or any number of isoprenyl units from 8-10, or 9-10 isoprenyl units. Coenzyme Q10 includes the fully oxidized version, also known as ubiquinone, the partially oxidized version, also known as semiquinone or ubisemiquinone, or the fully reduced version, also known as ubiquinol; or any mixtures or combinations thereof. In certain embodiments, the CoQ10 compound for treatment of cancer is ubiquinone. In certain embodiments, the CoQ10 compound for treatment of cancer is ubiquinol.

In certain embodiments of the present invention, the therapeutic agent is coenzyme Q10 (CoQ10). Coenzyme Q10, also referred to herein as CoQ10, is also known as ubiquinone, or ubidecarenone. Coenzyme Q10 is art-recognized and further described in International Publication No. WO 2005/069916 (Appln. No. PCT/US2005/001581, WO 2008/116135 (Appln. No. PCT/US08/57786), WO20101132507 (Appln. No. PCT/US2010/034453), WO 2011/112900 (Appln. No. PCT/US2011/028042), and WO2012/174559 (Appln. No. PCT/US2012/043001) the entire contents of each of which are expressly incorporated by reference herein. Coenzyme Q10 is one of a series of polyprenyl 2,3-dimethoxy-5-methylbenzoquinone (ubiquinone) present in the mitochondrial electron transport systems of eukaryotic cells. Human cells produce coenzyme Q10 exclusively and it is found in cell and mitochondrial membranes of all human cells, with the highest levels in organs with high energy requirements, such as the liver and the heart. The body pool of coenzyme Q10 has been estimated to be about 2 grams, of which more than 50% is endogenous. Approximately 0.5 grams of coenzyme Q10 is required from the diet or biosynthesis each day. Coenzyme Q10 is produced in ton quantities from the worldwide supplement market and can be obtained from Kaneka, with plants in Pasadena, Texas and Takasagoshi, Japan.

II. Compositions

The present disclosure provides compositions containing a CoQ10 compound for the treatment and prevention of cancer. The compositions of the present disclosure can be self-administered by a patient, or in pharmaceutical compositions where it is mixed with suitable carriers or excipient(s). In treating a patient exhibiting a disorder of interest. e.g., cancer, a therapeutically effective amount of the CoQ10 compound is administered. A therapeutically effective dose refers to that amount of the compound which results in at least stable disease or a prolongation of survival in a patient.

Suitable routes of administration of the present compositions of the invention may include parenteral delivery, including, intravenous infusion, preferably continuous infusion. In a preferred embodiment, the IV infusion comprises the active agent, e.g., coenzyme Q10, at approximately a 40 mg/mL (4% w/v) concentration. Where the composition is administered by IV infusion, it can be diluted in a pharmaceutically acceptable aqueous solution such as phosphate buffered saline or normal saline. In some embodiments, one or more routes of administration may be combined, such as, for example, intravenous and intratumoral, or intravenous and peroral, or intravenous and oral, or intravenous and topical, transdermal, or transmucosal. However, the methods provided herein include administration of coenzyme Q10 by continuous intravenous infusion.

For example, a CoQ10 compound can be formulated for parenteral delivery, e.g., for intravenous injection. The compositions may be administered in a single bolus, multiple injections, or by continuous infusion (for example, intravenously or by peritoneal dialysis). For parenteral administration, the compositions may be formulated in a sterilized pyrogen-free form.

Use of pharmaceutically acceptable carriers to formulate the compounds herein disclosed, for the practice of the present invention, into dosages suitable for systemic administration is within the scope of the present disclosure. With proper choice of carrier and suitable manufacturing practice, the compositions of the present disclosure, in particular, those formulated as solutions, may be administered parenterally, such as by intravenous injection.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices may be desirable. The data obtained from these cell culture assays and animal studies can be used in formulating a range of dosage for use in human. The dosage of such compounds may be within a range of circulating concentrations that include the ED50 with little or no toxicity. The dosage may vary within this range depending upon the dosage form employed and the route of administration utilized.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein, in addition to the active ingredients, these pharmaceutical compositions may contain suitable pharmaceutically acceptable carriers including excipients and auxiliaries which facilitate processing of the active compounds into preparations which can be used pharmaceutically. The preparations formulated for intravenous administration may be in the form of solutions of colloidal dispersion.

Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

III. Formulations

The active agent, e.g., a CoQ10 compound, can be delivered in any pharmaceutically acceptable carrier for the desired route of administration. As used herein, formulations including CoQ10 compounds are formulated for administration by injection or infusion. In certain embodiments, the CoQ10 compounds are not delivered orally.

Preferred therapeutic formulations for use in the methods of the invention comprise the active agent (e.g., a CoQ10 compound) in a microparticle formation, e.g., for intravenous administration. Such intravenous formulations are provided, for example, in WO2011/112900 (Appln. No. PCT/US2011/028042), the entire contents of which are expressly incorporated herein by reference, and an exemplary intravenous formulation as described in WO2011/112900 (Appln. No. PCT/US2011/028042) is used in the examples set forth below. Through high pressure homogenization, active agent (e.g., a CoQ10 compound) particles are reduced to produce particles that are small enough to pass through a 200-nm sterilizing filter. Particles that are small enough to pass through a 200-nm sterilizing filter can be injected intravenously. These particles are much smaller than blood cells and therefore will not embolize capillaries. Red blood cells for example are 6-micron×2-micron disks. The particles are dispersed to and are encased or surrounded by a stabilizing agent. While not wishing to be hound by any theory, it is believed that the stabilizing agents are attracted to the hydrophobic therapeutic agent such that the dispersed particles of the hydrophobic therapeutic agent are surrounded by the stabilizing agent forming a suspension or an emulsion. The dispersed particles in the suspension or emulsion comprises a stabilizing agent surface and a core consisting of the hydrophobic therapeutic agent, e.g., a CoQ10 compound, in a solid particulate form (suspension) or in an immiscible liquid form (emulsion). The dispersed particles can be entrenched in the lipophilic regions of a liposome.

Dispersed colloidal systems permit a high drug load in the formulation without the use of co-solvents. Additionally, high and relatively reproducible plasma levels are achieved without the dependence on endogenous low-density lipoprotein carriers. More importantly, the formulations allow sustained high drug levels in tumor cells due to the passive accumulation of the colloidal particles of the hydrophobic therapeutic agent.

A preferred intravenous formulation substantially comprises a continuous phase of water and dispersed solids (suspension) or dispersed immiscible liquid (emulsion). Dispersed colloidal systems, in which the particles are composed largely of the active agent (drug) itself, can often deliver more drug per unit volume than continuous solubilizing systems, if the system can be made adequately stable.

As the formulation medium, the aqueous solution may include Hank's solution, Ringer's solution, phosphate buffered saline (PBS), physiological saline buffer or other suitable salts or combinations to achieve the appropriate pH and osmolarity for parenterally delivered formulations. Aqueous solutions can be used to dilute the formulations for administration to the desired concentration. For example, aqueous solutions can be used to dilute a formulation for intravenous administration from a concentration of about 4% w/v to a lower concentration to facilitate administration of lower doses of coenzyme Q10. The aqueous solution may contain substances which increase the viscosity of the solution, such as sodium carboxymethyl cellulose, sorbitol, or dextral.

The active agent (e.g., a CoQ10 compound) is dispersed in the aqueous solution such that a colloidal dispersion is formed wherein the nano-dispersion particles of the hydrophobic therapeutic agent are covered or encased or encircled by the dispersion stabilizing agents to form nano-dispersions of the active agent (e.g., a CoQ10 compound) particles. The nano-dispersed active agent (e.g., a CoQ10 compound) particles have a core formed of the hydrophobic therapeutic agent that is surrounded by the stabilizing agent. Similarly, in certain aspects, the stabilizing agent is a phospholipid having both a hydrophilic and lipophilic portion. The phospholipids form liposomes or other nanoparticles upon homogenization. In certain aspects these liposomes are. In-layered unilamellar liposomes while in other embodiments the liposomes are bi-layered multi-lamellar liposomes. The dispersed active agent (e.g., a CoQ10 compound) particles are dispersed in the lipophilic portion of the bi-layered structure of the liposome formed from the phospholipids. In certain other aspects the core of the liposome, like the core of the nano-dispersion of active agent (e.g., a CoQ10 compound) particles, is formed of the hydrophobic therapeutic agent and the outer layer is formed of the bi-layered structure of the phospholipid. In certain embodiments the colloidal dispersions are treated by a lyophilization process whereby the nanoparticle dispersion is convened to a dry powder.

In some embodiments, the formulation for injection or infusion used is a 4% sterile aqueous colloidal dispersion containing coenzyme Q10 in a nanosuspension as prepared in WO2011/112900. In certain embodiments, the formulation includes an aqueous solution; a hydrophobic active agent, e.g., coenzyme Q10, a coenzyme Q10 precursor or metabolite or a coenzyme Q10 related compound, dispersed to form a colloidal nano-dispersion of particles; and at least one of a dispersion stabilizing agent and an opsonization reducer; wherein the colloidal nano-dispersion of the active agent is dispersed into nano-dispersion particles having a mean size of less than 200 nm.

In certain embodiments, the dispersion stabilizing agent includes, but is not limited to, pegylated castor oil, Cremophor® EL, Cremophor® RH 40, Pegylated vitamin E, Vitamin E, TPGS, and Dimyristoylphosphatidyl choline (DMPC).

In certain embodiments, the opsonization reducer is a poloxamer or a poloxamines.

In certain embodiments, the colloidal nano-dispersion is a suspension or an emulsion. Optionally, a colloidal nano-dispersion is in a crystalline form or a super-cooled melt form.

In certain embodiments, the formulation for injection or infusion includes a lyoprotectant such as a nutritive sugar including, but not limited to, lactose, mannose, maltose, galactose, fructose, sorbose, raffinose, neuraminic acid, glucosamine, galactosamine, N-methylglucosamine, mannitol, sorbitol, arginine, glycine, and sucrose; or any combination thereof.

In certain embodiments, the formulation for injection or infusion includes an aqueous solution; a hydrophobic active agent dispersed to form a colloidal nano-dispersion of particles; and at least one of a dispersion stabilizing agent and an opsonization reducer. The colloidal nano-dispersion of the active agent is dispersed into nano-dispersion particles having sizes of less than 200 nm. In some embodiments the dispersion stabilizing agent is selected from natural or semisynthetic phospholipids. For example, suitable stabilizing agents include polyethoxylated (a/k/a pegylated) castor oil (Cremophor® EL), polyethoxylated hydrogenated castor oil (Cremophor® RH 40). Tocopherol polyethylene glycol succinate (Pegylated vitamin E, Vitamin E TPGS), Sorbitan fatty acid esters (Spans®), bile acids and bile-acid salts, or dimyristoylphosphatidyl choline (DMPC). In some embodiments the stabilizing agent is DMPC.

In certain embodiments the formulation is suitable for parenteral administration, including intravenous, intraperitoneal, orthotopical, intracranial, intramuscular, subcutaneous, intramedullary injections, as well as intrathecal, direct intraventricular, intranasal, or intraocular injections. In certain embodiments, the formulation contains coenzyme Q10, dimyristoyl-phosphatidylcholine, and poloxamer 188 in a ratio of 4:3:1.5 respectively that is designed to stabilize the nanosuspension of the particles. In some embodiments, the formulation includes a phosphate buffer saline solution which contains sodium phosphate dibasic, potassium phosphate monobasic, potassium chloride, sodium chloride, and water for injection. In certain embodiments, the 4% sterile aqueous colloidal dispersion containing coenzyme Q10 in a nanosuspension is diluted in the phosphate buffered saline solution provided, e.g., 1:1, 1:2, 1:3, 1:4, 1:5, 1:6, 1:7, 1:8, 1:9, 1:10, 1.11, 1:12, 1:13, 1:14, 1:15, 1.16, 1:17, 1:18, 1:19, 1:20, or other appropriate ratio bracketed by any two of the values.

In some embodiments, a formulation for administration for use in the invention may include from about 0.001% to about 20% (w/w) of coenzyme Q10, about 0.01% to about 20% (w/w) of coenzyme Q10, about 0.1% to about 20% (w/w) of coenzyme Q10, more preferably about 0.01% to about 15% and even more preferably about 0.1% to about 10% (w/w) of coenzyme Q10, in certain embodiments, a formulation for any route of administration for use in the invention may include from about 1% to about 10% (w/w) of coenzyme Q10. In certain embodiments, a formulation for any route of administration for use in the invention may include from about 2% to about 8% (w/w) of coenzyme Q10. In certain embodiments, a formulation for any route of administration for use in the invention may include from about 2% to about 7% (w/w) of coenzyme Q10. In certain embodiments, a formulation for any route of administration for use in the invention may include from about 3% to about 6% (w/w) of coenzyme Q10. In certain embodiments, a formulation for any route of administration for use in the invention may include from about 3% to about 5% (w/w) of coenzyme Q10 In certain embodiments, a formulation for any route of administration for use in the invention may include from about 3.5% to about 4.5% (w/w) of coenzyme Q10. In certain embodiments, a formulation for any route of administration for use in the invention may include from about 3.5% to about 5% (w/w) of coenzyme Q10. In one embodiment a formulation includes about 4% (w/w) of coenzyme Q10. In one embodiment a formulation includes about 8% (w/w) of coenzyme Q10. In various embodiments, the formulation includes about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 7%, 8%, 9%, 10% 11%, 12%, 13%, 14%, 15%, 16%, 17%, 18%, 19% or 20% (w/w) of coenzyme Q10, or any range bracketed by any two values recited. In certain embodiments, the formulations can be prepared as a percent weight to volume rather than a percent weight to weight. Depending on the formulation, the concentration of coenzyme Q10 may be the same, or about the same in the w/w and the w/v percent formulations. Coenzyme Q10 can be obtained from Kaneka Q10 as Kaneka Q10 (USP UBIDECARENONE) in powdered form (Pasadena, Texas, USA). Coenzyme Q10 used in the methods exemplified herein have the following characteristics: residual solvents meet USP 467 requirement; water content is less than 0.0%, less than 0.05% or less than 0.2%; residue on ignition is 0.0%, less than 0.05%, or less than 0.2% less than; heavy metal content is less than 0.002%, or less than 0.001%; purity of between 98-100% or 99.9%, or 99.5%.

In certain embodiments, the concentration of coenzyme Q10 in the formulation is 1 mg/mL to 150 mg/mL In one embodiment, the concentration of coenzyme Q10 in the formulation is 5 mg/mL to 125 mg/mL. In one embodiment, the concentration of coenzyme Q10 in the formulation is 10 mg/mL to 100 mg/mL. In one embodiment, the concentration of coenzyme Q10 in the formulation is 20 mg/mL to 90 mg/mL. In one embodiment, the concentration of coenzyme Q10 is 30 mg/mL to 80 mg/mL. In one embodiment, the concentration of coenzyme Q10 is 30 mg/mL to 70 mg/mL. In one embodiment, the concentration of coenzyme Q10 is 30 mg/mL to 60 mg/mL. In one embodiment, the concentration of coenzyme Q10 is 30 mg/mL to 50 mg/mL. In one embodiment, the concentration of coenzyme Q10 is 35 mg/mL to 45 mg/mL. It should be understood that additional ranges having any one of the foregoing values as the upper or lower limits are also intended to be part of this invention, e.g., 10 mg/mL to 50 mg/mL, or 20 mg/mL to 60 mg/mL.

In certain embodiments, the concentration of coenzyme Q10 in the formulation is about 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90 or 95 mg/mL. In one embodiment, the concentration of coenzyme Q10 in the formulation is about 50 mg/mL. In one embodiment, the concentration of coenzyme Q10 in the formulation is about 60 mg/mL. In one embodiment, the concentration of coenzyme Q10 in the formulation is about 30 mg/mL. In a preferred embodiment, the concentration of coenzyme Q10 in the formulation is about 40 mg/mL. It should be understood that ranges having any one of these values as the upper or lower limits are also intended to be part of this invention, e.g. between 37 mg/mL and 47 mg/mL or between 31 mg/mL and 49 mg/mL.

It is understood that formulations can similarly be prepared containing coenzyme Q10 precursors, metabolites, and related compounds.

IV. Treatment of Cancer

The invention provides methods for the treatment of cancer by continuous infusion of coenzyme Q10. In certain embodiments, the cancer comprises a solid tumor. In certain embodiments, the cancer comprises a leukemia. In certain embodiments, the cancer is treated with coenzyme Q10 alone. In certain embodiments, the cancer is treated with coenzyme Q10 and an additional agent. In certain embodiments, the additional agent is a chemotherapeutic agent. In certain embodiments, treatment with the chemotherapeutic agent is initiated at the same time as treatment with the coenzyme Q10. In certain embodiments, the treatment with the chemotherapeutic agent is initiated after the treatment with coenzyme Q10 is initiated. In certain embodiments, treatment with the additional agent is initiated upon progression of the cancer during treatment with coenzyme Q10. In certain embodiment& treatment with the additional agent is initiated without progression of the cancer during treatment with coenzyme Q10. In certain embodiments, treatment with coenzyme Q10 is continued upon initiation of administration of the additional agent. In certain embodiment& treatment with coenzyme Q10 is stopped upon initiation of treatment with the additional agent.

In certain embodiment, formulations and methods of the present disclosure may be utilized for the treatment of solid tumors wherein the subject has failed at least one prior chemotherapeutic regimen. Accordingly, the present invention provides methods of treating cancer in a subject, wherein the subject has failed at least one prior chemotherapeutic regimen for the cancer, comprising administering the formulations of the invention to the subject by continuous infusion in an amount sufficient to treat the cancer, thereby treating cancer. The formulations of the invention may also be utilized for inhibiting tumor cell growth in a subject wherein the subject has failed at least one prior chemotherapeutic regimen. Accordingly, the invention further provides methods of inhibiting tumor cell growth in a subject, wherein the subject has failed at least one prior chemotherapeutic regimen, comprising administering the formulations of the invention to the subject, such that tumor cell growth is inhibited. In a preferred embodiment, inhibiting tumor growth includes achieving at least stable disease of the primary lesion by RECIST 1.1 criteria. In certain embodiments, the subject is a human subject.

Such formulations may include the hydrophobic therapeutic agent, e.g., coenzyme Q10, its metabolites, or coenzyme Q10 related compounds, in a pharmaceutically acceptable carrier, in some embodiments, such a formulation may include from about 0.001% to about 20% (w/w) of coenzyme Q10, more preferably between about 0.01% and about 15% and even more preferably between about 0.1% to about 10% (w/w) of coenzyme Q10. In one embodiment a formulation includes about 4% (w/w) of coenzyme Q10. In one embodiment a formulation includes about 8% (w/w) of coenzyme Q10. In various embodiments, the formulation includes about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19% or 20% (w/w) of coenzyme Q10, or any range bracketed by those values. In certain embodiments, the formulations can be prepared as a percent weight to volume rather than a percent weight to weight. Depending on the formulation, the concentration of coenzyme Q10 may be the same, or about the same in the w/w and the w/v percent formulations. As also noted herein, compositions of the present disclosure may be in a liquid form, capable of introduction into a subject by any means or route of administration within the purview of those skilled in the art. For example, compositions may be administered by routes of administration including, but not limited to, intravenous, intratumoral, combinations thereof, and the like.

In certain embodiments of the invention, methods are provided for treating or preventing cancer in a human by intravenously administering a coenzyme Q10, coenzyme Q10 precursor, metabolite, or related compound formulation to the human such that treatment or prevention occurs, wherein the human is administered the coenzyme Q10 compound, e.g., coenzyme Q10, by continuous infusion (e.g., for at least 24 hours, at least 48 hours, at least 72 hours, at least 96 hours or at least 144 hours) wherein a 24 hour dose (e.g., average 24 hour dose) of the coenzyme Q10 compound (e.g., coenzyme Q10) is administered in the range of about 0.5 mg/kg/dose to about 10,000 mg/kg/dose, about 5 mg/kg/dose to about 5,000 mg/kg/dose, about 10 mg/kg/dose to about 3,000 mg/kg/dose. In one embodiment, the formulation is administered such that, preferably, coenzyme Q10 is administered a 24 hour dose in the range of about 10 mg/kg/dose to about 1,400 mg/kg/dose. In one embodiment, the formulation is administered a 24 hour dose such that, preferably, coenzyme Q10 is administered in the range of about 10 mg/kg/dose to about 650 mg/kg/dose. In one embodiment, the formulation is administered such that, preferably, coenzyme Q10 is administered in the range of about 10 mg/kg/dose to about 200 mg/kg/dose. In one embodiment, the formulation is administered a 24 hour dose such that, preferably, coenzyme Q10 is administered in the range of about 10 mg/kg/dose to about 100 mg/kg/dose. In one embodiment, the formulation is administered a 24 hour dose such that, preferably, coenzyme Q10 is administered in the range of about 10 mg/kg/dose to about 75 mg/kg/dose. In one embodiment, the formulation is administered a 24 hour dose such that, preferably, coenzyme Q10 is administered in the range of about 10 mg/kg/dose to about 65 mg/kg/dose. In various embodiments, the formulation is administered a 24 hour dose such that, preferably, coenzyme Q10 is administered in the range of about 10 mg/kg/dose to about 15 mg/kg/dose, about 15 mg/kg/dose to about 20 mg/kg/dose, about 20 mg/kg/dose to about 25 mg/kg/dose, about 27 mg/kg/dose to about 35 mg/kg/dose, about 34 mg/kg/dose to about 42 mg/kg/dose, about 42 mg/kg/dose to about 52 mg/kg/dose, or about 53 mg/kg/dose to about 65 mg/kg/dose. In various embodiments, the formulation is administered such that, preferably, coenzyme Q10 is administered a 24 hour dose at a dose of about 2 mg/kg/dose, 5 mg/kg/dose, 10 mg/kg/dose, 15 mg/kg/dose, 20 mg/kg/dose, 25 mg/kg/dose, 30 mg/kg/dose, 35 mg/kg/dose, 40 mg/kg/dose, 45 mg/kg/dose, 50 mg/kg/dose, 55 mg/kg/dose, 56 mg/kg/dose, 57 mg/kg/dose, 58 mg/kg/dose, 59 mg/kg/dose, 60 mg/kg/dose, 65 mg/kg/dose, 70 mg/kg/dose, 75 mg/kg/dose, 76 mg/kg/dose, 77 mg/kg/dose, 78 mg/kg/dose, 79 mg/kg/dose, 80 mg/kg/dose, 85 mg/kg/dose, 90 mg/kg/dose, 95 mg/kg/dose, 100 mg/kg/dose, 101 mg/kg/dose, 102 mg/kg/dose, 103 mg/kg/dose, 104 mg/kg/dose, 105 mg/kg/dose, 106 mg/kg/dose, 107 mg/kg/dose, 108 mg/kg/dose, 109 mg/kg/dose, 110 mg/kg/dose, 120 mg/kg/dose, 130 mg/kg/dose, 140 mg/kg/dose, 150 mg/kg/dose, 160 mg/kg/dose, 170 mg/kg/dose, 180 mg/kg/dose, 190 mg/kg/dose, or 200 mg/kg/dose. In various embodiments, the formulation is administered a 24 hour dose such that, preferably, coenzyme Q10 is administered at a dose of at least 2 mg/kg/dose, 5 mg/kg/dose, 10 mg/kg/dose, 15 mg/kg/dose, 20 mg/kg/dose, 25 mg/kg/dose, 30 mg/kg/dose, 35 mg/kg/dose, 40 mg/kg/dose, 45 mg/kg/dose, 50 mg/kg/dose, 55 mg/kg/dose, 56 mg/kg/dose, 57 mg/kg/dose, 58 mg/kg/dose, 59 mg/kg/dose, 60 mg/kg/dose, 65 mg/kg/dose, 70 mg/kg/dose, 75 mg/kg/dose, 76 mg/kg/dose, 77 mg/kg/dose, 78 mg/kg/dose, 79 mg/kg/dose, 80 mg/kg/dose, 85 mg/kg/dose, 90 mg/kg/dose, 95 mg/kg/dose, 100 mg/kg/dose, 101 mg/kg/dose, 102 mg/kg/dose, 103 mg/kg/dose, 104 mg/kg/dose, 105 mg/kg/dose, 106 mg/kg/dose, 107 mg/kg/dose, 108 mg/kg/dose, 109 mg/kg/dose, 110 mg/kg/dose, 120 mg/kg/dose, 130 mg/kg/dose, 140 mg/kg/dose, 150 mg/kg/dose, 160 mg/kg/dose, 170 mg/kg/dose, 180 mg/kg/dose, 190 mg/kg/dose, or 200 mg/kg/dose, wherein the dose does not result in any limiting toxicities. It should be understood that ranges having any one of these values as the upper or lower limits of a 24 hour dose are also intended to be part of this invention, e.g., about 50 mg/kg/dose to about 200 mg/kg/dose, or about 650 mg/kg/dose to about 1400 mg/kg/dose, or about 55 mg/kg/dose to about 110 mg/kg/dose. In one embodiment the administered 24 hour dose is at least about 1 mg/kg/dose, at least about 5 mg/kg/dose, at least about 10 mg/kg/dose, at least about 12.5 mg/kg/dose, at least about 15 mg/kg/dose, at least about 20 mg/kg/dose, at least about 25 mg/kg/dose, at least about 30 mg/kg/dose, at least about 35 mg/kg/dose, at least about 40 mg/kg/dose, at least about 45 mg/kg/dose, at least about 50 mg/kg/dose, at least about 55 mg/kg/dose, at least about 60 mg/kg/dose, at least about 65 mg/kg/dose, at least about 75 mg/kg/dose, at least about 100 mg/kg/dose, at least about 125 mg/kg/dose, at least about 150 mg/kg/dose, at least about 175 mg/kg/dose, at least about 200 mg/kg/dose, at least about 300 mg/kg/dose, or at least about 400 mg/kg/dose. In certain embodiments, the administered 24 hour dose is no more than about 20 mg/kg/dose, about 25 mg/kg/dose, about 30 mg/kg/dose, about 35 mg/kg/dose, about 40 mg/kg/dose, about 45 mg/kg/dose, about 50 mg/kg/dose, about 55 mg/kg/dose, about 60 mg/kg/dose, about 75 mg/kg/dose, about 100 mg/kg/dose, about 125 mg/kg/dose, about 150 mg/kg/dose, about 175 mg/kg/dose, about 200 mg/kg/dose, about 300 mg/kg/dose, about 400 mg/kg/dose, about 500 mg/kg/dose, about 600 mg/kg/dose, about 700 mg/kg/dose, about 800 mg/kg/dose, about 900 mg/kg/dose, about 1000 mg/kg/dose, about 1100 mg/kg/dose, about 1200 mg/kg/dose, or about 1300 mg/kg/dose. It is understood that any of the lower limit values and upper limit values can be combined to create a range.

In certain embodiments, a dose can be a 48 hour dose (i.e., about 2 days) administered by continuous infusion in any of the foregoing amounts or ranges of amounts provided. In certain embodiments, the total 48 hour dose administered by continuous infusion is 2 times the amount administered in a 24 hour dose. In certain embodiments, the total 48 hour dose administered by continuous infusion is administered over 48 hours with an average dose over 24 hours of any of the foregoing amounts or ranges of amounts provided. In certain embodiments, the total 48 hour dose administered by continuous infusion is equivalent to any of the foregoing 24 hour doses, but is administered over 48 hours. In certain embodiments the total 48 hour dose is about 30 mg/kg to about 350 mg/kg, or about 30 mg/kg to about 300 mg/kg. In certain embodiments, the total 48 hour continuous infusion dose is about 50 mg/kg to about 250 mg/kg, in certain embodiments, the total 48 hour continuous infusion dose is about 38 mg/kg, about 50 mg/kg, about 66 mg/kg, about 88 mg/kg, about 110 mg/kg, about 137 mg/kg, about 171 mg/kg, or about 215 mg/kg.

In certain embodiments, a dose can be a 96 hour dose (i.e., about 4 days) administered by continuous infusion in any of the amounts or ranges of amounts provided. In certain embodiments, the total 96 hour dose administered by continuous infusion is four times the amount administered in a 24 hour dose. In certain embodiments, the 96 hour dose administered by continuous infusion is administered over 96 hours with an average dose over 24 hours of any of the foregoing amounts or ranges of amounts provided. In certain embodiments, the total 96 hour dose administered by continuous infusion is equivalent to any of the foregoing 24 hour doses, but is administered over 96 hours. In certain embodiments the total 16 hour dose is about 30 mg/kg to about 450 mg/kg, 30 mg/kg to about 400 mg/kg, about 30 mg/kg to about 350 mg/kg, or about 30 mg/kg to about 300 mg/kg. In certain embodiments, the total 96 hour continuous infusion dose is about 50 mg/kg to about 250 mg/kg. In certain embodiments the total 96 hour dose is about 100 mg/kg to about 430 mg/kg, 100 mg/kg to about 200 mg/kg, about 200 mg/kg to about 350 mg/kg, or about 300 mg/kg to about 450 mg/kg. In certain embodiments, the total 96 hour continuous infusion dose is about 38 mg/kg, about 50 mg/kg, about 66 mg/kg, about 88 mg/kg, about 110 mg/kg, about 137 mg/kg, about 171 mg/kg, about 215 mg/kg, about 100 mg/kg, about 132 mg/kg, about 176 mg/kg, about 220) mg/kg, about 274 mg/kg, about 342 mg/kg, or about 430 mg/kg.

In certain embodiments, a dose can be a 72 hour dose (i.e., about 3 days) administered by continuous infusion in any of the amounts or ranges of amounts provided. In certain embodiments, the total 72 hour dose administered by continuous infusion is 3 times the amount administered in a 24 hour dose. In certain embodiments, the 72 hour dose administered by continuous infusion is administered over 72 hours with an average dose over 24 hours of any of the foregoing amounts or ranges of amounts provided, in certain embodiments, the total 72 hour dose administered by continuous infusion is equivalent to any of the foregoing 24 hour doses, but is administered over 72 hours. In certain embodiments the total 72 hour dose is about 30 mg/kg to about 350 mg/kg, or about 30 mg/kg to about 300 mg/kg. In certain embodiments, the total 72 hour continuous infusion dose is about 50 mg/kg to about 250 mg/kg. In certain embodiments, the total 72 hour continuous infusion dose is about 38 mg/km, about 50 mg/kg, about 66 mg/kg, about 88 mg/kg, about 110 mg/kg, about 137 mg/kg, about 171 mg/kg, or about 215 mg/kg.

In certain embodiments, a dose can be a 144 hour dose (i.e., about 6 days) administered by continuous infusion in any of the foregoing amounts or ranges of amounts provided. In certain embodiments, the total 144 hour dose administered by continuous infusion is 6 times the amount administered in a 24 hour dose. In certain embodiments, the 144 hour dose administered by continuous infusion is administered over 144 hours with an average dose over 24 hours of any of the foregoing amounts or ranges of amounts provided. In certain embodiments, the total 144 hour dose administered by continuous infusion is equivalent to any of the foregoing 24 hour doses, but is administered over 144 hours. In certain embodiments the total 144 hour dose is about 30 mg/kg to about 350 mg/kg, or about 30 mg/kg to about 300 mg/kg. In one embodiment the total 144 hour dose is about 75 mg/kg to about 350 mg/kg, in certain embodiments, the total 144 hour continuous infusion dose is about 50 mg/kg to about 250 mg/kg. In certain embodiments, the total 144 hour continuous infusion dose is about 38 mg/kg, about 50 mg/kg, about 66 mg/kg, about 88 mg/kg, about 110 mg/kg, about 137 mg/kg, about 171 mg/kg, or about 215 mg/kg, in certain embodiments, the total 144 hour continuous infusion dose is about 76 mg/kg, about 100 mg/kg, about 132 mg/kg, about 176 mg/kg, about 220 mg/kg, about 274 mg/kg, or about 342 mg/kg. In one embodiment, the coenzyme Q10 formulation is administered one time per week, in one embodiment, the coenzyme Q10 formulation is administered two times per week. In one embodiment, the coenzyme Q10 formulation is administered 3 times per week. In one embodiment, the coenzyme Q10 formulation is administered four times per week. In another embodiment, the coenzyme Q10 formulation is administered 5 times per week. In one embodiment, the coenzyme Q10 formulation is administered once per day. In certain embodiments, the formulation is administered over more than 4 hours. In certain embodiments, the formulation is administered over 8 or more hours. In certain embodiments, the formulation is administered over 12 hours or more hours. In certain embodiments, the formulation is administered over 18 or more hours. In certain embodiments, the formulation is administered over 24 or more hours (i.e., by continuous infusion). In certain embodiments, the formulation is administered over about 24 hours. In certain embodiments, the formulation is administered over at least about 48 hours, 72 hours, 96 hours, 120 hours, 144 hours, 168 hours, 192 hours, 216 hours, 240 hours, 264 hours, 288 hours, 312 hours, 336 hours, 360 hours, 384 hours, 408 hours, 432 hours, 456 hours, or 480 hours. In certain embodiments, the formulation is administered over about 48 hours, 72 hours, 96 hours, 120 hours, 144 hours, 168 hours, 192 hours, 216 hours, 2441 hours, 264 hours, 288 hours, 312 hours, 336 hours, 360 hours, 384 hours, 408 hours, 432 hours, 456 hours, or 480 hours. Any of these values may be used to define a range for the number of hours over which the dose is administered. For example, the formulation may be administered over about 48 hours to about 480 hours, over about 48 hours to about 144 hours, or over about 48 hours to about 96 hours.

In certain embodiments, the amount of coenzyme Q10 administered is the same for each 24 hour period regardless of the rate(s) of administration during each 24 hour period of the continuous infusion. In certain embodiments, the amount of coenzyme Q10 administered varies for one or more 24 hour period of the continuous infusion. In certain embodiments, the amount of coenzyme Q10 administered during the first 24 hours is different from the amount of coenzyme Q10 administered during the remaining 24 hour periods in the continuous infusion. In certain embodiments, the amount of coenzyme Q10 administered is the same for all 24 hour periods, but the rate(s) of administration of coenzyme Q10 is different for the first 24 hour period as compared to the remaining 24 hour periods of the continuous infusion.

In certain embodiments, the continuous infusion is initiated with a loading dose of coenzyme Q10. In a preferred embodiment, the dosage administered in the 24, 48, or 72 hours is initially administered at a higher rate than the remainder of the 24, 48, or 72 hour infusion. In certain embodiments, at least 5% of the dose for the first 24, 48, or 72 hours is administered at the higher rate during the first hour of administration. In certain embodiments, at least 6% of the dose for the first 24, 48, or 72 hours is administered at the higher rate during the first hour of administration, in certain embodiments, at least 7% of the dose for the first 24, 48, or 72 hours is administered at the higher rate during the first hour of administration. In certain embodiments, at least 8% of the dose for the first 24, 48, or 72 hours is administered at the higher rate during the first hour of administration. In certain embodiments, at least 9% of the dose for the first 24, 48, or 72 hours is administered at the higher rate during the first hour of administration. In certain embodiments, at least 10% of the dose for the first 24, 48, or 72 hours is administered at the higher rate during the first hour of administration. In certain embodiments, at least 8% of the dose for the first 24, 48, or 72 hours is administered at the higher rate during the first hour of administration. In certain embodiments, at least 15% of the dose for the first 24, 48, or 72 hours is administered at the higher rate during the first hour of administration. In certain embodiments, at least 17.5% of the dose for the first 24, 48, or 72 hours is administered at the higher rate during the first hour of administration. In certain embodiments, at least 20% of the dose for the first 24, 48, or 72 hours is administered at the higher rate during the first hour of administration. In certain embodiments, at least 22.5% of the dose for the first 24, 48, or 72 hours is administered at the higher rate during the first hour of administration. In certain embodiments, at least 25% of the dose for the first 24, 48, or 72 hours is administered at the higher rate during the first hour of administration. After administration of a portion of the dose at a higher rate for the first of the 24, 48, or 72 hours, the remainder of the dose is administered at a second, lower rate for the remaining 23, −47, or 73 hours. Typically, the continuous infusion is continued to provide a continuous infusion of at least 96 hours (i.e. two 48 hour infusions with a short break between the two infusions) or at least 144 hours (i.e. two 72 hour infusions with a short break between the two infusions). This continuation may be at a third infusion rate, which is between the two prior infusion rates used such that the amount of coenzyme Q10 administered each 48 hours (for the 96 hour infusion) or each 72 hours (for the 144 hour infusion) is the same. Methods to adjust infusion rates to provide a loading dose at the beginning of the infusion are well within the ability of those of skill in the art.

In certain embodiments, the infusion rate for the loading dose for the first hour of the continuous administration is about 0.1 ml/min to about 1.5 ml/min. For example, the loading dose of the first hour of the infusion can be about 0.1 ml/min, 0.15 ml/min, 0.2 ml/min, 0.25 ml/min, 0.3 ml/min, 0.35 ml/min, 0.4 ml/min, 0.45 ml/min, 0.50 ml/min, 0.55 ml/min, 0.6 ml/min, 0.65 ml/min, 0.7 ml/min, 0.75 ml/min, 0.8 ml/min, 0.85 ml/min, 0.9 ml/min, 0.95 ml/min, 1.0 ml/min, 1.1 ml/min, 1.2 ml/min, 1.3 ml/min, 1.4 ml/min, 1.5 ml/min, or more, or any range bracketed by any of two values provided.

In certain embodiments (e.g., for a 96 hr continuous infusion), the loading dose rate (the first rate) for coenzyme Q10 administration is at least 1 mg/kg/hr, at least 2 mg/kg/hr, at least 3 mg/kg/hr, at least 4 mg/kg/hr, at least 5 mg/kg/hr, at least 6 mg/kg/hr, at least 7 mg/kg/hr, at least 8 mg/kg/hr, at least 9 mg/kg/hr, at least 10 mg/kg/hr, at least 11 mg/kg/hr, at least 12 mg/kg/hr, at least 13 mg/kg/hr, at least 14 mg/kg/hr, at least 15 mg/kg/hr, at least 16 mg/kg/hr, at least 17 mg/kg/hr, at least 18 mg/kg/hr, at least 19 mg/kg/hr, at least 20 mg/kg/hr, at least 25 mg/kg/hr, at least 30 mg/kg/hr, at least 35 mg/kg/hr, at least 40 mg/kg/hr, at least 45 mg/kg/hr, or at least 50 mg/kg/hr, where “km” is the body weight of the subject being treated. In particular embodiments, the loading dose rate for coenzyme Q10 administration is about 3.1 mg/kg/hr, about 4.2 mg/kg/hr, about 5.5 mg/kg/hr, about 7.4 mg/kg/hr, about 9.2 mg/kg/hr, about 11 mg/kg/hr, about 14 mg/kg/hr, or about 18 mg/kg/hr. In particular embodiments (e.g., for a 144 hr continuous infusion), the loading dose rate for coenzyme Q10 administration is about 3.1 mg/kg/hr, about 4.1 mg/kg/hr, about 5.4 mg/kg/hr, about 7.2 mg/kg/hr, about 9.0 mg/kg/hr, about 11.2 mg/kg/hr, about 14.0 mg/kg/hr, or about 17.6 mg/kg/hr. Any of these values may be used to define a range for the loading dose rate for coenzyme Q10 administration. For example, the loading dose rate (first rate) may range from about 1 mg/kg/hr to about 50 mg/kg/hr, from about 1 mg/kg/hr to about 20 mg/kg/hr, from about 3 mg/kg/hr to about 15 mg/kg/hr, from about 5 mg/kg/hr to about 20 mg/kg/hr, or from about 3.1 mg/kg/hr to about 18 mg/kg/hr.

In a preferred embodiment, the dose rate for the loading dose (first rate) does not exceed 26.0) mg/kg/hr. In a preferred embodiment, the dose rate does not exceed 19.6 mg/kg/hr. In a preferred embodiment, the dose rate does not exceed 14.5 mg/kg/hr.

In certain embodiments, the rate of the infusion for the remaining 23 hours of the first 24 hours of the dose, the remaining 47 hours of the first 48 hours of the dose, or the remaining 71 hours of the first 72 hours of the dose is about 0.02 ml/min to about 0.4 ml/min. In certain embodiments, the rate of infusion is about 0.02 ml/min, 0.03 ml/min, 0.04 ml/min, 0.05 ml/min, 0.06 ml/min, 0.07 ml/min, 0.08 ml/min, 0.09 ml/min, 0.1 ml/min, 0.11 ml/min, 0.12 ml/min, 0.13 ml/min, 0.14 ml/min 0.15 ml/min, 0.16 ml/min, 0.17 ml/min, 0.18 ml/min, 0.19 ml/min, 0.20 ml/min, 0.21 ml/min, 0.22 ml/min, 0.23 ml/min, 0.24 ml/mm, 0.25 ml/min, 0.30 ml/min 0.35 ml/min, or mom or any range bracketed by any of two values provided.

In certain embodiments, the dose rate for the remaining 23 hours of a first 24 hour infusion, the remaining 47 hours of a first 48 hour infusion, or the remaining 71 hours of a first 72 hour infusion (i.e., the second dose rate) is at least 0.1 mg/kg/hr, at least (1.2 mg/kg/hr, at least 0.3 mg/kg/hr, at least 0.4 mg/kg/hr, at least 0.5 mg/kg/hr, at least 0.6 mg/kg/hr, at least 0.7 mg/kg/hr, at least 0.8 mg/kg/hr, at least 0.9 mg/kg/hr, at least 1.0 mg/kg/hr, at least 1.5 mg/kg/hr, at least 2.0 mg/kg/hr, at least 2.5 mg/kg/hr, at least 3.0 mg/kg/hr, at least 3.5 mg/kg/hr, at least 4.0 mg/kg/hr, at least 4.5 mg/kg/hr, at least 5.0 mg/kg/hr, at least 6.0 mg/kg/hr, at least 7.0 mg/kg/her, at least 8.0 mg/kg/hr, at least 9.0 mg/kg/hr or at least 10.0 mg/kg/hr. In particular embodiments, the second rate (e.g., for a 48 hour infusion of coenzyme Q10) is about 3.1 mg/kg/hr, about 4.2 mg/kg/hr, about 5.5 mg/kg/hr, about 7.4 mg/kg/hr, about 9.2 mg/kg/hr, about 11 mg/kg/hr, about 14 mg/kg/hr, or about 18 mg/kg/hr. In particular embodiments, the second rate (e.g., for a 72 hour infusion of coenzyme Q10) is about 0.49 mg/kg/hr, about 0.65 mg/kg/hr, about (1.85 mg/kg/hr, about 1.14 mg/kg/hr, about 1.42 mg/kg/hr, about 1.77 mg/kg/hr, about 2.21 mg/kg/hr, or about 2.78 mg/kg/hr. Any of these values may be used to define a range for the second dose rate for coenzyme Q10 administration. For example, the second dose rate may range from about 0.1 mg/kg/hr to about 10 mg-kg/hr, from about 3.1 mg/kg/hr to about 18 mg/kg/hr, from about 0.49 mg/kg/hr to about 2.78 mg/kg/hr. from about 0.5 mg/kg/hr to about 2.5 mg/kg/hr, from about 0.1 mg/kg/hr to about 5 mg/kg/hr, from about 0.1 mg/kg/hr to about 3 mg/kg/hr, or from about 0.5 mg/kg/hr to about 2.2 mg/kg/hr.

In certain embodiments, the second dose rate does not exceed 35.8 mg/kg/hr. In certain embodiments, the second dose rate does not exceed 25.7 mg/kg/hr. In certain embodiments, the second dose rate does not exceed 26 mg/kg/hr. In certain embodiments, the second dose rate does not exceed 22.9 mg/kg/hr. In certain embodiments, the second dose rate does not exceed 19.6 mg/kg/hr. In certain embodiments, the second dose rate does not exceed 18.4 mg/kg/hr. In certain embodiments, the second dose rate does not exceed 14.5 mg/kg/hr. In certain embodiments, the second dose rate does not exceed 11 mg/kg/hr. In certain embodiments, the second dose rate does not exceed 9.2 mg/kg/hr. In certain embodiments, the second dose rate does not exceed 8.3 mg/kg/hr. In certain embodiments, the second dose rate does not exceed 7.4 mg/kg/hr. In certain embodiments, the second dose rate does not exceed 5.5 mg/kg/hr. In certain embodiments, the second dose rate does not exceed 4.2 mg/kg/hr.

Coenzyme Q10 may also be administered at a third rate, i.e., the rate for the second infusion following a short break (e.g., the second 24 hour infusion of a 48 hour infusion, the second 48 hour infusion of a 96 hour continuous infusion, or the second 72 hour infusion of a 144 hour continuous infusion). In certain embodiments, the third rate of infusion is about 0.03 ml/min to about 0.4 ml/min. In certain embodiments, the third rate of infusion is about 0.03 ml/min, 0.04 ml/min, 0.05 ml/min, 0.06 ml/min, 0.07 ml/min, 0.08 ml/min, 0.09 ml/min, 0.1 ml/min, 0.11 ml/min, 0.12 ml/min, 0.13 ml/min, 0.14 ml/min, 0.15 ml/min, 0.16 ml/min, 0.17 ml/min, 0.18 ml/min, 0.19 ml/min, 0.20 ml/min, 0.21 ml/min, 0.22 ml/min, 0.23 ml/min, 0.24 ml/min, 0.25 ml/min, 0.30 ml/min, 0.35 ml/mm, or more, or an range bracketed by any of two values provided.

In certain embodiments the third dose rate is at least 0.1 mg/kg/hr, at least 0.2 mg/kg/hr, at least 0.3 mg/kg/hr, at least 0.4 mg/kg/hr, at least 0.5 mg/kg/hr, at least 0.6 mg/kg/hr, at least 0.7 mg/kg r, at least 0.8 mg/kg/hr, at least 0.9 mg/kg/hr, at least 1.0 mg/kg/hr, at least 1.5 mg/kg/hr, at least 2.0 mg kg/hr, at least 2.5 mg/kg/hr, at least 3.0 mg/kg/hr, at least 3.5 mg/kg/hr, at least 4.0 mg/kg/hr, at least 4.5 mg/kg/hr, at least 5.0 mg/kg/hr, at least 6.0 mg/kg/hr, at least 7.0 mg/kg/her, at least 8.0 mg/kg/hr, at least 9.0 mg/kg/hr or at least 10.0 mg/kg/hr. In particular embodiments, the third dose rate (e.g., for a second 48 hour dose of a 96 hour continuous infusion) is about 0.80 mg/kg/hr, about 1.05 mg/kg/hr, about 1.38 mg/kg/hr, about 1.83 mg/kg/hr, about 2.29 mg/kg/hr, about 2.85 mg/kg/hr, about 3.56 mg/kg/hr, or about 4.48 mg/kg/hr. In particular embodiments, the third dose rate (e.g., for a second 72 hour dose of a 144 hour continuous infusion) is about 0.53, about 0.69 mg/kg/hr, about 0.92 mg/kg/hr, about 1.22 mg/kg/hr, about 1.53 mg/kg/hr, about 1.90 mg g/hr, about 2.38 mg/kg/hr, or about 2.99 mg/kg/hr. Any of these values may be used to define a range for the third dose rate. For example, the third dose rate may range from about 0.1 mg/kg/hr to about 10 mg/kg/hr, from about 0.80 mg/kg/hr to about 4.48 mg/kg/hr, or from about 0.53 mg/kg/hr to about 2.99 mg/kg/hr.

In certain embodiments, the third dose rate does not exceed 35.8 mg/kg/hr. In certain embodiments, the third dose rate does not exceed 28.7 mg/kg/hr. In certain embodiments, the third dose rate does not exceed 26 mg/kg/hr. In certain embodiments, the third dose rate does not exceed 22.9 tug/kg/hr. In certain embodiments, the third dose rate does not exceed 19.6 mg/kg/hr. In certain embodiments, the third dose rate does not exceed 18.4 mg/kg/hr. In certain embodiments, the third dose rate does not exceed 14.5 mg/kg/hr. In certain embodiments, the third dose rate does not exceed 11 mg/kg/hr. In certain embodiments, the third dose rate does not exceed 9.2 mg/kg/hr. In certain embodiments, the third dose rate does not exceed 8.3 mg/kg/hr. In certain embodiments, the third dose rate does not exceed 7.4 mg/kg/hr. In certain embodiments, the third dose rate does not exceed 5.5 mg/kg/hr. In certain embodiments, the third dose rate does not exceed 4.2 mg/kg/hr.

Coenzyme Q10 may be administered at different daily doses depending on the dosing regimen. For example, in certain embodiments, the daily dose of coenzyme Q10 for the first day of infusion (i.e., the first 24 hours of infusion) is higher than the daily dose for the second day of infusion (i.e., the second 24 hours of infusion) if a loading dose is used. In certain embodiments, the daily dose for the third day of infusion (e.g. hours 49-72 of a 72-hour infusion) is lower than the daily dose for the first day of infusion, and higher than the daily dose for the second day of infusion. In certain embodiments, coenzyme Q10 is administered at a dose of at least 1 mg/kg/day (24 hours), at least 5 mg/kg/day (24 hours), at least 10 mg/kg/day (24 hours), at least 15 mg/kg/day (24 hours), at least 20 mg/kg/day (24 hours), at least 25 mg/kg/day (24 hours), at least 30 mg/kg/day (24 hours), at least 35 mg/kg/day (24 hours), at least 40 mg/kg/day (24 hours), at least 45 mg/kg/day (24 hours), at least 50 mg/kg/day (24 hours), at least 55 mg/kg/day (24 hours), at least 60 mg/kg/day (24 hours), at least 65 mg/kg/day (24 hours), at least 70 mg/kg/day (24 hours), at least 75 mg/kg/day (24 hours), at least 80 mg/kg/day (24 hours), at least 85 mg/kg/day (24 hours), at least 90 mg/kg/day (24 hours), at least 95 mg/kg/day (24 hours), at least 100 mg/kg/day (24 hours), at least 110 mg/kg/day (24 hours), at least 120 mg/kg/day (24 hours), at least 130 mg/kg/day (24 hours), at least 140 mg/kg/day (24 hours), at least 150 mg/kg/day (24 hours), at least 200 mg/kg/day (24 hours), at least 250 mg/kg/day (24 hours), at least 300 mg/kg/day (24 hours), at least 400 mg/kg/day (24 hours), or at least 500 mg/kg/day (24 hours). In particular embodiments, coenzyme Q10 is administered at at least one dose selected from the group consisting of about 11.8 mg/kg/day (24 hours), about 12.5 mg/kg/day (24 hours), about 14.4 mg/kg/day (24 hours), about 15.6 mg/kg (24 hours), about 16.5 mg/kg/day (24 hours), about 19 mg/kg/day (24 hours), about 20.4 mg/kg/day (24 hours), about 22 mg/kg/day (24 hours), about 25 mg/kg/day (24 hours), about 27.5 mg/kg/day (24 hours), about 29.3 mg/kg/day (24 hours), about 33 mg/kg/day (24 hours), about 34.2 mg/kg/day (24 hours), about 36.7 mg/kg/day (24 hours), about 41.7 mg/kg/day (24 hours), 42.8 mg/kg/day (24 hours), about 44 mg/kg/day, (24 hours), about 45.7 mg/kg/day (24 hours), about 51.9 mg/kg/day (24 hours), about 53.8 mg/kg/day (24 hours), about 55 mg/kg/day (24 hours), about 57 mg/kg/day (24 hours), about 58.7 mg/kg/day (24 hours), about 64.8 mg/kg/day (24 hours), about 66.7 mg/kg/day (24 hours), about 68.5 mg/kg/day (24 hours), about 71.7 mg/kg/day (24 hours), about 73.4 mg/kg/day (24 hours), about 81.5 mg/kg/day (24 hours), about 85.5 mg/kg/day (24 hours), about 91.7 mg/kg/day (24 hours), about 107.5 mg/kg/day (24 hours), about 114.6 mg/kg/day (24 hours), and about 143.3 mg/kg/day (24 hours). Any of these values may be used to define a range for the daily dose of coenzyme Q10. For example, the daily dose of coenzyme Q10 may range from 1 mg/kg/day (24 hours) to 500 mg/kg/day (24 hours), from 10 mg/kg/day (24 hours) to 150 mg/kg/day (24 hours), or from 11.8 mg/kg/day (24 hours) to 143.2 mg/kg/day (24 hours).

In one embodiment, the daily dose (e.g., average daily dose) of coenzyme Q10 for a continuous infusion regimen of the invention (e.g., a 48 hour, 72 hour, 96 hour or 144 hour continuous infusion) ranges from 10-65 mg/kg per day (24 hours), from 10-15 mg/kg per day (24 hours), from 15-20 mg/kg per day (24 hours), from 20-25 mg/kg per day (24 hours), from 25-35 mg/kg per day (24 hours), from 35-42 mg/kg per day (24 hours), from 42-52 mg/kg per day (24 hours), or from 52-65 mg/kg per day (24 hours).

In certain embodiments, the formulation, preferably a coenzyme Q10 formulation, can be administered in one or more cycles. For example, the coenzyme Q10 can be administered for 2, 3, 4, 5, 6, 7, 8, or more weeks consecutively, and then not administered for a period of 1, 2, 3, 4, or more weeks, providing a cycle of administration. In certain embodiments, the cycles are administered without a pause between cycles. In certain embodiments, at the end of one or more cycles, the patient is assessed to determine treatment efficacy, toxicity, and assess if the treatment should be continued, modified, or ended. In certain embodiments, one or more cycles of coenzyme Q10 treatment are administered with one or more cycles of at least one anticancer agent. In certain embodiments, treatment with the additional anti-cancer agent is initiated after the first cycle of treatment with coenzyme Q10. In certain embodiments, treatment with the additional anti-cancer agent is initiated after at least one cycle of treatment with coenzyme Q10. In certain embodiment& treatment with the additional anti-cancer agent is initiated after cancer progression in the subject after treatment with coenzyme Q10. In certain embodiments, treatment with the additional anti-cancer agent is initiated without cancer progression in the subject after treatment with coenzyme Q10.

The number of cycles of administration depends, for example, on the response of the subject, the severity of disease, other therapeutic interventions used on the subject, or any adverse response of the subject. In certain embodiments, the coenzyme Q10 formulation is administered as long as the subject is exhibiting at least a stable response to treatment with no serious adverse events, e.g., dose limiting toxicities, grade IV toxicities, or persistent grade III toxicities that cannot be mitigated by the use of other interventions.

In certain embodiments, the coenzyme Q10 is administered for at least 1, 2, 3, 4, 5, 6, 7, 8, 9, 10, 11, 12, 13, 14, 15, 16, 17, 18, 19, or 20 cycles. In certain embodiments, the coenzyme Q10 is administered for no more than 1, 2, 3, 4, 5, 6, 7, 8, 9, 10, 11, 12, 13, 14, 15, 16, 17, 18, 19, or 20 cycles. Any of these values may be used to define a range for the number of cycles. For example, the number of cycles may range from 1-20, from 2-10, or from 4-8.

In another embodiment, the formulation, preferably, a coenzyme Q10 formulation, is administered in the form of a coenzyme Q10 IV formulation at a dosage of between about 10 mg/kg/dose and about 10,000 mg/kg/dose of coenzyme Q10, about 20 mg/kg/dose to about 5000 mg/kg/dose, about 50 mg/kg/dose to about 3000 mg/kg/dose, about 100 mg/kg/dose to about 2000 mg/kg/dose, about 200 mg/kg/dose to about 1000 mg/kg/dose, about 300 mg/kg/dose to about 500 mg/kg/dose, or about 55 mg/kg/dose to about 110 mg/kg/dose wherein the coenzyme Q10 formulation comprises between about 1% and 10% of coenzyme Q10 (w/v). In one embodiment, the coenzyme Q10 formulation comprises about 4% of coenzyme Q10 (w/v). In one embodiment, the coenzyme Q10 IV formulation comprises about 8% of coenzyme Q10 (w/v). In other embodiments, the coenzyme Q10 IV formulation comprises about 0.1%, 0.2%, 0.3%, 0.4%, 0.5%, 0.6%, 0.7%, 0.8%, 0.9%, 1%, 1.5%, 2%, 2.3%, 3%, 3.3%, 4% 4.3%, 5%, 5.3%, 6% 6.3%, 7%, 7.3%, 8%, 8.3%, 9%, 9.3% or 10% of coenzyme Q10 (w/v). It should be understood that ranges having any one of these values as the upper or lower limits are also intended to be part of this invention.

In the treatment of cancer, the formulations may be in a pharmaceutically acceptable carrier that may be administered in a therapeutically effective amount to a subject as either a mono-therapy, in combination with at least one other anticancer agent, e.g., chemotherapeutic agent, for a given indication, in combination with radiotherapy, following surgical intervention to radically remove a tumor, in combination with other alternative and/or complementary acceptable treatments for cancer, and the like.

In general, the coenzyme Q10 formulations and methods described herein may be used to treat any neoplasm. In a particular embodiment, the formulations and methods are used to treat a solid tumor in a subject. In certain embodiment, the formulations and methods are used to treat a non-solid tumor in a subject, e.g., a leukemia. In certain embodiments, the subject has failed at least one chemotherapeutic regimen prior to treatment with coenzyme Q10.

Without wishing to be bound by mechanism, in certain embodiments, the effect coenzyme Q10 may have on cancer cells may depend, in part, on the various states of metabolic and oxidative flux exhibited by the cancer cells. Coenzyme Q10 may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the viability or proliferative capacity of a cancer cell. In some embodiments, the interaction of coenzyme Q10 with glycolytic and oxidative flux factors may enhance the ability of coenzyme Q10 to exert its restorative apoptotic effect in cancer. While the present disclosure has focused on coenzyme Q10 and its metabolites, other compounds related to coenzyme Q10 which may be administered instead of, or in combination with, coenzyme Q10 include, but are not limited to, benzoquinones, isoprenoids, farnesols, farnesyl acetate, farnesyl pyrophosphate, 1-phenylalanine, d-phenylalanine, dl-phenylalanine, 1-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like.

In one embodiment, administration of coenzyme Q10 as described herein, achieves at least stable disease, reduces tumor size, inhibits tumor growth and/or prolongs the survival time of a tumor-bearing subject as compared to an appropriate control. Accordingly, this invention also relates to a method of treating tumors in a human or other animal, including a subject, who has failed at least one prior chemotherapeutic regimen, by administering to such human or animal an effective, non-toxic amount of coenzyme Q10, for example, by administering an effective dose by IV administration, preferably continuous IV administration. One skilled in the art would be able, by routine experimentation with the guidance provided herein, to determine what an effective, non-toxic amount of coenzyme Q10 for continuous IV administration would be for the purpose of treating malignancies including in a subject who has railed at least one prior chemotherapeutic regimen. For example, a therapeutically active amount of coenzyme Q10 may vary according to factors such as the disease stage (e.g., stage I versus stage IV), age, sex, medical complications (e.g., immunosuppressed conditions or diseases, coagulopathies) and weight of the subject, and the ability of the coenzyme Q10 to elicit a desired response in the subject. The dosage regimen may be adjusted to provide the optimum therapeutic response. For example, several divided doses may be administered daily, the dose may be administered by continuous infusion, or the dose may be proportionally reduced as indicated by the exigencies of the therapeutic situation.

In certain embodiments of the invention, the methods further include a treatment regimen which includes any one of or a combination of surgery, radiation, chemotherapy, e.g., hormone therapy, antibody therapy, therapy with growth factors, cytokines, and anti-angiogenic therapy.

It is understood that such treatment methods can similarly be performed by administration of coenzyme Q10 precursors, metabolites, and related compounds.

In certain embodiments of the invention, the methods further comprise monitoring the subject for decreased coagulation. In certain embodiments, the subject is monitored for decreased coagulation before administering coenzyme Q10 to the subject. In certain embodiments, the subject is monitored for decreased coagulation after administering coenzyme Q10 to the subject. In certain embodiments, the subject is monitored for decreased coagulation before administering coenzyme Q10 to the subject and after administering coenzyme Q10 to the subject. In certain embodiments, monitoring for decreased coagulation comprises assessing the PT/PTT, INR and/or platelet count. In certain embodiments, decreased coagulation comprises an INK of greater than 2 and normal coagulation comprises an INR of 2 or less. In certain embodiments, the decreased coagulation comprises an INR of greater than 3 and normal coagulation comprises an INR of 3 or less. In certain embodiments, decreased coagulation comprises a platelet threshold less than 50,000/μL. In certain embodiments, normal coagulation comprises a platelet threshold of at least 50,000/μL.

In certain embodiments, the methods further comprise administering an agent to increase coagulation in a subject identified as having decreased coagulation. In certain embodiments, the agent to increase coagulation is administered before administering coenzyme Q10 to the subject. In certain embodiments, the agent to increase coagulation is administered after administering coenzyme Q10 to the subject. In a particular embodiment, the agent to increase coagulation comprises vitamin K. In certain embodiments, the vitamin K is administered by oral, intravenous, intramuscular, or subcutaneous administration. In a particular embodiment, the agent to increase coagulation comprises cryoprecipitate or fresh frozen plasma.

In certain embodiments, the methods further comprise discontinuing treatment with coenzyme Q10 in a subject identified as having decreased coagulation. In certain embodiments, the methods further comprise confirming the subject has normal coagulation and starting treatment with coenzyme Q10. In certain embodiments, coenzyme Q10 is administered to the subject if the INR, PT, and PIT are less than or equal to 1.5 times the upper limit of normal and the platelet count is greater than or equal to 50,000/μL. In certain embodiments, the methods further comprise confirming the subject has normal coagulation and continuing treatment with coenzyme Q10. In certain embodiments, the coenzyme Q10 is administered at two, three, four or five different rates. In certain embodiments, the coenzyme Q10 is administered at two or more different rates, three or more different rates, four or more different rates, or five or more different rates. In certain embodiments, the coenzyme Q10 is administered for at least 24 hours, at least 48 hours, at least 72 hours, at least 96 hours, at least 120 hours, at least 144 hours, at least 168 hours, at least 192 hours, at least 216 hours, at least 240 hours, at least 264 hours, at least 288 hours, at least 312 hours, at least 336 hours, at least 360 hours, at least 384 hours, at least 408 hours, at least 432 hours, at least 456 hours, or at least 480 hours. Cancers for treatment using the methods of the invention include, for example, all types of cancer or neoplasm or malignant tumors found in mammals, including, but not limited to: leukemias, lymphomas, melanomas, carcinomas and sarcomas. In one embodiment, cancers for treatment using the methods of the invention include melanomas, carcinomas and sarcomas. In preferred embodiments, the coenzyme Q10 compositions are used for treatment, of various types of solid tumors, for example breast cancer, bladder cancer, colon and rectal cancer, endometrial cancer, kidney (renal cell) cancer, lung cancer, melanoma, pancreatic cancer, prostate cancer, thyroid cancer, skin cancer, bone cancer, brain cancer, cervical cancer, liver cancer, stomach cancer, mouth and oral cancers, neuroblastoma, testicular cancer, uterine cancer, thyroid cancer, head and neck, kidney, lung, non-small cell lung, melanoma, mesothelioma, ovary, sarcoma, stomach, uterus and medulloblastoma, and vulvar cancer. In certain embodiments, solid tumors include breast cancer, including triple negative breast cancer. In certain embodiments, skin cancer includes melanoma, squamous cell carcinoma, cutaneous T-cell lymphoma (CTCL). In certain embodiments, the cancer includes leukemia. In certain embodiments, leukemias include acute leukemias. In certain embodiments, leukemias include chronic leukemias. In certain embodiments, leukemias include acute lymphocytic (or lymphoblastic) leukemia (ALL), acute myelogenous (or myeloid or non-lymphatic) leukemia (AML), chronic lymphocytic leukemia (CLL), and chronic myelogenous leukemia (CML). Further types of leukemia include Hairy cell leukemia (HCL), T-cell prolymphocytic leukemia (T-PLL), large granular lymphocytic leukemia, and adult T-cell leukemia. However, treatment using the coenzyme Q10 compositions are not limited to these types of cancers.

As used herein, the terms "cancer." "neoplasm," and "tumor." are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. Leukemia is clinically detectable using one or more of complete blood counts, pallor, blood smears, and bone marrow smears. Advanced leukemias in certain subjects can manifest solid tumors.

Examples of non-solid tumors, e.g., leukemias, that cannot be detected by imaging or palpation can be detected, for example, by neutrophil counts, platelet counts, and by detection of abnormal cells in the bone marrow, e.g., the presence of blasts that cannot be other wise explained (e.g., bone marrow regeneration after consolidation therapy), the presence of Auer rods, or the appearance of new dysplastic changes.

The term "sarcoma" generally refers to a tumor which is made up of a substance like the embryonic connective tissue and is generally composed of closely packed cells embedded in a fibrillar or homogeneous substance. Examples of sarcomas which can be treated with the present compositions and optionally an additional anticancer agent, e.g., a chemotherapeutic agent, include, but are not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions of the invention and optionally an additional anticancer agent, e.g., a chemotherapeutic agent, include but are not limited to, for example, acral-lentiginous melanoma, amelanotic melanoma, benign juvenile melanoma, Cloudman's melanoma, S91 melanoma, Harding-Passer melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions of the invention and optionally an additional anticancer agent, e.g., a chemotherapeutic agent, include but are not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "leukemia" refers to a type of cancer of the blood or bone marrow characterized by an abnormal increase of immature white blood cells called "blasts". Leukemia is a broad term covering a spectrum of diseases. In turn, it is part of the even broader group of diseases affecting the blood, bone marrow, and lymphoid system, which are all known as hematological neoplasms. Leukemias can be divided into four major classifications, acute lymphocytic (or lymphoblastic) leukemia (ALL), acute myelogenous (or myeloid or non-lymphatic) leukemia (AML), chronic lymphocytic leukemia (CLL), and chronic myelogenous leukemia (CML), Further types of leukemia include Hairy cell leukemia (HCL), T-cell prolymphocytic leukemia (T-PLL), large granular lymphocytic leukemia, and adult T-cell leukemia.

"Acute leukemia" is characterized by a rapid increase in the number of immature blood cells. Crowding due to such cells makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children.

"Chronic leukemia" is characterized by the excessive build up of relatively mature, but still abnormal, white blood cells. Typically taking months or years to progress, the cells are produced at a much higher rate than normal, resulting in many abnormal white blood cells. Whereas acute leukemia must be treated immediately, chronic forms are sometimes monitored for some time before treatment to ensure maximum effectiveness of therapy.

Lymphoblastic or lymphocytic leukemias are due to hyperproliferation of bone marrow cells that produce lymphocytes (white blood cells), typically B cells.

Myeloid or myelogenous leukemias are due to hyperproliferation of bone marrow cells that produce red blood cells, some other types of white cells, and platelets.

Additional cancers which can be treated with the compositions of the invention include, for example, Hodgkin's disease, von-Hodgkin's lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, prostate cancer, pancreatic cancer, uterine sarcoma, myxoid liposarcoma, leiomyosarcoma, chondrosarcoma, osteosarcoma, colon adenocarcinoma of colon, cervical squamous cell carcinoma, tonsil squamous cell carcinoma, papillary thyroid cancer, adenoid cystic cancer, synovial cell sarcoma, malignant fibrous histiocytoma, desmoplastic sarcoma, hepatocellular carcinoma, spindle cell sarcoma, cholangiocarcinoma, and triple negative breast cancer. In one embodiment, actinic keratosis may be treated or prevented from progressing to a cancer according to the methods of the invention.

V. Combination Therapies

In certain embodiments, the formulations and methods of the invention can be used in combination therapy with at least one additional anticancer agent, e.g., chemotherapeutic agent. In certain embodiments, treatment with the chemotherapeutic agent is initiated at the same time as treatment with the coenzyme Q10. In certain embodiments, the treatment with the chemotherapeutic agent is initiated after the treatment with coenzyme Q10 is initiated. In certain embodiments, treatment with the additional agent is initiated upon progression of the cancer during treatment with coenzyme Q10. In certain embodiments, treatment with the additional agent is initiated without progression of the cancer during treatment with coenzyme Q10. In certain embodiments, treatment with coenzyme Q10 is continued upon initiation of administration of the additional agent, in certain embodiments, treatment with coenzyme Q10 is stopped upon initiation of treatment with the additional agent.

The methods of treatment of cancer by continuous infusion of coenzyme Q10 provided herein include combination therapies with additional anticancer agents or interventions (e.g., radiation, surgery, bone marrow transplant). In certain embodiments, "combination therapy" includes a treatment with coenzyme Q10 to decrease tumor burden and/or improve clinical response. Administration of coenzyme Q10 with palliative treatments or treatments to mitigate drug side effects (e.g., to decrease nausea, pain, anxiety, or inflammation, to normalize clotting) is not considered to be a combination treatment of the cancer.

In a preferred embodiment, treatment with coenzyme Q10 by continuous infusion is combined with the standard of care for treatment of the particular cancer to be treated. The standard of care for a particular cancer type can be determined by one of skill in the art based on, for example, the type and severity of the cancer, the age, weight, gender, and/or medical history of the subject, and the success or failure of prior treatments.

In certain embodiments, treatment of subjects with leukemia, particularly ALL or AML, continuous infusion of coenzyme Q10 is combined with one, or preferably both, of the following treatments.

1. Fludarabine, preferably at a dose of 15 mg/m administered intravenously over 15-30 minutes±15 minutes, every 12 hours for 5 days (or for 4 days in patients over 65 years of age or with ECOG Performance Status of 3).
2. Cytarabine, preferably administered at 0.5 g/$m^2$ in 250 ml of normal saline administered intravenously over 2 hours±20 minutes every 12 hours±2 hours for 5 days (or for 4 days in patients over 65 years of age or with ECOG Performance Status of 3).

In certain embodiments, the fludarabine and/or cytarabine will be administered on days 1-5 of an 18 day continuous infusion of coenzyme Q10. In a preferred embodiment, treatment with fludarabine and/or cytarabine is initiated after completion an 18 day continuous infusion of coenzyme Q10 alone. In certain embodiments, 1, 2, 3, 4, or 5 cycles of the combination therapy are administered to the subject. The subject is assessed for response criteria at the end of each cycle. The subject is also monitored throughout each cycle for adverse events (e.g., clotting, anemia, liver and kidney function, etc.) to ensure that the treatment regimen is being sufficiently tolerated.

In certain embodiments, treatment of subjects with solid tumors by continuous infusion of coenzyme Q10 is combined with one or more of the following treatments.

1. Gemcitabine, preferably by intravenous administration at a weekly dose starting at 600 mg/$m^2$, with the dose being adjusted based on the tolerance of the subject to the drug.
2. 5-Fluorouracil (5-FU), preferably by intravenous administration at a weekly starting dose of 350 mg/$m^2$, with the dose being adjusted based on the tolerance of the subject to the drug, in combination with leucovorin at 100 mg/$m^2$.
3. Docetaxel, preferably by intravenous administration once weekly at a starting dose of 20 mg/$m^2$, with the dose being adjusted based on the tolerance of the subject to the drug.

In certain embodiments, the gemcitabine, 5-FU and leucovorin, and/or docetaxel are administered on day 1-5 of a 96 hour continuous infusion of coenzyme Q10. In a preferred embodiment, treatment with gemcitabine, 5-FU and leucovorin, and/or docetaxel is initiated after completion of an 18 day continuous infusion of coenzyme Q10 alone. In certain embodiments, 1, 2, 3, 4, or 5 cycles of the combination therapy are administered to the subject. The subject is assessed for response criteria at the end of each cycle. The subject is also monitored throughout each cycle for adverse events (e.g., clotting, anemia, liver and kidney function, etc.) to ensure that the treatment regimen is being sufficiently tolerated.

In certain embodiments, coenzyme Q10 is administered in an amount that would be therapeutically effective if delivered alone, i.e., coenzyme Q10 is administered and/or acts as a therapeutic agent, and not predominantly as an agent to ameliorate side effects of other chemotherapy or other cancer treatments, coenzyme Q10 and/or pharmaceutical formulations thereof and the other therapeutic agent can act additively or, more preferably, synergistically. In one embodiment, coenzyme Q10 and/or a formulation thereof is administered concurrently with the administration of an additional anticancer (e.g., chemotherapeutic, anti-angiogenic) agent. In another embodiment, a compound and/or pharmaceutical formulation thereof is administered prior or subsequent to administration of another anticancer agent wherein both agents are present in the subject at the same time or have therapeutic activity in the subject at the same time. In one embodiment, the coenzyme Q10 and additional anticancer agent act synergistically. In one embodiment, the coenzyme Q10 and additional anticancer agent act additively.

In one embodiment, the therapeutic methods of the invention further comprise administration of one or more additional therapeutic agents, e.g., one or more anticancer agents, e.g., anti-angiogenic agents, chemotherapeutic agents, e.g., small molecule anticancer agents, biologic anticancer agents including both protein based and nucleic acid based therapeutics. For example, in one embodiment, an additional anticancer agent for use in the therapeutic methods of the invention is a chemotherapeutic agent.

Small molecule chemotherapeutic agents generally belong to various classes including, for example: 1. Topoisomerase II inhibitors (cytotoxic antibiotics), such as the anthracyclines/anthracenediones, e.g., doxorubicin, epirubicin, idarubicin and nemorubicin, the anthraquinones, e.g., mitoxantrone and losoxantrone, and the podophillotoxines. e.g., etoposide and teniposide; 2. Agents that affect microtubule formation (mitotic inhibitors), such as plant alkaloids (e.g., a compound belonging to a family of alkaline, nitrogen-containing molecules derived from plants that are biologically active and cytotoxic). e.g., taxanes, e.g., paclitaxel and docetaxel, and the vinka alkaloids, e.g., vinblastine, vincristine, and vinorelbine, and derivatives of podophyllotoxin; 3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan; 4. Antimetabolites (nucleoside inhibitors), for example, folates, e.g., folic acid, fluropyrimidines, purine or pyrimidine analogues such as 5-fluorouracil, capecitabine, gemcitabine, methotrexate, and edatrexate; 5. Topoisomerase I inhibitors, such as topotecan, irinotecan, and 9-nitrocamptothecin, camptothecin derivatives, and retinoic acid; and 6. Platinum compounds/complexes, such as cisplatin, oxaliplatin, and carboplatin, Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxa), docetaxel (taxotere), aldesleukin, asparaginase, busulfan, carboplatin, cladribine, camptothecin, CPT-I1, 1O-hydroxy-7-ethylcamptothecin (SN38), dacarbazine, S-I capecitabine, florafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epinibicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rumantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna innotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof which are readily apparent to one of skill in the art based on the appropriate standard of care for a particular tumor or cancer.

In another embodiment, an additional chemotherapeutic agent for use in the combination therapies of the invention is a biologic agent.

Biologic agents (also called biologics) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below, and generally belong to various classes including, for example: 1. Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leutinizing hormones; and 2. Enzymes, proteins, peptides, polyclonal and/or monoclonal antibodies, such as interleukins, interferons, colony stimulating factor, etc.

In one embodiment, the biologic is an interferon. Interferons (IFN) are a type biologic agent that naturally occurs in the body. Interferons are also produced in the laboratory and given to cancer patients in biological therapy. They have been shown to improve the way a cancer patient's immune system acts against cancer cells.

Interferons may work directly on cancer cells to slow their growth, or they may cause cancer cells to change into cells with more normal behavior. Some interferons may also stimulate natural killer cells (NK) cells. T cells, and macrophages which are types of white blood cells in the bloodstream that help to fight cancer cells.

In one embodiment, the biologic is an interleukin. Interleukins (IL) stimulate the growth and activity of man immune cells. They are proteins (cytokines and chemokines) that occur naturally in the body, but can also be made in the laboratory. Some interleukins stimulate the growth and activity of immune cells, such as lymphocytes, which work to destroy cancer cells.

In another embodiment, the biologic is a colony-stimulating factor. Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Paris of the immune system cannot function without blood cells, thus colony-stimulating factors encourage the bone marrow stem cells to produce white blood cells, platelets, and red blood cells.

With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells.

Monoclonal antibody agents do not destroy healthy cells. Monoclonal antibodies achieve their therapeutic effect through venous mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Examples of antibodies which may be used in the combination treatment of the invention include anti-CD20 antibodies, such as, but not limited to, cetuximab. Tositumomab, rituximab, and Ibritumomab. Anti-HER2 antibodies may also be used in combination with coenzyme Q10 for the treatment of cancer. In one embodiment, the anti-HER2 antibody is Trastuzumab (Herceptin). Other examples of antibodies which may be used in combination with coenzyme Q10 for the treatment of cancer include anti-CD52 antibodies (e.g., Alemtuzumab), anti-CD-22 antibodies (e.g., Epratuzumab), and anti-CD33 antibodies (e.g., Gemtuzumab ozogamicin). Anti-VEGF antibodies may also be used in combination with coenzyme Q10 for the treatment of cancer, in one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab. Numerous other anti-tumor antibodies are known in the art and would be understood by the skilled artisan to be encompassed by the present invention.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary, cancer treatment). Cytokine therapy reaches all parts of the body to kill cancer cells and prevent tumors from growing.

In another embodiment, the biologic is a fusion protein. For example, recombinant human Apo2L/TRAIL (GENETECH) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is a therapeutic nucleic acid molecule. Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. Therapeutic nucleic acids can be directed against essentially any target nucleic acid sequence in a cell. In certain embodiments, the nucleic acid therapeutic is targeted against a nucleic acid sequence encoding a stimulator of angiogenesis, e.g., VEGF, FGF, or of tumor growth, e.g., EGFR.

Antisense nucleic acid therapeutic agents are single stranded nucleic acid therapeutics, typically about 16 to 30 nucleotides in length, and are complementary to a target nucleic acid sequence in the target cell, either in culture or in an organism.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. The entire contents of each of the patents listed in this paragraph are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide, in addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference.

Additional exemplary biologic agents for use in the methods of the invention include, but are not limited to, gefitinib (Iressa), anastrazole, diethylstilboesterol, estradiol, premarin, raloxifene, progesterone, norethynodrel, ethisterone, dimesthisterone, megestrol acetate, medroxyprogesterone acetate, hydroxyprogesterone caproate, norethisterone, methyltestosterone, testosterone, dexamthasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-IBB, anti-4-IBBL, anti-CD40, anti-CD 154, anti-OX40, anti-OX40L, anti-CD28, anti-CD80, anti-CD86, anti-CD70, anti-CD27, anti-HVEM, anti-LIGHT, anti-GITR, anti-GITRL, anti-CTLA-4, soluble OX40L, soluble 4-IBBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble firms of agents may be made as, for example fusion proteins, by operatively linking the agent with, for example, Ig-Fc region.

It should be noted that more than one additional anticancer agents, e.g., 2, 3, 4, 5, or more, may be administered in combination with the coenzyme Q10 formulations provided herein. For example, in one embodiment two additional chemotherapeutic agents may be administered in combination with coenzyme Q10. Appropriate doses and routes of administration of the chemotherapeutic agents provided herein are known in the art.

VI. Reduction of Myelosuppression

Myelosuppression is known to be a side effect of many chemotherapeutic agents. Myelosuppression-induced disorders can produce side effects ranging from tiredness and to dose limiting toxicities. Although agents such as pegfilgrastim can be used to stimulate blood cell production in bone marrow to reduce the risk of infection due to chemotherapy induced neutropenia in subjects with solid tumors, such agents cannot be used in a subject suffering from leukemia and have their own adverse side effects. The combination therapies provided herein including the continuous infusion of coenzyme Q10 may reduce the risk of or prevent myelosuppression induced disorders in a subject being treated with a chemotherapeutic agent that induces myelosuppression.

As used herein, a "myelosuppression-induced disorders" includes those disorders and symptoms of the disorders that occur as a result of chemotherapy-induced myelosuppression. Examples of myelosuppression-induced disorders includes myelosuppression-induced anemia (which include such symptoms as, for example, weakness, fatigue, malaise, poor concentration, shortness of breath, heart palpitations, angina, pallor, tachycardia, and cardiac enlargement), myelosuppression-induced neutropenia (which includes such symptoms as, for example, an increase risk of severe infection or sepsis, fevers, mouth ulcers, diarrhea and sore throat) or myelosuppression-induced thrombocytopenia (which include such symptoms as for example, an increased risk of bleeding, purpura, nosebleeds, and bleeding gums).

In one embodiment, the myelosuppression-induced disorder is myelosuppression-induced neutropenia. In yet another embodiments, the myelosuppression-induced disorder is myelosuppression-induced infection, myelosuppression-induced fevers, myelosuppression-induced mouth ulcers, myelosuppression-induced diarrhea, and myelosuppression-induced sore throat. The language "myelosuppression induced infection" includes infections (e.g., sepsis) that occur as a result of chemotherapy induced myelosuppression and/or chemotherapy induced neutropenia.

In some embodiments, co-administration of coenzyme Q10 by the continuous infusion methods provided herein can prevent or ameliorate depletion of neutrophils in a subject being treated with a chemotherapeutic agent. A used herein "preventing depletion of neutrophils" includes the arresting or suppression of the loss of neutrophils in a subject that can occur as a result of treating the subject with a chemotherapeutic agent. In some embodiments, the methods of the invention prevent the depletion of neutrophils by at least about 5%, about 10%, about 15%, about 20%, about 25%, about 30%, by about 35%, by about 40%, by about 45%, by about 50%, by about 33%, by about 60% by about 65%, by about 70%, by about 75%, by about 80%, by about 85%, by about 90%, by about 95% or by about 100%.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Each patent, publication, and reference cited herein is incorporated herein by reference in their entirety. Further, WO 2008/116135 (PCT Appln. No. PCT/US2008/116135), WO2010/132507 (PCT Appln. No. PCT/US2010/034453), WO2011/11290 (PCT Appln. No PCT/US2011/028042), WO2012/174559 (PCT Appln. No. PCT/US2012/043001), and US Patent Application Publication No.: US2011/0027247 are hereby incorporated by reference in their entirety.

Example 1—Parenteral Coenzyme Q10 Formulation Significantly Improves Survival in Animal Model of Leukemia Including the Resolution of Paraplegia Due to Brain Metastasis Leukemia cells exhibit alterations in intermediary metabolism similar to other cancers, wherein ATP sourcing is shunted from mitochondria) oxphos towards glycolytic preponderance (Warburg Effect) to meet oncogenic proliferative demands. A consequence of this metabolic switch is the simultaneous short-circuit of the programmed death pathways, leading to a immortalization program in cancer cells including leukemia. Delivery of high levels of coenzyme Q10 in a lipid nanodispersion mixture has been demonstrated to preferentially shift metabolic networks from glycolysis towards mitochondrial-centric oxphos and recapitulation of apoptotic pathways in various cancers in vitro and in vivo models. Given the centrality of the Bcl-2 involvement in the etiology of leukemia, this study focused on investigation of the effectiveness of Coenzyme Q10 in animal models of erythroid and myeloid leukemia.

Human acute erythro-leukemia (K562) and acute myeloid leukemia (KG1) cells ($1\times10^6$) were injected intraperitoneally in immune-compromised mice. Engraftment was confirmed by complete blood counts, presence of anemia, and clinical assessment of animal behavior.

The mice (total n=120 for each model respectively) were randomized into four (n=30/group) treatment groups. Each treatment regimen was administered in a four week cycle with three weeks of treatment, one week off:

1. Untreated (control)
2. Coenzyme Q10 (4%, administered at 75 mg/kg, once/day by continuous infusion)
3. Chemotherapy (cytarabine/AraC 25 mg/kg, 5×/week; and adriamycin/daunorubicin 5 mg/kg; 1×/wk)
4. Coenzyme Q10 (4%, administered at 75 mg/kg, once/day by continuous infusion)+chemotherapy (cytarabine/AraC 25 mg/kg, 5×/week; and adriamycin/daunorubicin 5 mg/kg; 1×/wk)

Figure 4:
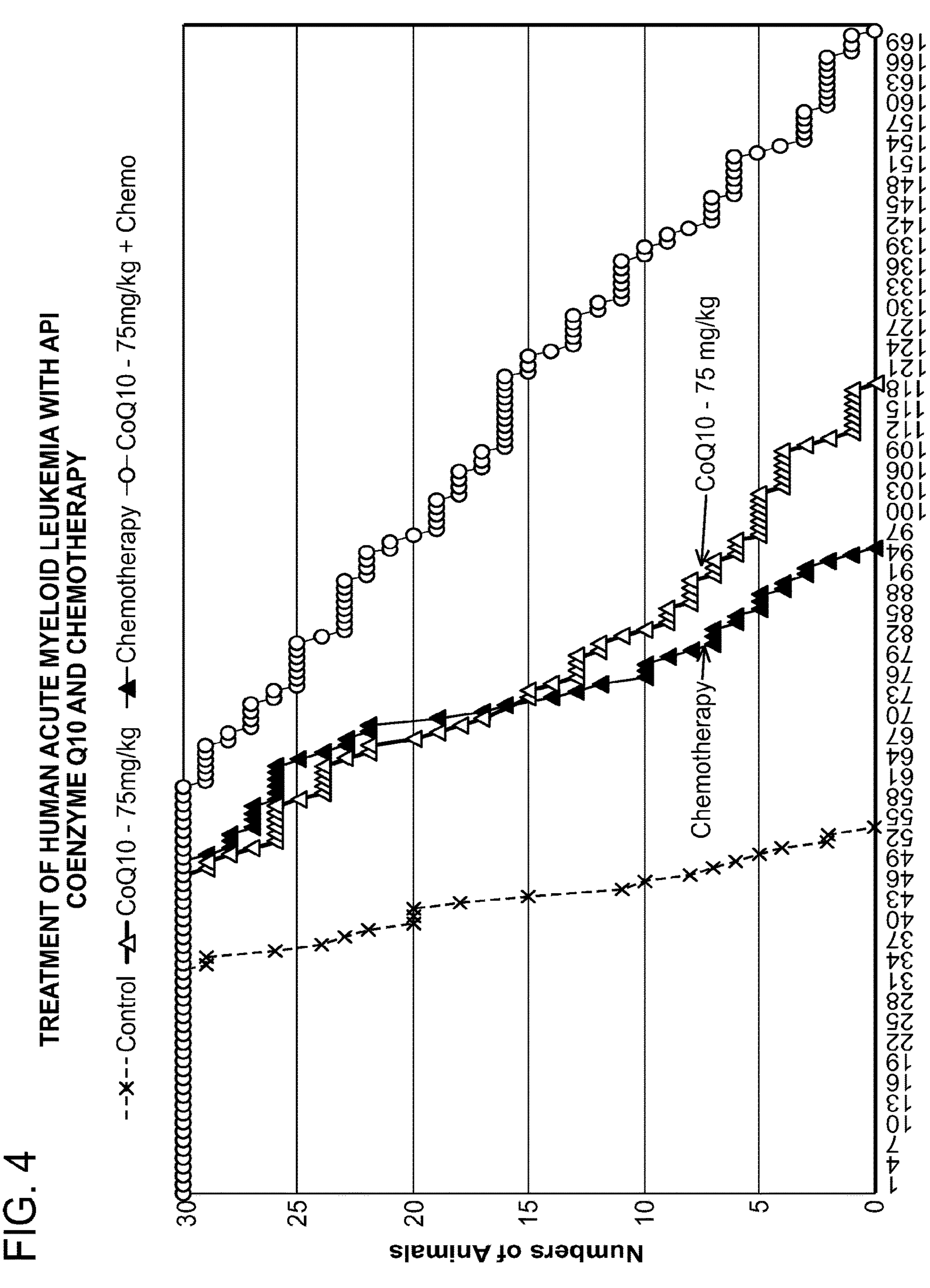
FIG. 4 shows survival results from the study of mice with acute myeloid leukemia. The x axis represents the number of days from start of treatment, where day 1 is the first day of treatment, and they axis represents the number of surviving animals.
Figure 5:
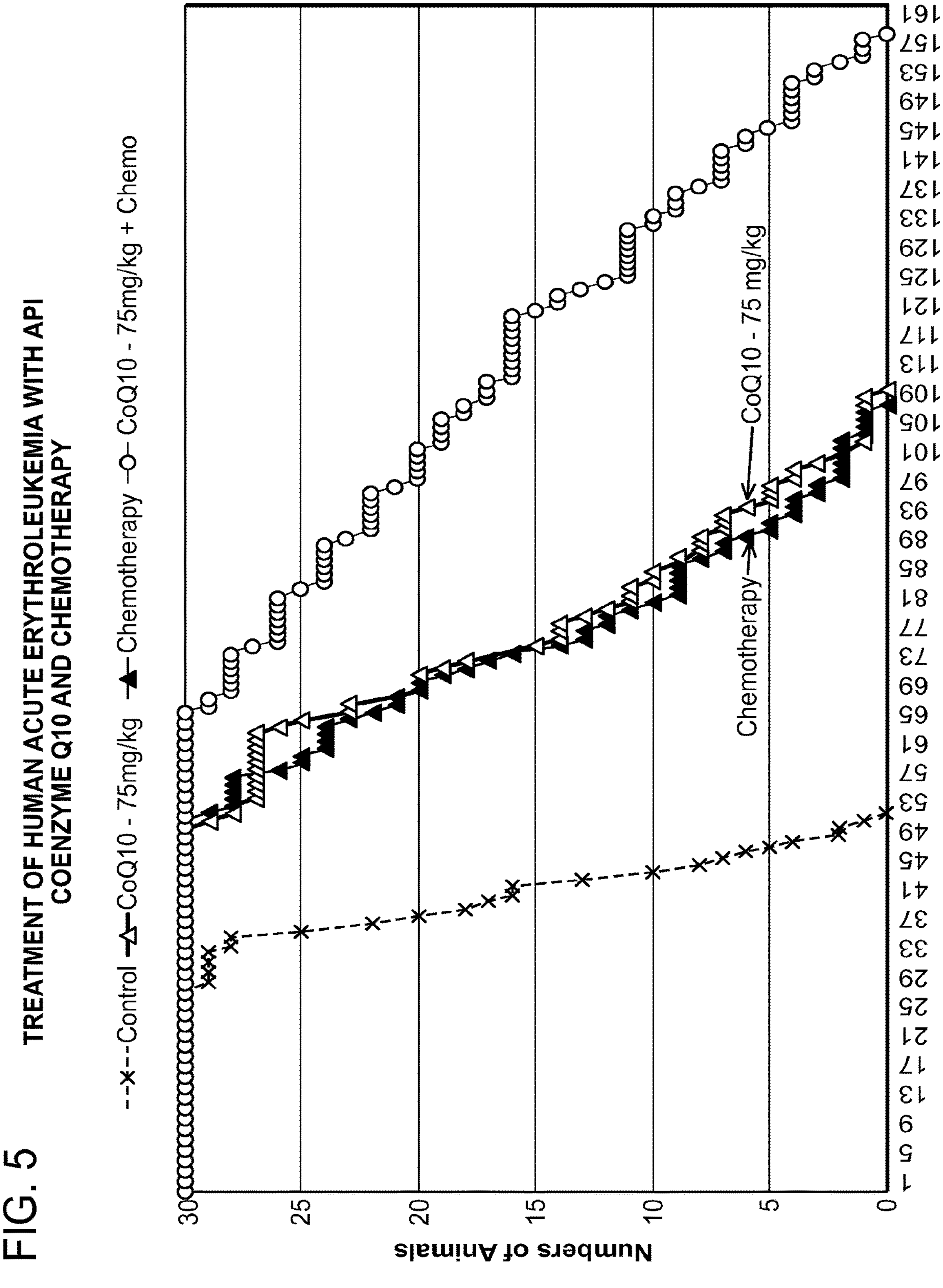
FIG. 5 shows survival results from the study of mice with acute erythroleukemia. The x axis represents the number of days from start of treatment, where day 1 is the first day of treatment, and they axis represents the number of surviving animals.

All dosings were intravenous and followed a protocol of 3 week treatment followed by 1 week rest. Leukemia was monitored by pallor and blood smears, and hone marrow smears were performed post-mortem for analysis using Wright's stain. Survival results from the study of mice with acute myeloid leukemia are provided in FIG. 4. Survival results from the study of mice with acute erythroleukemia are show in FIG. 5. Day 1 is the first day of treatment with coenzyme Q10 and/or chemotherapy.

In both leukemia models, combination of coenzyme Q10 with chemotherapy was associated with significant increase in survival compared to other groups including the corresponding chemotherapy alone cohorts ($p<0.00001$). Coenzyme Q10 alone improved survival compared to chemotherapy in myeloid leukemia, but not in the erythroleukemia model, where coenzyme Q10 alone showed relatively similar survival compared to chemotherapy alone.

These results demonstrate that coenzyme Q10, either alone or in combination with standard chemotherapeutic agents, is effective in the treatment of leukemias, particularly acute leukemias.

In a separate study, a rat (Fisher 344) chloroleukemia (MIA C51) model of CNS leukemia was developed that demonstrated paraplegia and urinary retention as a result of brain metastasis. Administration of coenzyme Q10 (St) mg/kg/day, IP) was associated with complete resolution of limb paralysis demonstrating the ability of coenzyme Q10 in penetrating into the CNS. Moreover, coenzyme Q10 (50 mg/kg/day, IP) administration was associated with significant increase in survival in animals with metastasis to the lungs and liver. The data provides encouraging evidence of the potential translational use of coenzyme Q10 in the treatment of leukemia. The results from this study are discussed in detail in WO2012/1314765, which is incorporated herein by reference in its entirety.

Figure 6:
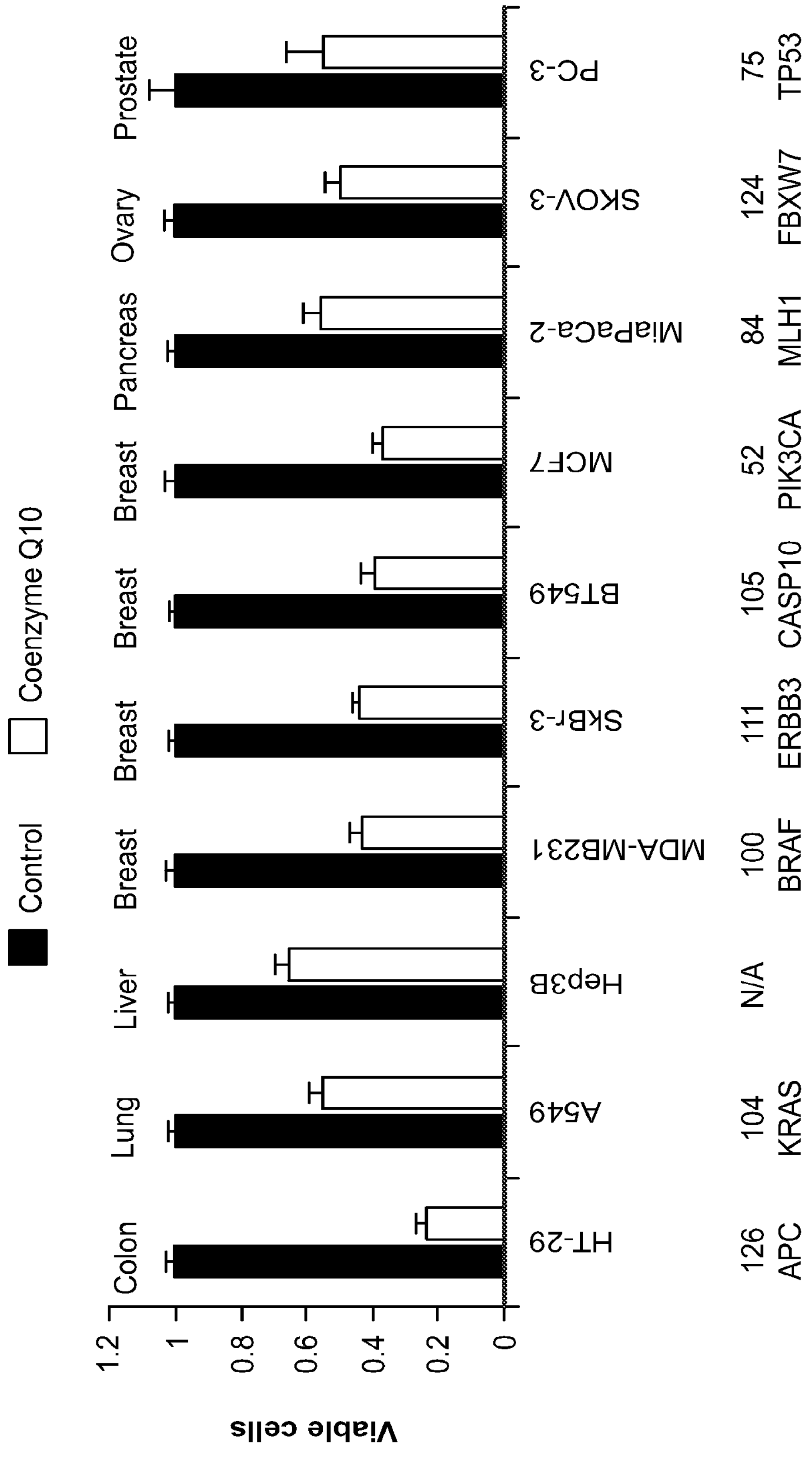
FIG. 6 shows the effect of coenzyme Q10 on viability of cancer cells lines. Each of the cell lines was treated with a fixed dose (100 μM) of coenzyme Q10. The data represents cell viability in the absence and presence of coenzyme Q10 at 48 or 72 hour exposures.

Example 2—Coenzyme Q10 Treatment Reduces Viability of Various Cancer Cells In Vitro Various cancer cell lines were treated with coenzyme Q10 at 100 μM concentration to determine the effect on cancer cell viability. The cancer cell lines tested were HT-29 (colon), A549 (lung), Hep3B (liver), MDA-MB231 (breast), SkBr-3 (breast), MCF7 (breast), MiaPaCa-2 (pancreas), SKOV-3 (ovary), and PC-3 (prostate). Cell viability was measured between 24 and 72 hours. In all cancer cell lines tested, a decrease in cell viability in response to coenzyme Q10 was evident as early as 24 hours and increased progressively between 48 and 72 hours. For example. FIG. 6 shows cell viability with and without coenzyme Q10 treatment at 48 hours of exposure (for cell lines HT-29, A549, Hep3B, MDA-MB231, SkBr-3 and BT549) or 72 hours of exposure (for cell lines MCF7, MiaPaca-2, SKOV-3, and PC-3). The text at the bottom of the graph in FIG. 6 represents the gene mutation and mutation rate for each cell line. For example, the HT-29 cell line contains the APC mutation with a mutation rate of 126.

There was a consistent decrease in cell viability in the cancer cell lines tested independent of the mutational status. In each of the cell lines, the extent of the effect of coenzyme Q10 on cell viability was associated with duration of exposure, with some cell lines exhibiting higher sensitivity at 48 hours and other cancer cell lines exhibiting a decrease in cell viability at 72 hours. This data suggests that the duration of exposure, an indirect measure of drug-cell contact, is an important component of the effect of coenzyme Q10 on the viability of cancer cells of different lineage.

Example 3—Continuous Infusion of Coenzyme Q10 Improves Survival in Animal Models of Pancreatic, Prostate, and Lung Cancer Several studies were undertaken to determine the effect of different dosing regimens of a coenzyme Q10 nanosuspension formulation on animal survival in animal models of various cancers.

Figure 7:
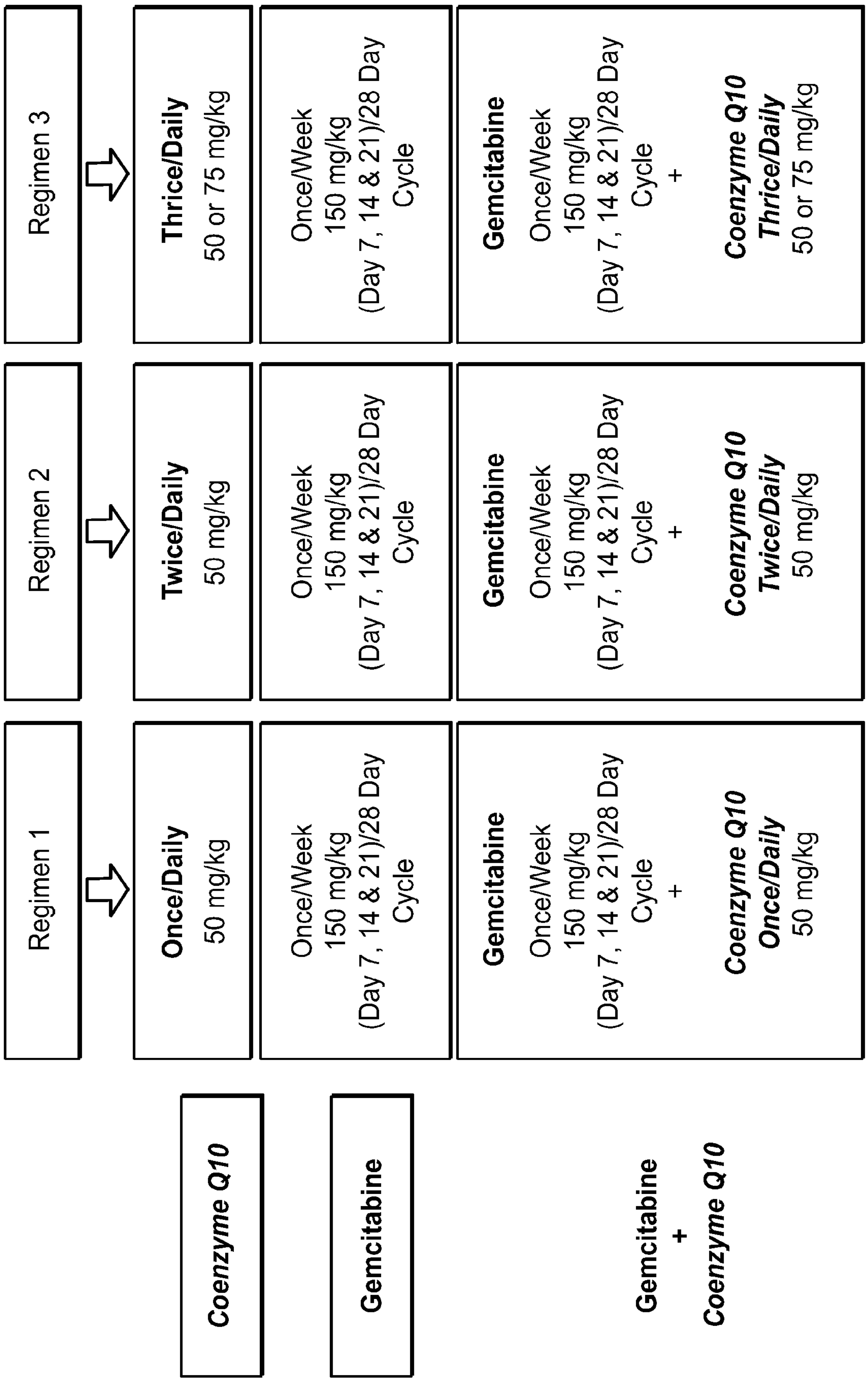
FIG. 7 shows three regimens utilized for evaluating the effect of coenzyme Q10 alone or in combination with gemcitabine on total survival in a preclinical animal model of pancreatic cancer. The study included once/daily, twice/daily or thrice/daily dosing of coenzyme Q10 at 50 mg/kg body weight (Regimen 1 and Regimen 2) or 50 mg/kg or 75 mg/kg body weight (Regimen 3) alone or in combination with gemcitabine (150 mg/kg body weight).

For example, FIG. 7 is a schematic describing a study investigating three different dosing regimens for coenzyme Q10 in an animal model of pancreatic cancer. The effect of coenzyme Q10 alone or in combination with gemcitabine on total survival in a preclinical mouse model of pancreatic cancer was evaluated.

Equal numbers of MIAPaCa-2 human pancreatic tumor cells were suspended in MATRIGEL® and injected into NOD scid gamma (NSG) mice. The NSG mouse model is devoid of innate and adaptive immune systems and provides a biological environment suitable for the growth of human tumors in vivo. The MIAPaCa-2 is a well established human derived pancreatic carcinoma cell line that can be used to establish pancreatic tumors in immunosuppressed animals. MIAPaca-2 tumors were allowed to develop for, on average, at least 3 weeks in mice prior to initiation of treatment. Animals with palpable tumors were randomized into treatment groups.

Figure 8A:
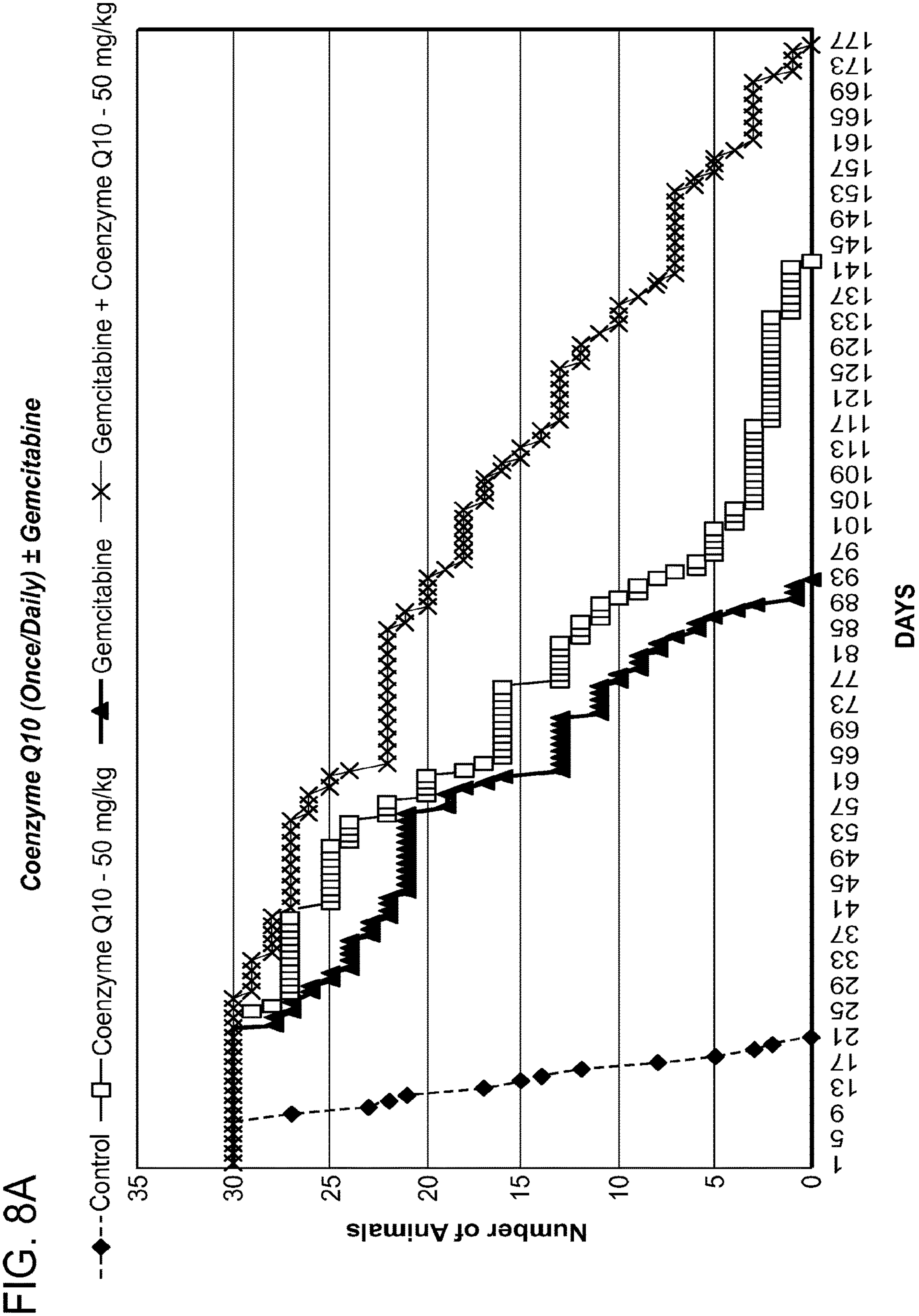
FIG. 8A-8C shows the effect of gemcitabine, coenzyme Q10 (50 mg/kg body weight dose) and a combination of gemcitabine+coenzyme Q10 on survival in a pancreatic cancer animal model. Survival profiles of animals treated with once/daily coenzyme Q10 (FIG. 8A), twice/daily coenzyme Q10 (FIG. 8B) and thrice/daily coenzyme Q10 (FIG. 8C) alone or in combination with gemcitabine are shown. The x axis represents the number of days from start of treatment and they axis represents the number of surviving animals.
Figure 8B:
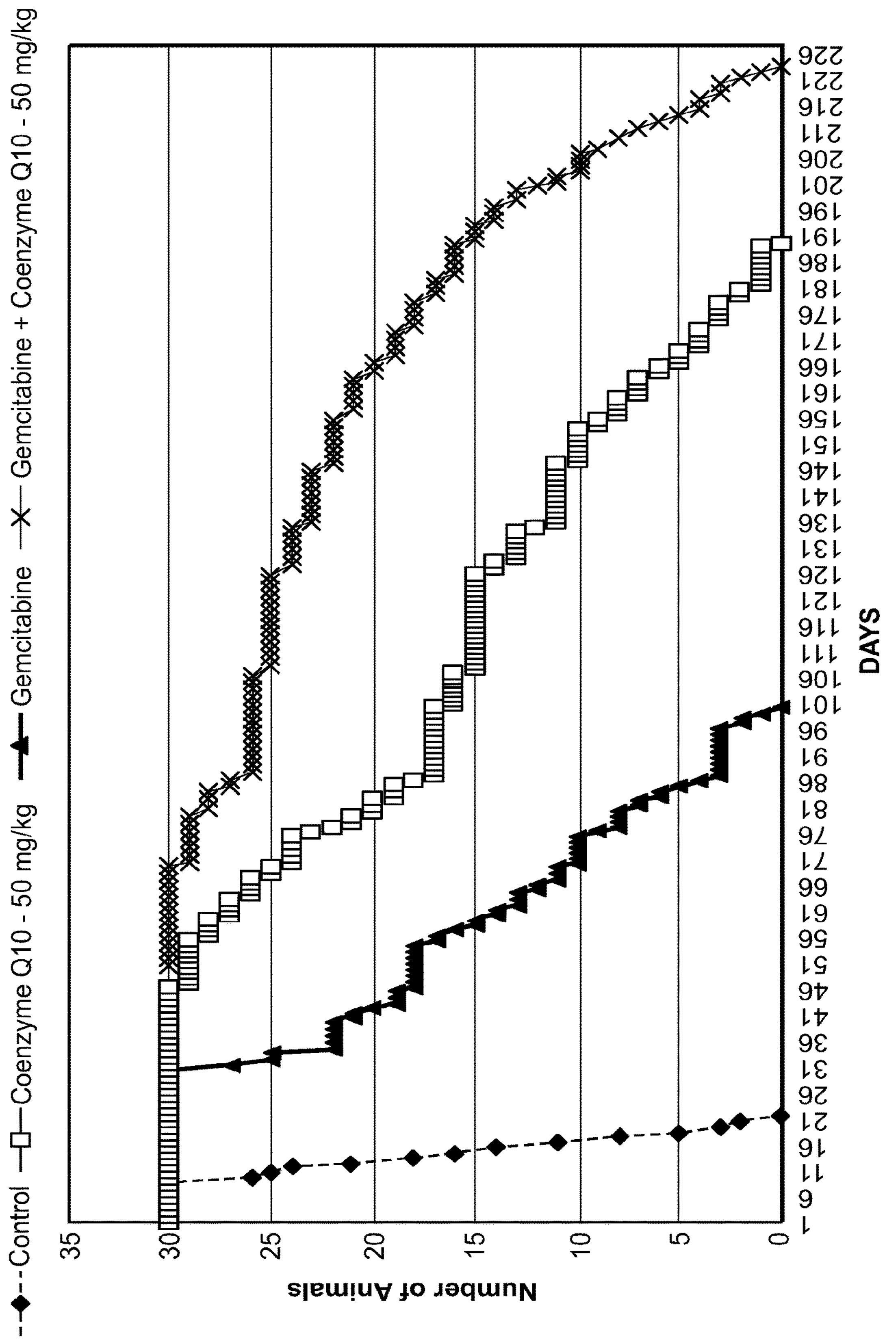
Figure 8C:
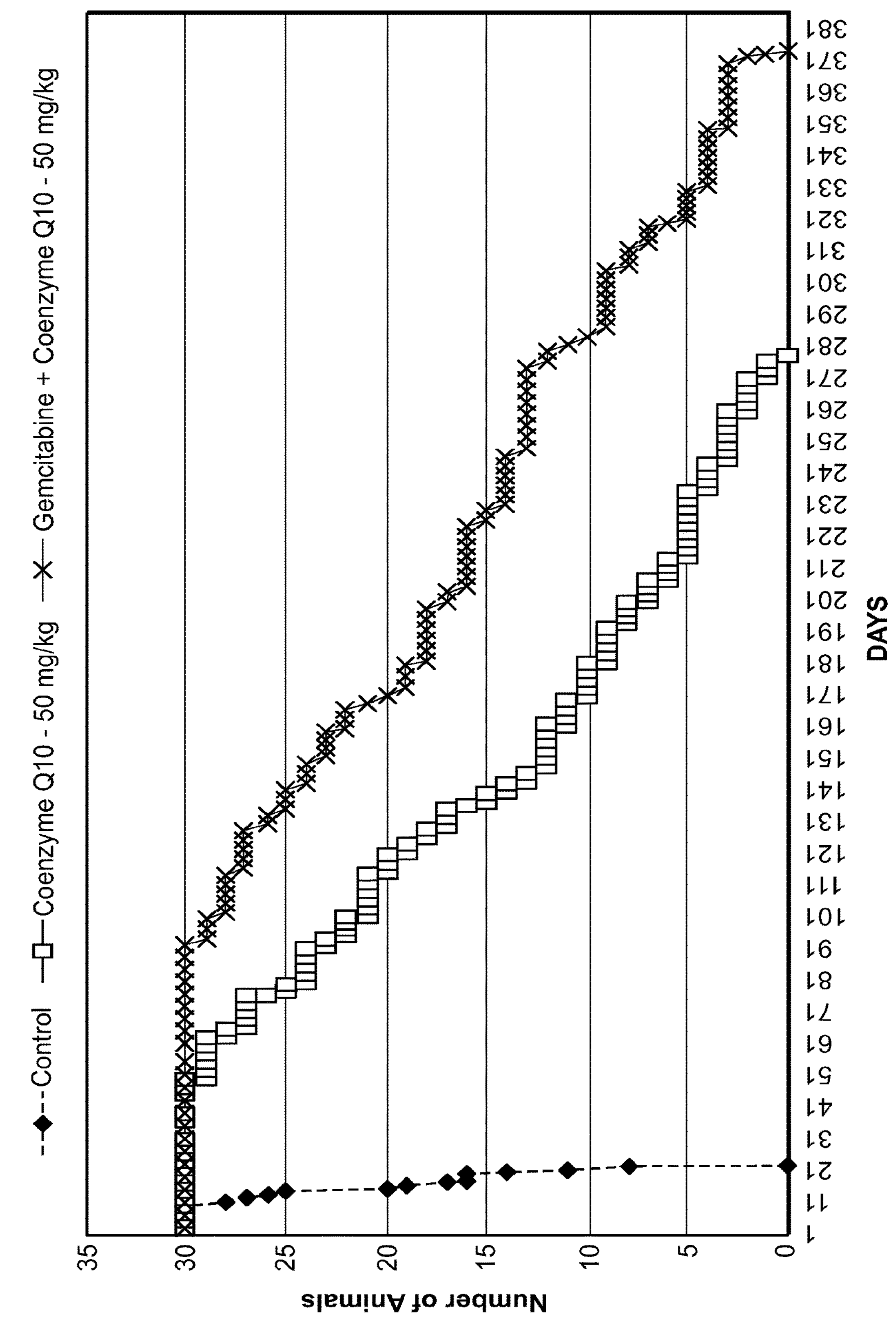

The three treatment regimens utilized for the study included once/daily, twice/daily or thrice/daily dosing of coenzyme Q10 at either 50 mg/kg body weight (Regimen 1 & Regimen 2) or 50 mg/kg or 75 mg/kg body weight (Regimen 3) alone or in combination with a fixed dose of gemcitabine (150) mg/kg body weight). For example, mice treated twice/daily received two 50 mg/kg doses of coenzyme Q10, for a total of 100 mg/kg/day, and mice treated thrice daily received three 50 mg/kg doses of coenzyme Q10 for a total of 150 mg/kg/day. Each group of animals received chemotherapeutic treatment for a minimum of three cycles and was maintained to determine outcomes. In each of the cohorts tested, animals treated with coenzyme Q10 alone exhibited an increase in survival compared to untreated animals or animals treated with chemotherapy alone. See FIGS. 8A-C. The combination therapy of coenzyme Q10 and gemcitabine resulted in higher survival rates than coenzyme Q10 alone or gemcitabine alone, indicating that the coenzyme Q10 and gemcitabine treatments had an additive effect. FIGS. 8A-C also provide evidence that increasing doses of coenzyme Q10 from once/daily to three times per day was associated with significant improvement in animal survival. Thus, the improvement in and maintenance of animals administered 50 mg/kg dose of coenzyme Q10 in multiple bolus may be due to a relatively constant level of coenzyme Q10 in the blood for longer duration than can be achieved with a single daily administration.

Figure 9:
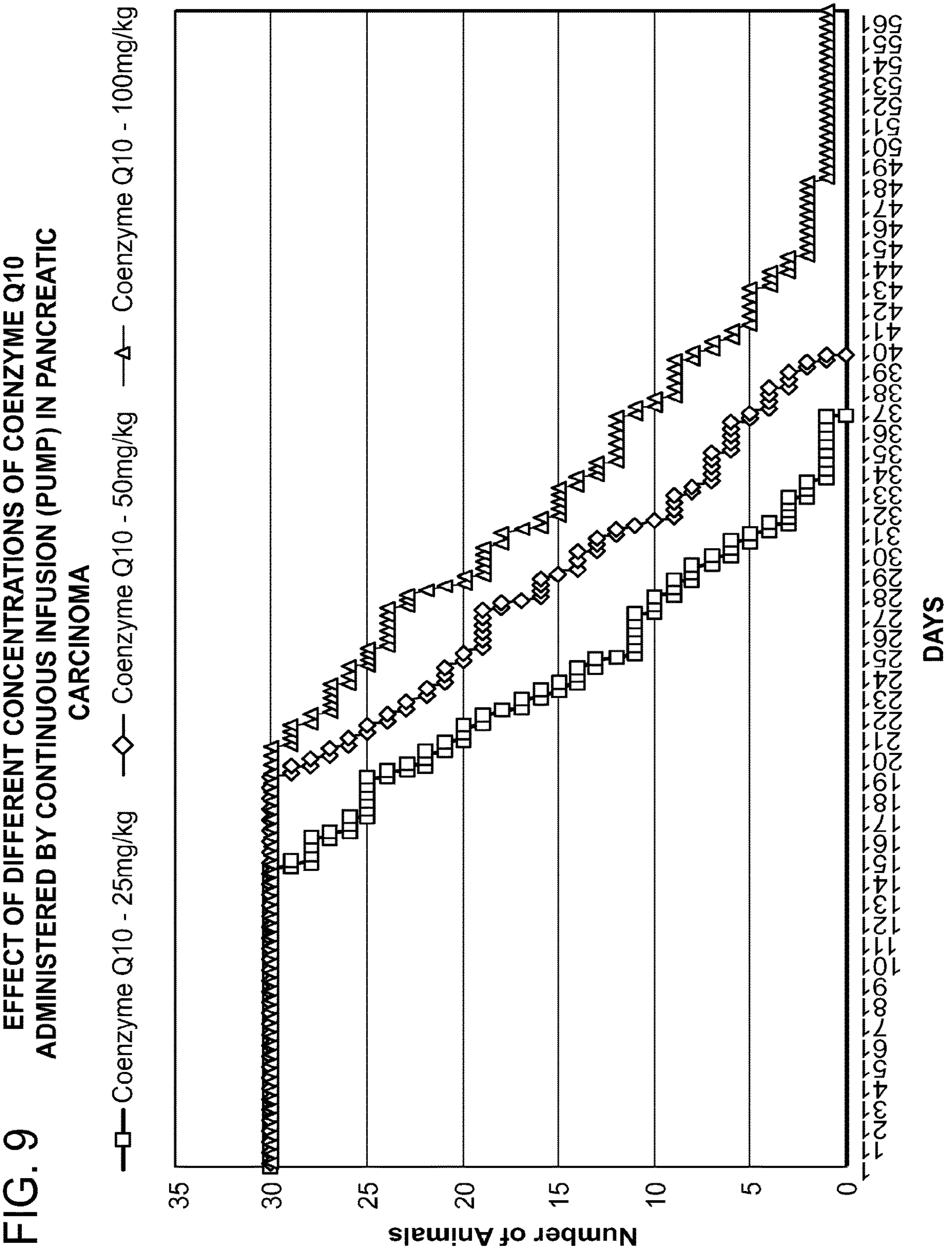
FIG. 9 shows the effect of continuous infusion of various concentrations of coenzyme Q10 on the duration of survival in an animal model of pancreatic cancer. An infusion pump was surgically installed in the animals to facilitate continuous infusion of coenzyme Q10 at doses of 25 ma/kg, 50 mg/kg or 100 mg/kg body weight per day. The x axis represents the number of days from start of treatment and the y axis represents the number of surviving animals.

Next, a continuous infusion protocol was implemented to determine the effect of constant coenzyme Q10 administration on survival in an animal model of pancreatic cancer. An infusion pump was surgically installed in the animals to facilitate continuous infusion of coenzyme Q10 at a dose of 25 mg/kg, 50 mg/kg or 100 mg/kg body weight per day. Treatment was continued throughout the entire duration of the study. FIG. 9 shows the effect of continuous infusion of increasing concentrations of coenzyme Q10 on duration of survival in an animal model of pancreatic cancer. Animals treated with continuous infusion of coenzyme Q10 at a dose of 25 mg/kg body weight per day (FIG. 9) exhibited a higher survival rate than animals administered 50 mg/kg body weight per day in three doses (FIG. 8C). Thus, continuous infusion of coenzyme Q10 at the 25 mg/kg body weight dose over a 24 hour duration resulted in a higher survival rate than treatment with a higher dose of coenzyme Q10 (i.e. 50 mg/kg body weight) three times per day.

Furthermore, the overall survival in the pancreatic cancer model is substantially improved by increasing the dose of coenzyme Q10 using the continuous infusion mode of administration. For example, animals treated with a continuous infusion of coenzyme Q10 at a total dose of lot) mg/kg had higher survival rates than those treated with continuous infusion of 50 mg/kg or 25 mg/kg. See FIG. 9. Thus the effect of coenzyme Q10 on animal survival was dose dependent.

Figure 10:
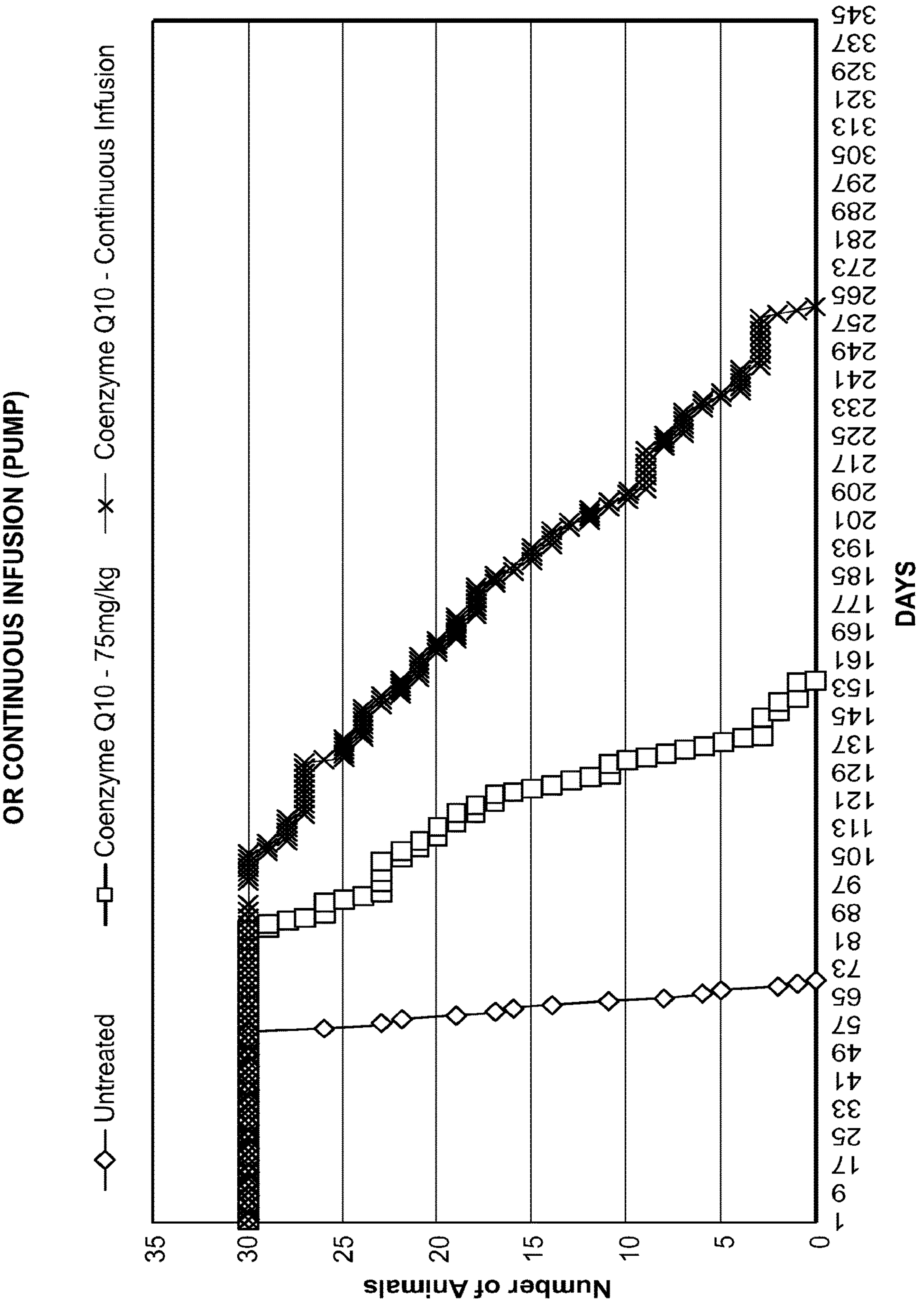
FIG. 10 shows the effect of continuous infusion of various concentrations of coenzyme Q10 on survival in an animal model of prostate cancer. Coenzyme Q10 was administered using two different dosing regimens, 75 mg/kg body weight per day (dosed as 25 mg/kg bode weight every 1 hours), or a continuous infusion of coenzyme Q10 at a dose of 75 mg/kg body weight per day. Treatment was continued throughout the entire duration of the study. The x axis represents the number of days from start of treatment and the y axis represents the number of surviving animals.

The observed improvement in animal cohorts administered coenzyme Q10 as a continuous infusion was repeated in other animal models of cancer. For example. FIG. 10 shows the effect of continuous infusion of coenzyme Q10 on the duration of survival in a prostate cancer animal model. LnCaP human prostate adenocarcinoma cells were injected into immunocompromised mice. Coenzyme Q10 was administered using two different dosing regimens. One cohort was administered a total dose of 75 mg/kg body weight per day by dosing 25 mg/kg body weight every 8 hours (multiple bolus regimen). In a second cohort, an infusion pump was surgically installed in the animals to facilitate continuous infusion of coenzyme Q10 at a total dose of 75 mg/kg body weight per day. Treatment was continued throughout the entire duration of the study. The cohorts treated with coenzyme Q10 administered 75 mg/kg body weight every 8 hours (multiple bolus regimen) exhibited a higher survival rate than the untreated control. See FIG. 10. However, the animal cohorts administered coenzyme Q10 at the same dose as a continuous infusion demonstrated an even higher survival rate when compared to the multiple bolus regimen.

The data in FIG. 10 show that for a given dose, e.g., 75 mg/kg body weight per day, the dosing regimen of coenzyme Q10 is an important component that significantly impacts animal survival. The continuous infusion of coenzyme Q10 (75 mg/kg body weight over 24 hours) was superior to three bolus treatments administered over the same time period at the same total dose. This result suggests that maintenance of constant levels of coenzyme Q10 in the blood can potentially be achieved using a continuous infusion protocol.

Figure 12:
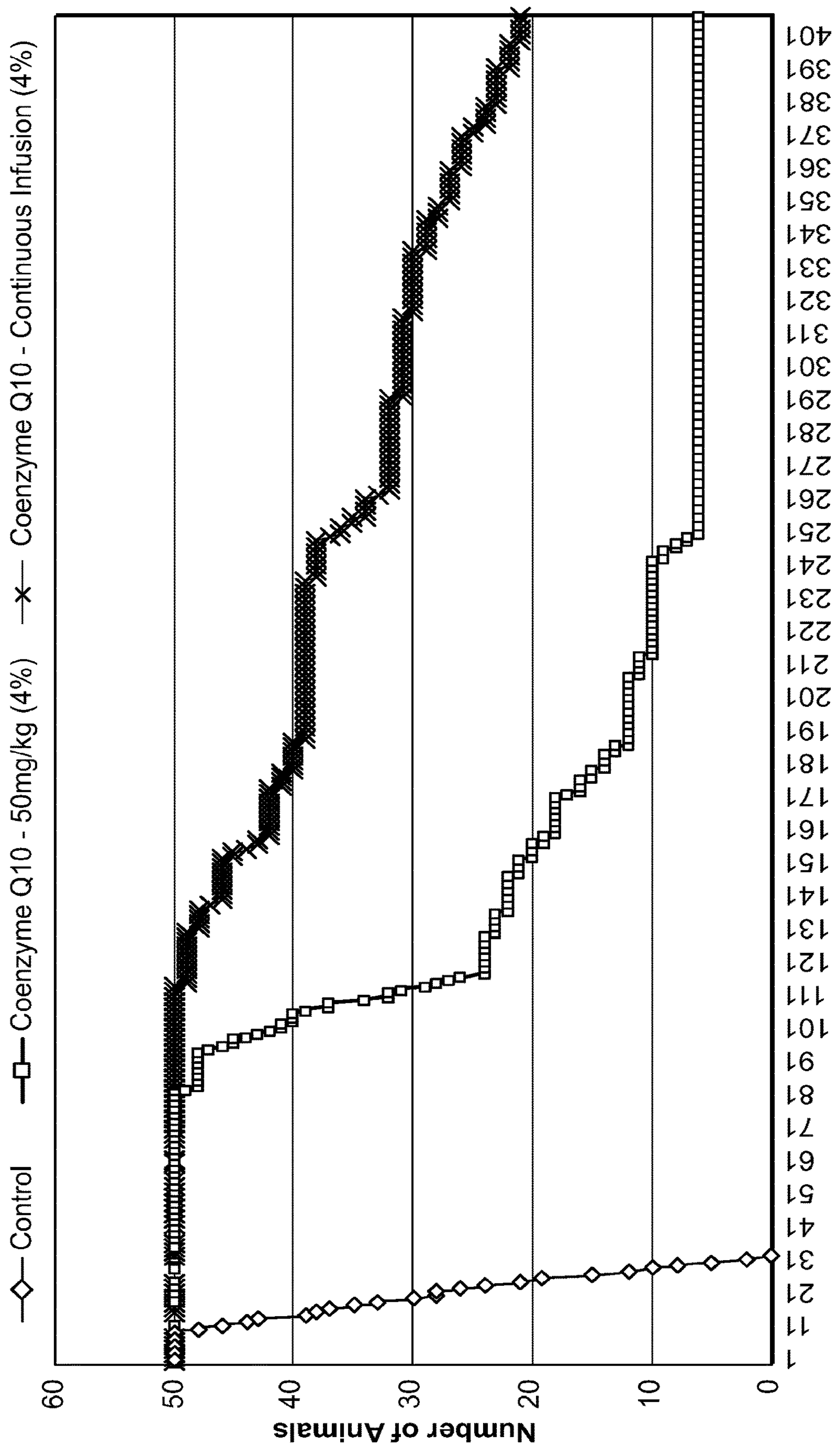
FIG. 12 shows the effect of three times daily treatment with coenzyme Q10 and continuous infusion of coenzyme Q10 in rats injected with a lung chloroma. The x axis represents the number of days from start of treatment and the y axis represents the number of surviving animals.
Figure 13:
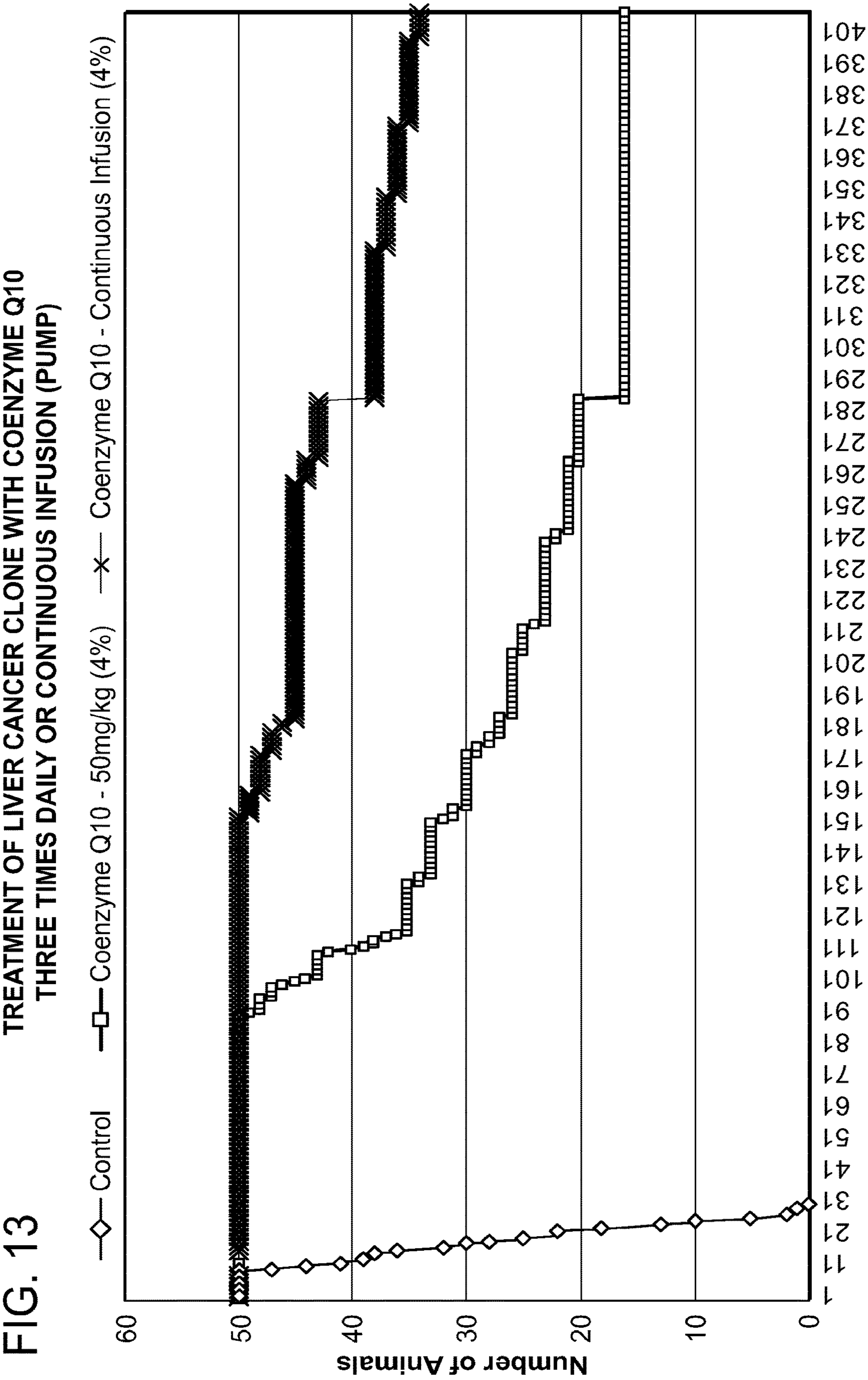
FIG. 13 shows the effect of three times daily treatment with coenzyme Q10 and continuous infusion of coenzyme Q10 in rats injected with a liver chloroma. The x axis represents the number of days from start of treatment and the y axis represents the number of surviving animals.

The effect of dosing schedule of coenzyme Q10 was also investigated in rats bearing liver or lung chloromas. Rats were transplanted with liver or lung clones of malignant chloromas derived from a stable myelogenous leukemia (chloroleukemia) cell line, MIA C51 (see. e.g., Jimenez and Yunis (1987) *Science* 238: 1278-1280). The clones have been selected to home to and form tumors in the liver or lungs, respectively. Rats were randomized to receive either no treatment, injection 3 times a day with 40 mg/mL (4%) coenzyme Q10, or continuous infusion of 40 mg/mL (4%) coenzyme Q10 via an implanted pump, to deliver for each regimen a total dose of 50 mg/kg body weight per day. In rats with liver chloromas, the 40 mg/mL coenzyme Q10 significantly prolonged survival in both the continuous infusion pump dosing group and the injection 3 times a day dosing group compared to control. However, the continuous infusion regimen was much more effective than the injection regimen for both the lung (FIG. 12) and liver (FIG. 13) chloromas. For example, at Day 189 in the liver chloroma model, 45 of 50 rats were alive in the continuous infusion treatment group compared with 26 of 50 rats alive in the injection treatment group. All control animals were dead at Day 30. See FIG. 13.

Figure 14:
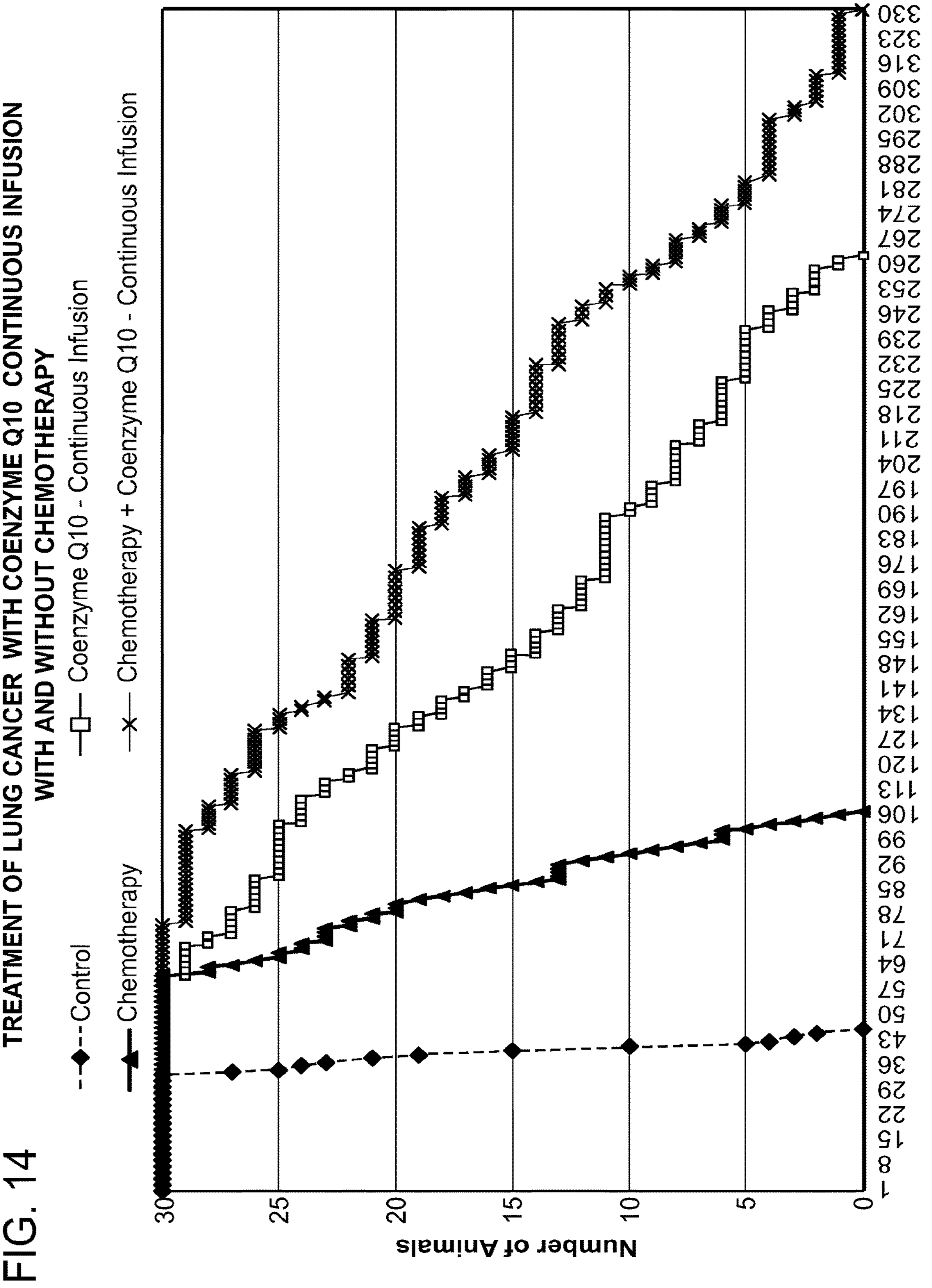
FIG. 14 shows the effect of continuous infusion of coenzyme Q10 alone, chemotherapy alone, or a combination of chemotherapy and continuous infusion of coenzyme Q10 in rats injected with human lung cancer cells. The dose of coenzyme Q10 is 50 mg/kg and the concentration is 4%. The chemotherapy was repeated on a three week cycle as follows: week 1: I. V. Cyclophosphamide, 35 mg/kg, 1×/wk and I.V. Doxorubicin 2.5 mg/kg, 3×/wk, Weeks 2-3: no treatment. The x axis represents the number of days from start of treatment and the y axis represents the number of surviving animals.

The effect of coenzyme Q10 dosing regimens was further investigated in rats implanted with H522 human lung cancer cells. Rats were randomized to receive either no treatment (control), continuous infusion with coenzyme Q10, chemotherapy, or a combination of coenzyme Q10 and chemotherapy. The dose of coenzyme Q10 was 50 mg/kg per day over 24 hours and the concentration was 4%. The chemotherapy was repeated on a three week cycle as follows: week 1: I.V. Cyclophosphamide, 35 mg/kg, 1×/wk and I.V. Doxorubicin 2.5 mg/kg, 3×/wk; Weeks 2-3: no treatment. As shown in FIG. 14, continuous infusion of CoQ10 alone was more effective than chemotherapy alone in increasing animal survival. Moreover, continuous infusion of the combined coenzyme Q10 and chemotherapy was more effective than either treatment alone.

In summary, these data indicate that both dose and dosing regimen are important parameters associated with survival outcomes in preclinical models of cancer. First, increased dose of coenzyme Q10 is associated with significant improvement in duration of survival in animal models of cancer. Furthermore, these data provide evidence that continuous infusion of coenzyme Q10 is associated with significant improvement in survival in cancer models. Thus, the ability to maintain relatively constant blood concentration of coenzyme Q10 using a continuous infusion protocol appears to be an important criterion for improving overall survival in cancer models.

Example 4—Coenzyme Q10 Nanosuspension for Intravenous Injection Pharmacokinetic, Pharmacodynamic, and Safety Studies The first-in-human Phase 1 study with coenzyme Q10 nanosuspension (40 mg/ml) was conducted in 50 patients with advanced solid tumors. The objectives were to assess the safety, maximum tolerated dose, PK and PD of coenzyme Q10, specifically a 4% coenzyme Q10 nanosuspension formulation (as described in WO 2011/112900, the entire contents of which are expressly incorporated herein by reference), administered as a 4-hour IV infusion 3 times weekly in 28-day cycles. Nine dose levels were explored ranting from 5.62 to 139 mg/kg. Plasma concentration profiles and PK parameters were determined from blood samples collected pre-dose and at intervals to 48 hours post-dose.

Evaluation of the PK parameters indicated linear or dose to linear dose-proportionality with the 4-hour infusion schedule. The curves are similar for all doses. There was some evidence of non-linearity at the lowest dose levels. However, for doses of 22.5 mg/kg or higher, dose-proportionality appeared linear.

$T_{max}$ and $C_{max}$ were generally associated with the end of the infusion. The $t_{1/2}$ ranged from 2.18 to 18.0 hr, with little or no dependence of $t_{1/2}$ on dose. Considering all dose groups, there was no apparent accumulation with increasing duration of dosing.

The majority of adverse events (AEs) during the study were Common Terminology Criterial of Adverse Events (CTCAE) grade 1 or 2, with the most common non-laboratory AEs (all causalities combined) being fatigue; nausea; dyspnea; abdominal pain, fever, tachycardia, vomiting, anorexia, and diarrhea. Of these, AEs related to coenzyme Q10 included fatigue (24%), headache (10%), nausea (8%), fever (8%), chills (6%) and arthritis (4%).

The most common laboratory AEs (all causalities combined) were: anemia (98%), hyperglycemia (88%), PIT prolonged (82%), INR increased (76%); hypoalbuminemia (70%), AST increased (66%), alkaline phosphatase increased (62%), platelet count decreased (58%), and hypocalcemia (42%). Of these laboratory AEs, those judged to be coenzyme Q10-related included PTT prolonged (80%), platelet count decreased (14%), AST increased (8%), and alkaline phosphatase increased (2%). In addition, 38 patients experienced abnormal INR values, and in 34 of these patients (68%) the increased INR was considered related to coenzyme Q10. Increased INR was clinically significant in 14 of the patients, having increased to grade 3 or caused a bleeding event. When Vitamin K was administered, all INRs decreased to grade 1 or resolved. Seven of the 14 patients with clinically significant increased INR had a medical history of bleeding events or increased coagulopathy prior to the study.

Although no dose limiting toxicities (DLTs) were identified with the 4-hour infusion schedule, 2 patients had serious bleeding events associated with increased INR at the 104.3 mg/kg dose level. One of these serious adverse events (SAEs) resulted in the patient's death due to hemothorax.

Twenty patients died due to disease progression or intercurrent illness during the study. Four patients discontinued treatment due to AEs reported as unrelated to treatment; grade 2 infection at the tumor site (1), grade 3 thrombocytopenia (2), and grade 4 AST increased (1). Three patients were actively being treated at the time of the study hold; 2 patients at the 104.3 mg/kg dose level and 1 patient had received 2 doses at the 139 mg/kg dose level.

Two SAEs were reported as possibly related to coenzyme Q10; grade 3 APTT prolonged and grade 3 hematuria. No clinically significant changes in vital signs or physical examination findings were observed. The best response to coenzyme Q10 was stable disease (23 of 50 patients, 46%). One patient with a sarcoma had a partial response, and 15 patients (30%) had progressive disease. These results demonstrate a clinical response in a phase 1 dose-escalating trial, in which the primary objective was not treatment, in some patients to coenzyme Q10 administered intravenously three times per week delivered over a four hour infusion. Adverse events and dose limiting toxicities included bleeding events and elevated INR at higher dosage levels.

Example 5—Coenzyme Q10 Nanosuspension for Intravenous Injection to Patients with Solid Tumors A Phase 1a/b Non-randomized. Dose Escalation Study of the Safety Pharmacokinetics, and Pharmacodynamics of Sterile Coenzyme Q10 (Ubidecarenone, LISP) Nanosuspension Injection Administered Intravenously to Patients With Solid Tumors.

A phase 1 clinical trial for treatment of metastatic cancer or refractory solid tumors using coenzyme Q10 monotherapy and coenzyme Q10 in combination with chemotherapy is ongoing. The coenzyme Q10 is provided as a 4% coenzyme Q10 nanosuspension formulation as described in WO 2011/112900, the entire contents of which are expressly incorporated herein by reference. The study is an open label, non-randomized safety study with crossover assignments. The estimated enrollment for the study is up to 45 subjects for the monotherapy and up to 120 subjects for the combination therapy.

The study is designed with a longer dosing schedule (e.g., 24-hour infusion, 48-hour infusion, or 96-hour continuous infusion) as compared to the study described in the previous example (4-hour infusion). This extended dosage schedule is intended to decrease coenzyme Q10 $C_{max}$ values and maintain steady-state levels. Without being bound by mechanism, it is proposed that the prolonged dosing schedule and/or decreased infusion rates avoid potential toxicity presumably related to high $C_{max}$ levels, thereby increasing the therapeutic range of coenzyme Q10 administered over a shorter dosing period and/or at a higher infusion rate.

To improve compliance over thrice weekly 4-hour infusions and to potentially reduce drug-related coagulation AEs, a 48-hour dosing schedule consisting of a loading dose (over 1 hour) followed by infusion of the remainder of the dose over 47-hours is used. In this outpatient dosing plan, the patient returns to the clinic toward the end of each 48-hour treatment, the infusion is disconnected, and the patient is reassessed. If the patient continues to meet the requirements for coenzyme Q10 treatment, the infusion pump is refilled with a second 48-hour dose for administration at a uniform rate to continue at home. Such a dosing regimen is considered effectively to be a 96-hour continuous infusion despite the short pause in infusion.

On this schedule doses are started on Days 1, 3, 8, 10, 15, 17, 22, and 24 of every 28-day cycle for patient convenience and compliance, particularly for outpatients as it requires a minimal amount of time at the clinic.

Concentrations with Two 48-Hour Infusions Schedule

The proposed coenzyme Q10 infusion schedule utilized the available data from Study CTL0510, discussed in the Example above, for the 58.7, 78.2, and 104.3 mg/kg doses given as 4-hour infusions 3 times per week to develop an infusion schedule of two 48-hour infusions given on Monday and Wednesday for 4 weeks. The total weekly doses are 176, 235, and 313 mg/kg, respectively (equivalent to about 44 mg/kg, 58.75 mg/kg, and 78.35 mg/kg per 24 hour period) Projections were made for the Monday-Wednesday continuous infusions utilizing total weekly doses of 176 (3×58.7), 235 (3×78.2) and 313 (3×104.3) mg/kg as follows:

- Two 48-hour infusions starting on Monday and Wednesday (equivalent to a 96-hour once weekly infusion) with a short, 30-minute break to change the pump and attach the second bag of infusate. Such a dosing regimen is considered to be a 96-hour continuous infusion despite the short pause in infusion.
- Part of the weekly dose is to be used as a loading dose on each Monday of the cycle.
- The loading dose is about 1-hour in duration and the infusion rate is not greater than the infusion rates used for the 4-hour infusions at the doses of 58.7, 78.2, and 104.3 mg/kg.
- For the examples of 58.7, 78.2, and 104.3 mg/kg doses, the maximum 1-hour rates are 14.5, 19.6, and 26.0 mg/kg/hr, respectively.

In all cases the concentrations of coenzyme Q10 would be negligible on Sundays. Table 1 below shows the weekly $C_{max}$ and AUC values for three 4-hour infusions on Monday, Wednesday, and Friday (using mean data from Study CTL0510 for Monday) with projections for two 48-hour infusions on Monday and Wednesday. The total weekly dose was the same in all cases. As expected, $C_{max}$ values were higher with the 4-hour infusions because the infusion rate was faster. The AUC values were also higher with 4-hour infusions, which were not expected. Theoretically, they would be expected to be the same because the doses are the same.

In conclusion, 48-hour infusions 2× per week are a viable alternative to 4-hour infusions 3× per week, producing more sustained plasma concentrations during the week.

TABLE 1

Estimated Weekly $C_{max}$ and AUC Values

| Schedule | Weekly Dose (mg/kg) | $C_{max}$ (μg/mL | $AUC_{0-168}$ (μg*hr/mL) |
|---|---|---|---|
| 48-hr Infusions on | 176 | 435 | 45,119 |
| Monday and | 235 | 582 | 60,398 |
| Wednesday | 313 | 774 | 80,240 |
| 4-hr Infusions on | 176 | 1,558 | 68,787 |
| Monday, Wednesday | 235 | 1,592 | 74,640 |
| and Friday | 313 | 2,198 | 125,953 |

Assessment of Maximum Tolerated Dose (MTD)

The primary outcome measures include determination of the Maximum Tolerated Dose (MTD) of coenzyme Q10 intravenous formulation at each week of treatment for the duration of Cycle 1 up to 4 weeks on Arm 1 and 6 weeks for Arm 2.

Dose limiting toxicities are assessed during Cycle 1 (first four weeks of Arm 1 and 6 weeks for Arm 2) of the study. Blood samples for pharmacokinetic and pharmacodynamic analyses are collected during each cycle of monotherapy and combination therapy. Urine samples for determination of coenzyme Q10 renal clearance are collected only during Cycle 1 of monotherapy and combination therapy. A PET scan is performed within 2 weeks prior to starting treatment and after 2 weeks of coenzyme Q10 treatment, and 8 weeks of treatment on Arm 1 or 10 weeks of treatment on Arm 2. Core biopsies (2-3) are performed at the time of baseline and Week 2 PET scan for patients who opt-in to participate in these exploratory studies.

Secondary outcome measures include evaluation of plasma pharmacokinetics (PK) of coenzyme Q10 at each cycle (every 4 weeks) for up to 1 year. To evaluate plasma pharmacokinetics (PK) of coenzyme Q10 monotherapy and coenzyme Q10 in combination with chemotherapy when administered as a 96-hour IV infusion in patients with solid tumors. Urine samples for determination of coenzyme Q10 renal clearance are collected only during Cycle 1 of monotherapy and combination therapy. A PET scan is performed within 2 weeks prior to starting treatment and after 2 weeks of coenzyme Q10 treatment, and 8 weeks of treatment on Arm 1 or 10 weeks of treatment on Arm 2. Core biopsies (2-3) are performed at the time of baseline and Week 2 PET scan for patients who opt-in to participate in these exploratory studies.

The treatment arms are as follows:

TABLE 2

| Treatment Arms | |
|---|---|
| Arms | Assigned intervention |
| Experimental: Coenzyme Q10 monotherapy<br>patients who meet eligibility parameters receive 2 consecutive 48-hour infusions of Coenzyme Q10 twice weekly on Monday and Wednesday (i.e., Days 1, 3, 8, 10, 15, 17, 22, and 24), essentially receiving Coenzyme Q10 treatment for 96 hours per week of each 28-day cycle. | Drug: Coenzyme Q10 monotherapy |
| Active Comparator: Coenzyme Q10 in combination with chemotherapy<br>treatment Arm 2 will enroll and treat patients with Coenzyme Q10 at the evaluated and confirmed safe dose in combination with one of 3 chemotherapies::<br>Gemcitabine IV once weekly at a starting dose of 600 $mg/m^2$;<br>5-Fluorouracil (5-FU) IV once weekly at a starting dose of 350 $mg/m^2$ with leucovorin (LV) 100 $mg/m^2$;<br>Docetaxel IV once weekly at a starting dose of 20 $mg/m^2$ | Drug: Coenzyme Q10 in combination with chemotherapy |

Study Objectives

The primary objective of the study is to determine the maximum tolerated dose (MTD) and assess the safety and tolerability of monotherapy coenzyme Q10 and coenzyme Q10 in combination with chemotherapy when administered as a 96-hour intravenous (IV) infusion in patients with solid tumors.

The secondary objective of the study is to evaluate plasma pharmacokinetics (PK) and estimate renal clearance of coenzyme Q10 monotherapy and coenzyme Q10 in combination with chemotherapy when administered as a 96-hour IV infusion in patients with solid tumors.

The exploratory objectives of the study are:

- To evaluate the pharmacodynamic (PD) correlates of coenzyme Q10 activity in plasma as monotherapy and in combination with chemotherapy.
- To evaluate the effects of coenzyme Q10 on shifting tumors to aerobic respiration by PET imaging.
- To assess tumor vascularity (using DCE-MRI) in at least 6 subjects who received coenzyme Q10 at the MID, within 24 hours pre-dose and post-dose.
- To evaluate tumor response (preliminary antitumor activity) after repeat administration of coenzyme Q10.
- Progression-free survival (PFS) and time to progression (TIP) are assessed for each treatment group.
- Myelosuppression recorded for the combination treatment arm is compared to historical data for each treatment.
- Long-term safety and tolerability of coenzyme Q10 are assessed after repeat administration as monotherapy and in combination with chemotherapy.

Study Eligibility Criteria

Subjects in the study are both male and female adults at least 18 years of age with a clinically diagnosed solid tumor.

Inclusion Criteria:

- The patient has a histologically confirmed solid tumor that is metastatic or unresectable for which standard measures do not exist or are no longer effective. (Patients with primary brain cancer or lymphoma are permitted. Patients with brain metastases are allowed if whole brain radiation was performed and is documented stable for ≥6 weeks)
- The patient has an ECOG performance status≤2
- The patient has a life expectancy of >3 months.
- Sexually active patients and their partners agree to use an accepted method of contraception during the course of the study
- Female patients of childbearing potential must have a negative pregnancy test within 1 week prior to beginning study treatment.
- The patient has adequate organ and marrow function as follows;
- ANC≥1500 $min^3$, platelets≥100,000/$mm^3$, hemoglobin≥9 g/dL,
- serum creatinine≤18 mg/dL or creatinine clearance>50 mL/min;
- bilirubin≤1.5 mg/dL; alanine aminotransferase (ALT), aspartate transaminase (AST)≤2.5 times the upper limit of normal if no liver involvement or ≤5 times the upper limit of normal with liver involvement.
- The patient has serum electrolytes (including calcium, magnesium, phosphorous, sodium and potassium) within normal limits (supplementation to maintain normal electrolytes is allowed).
- The patient has adequate coagulation: prothrombin time (PT), partial thromboplastin time (PTT), and an International Normalized Ratio within normal limits.
- The patient is capable of understanding and complying with the protocol and has signed the informed consent document.

Exclusion Criteria:

- The patient has uncontrolled intercurrent illness including, but not limited to uncontrolled infection, symptomatic congestive heart failure (NYHA class III and IV), uncontrolled cardiac arrhythmia, or psychiatric illness/social situations that would limit compliance with study requirements
- The patient has active heart disease including myocardial infarction within previous 3 months, symptomatic coronary artery disease, arrhythmias not controlled by medication, unstable angina pectoris, or uncontrolled congestive heart failure (NYHA class III and IV)
- The patient has received chemotherapy or radiotherapy within 4 weeks or has received nitrosoureas or mitomycin C within 6 weeks prior to the first dose of study drug.

The patient has received radiation to ≥25% of his or her bone marrow within 4 weeks of the first dose of study drug.

The patient has received an investigational drug within 30 days of the first dose of study drug.

The patient has not recovered to grade≤1 from adverse events (AEs) due to investigational drugs or other medications, which were administered more than 4 weeks prior to the first dose of study drug.

The patient is pregnant or lactating.

The patient is known to be positive for the human immunodeficiency virus (HIV). The effect of coenzyme Q10 on HIV medications is unknown. Note HIV testing is not required for eligibility, but if performed previously and was positive, the patient is ineligible for the study.

The patient has an inability or unwillingness to abide by the study protocol or cooperate fully with the investigator or designee.

The patient is taking HMG-CoA reductase inhibitors (Statin drugs).

The patient is receiving digoxin, digitoxin, lanatoside C, or any type of digitalis alkaloids.

The patient is receiving colony stimulating factors (CSFs) that cannot be held during the monitoring period for dose-limiting toxicities (DLT).

The patient has uncontrolled or severe coagulopathies or a history of clinically significant bleeding within the past 6 months, such as hemoptysis, epistaxis, hematochezia, hematuria, or gastrointestinal bleeding.

The patient has a known predisposition for bleeding such as von Willebrand's disease or other such condition.

The patient requires therapeutic doses of any anticoagulant, including low molecular weight heparin (LMWH). Concomitant use of warfarin, even at prophylactic doses, is prohibited.

Assessment of measurable lesions to determine eligibility are based on the following criteria.

TABLE 3

| Baseline Eligibility. | |
|---|---|
| Measurable Disease: | Tumor lesions: Must be accurately measured in at least one dimension (longest diameter in the plane of measurement is to be recorded) with a minimum size of:<br>10 mm by CT scan (CT scan slice thickness no greater than 5 mm).<br>10 mm caliper measurement by clinical exam (lesions that cannot be accurately measured with calipers should be recorded as non-measurable).<br>20 mm by chest x-ray.<br>Skin lesions: Documentation by color photography, including a ruler to estimate the size of the lesion, is recommended.<br>Malignant lymph nodes: To be considered pathologically enlarged and measurable, a lymph node must be >15 mm in short axis when assessed by CT scan. At baseline and in follow-up, only the short axis will be measured and followed. |
| Non-Measurable Disease: | All other lesions, including small lesions (longest diameter <10 mm or pathological lymph nodes with >10- to <15-mm short axis) as well as truly non-measurable lesions. Lesions considered truly non-measurable include: leptomeningeal disease, ascites, pleural or pericardial effusion, inflammatory breast disease, and lymphangitic involvement of skin or lung, abdominal masses, abdominal organomegaly identified by physical exam that is not measurable by reproducible imaging requirements. |
| Target Lesions: | The most reproducible measurable lesions, up to a maximum of 2 lesions per organ and 5 lesions in total, representative of all involved organs should be identified as target lesions and recorded and measured at baseline.<br>Target lesions should be selected on the basis of their size (lesions with the longest diameter), should be representative of all involved organs, and in addition should be those that lend themselves to reproducible repeated measurements. Pathological nodes which are defined as measurable and that may be identified as target lesions must meet the criterion or a short axis of >15 mm by CT scan. A sum of the diameters (longest for non-nodal lesions, short axis for nodal lesions) for all target lesions is calculated and reported as the baseline sum diameters. If lymph nodes are to be included in the sum, then as noted above, only the short axis is added into the sum. The baseline sum diameters is used as reference to further characterize any objective tumor response. |
| Non-Target Lesions: | All other lesions should be identified as non-target lesions at baseline. Measurements of these lesions are not required, but the presence or absence of each should be noted throughout follow-up. |

TABLE 4

| Guidelines for Evaluation of Measurable Disease. | |
|---|---|
| Clinical Lesions: | Clinical lesions are only be considered measurable when they are superficial (eg, skin nodules and palpable lymph nodes). In the case of skin lesions, documentation by color photography, including a ruler to estimate the size of the lesion, is recommended. |
| Chest X-ray: | Lesions on chest X-ray are acceptable as measurable lesions when they are clearly defined and surrounded by aerated lung. However, CT is preferable. |

TABLE 4-continued

| Guidelines for Evaluation of Measurable Disease. | |
|---|---|
| Conventional CT and MRI: | CT and MRI are the best currently available and reproducible methods to measure target lesions selected for response assessment. Conventional CT and MRI are performed with cuts of 10 mm or less in slice thickness, contiguously. Spiral CT scan are performed using a 5-mm contiguous reconstruction algorithm. This applies to tumors of the chest, abdomen, and pelvis. Head and neck tumors and those of extremities usually require specific protocols. |
| Ultrasound: | When the primary trial endpoint is objective response, ultrasound should not be used to measure tumor lesions. It is, however, a possible alternative to clinical measurements of superficial palpable lymph nodes, subcutaneous lesions, and thyroid nodules. Ultrasound may also be useful to confirm the complete disappearance of superficial lesions usually assessed by clinical examination. |
| Endoscopy and Laparoscopy: | Use of endoscopy and laparoscopy for objective tumor evaluation has not yet been fully and widely validated. Therefore, use of these techniques for objective tumor response should be restricted to validation purposes in specialized centers. Such techniques can be useful in confirming complete pathological response when biopsies are obtained. |
| Tumor Markers: | Tumor markers alone cannot be used to assess response. If markers are initially above the upper limit of normal, they must normalize for a patient to be considered in complete clinical response when all lesions have disappeared. |
| Cytology and Histology: | Cytology and histology can be used to differentiate between PR and CR in rare cases (eg, after treatment to differentiate between residual benign lesions and residual malignant lesions in tumor types such as germ cell tumors). |

Trial Design

This is a Phase 1a/b multicenter, open-label, non-randomized, dose-escalation study to examine the dose limiting toxicities (DLT) of coenzyme Q10 administered as a 96-hour continuous intravenous (IV) infusion as monotherapy (treatment Arm 1) and in combination with chemotherapy (treatment Arm 2) in patients with solid tumors. In the Phase 1a portion of the trial, patients who meet eligibility parameters receive 2 consecutive 48-hour infusions of coenzyme Q10 twice weekly on Monday and Wednesday (i.e., Days 1, 3, 8, 10, 15, 17, 22, and 24), essentially receiving coenzyme Q10 treatment for 96 hours per week of each 28-day cycle. At each dose level of Arm 1 and Arm 2, patients are treated for either 8 hours at minimum of outpatient monitoring or inpatient monitoring for the first 24-hrs of the first infusion of Cycle 1. All other treatments are administered in an outpatient setting. Dose limiting toxicities are assessed during Cycle 1.

The study is a standard 3+3 dose escalation design with the dose escalated in successive cohorts of 3 to 6 patients each. Toxicity at each dose level is graded according to National Cancer Institute Common Terminology Criteria for Adverse Events (CTCAE v4.02). Safety oversight is provided by the Cohort Review Committee (CRC). The CRC reviews and confirms all DLTs and monitor safety throughout the study (including Arm 2).

Assessments of the antitumor activity of coenzyme Q10 is performed at the end of Cycle 2 and every 2 cycles thereafter using standard techniques such as computerized tomography (CT) or magnetic resonance imaging (MRI) for patients with measurable disease. Response is evaluated using Response Evaluation Criteria in Solid Tumors (RECIST) v1.1. Patients who experience no unacceptable toxicity or disease progression, may receive additional 28-day cycles for up to 1 year on Arm 1 or 2. Patients on Arm 1 who progress may elect to continue coenzyme Q10 treatment in combination with gemcitabine, 5-FU, or docetaxel at the treating physician's discretion. Once a dose level of coenzyme Q10 monotherapy is evaluated and the CRC determines it safe to escalate to the next dose level, Cohort 1 of Treatment Arm 2 of coenzyme Q10 in combination with chemotherapy will open to accrual. Cohort 1 of Arm 2 patients are enrolled onto one of 3 chemotherapies, gemcitabine, 5-FU, or docetaxel. Cycle 1 of combination therapy (Arm 2) is 6 weeks in duration for patients with coenzyme Q10 administered twice weekly on Mondays and Wednesday for 6 weeks and chemotherapy administered on Fridays, Days 19, 26 and 33. Cycles 2-12 are 4 weeks in duration with coenzyme Q10 administered twice weekly on Mondays and Wednesdays for 4 weeks and chemotherapy administered on Fridays, Days 5, 12 and 19. Dose limiting toxicities are assessed during Cycle 1. Response is assessed after Cycle 2 (10 weeks) and responders who continue onto Cycles 2-12 are assessed every 2 cycles (8 weeks). Patients can continue coenzyme Q10 in combination with chemotherapy for a maximum of 12 cycles in the absence of intolerable toxicity and progression. Patients on Arm 2 who progress on one type of chemotherapy may not switch to one of the other chemotherapy agents in combination with coenzyme Q10. However, if the chemotherapy component (i.e., 5-FU, gemcitabine, or docetaxel) of combination therapy is discontinued due to chemotherapy-related toxicity, patients may continue to receive coenzyme Q10 as monotherapy.

Once the maximum tolerated dose (MTD) of coenzyme Q10 as monotherapy and in combination with chemotherapy are established, an expansion cohort is enrolled (a total of 12-15 patients for monotherapy and a total of 10 patients for each combination therapy)

PK/PD Assessments

Blood samples for pharmacokinetic and pharmacodynamic analyses are collected during each cycle of monotherapy and combination therapy. Urine samples for determination of coenzyme Q10 renal clearance are collected only during Cycle 1 of monotherapy and combination therapy. A PET scan is performed within 2 weeks prior to starting treatment and after 2 weeks of coenzyme Q10 treatment, and 8 weeks of treatment on Arm 1 or 10 weeks of treatment on Arm 2. Core biopsies (2-3) are performed at the time of baseline and Week 2 PET scan for patients who opt-in to participate in these exploratory studies.

Number of Patients

Up to 45 patients are enrolled onto treatment Arm 1, the single-agent coenzyme Q10 dose escalation and expansion portion of the study, and up to 120 patients onto treatment Arm 2, coenzyme Q10 in combination with chemotherapy dose escalation and expansion portion. The exact number will be determined by the number of dose escalations until the MID is reached. Therefore, up to 165 patients may be enrolled.

Trial Drugs, Dose, and Mode of Administration

Coenzyme Q10 Nanosuspension for Injection (40 mg/mL) is administered IV over 96 hours at the starting dose of 66 mg/kg per 96 hour dose. Each patient receives 2 consecutive 48-hour infusions per week (Monday-Wednesday and Wednesday-Friday) during each 28-day cycle. The dose may be escalated 25% in subsequent cohorts until the MTI) is reached.

Upon safe completion of a coenzyme Q10 dose level as monotherapy, treatment Arm 2 will enroll and treat patients with coenzyme Q10 at the evaluated and confirmed safe dose in combination with one of three chemotherapies:

- Gemcitabine IV once weekly at a starting dose of 600 $mg/m^2$;
- 5-Fluorouracil (5-FU) IV once weekly at a starting dose of 350 $mg/m^2$ with leucovorin (LV) 100 $mg/m^2$;
- Docetaxel IV once weekly at a starting dose of 20 $mg/m^2$ Duration of Therapy The minimum duration of therapy is 8 weeks (2 cycles) for treatment Arm 1 and 10 weeks for treatment Arm 2.

For patients who do not progress on single agent coenzyme Q10 treatment after 2 cycles (8 weeks), treatment may continue for up to 12 cycles or until any of the discontinuation criteria are met. Patients who progressed after 2 cycles (8 weeks) and do not have unacceptable toxicity may continue to receive coenzyme Q10 in combination with gemcitabine, 5-FU, or docetaxel.

For patients treated with the combination of coenzyme Q10 plus chemotherapy, treatment may continue for up to 12 cycles in the absence of progressive disease, unacceptable toxicity, or until any of the discontinuation criteria are met. At the discretion of the Cohort Review Committee (CRC), eligible subjects may continue to receive coenzyme Q10 treatment beyond 1 year, under a separate protocol.

Dose-Limiting Toxicity

Adverse events are graded according to CTCAE v4.02. A copy of this grading scale can be accessed at the URL ctep.cancer.gov.

A dose-limiting toxicity (DLT) is defined as a clinically significant adverse event or abnormal laboratory value that is at least possibly related to coenzyme Q10 occurring during Cycle 1 that meets any of the following criteria:

- A treatment-related AE that, in the opinion of the CRC, is of potential clinical significance such that further dose escalation would expose patients in higher dose cohorts to risk of irreversible medical harm or require medical treatment to avoid irreversible medical harm.
- Any≥grade 3 non-hematologic toxicities that are at least possibly related to study drug with the exception of alopecia and grade 3 diarrhea, nausea, and vomiting that resolves to grade 2 or less within 48 hours of institution of supportive care.
- Grade 3 thrombocytopenia with clinically significant bleeding.
- Any≥grade 4 hematologic toxicities including, but not limited to, death, grade 4 anemia of any kind, grade 4 thrombocytopenia, grade 4 neutropenia of >5 days duration, or grade 4 neutropenia of any duration with fever or documented infection will all be considered DLT
- Grade 2 INR/PTT elevation with clinically significant bleeding.
- Grade 3 INR/PTT abnormalities (with or without bleeding)
- Concomitant elevations of transaminases and bilirubin that meet Hy's Law criteria.
- ≥Grade 3 electrolyte abnormalities.
- Any grade 3 hypokalemia or hypomagnesemia if standard measures have not reduced these to a grade 2 or better in 7 days or less
- ≥Grade 4 (life threatening) hypokalemia or hypomagnesemia of any duration.
- Grade 3 deterioration of kidney and liver function of any duration.

A table of non-limiting, standard laboratory assessments are provided below.

TABLE 5

Laboratory Panels.

| | |
|---|---|
| Hematology | CBC with differential, platelets |
| Coagulation | PT/PTT/INR |
| Serum Chemistry | Albumin, alkaline phosphatase, ALT, AST, blood urea nitrogen (BUN), calcium, carbon dioxide, chloride, creatinine, gamma-glutamyl transferase (GGT), glucose, lactate dehydrogenase, phosphorus, potassium, sodium, total bilirubin, total protein, serum magnesium, cholesterol, triglycerides |
| Urinalysis | Appearance, color, pH, specific gravity, ketones, protein, glucose, bilirubin, nitrite, urobilinogen, and occult blood (microscopic examination of sediment are performed only if the results of the urinalysis dipstick evaluation are positive) |
| Laboratory work-up for any >grade 2 INR | LFTs, levels of Vitamin-K dependent coagulation factors (II, VII, IX, X), Protein C, and Protein S. If >grade 2 INR is not corrected following administration of Vitamin K, cryoprecipitate or fresh frozen plasma, additional tests such as mixing studies, fibrinogen level, D-dimer and fibrin split products are performed. |

Determination of DLT

The patient population used fir determination of DLT consists of patients who have met the minimum safety evaluation requirements of the trial. To be considered eligible for DLT assessment during Cycle 1 of treatment, patients must either have had a DLT (irrespective of the number of doses received) or have completed the first cycle and received at least 80% of the scheduled doses of coenzyme Q10 for Arm 1 and coenzyme Q10+, chemotherapy in Arm 2.

Patients who discontinue treatment early due to disease progression or withdrawal are asked to have all End-of-Treatment safety evaluations performed. If a patient withdraws from treatment during Cycle 1 due to any reason other than a DLT and does not meet the minimum safety evaluation requirements described above, that patient is replaced.

Maximum Tolerated Dose

The MID is the highest dose at which≤1 of 6 patients experience a DLT during Cycle 1 (28 days for Arm 1 or 6 weeks for Arm 2) of coenzyme Q10 therapy. If 2 or more patients in a dosing group experience a DLT, the MTD has been exceeded.

Expansion after Determination of the MTD

A total of 12 to 15 patients are evaluated at the MTD for coenzyme Q10 monotherapy and up to 10 patients are evaluated at the MTD fix coenzyme Q10 in combination with one of each chemotherapy to confirm the safety and tolerability, PK and PI) of coenzyme Q10 at that dose.

Initiation of Combination Chemotherapy Cohort

Once a dose level of coenzyme Q10 monotherapy is evaluated and the CRC determines it safe to escalate to the next dose level, treatment Arm 2 of coenzyme Q10 in combination with chemotherapy will open to accrual at a reduced dose level. Arm 2 patients are enrolled onto one of 3 chemotherapies, gemcitabine, 5-FU, or docetaxel according to the dose levels provided herein. Cycle 1 is 6 weeks in duration for Arm 2 patients with coenzyme Q10 administered twice weekly on Mondays and Wednesday for 6 weeks and chemotherapy administered on Fridays. Days 19, 26 and 33. Cycles 2-12 are 4 weeks in duration with coenzyme Q10 administered twice weekly on Mondays and Wednesdays for 4 weeks and chemotherapy administered on Fridays. Days 5, 12 and 19. Dose limiting toxicities are assessed during Cycle 1. Response is assessed after Cycle 2 (10 weeks) and responders who continue onto Cycles 2-12 are assessed every 2 cycles (8 weeks). Patients continue coenzyme Q10 in combination with chemotherapy for a maximum of 12 cycles in the absence of intolerable toxicity and progression.

Dose Cohorts

Single Agent Coenzyme Q10 (Treatment Arm 1)

The starting dose level of coenzyme Q10 is 66 mg/kg per 96 hour dose administered by IV infusion over 48 hours 2 times per week of each 28-day cycle (Table 3). The 2 doses are administered over 4 consecutive days, i.e., the first dose on Monday-Wednesday and the second dose on Wednesday-Friday of each week. The study drug is administered undiluted via a central venous access device and the infusion rate is controlled by a programmable ambulatory infusion pump such as the CADD Prizm VIP (model 6101) ambulatory pump.

For the first dose of each week (i.e., on Days 1, 8, 15, and 22 of the cycle) a loading dose using the CADD pump is infused over 1 hour with the remainder of the dose volume infused over 47 hours using the same CADD pump as indicated in Table 6 below, Coenzyme Q10 Nanosuspension for Injection Dose Cohorts (Arm 1; Monotherapy). At each dose level of Arm 1 and Arm 2, patients are treated for either 8 hours at minimum of outpatient monitoring or inpatient monitoring for the first 24-hrs of the first infusion of Cycle 1. Patients are monitored for dose-limiting toxicity (DLT) or an AE that requires prolonged hospitalization. If no reaction to coenzyme Q10 develops, the patient will be discharged.

For the second dose of each week (i.e., on Days 3, 10, 17, and 24 of the cycle) the total dose volume are given over 48 hours with no loading dose as indicated in Table 6 below. Coenzyme Q10 Nanosuspension for Injection Dose Cohorts (Arm 1; Monotherapy).

Patients are dosed at their assigned dose cohort for the duration of their treatment. Intra-patient dose escalation is not allowed. If the starting dose of 66 mg/kg exceeds the MTD of coenzyme Q10, the dose is reduced to 50 mg/kg for Cohort−1. No more than 2 dose reductions are allowed during the study. The minimum dose is Dose Level −1.

TABLE 6

Coenzyme Q10 Nanosuspension for Injection Dose Cohorts (Arm 1; Monotherapy).

| | | | Monday-Wednesday Over 48 Hrs | | | | | |
|---|---|---|---|---|---|---|---|---|
| | Total Dose 2x per Week | | Loading Dose Over 1 Hr | | Remainder Over 47 Hrs | | Wednesday-Friday Over 48 Hrs | |
| Cohort | Dose | Volume* | Volume* | Infusion Rate | Volume* | Infusion Rate | Volume* | Infusion Rate |
| −1 | 50 mg/kg | 88 mL | 7.4 mL | 4.2 mg/kg/hr | 81 mL | 0.98 mg/kg/hr | 88 mL | 1.05 mg/kg/hr |
| 1 | 66 mg/kg | 116 mL | 9.6 mL | 5.5 mg/kg/hr | 106 mL | 1.29 mg/kg/hr | 116 mL | 1.38 mg/kg/hr |
| 2 | 88 mg/kg | 154 mL | 13.0 mL | 7.4 mg/kg/hr | 141 mL | 1.71 mg/kg/hr | 154 mL | 1.83 mg/kg/hr |
| 3 | 110 mg/kg | 193 mL | 16.1 mL | 9.2 mg/kg/hr | 176 mL | 2.14 mg/kg/hr | 193 mL | 2.29 mg/kg/hr |
| 4 | 137 mg/kg | 240 mL | 19.3 mL | 11 mg/kg/hr | 221 mL | 2.68 mg/kg/hr | 240 mL | 2.85 mg/kg/hr |
| 5 | 171 mg/kg | 299 mL | 24.5 mL | 14 mg/kg/hr | 275 mL | 3.34 mg/kg/hr | 299 mL | 3.56 mg/kg/hr |
| 6 | 215 mg/kg | 376 mL | 31.5 mL | 18 mg/kg/hr | 345 mL | 4.19 mg/kg/hr | 376 mL | 4.48 mg/kg/hr |

*Assuming a 70 kg patient

Treatment Arm 2 Combination Chemotherapy

Once a dose level of coenzyme Q10 monotherapy is evaluated and the CRC determines it safe to escalate to the next dose level, Arm 2 of coenzyme Q10 in combination with chemotherapy will open to accrual at a reduced dose level (see Table 7, Coenzyme Q10 Nanosuspension for Injection Dose Cohorts (Arm 2; Combination Therapy). A standard 3+3 design is used for Arm 2 of the study, and the definition of DLT is the same as that used in Arm 1. Coenzyme Q10 is started at one dose level below the dose that has been studied and determined to be safe in the monotherapy portion of the trial. Arm 2 patients are enrolled onto one of 3 chemotherapies, gemcitabine, 5-FU, or docetaxel according to the dose levels below and the following schedule (see Tables 7-10 with dosages for Arm 2 chemotherapy combinations).

Gemcitabine IV once weekly at a starting dose of 600 $mg/m^2$,

5-Fluorouracil (5-FU) IV once weekly at a starting dose of 350 $mg/m^2$ with leucovorin (LV) 100 $mg/m^2$; OR Docetaxel IV once weekly at a starting dose of 20 $mg/m^2$ Note: Both coenzyme Q10 and the chemotherapy agent can escalate simultaneously in Cohorts 3 and 4 only if there are no DLTs observed in the previous cohorts. If one or more DLTs is observed, then intermediate dose levels are added where one agent is escalated.

Once assigned, patients may not switch to an alternative cohort. Arm 2 is expanded at the MTD dose to 10 patients for each chemotherapy combination to ensure safety and for additional PK modeling (a total of 30 additional patients).

Note: Patients on Arm 2 who progress on one type of chemotherapy may not switch to one of the other chemotherapy agents in combination with coenzyme Q10. However, if the chemotherapy component (i.e., 5-FU, gemcitabine, or docetaxel) of combination therapy is discontinued due to chemotherapy-related toxicity, patients may continue to receive coenzyme Q10 as monotherapy.

Cycle 1 is 6 weeks in duration for Arm 2 patients. Coenzyme Q10 is administered twice weekly on Mondays and Wednesday for 6 weeks and chemotherapy administered on Fridays, Days 19, 26 and 33. Chemotherapy is administered by IV infusion over 30 minutes at the clinic. Dose limiting toxicities are assessed during Cycle 1. Response is assessed after Cycle 2 (10 weeks) and responders who continue onto Cycles 3-12 are assessed every 2 cycles (8 weeks). Cycles 2-12 are 4 weeks in duration with coenzyme Q10 administered twice weekly on Mondays and Wednesdays for 4 weeks and chemotherapy administered on Fridays, Days 5, 12 and 19.

TABLE 7

| Coenzyme Q10 Nanosuspension for Injection Dose Cohorts (Arm 2; Combination Therapy) | | | | | | | | | |
|---|---|---|---|---|---|---|---|---|---|
| | | | Monday-Wednesday Over 48 Hrs | | | | | | |
| Co- | Total Dose 2× per Week | | Loading Dose Over 1 Hr | | Remainder Over 47 Hrs | | Wednesday-Friday Over 48 Hrs | | |
| hort | Dose | Volume* | Volume* | Infusion Rate | Volume* | Infusion Rate | Volume* | Infusion Rate | |
| −1 | 38 mg/kg | 67 mL | 5.5 mL | 3.1 mg/kg/hr | 61 mL | 0.74 mg/kg/hr | 67 mL | 0.80 mg/kg/hr | |
| 1 | 50 mg/kg | 88 mL | 7.4 mL | 4.2 mg/kg/hr | 81 mL | 0.98 mg/kg/hr | 88 mL | 1.05 mg/kg/hr | |
| 2 | 66 mg/kg | 116 mL | 9.6 mL | 5.5 mg/kg/hr | 106 mL | 1.29 mg/kg/hr | 116 mL | 1.38 mg/kg/hr | |
| 3 | 88 mg/kg | 154 mL | 13.0 mL | 7.4 mg/kg/hr | 141 mL | 1.71 mg/kg/hr | 154 mL | 1.83 mg/kg/hr | |
| 4 | 110 mg/kg | 193 mL | 16.1 mL | 9.2 mg/kg/hr | 176 mL | 2.14 mg/kg/hr | 193 mL | 2.29 mg/kg/hr | |
| 5 | 137 mg/kg | 240 mL | 19.3 mL | 11 mg/kg/hr | 221 mL | 2.68 mg/kg/hr | 240 mL | 2.85 mg/kg/hr | |
| 6 | 171 mg/kg | 299 mL | 24.5 mL | 14 mg/kg/hr | 275 mL | 3.34 mg/kg/hr | 299 mL | 3.56 mg/kg/hr | |

*Assuming a 70 kg patient

TABLE 8

| Arm 2 Combination of Coenzyme Q10 and Gemcitabine. | | |
|---|---|---|
| Cohort | Gemcitabine Dose | Coenzyme Q10 Dose |
| −1 | 600 mg/m$^2$ | 38 mg/kg |
| 1 | 600 mg/m$^2$ | 50 mg/kg |
| 2 | 600 mg/m$^2$ | 66 mg/kg |
| 3 | 800 mg/m$^2$ | 88 mg/kg |
| 4 | 1000 mg/m$^2$ | 110 mg/kg |
| 5 | 1000 mg/m$^2$ | 137 mg/kg |
| 6 | 1000 mg/m$^2$ | 171 mg/kg |

TABLE 9

| Arm 2 Combination of Coenzyme Q10 and 5-Fluorouracil. | | |
|---|---|---|
| Cohort | 5-FU + Leucovorin Dose [a] | Coenzyme Q10 Dose |
| −1 | 350 mg/m$^2$/LV 100 mg/m$^2$ | 38 mg/kg |
| 1 | 350 mg/m$^2$/LV 100 mg/m$^2$ | 50 mg/kg |
| 2 | 350 mg/m$^2$/LV 100 mg/m$^2$ | 66 mg/kg |
| 3 | 450 mg/m$^2$/LV 100 mg/m$^2$ | 88 mg/kg |
| 4 | 500 mg/m$^2$/LV 100 mg/m$^2$ | 110 mg/kg |
| 5 | 500 mg/m$^2$/LV 100 mg/m$^2$ | 137 mg/kg |
| 6 | 500 mg/m$^2$/LV 100 mg/m$^2$ | 171 mg/kg |

[a] Leucovorin may be administered prior to 5-FU or both drugs may be given concurrently.

TABLE 10

| Arm 2 Combination of Coenzyme Q10 and Docetaxel. | | |
|---|---|---|
| Cohort | Docetaxel Dose | Coenzyme Q10 Dose |
| −1 | 20 mg/m$^2$ | 38 mg/kg |
| 1 | 20 mg/m$^2$ | 50 mg/kg |
| 2 | 20 mg/m$^2$ | 66 mg/kg |
| 3 | 25 mg/m$^2$ | 88 mg/kg |
| 4 | 30 mg/m$^2$ | 110 mg/kg |

TABLE 10-continued

| Arm 2 Combination of Coenzyme Q10 and Docetaxel. | | |
|---|---|---|
| Cohort | Docetaxel Dose | Coenzyme Q10 Dose |
| 5 | 30 mg/m$^2$ | 137 mg/kg |
| 6 | 30 mg/m$^2$ | 171 mg/kg |

Dose Escalation of Coenzyme Q10 Monotherapy (Arm 1) & Combination Therapy (Arm 2)

The study is a standard 3+3 design with the dose of coenzyme Q10 escalated in successive dose cohorts of 3 patients each. Up to 3 to 6 patients are dosed at each dose level and in no case will cohorts contain more than 6 patients. If none of the 3 patients in a cohort experiences DLT during Cycle 1, then 3 new patients may be entered at the next higher dose level following CRC review of safety and PK data from lower cohorts.

A cohort may be expanded up to 6 patients from the normal 3 patient accrual with approval of the CRC or if 1 of 3 patients experiences DLT. If 1 of 3 patients experiences a DLT in Cycle 1, the cohort is expanded up to 6 patients. If no additional patient experiences a DLT at that dose, the next cohort opens to accrual and the dose escalated. If 2 or more patients in a cohort experience DLT during Cycle 1, no further patients are started at that dose.

The dose for subsequent cohorts is escalated only after the safety of the previous dose level has been established.

Dose escalation occurs in 25% increments from the immediate prior dose group in the absence of DLTs at the previous dose level.

Continuous Infusion Administration Methods and Devices

Chemotherapeutic agents are administered using routine methods well known in the art. The following exemplar devices and methods are provided for continuous infusion of coenzyme Q10. It is understood that other devices and methods can accomplish the same outcome at those provided in the table below. The exemplary devices provided are not limiting.

TABLE 11

| Materials Used to Prepare Coenzyme Q10 for IV Infusion. | | |
|---|---|---|
| Description | Manufacturer/Part No. | Container Type |
| Empty sterile Hospira IV infusion bags for use with Gemstar primary administration set | Hospira 510K: K771228 or equivalent | 250 mL Plastic Bag (7951-12)[a] |
| 250 mL ambulatory IV medication reservoir cartridge for use with CADD ambulatory infusion pump | Smith Medical 21-7308-24 - Medication Cassette Reservoir 510K # K081156 | Cartridge with PVC bag lining[b] |

TABLE 11-continued

Materials Used to Prepare Coenzyme Q10 for IV Infusion.

| Description | Manufacturer/Part No. | Container Type |
| --- | --- | --- |
| IV Administration Set for use with Gemstar ambulatory infusion pump | Hospira LifeShield Gemstar Primary IV tubing set; No 13758-28 | Primary Microbore Gemstar IV Set with non-DEHP tubing, nonvented piercing pin, cassette, slide clamp, Secure Lock and anti-siphon valve. Latex-Free, [c] |
| Infusion tubing extension set for 250 mL CADD cassette | Smith Medical CADD ® 21-7060-24-30-inch | 30" tubing extension Set with male luer, clamp, and integral anti-siphon valve with male luer [d] |
| Infusion tubing extension set for 250 mL CADD cassette | Smith Medical CADD ® 21-7061-24 -45-inch | 45" tubing extension set with male luer, clamp, and integral anti-siphon valve with male luer [d] |
| PharmAssure ® Syringe Filter with 5 um pore size for use with 100 mL drug vials | PALL ® Life Sciences HP4640 | Supor ® PES Membrane [e] |
| PharmAssure ® Syringe Filter with 5 um pore size for use with 20 mL drug vials | PALL ® Life Sciences HP1050 | Supor ® PES Membrane [e] |

[a]Plastic bag of polyvinyl chloride (PVC), contains Bis-2-ethylhexyl-phthalate (DEHP), latex free.
[b]PVC, plasticized with TOTM (Trioctyl Trimellitate).
[c] IV administration set only for use with Gemstar ambulatory infusion pump
[d] Plastic tubing of PVC, DEHP free, latex free.
[e] Plastic housing of modified acrylic with a Supor ® membrane.

Hematologic Toxicity

The Baseline Laboratory Requirements are ANC≥1500 $mm^3$, platelets $100,000/mm^3$, hemoglobin≥9 g/dL and INR, PT and PTT within normal limits. Hematology and chemistry is preferably assessed weekly (Mondays) and coagulation should be repeated within 24-72 hours prior to initiation of each dose. Coenzyme Q10 must be held for any grade 3 or 4 hematologic toxicity that is at least possibly drug-related. Any grade 3 or 4 hematologic toxicity must return to a grade 1 or resolved with the exception of INR, PT and PTT which must be within normal limits prior to administration of coenzyme Q10 in Cycles 2-12. Coenzyme Q10 may be resumed at a reduced dose.

To monitor and mitigate coenzyme Q10-associated coagulopathies, PT, PTT, INR and platelet count must be assessed prior to administering each dose of coenzyme Q10. An INR value of ≥grade 2 requires immediate treatment with Vitamin K, cryoprecipitate or fresh frozen plasma as clinically indicated. Any AE must decrease to ≤grade 1 and the INR must be normal before resuming coenzyme Q10 treatment.

If a second adverse event of grade 3 INR or PTT elevation occurs, permanently discontinue coenzyme Q10.

Permanently discontinue coenzyme Q10 in patients who experience clinically significant bleeding in conjunction with a ≥grade 2 elevation in INR or PTT.

Non-Hematologic Toxicity

A grade 3 or 4 non-hematologic toxicity that is at least possibly drug-related must return to grade 1 or resolve prior to administration of coenzyme Q10 in Cycles 2-12 Coenzyme Q10 may be resumed at a reduced dose.

Patients with toxicities that are manageable with supportive therapy may not require dose reductions. Patients requiring greater than 2 dose reductions of coenzyme Q10 should be withdrawn from the study.

At the end of the study, patients are assessed for response by RECIST criteria to treatment with either coenzyme Q10 monotherapy or coenzyme Q10 combination therapy with chemotherapeutic agents. The frequency, duration, and extent of response is compared to a population or historical control to determine benefit of the subject to the treatment regimen. Subjects are demonstrated to achieve clinically relevant outcomes based on RECIST criteria described herein. Subjects are also assessed for adverse outcomes as compared to subjects treated with intravenously administered coenzyme Q10 delivered in a four hour infusion at a higher infusion rate than is used in this clinical trial. Increased infusion duration is found to decrease adverse events in subjects, thereby increasing the therapeutic range of coenzyme Q10, allowing subjects to receive higher doses and/or more doses of coenzyme Q10 without significant adverse events, e.g., adverse events that would require the subject to terminate treatment and/or withdraw from the study. Subjects are also assessed for myelosuppression, particularly in the combination therapy cohorts. Levels of myelosuppression in subjects in this study are compared to historical controls to identify decreases in myelosuppression in coadministration regimens with coenzyme Q10.

Example 6—Safety and Efficacy Results for Ongoing Phase 1a/b Study of Coenzyme Q10 Nanosuspension for Intravenous Injection to Patients with Solid Tumors Interim results for the Phase lab non-randomized, dose escalation study of the safety, pharmacokinetics, and pharmacodynamics of coenzyme Q10 nanosuspension injection administered intravenously to patients with solid tumors described in Example 5 are provided below.

Forty-two subjects have been enrolled and treated thus far, 17 subjects in the monotherapy arm and 25 subjects in the combination arm:

Monotherapy Arm

- Dose Level 1 (66 mg/kg): 9 subjects enrolled, 1 active and 8 off study. 1 dose-limiting toxicity (DLT), grade 3 GGT. Dose level cleared
- Dose Level 2 (88 mg/kg): 4 subjects enrolled, 0 active (1 crossover to gemcitabine). 0 DLT. Dose level cleared.
- Dose Level 3 (110 mg/kg): 4 subjects enrolled, 10 active. 0 DLT. 2 subjects replaced, 1 slot open. Evaluation ongoing.

Three additional dose levels are to be evaluated.

Combination Arm 25 subjects enrolled, 12 active. 1 crossover subject, 13 off study.

Gemcitabine Cohort

Dose level 1 (50 mg/kg) closed. Mild to moderate thrombocytopenia (a gemcitabine-related adverse event) was observed, but with no DLT Dose level cleared.

Dose level 2 (66 mg/kg) open, 3 subjects enrolled.

Four additional dose levels are to be evaluated.

5-Fluorouracil (5FU) Cohort

Dose level 1 (50 mg/kg) fully accrued. No 5FU-related issued. Dose level cleared Dose level 2 (66 mg/kg) fully accrued. Dose level cleared.

Dose level 3 (kg mg/kg) open, all slots filled. Evaluation ongoing.

Three additional dose levels are to be evaluated.

Docetaxel Cohort

Dose level 1 (50 mg/kg) fully accrued. No docetaxel-related issued. Dose level cleared.

Dose level 2 (66 mg/kg) fully accrued. No issues or DLTs. Dose level cleared.

Dose level 3 (kg mg/kg) fully accrued. No issues or DLTs. Evaluation ongoing.

Three additional dose levels are to be evaluated.

The drug has been observed to be safe at the current levels. In particular, with the continuous infusion protocol, there were minimal coagulation abnormalities with aggressive pre-loading or treatment with Vitamin K. No bleeding events were reported. Transient elevation of triglycerides was observed, but with no clinical significance (as confirmed by in-house lipidomics evaluation). Mild to moderate Thrombocytopenia was observed after Gemcitabine treatment with no DLT at the initial dose. Pharmacokinetic studies at the initial tested doses showed linear distribution.

Coenzyme Q10 showed early activity at low doses in a variety of solid tumors including gastric, pancreatic, colon, head and neck, non-small cell lung cancer (NSCLC), mesothelioma and triple-negative (TN) Breast Cancer. Eight out of twelve patients (75%) that were evaluable for efficacy after dose level 2 showed various responses including, tumor reductions, decrease FDG, arrested tumor progression, stable disease, decrease in tumor markers, clinical improvements reflected on quality of life (QOL) (i.e. reduction of pain, increased energy, decrease in serous drainage, etc.). Two exemplary patients are described below Patient 1

Figure 11:
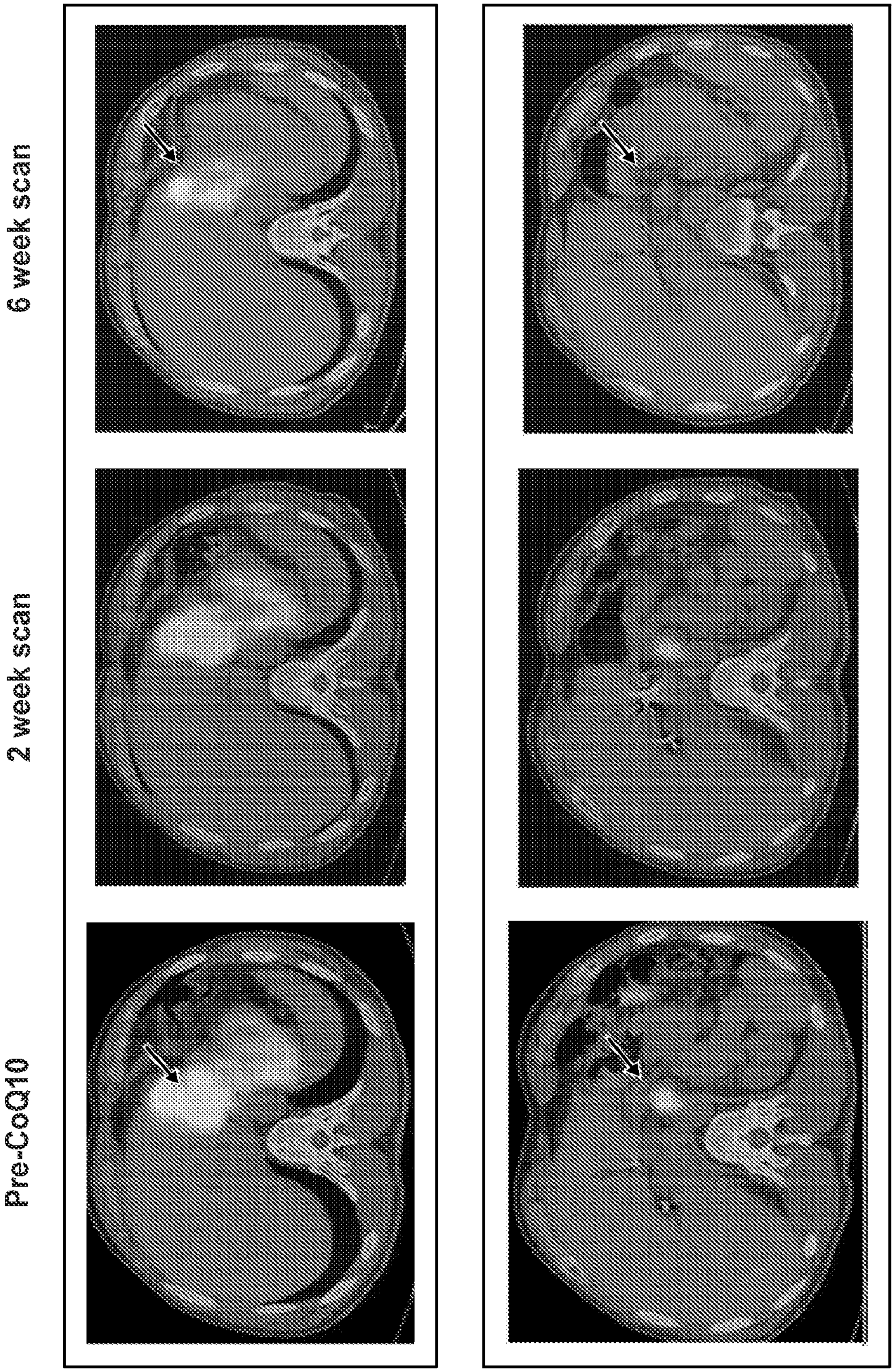
FIG. 11 shows a PET scan demonstrating early response to coenzyme Q10 at a 66 mg/kg/week dose in a relapsed, heavily pre-treated gastric cancer patient.

A 53 year-old Asian male with gastric adenocarcinoma with liver and lymph node metastases received Coenzyme Q10 at dose level 1 (66 mg/kg week). He was heavily previously treated, having received epirubicin, capecitabine, oxaliplatin, docetaxel, cisplatin and irinotecan. Radiographic PET response was identified at the end of two cycles with decrease on PET-SUV by 40% (see FIG. 11) with minimal changes in the size of the target lesion and disappearance of cervical lymph node metastases. This PET response was associated with clinical improvement in symptoms of early satiety. Multiomics tissue analysis demonstrated a switch from anaerobic driven markers to oxidative phosphorylation. Also a 15-fold increase in the intratumor concentration of Coenzyme Q11) was observed. The patient subsequently showed progression of disease after 4 additional weeks and was switched to the combination arm adding weekly docetaxel and again showed metabolic responses by PET/CT. The patient progressed after 2 cycles of the combination and was taken off the study after 6.5 months.

Patient 2

A 70 year old with metastatic bladder cancer to the abdomen/peritoneum, lung and bone was treated in the Gemcitabine/Coenzyme Q10 combo cohort at 66 mg/kg. Coenzyme Q10. The patient had received multiple previous therapies including radical cystoprostatectomy with cutaneous diversion, brachytherapy, and chemotherapy (pemetrex, MTX, docetaxel). The patient was doing well on the third cycle of treatment and was feeling better.

The Standardized Uptake Value (SUV) was increasing before therapy and at the 2-week scan. Week 10 PET scan showed that Omentum lesion 1 appeared less dense with no appreciable fluorodeoxyglucose (FDG) uptake. The Max SUV decreased to 0.8 from a previous value of 1.7. For Omentum lesion 2, the Max SUV decreased to 2.8 from 3.5, representing normal bowel uptake. For the Right iliac bone lesion, the Max SUV decreased to 1.9 from 2.3. There was a complete response in one of the non-target lesions in the abdomen. There was a continued decrease in degree of peritoneal disease with no definite identifiable FDG avid foci of peritoneal diseases currently identified.

The initial results described above indicate that Coenzyme Q10 appears safe and well tolerated in monotherapy and combination therapy, initial clinical and radiographic responses at low levels in monotherapy and combination therapy were seen in a variety of relapse/refractory, heavily pre-treated solid tumor patients. Multiomics tissue analysis demonstrated a switch from anaerobic driven markers to oxidative phosphorylation (i.e. reversal of the Warburg effect).

Example 7—A Phase 1a/b Non-Randomized, Dose Escalation Study of the Safety, Pharmacokinetics, and Pharmacodynamics of Sterile Coenzyme Q10 Nanosuspension Injection Administered Intravenously to Patients with Solid Tumors-144-Hour (6 Day) Continuous Infusion A phase 1 clinical trial evaluating a 144-hour (6 day) continuous infusion of coenzyme Q10 for treatment of solid tumors is earned out. Coenzyme Q10 is administered as a monotherapy (Arm 1) or in combination with chemotherapy (Arm 2). The coenzyme Q10 is provided as a 4% coenzyme Q10 nanosuspension formulation as described in WO 2011/112900, the entire contents of which are expressly incorporated herein by reference. The study is an open label, non-randomized dose-escalation study. The estimated enrollment is 45 patients for monotherapy (Arm 1), and up to 120 patients for combination therapy (Arm 2).

The study is designed with a longer dosing schedule (144-hour infusion) compared to the study described in Examples 5 and 6 (96-hour infusion). This extended dosing schedule is designed to further decrease coenzyme Q10 $C_{max}$ values and maintain coenzyme Q10 steady state levels for longer periods. Without being bound by mechanism, it is proposed that the prolonged dosing schedule and/or decreased infusion rates avoid potential toxicity presumably related to high $C_{max}$ levels, thereby increasing the therapeutic range of coenzyme Q10 administered over a shorter dosing period and/or at a higher rate of infusion.

A dosing schedule of two 72-hour doses is used. For the first 72-hour dose, a loading dose over 1 hour is followed by infusion of the remainder of the dose over 71 hours at a lower rate. The patient returns to the clinic toward the end of the first 72-hour treatment and the patient is reassessed. If the patient continues to meet the requirements for coenzyme Q10 treatment, the infusion pump is refilled with a second 72-hour dose for administration at a uniform rate at home.

The treatment arms are as follows:

Arm 1 (Coenzyme Q10 monotherapy) Patients who meet eligibility parameters receive 2 consecutive 72-hour infusions of coenzyme Q10 twice weekly on Tuesday and Friday (i.e., Days 1, 4, 8, 11, 15, 18, 22, and 25), essentially receiving coenzyme Q10 treatment for 144 hours per week of each 28-day cycle.

Arm 2 (Coenzyme Q10 in combination with chemotherapy)

Upon safe completion of a coenzyme Q10 dose level as monotherapy, treatment Arm 2 is enrolled and patients are treated with coenzyme Q10 at the evaluated and confirmed safe dose in combination with one of 3 chemotherapies:

Gemcitabine IV once weekly at a starting dose of 600 $mg/m^2$;

5-Fluorouracil (5-FU) IV once weekly at a starting dose of 350 $mg/m^2$ with leucovorin (LV) 100 mg/m2;

Docetaxel IV once weekly at a starting dose of 20 $mg/m^2$

Cycle 1 of combination therapy (Arm 2) is 6 weeks in duration for patients with coenzyme Q10 administered twice weekly on Tuesday and Friday for 6 weeks and chemotherapy administered on Mondays, Days 21, 28 and 35. Cycles 2-12 are 4 weeks in duration with coenzyme Q10 administered twice weekly on Tuesday and Friday for 4 weeks and chemotherapy administered on Mondays, Days 7, 14 and 21.

Study Objectives

The primary objectives of the study are to determine the maximum tolerated dose (MTD) and assess the safety and tolerability of monotherapy coenzyme Q10 and coenzyme Q10 in combination with chemotherapy when administered as a 144-hour intravenous (IV) infusion in patients with solid tumors.

The secondary objective is to evaluate plasma pharmacokinetics (PK) and estimate renal clearance of coenzyme Q10 monotherapy and coenzyme Q10 in combination with chemotherapy when administered as a 144-hour IV infusion in patients with solid tumors.

The exploratory objectives are:

To evaluate the pharmacodynamic (PD) correlates of coenzyme Q11) activity in plasma as monotherapy and in combination with chemotherapy.

To evaluate the elects of coenzyme Q10 on shifting tumors to aerobic respiration by PET imaging To assess tumor vascularity (using DCE-MRI) in at least 6 subjects who received coenzyme Q10 at the MTD, within 24 hours pre-dose and post-dose.

To evaluate tumor response (preliminary antitumor activity) after repeat administration of coenzyme Q10.

To assess progression-free survival (PFS) and time to progression (TTP) for each treatment group.

To compare myelosuppression recorded for the combination treatment arm to historical data for each treatment.

To assess long-term safety and tolerability of coenzyme Q10 after repeat administration as monotherapy and in combination with chemotherapy.

Study Eligibility Criteria

Inclusion Criteria:

Patients must meet the following criteria in order to be included in the clinical trial:

1. The patient has a histologically confirmed solid tumor that is metastatic or unresectable for which standard measures do not exist or are no longer effective. (Patients with primary brain cancer or lymphoma are permitted. Patients with brain metastases are allowed if whole brain radiation was performed and is documented stable for ≥6 weeks).
2. The patient is at least 18 years old.
3. The patient has an Eastern Cooperative Oncology Group (ECOG) performance status≤2.
4. The patient has a life expectancy of >3 months
5. Sexually active patients and their partners agree to use an accepted method of contraception during the course of the study.
7. Female patients of childbearing potential must have a negative pregnancy test within 1 week prior to beginning study treatment.
8. The patient has adequate organ and marrow function as follows:

ANC≥1500 mm3, platelets≥100,000/mm3, hemoglobin≥9 g/dL, serum creatinine≤1.8 mg/dL or creatinine clearance>50 mL/min;

bilirubin≤1.5 mg/dL; alanine aminotransferase (ALT), aspartate transaminase (AST)≤2.5 times the upper limit of normal if no liver involvement or ≤5 times the upper limit of normal with liver involvement.

9. The patient has serum electrolytes (including calcium, magnesium, phosphorous, sodium and potassium) within normal limits (supplementation to maintain normal electrolytes is allowed).
11. The patient has adequate coagulation: prothrombin time (PT) and an International Normalized and partial thromboplastin time (PTT)≤1.5 times the upper limit of normal.

12 The patient is capable of understanding and complying with the protocol and has signed the informed consent document.

Exclusion Criteria:

The patient is excluded from study participation if any of the following criteria are met:

1. The patient has uncontrolled intercurrent illness including, but not limited to uncontrolled infection, symptomatic congestive heart failure (NYHA class III and IV), uncontrolled cardiac arrhythmia, or psychiatric illness/social situations that would limit compliance with study requirements.

2. The patient has active heart disease including myocardial infarction within previous 3 months, symptomatic coronary artery disease, arrhythmias not controlled by medication, unstable angina pectoris, or uncontrolled congestive heart failure (NYHA class III and IV).

3 The patient has received chemotherapy or radiotherapy within 4 weeks prior to the first dose of study drug.

4. The patient has received radiation to ≥25% of his or her bone marrow within 4 weeks of the first dose of study drug.
5. The patient has received an investigational drug within 30 days of the first dose of study drug.
6. The patient has not recovered to grade≤1 adverse events (AEs) due to investigational drugs or other medications, administered more than 2 weeks prior to the first dose of study drug, with the exception of neurotoxicity attributed to oxaliplatin or taxanes, which must have recovered to <2 prior to study initiation.
7. The patient is pregnant or lactating.
8. The patient is known to be positive for the human immunodeficiency virus (HIV). The effect of coenzyme Q10 on HIV medications is unknown. Note: HIV testing is not required for eligibility, but if performed previously and was positive, the patient is ineligible for the study.

9. The patient has an inability or unwillingness to abide by the study protocol or cooperate fully with the investigator or designee
10. The patient is receiving digoxin, digitoxin, lanatoside C or any type of digitalis alkaloids.
11. The patient is receiving colony stimulating factors (CSFs) that cannot be held during the monitoring period for dose-limiting toxicities (DLT).
12. The patient has uncontrolled or severe coagulopathies or a history of clinically significant bleeding within the past 6 months, such as hemoptysis, epistaxis, hematochezia, hematuria, or gastrointestinal bleeding.
13. The patient has a known predisposition for bleeding such as von Willebrand's disease or other such condition.
14 The patient requires therapeutic doses of any anticoagulant, including low molecular weight heparin (LMWH). Concomitant use of warfarin, even at prophylactic doses, is prohibited.

Assessment of measurable lesions to determine eligibility are based on the criteria described in Example 4, Tables 3 and 4.

Trial Design

A phase 1 clinical trial for treatment of solid tumors using coenzyme Q10 monotherapy and coenzyme Q10 in combination with chemotherapy is carried out. The study is a multicenter, open-label, non-randomized, dose-escalation study to examine the dose limiting toxicities (DLT) of coenzyme Q10 administered as a 144-hour continuous intravenous (IV) infusion as monotherapy (treatment Arm 1) and in combination with chemotherapy (treatment Arm 2) in patients with solid tumors. In the Phase 1a portion of the trial, patients who meet eligibility parameters receive 2 consecutive 72-hour infusions of coenzyme Q10 twice weekly on Tuesday and Friday (i.e., Days 1, 4, 8, 11, 15, 18, 22, and 25), essentially receiving coenzyme Q10 treatment for 144 hours per week of each 28-day cycle. At each dose level of Arm 1 and Arm 2, patients are treated for either 8 hours at minimum of outpatient monitoring or inpatient monitoring for the first 24-hrs of the first infusion of Cycle 1. All other treatments are administered in an outpatient setting. Dose limiting toxicities are assessed during Cycle 1.

The study is a standard 3+3 dose escalation design with the dose escalated in successive cohorts of 3 to 6 patients each. Toxicity at each dose level is graded according to National Cancer Institute Common Terminology Criteria for Adverse Events (CTCAE v4.02). Safety oversight is provided by the Cohort Review Committee (CRC). The CRC reviews and confirms all DLTs and continue to monitor safety throughout the study (including Arm 2).

Assessments of the antitumor activity of coenzyme Q10 are performed at the end of Cycle 2 and every 2 cycles thereafter using standard techniques such as computerized tomography (CT) or magnetic resonance imaging (MRI) for patients with measurable disease. Response is evaluated using Response Evaluation Criteria in Solid Tumors (RECIST) v1.1. Patients who experience no unacceptable toxicity or disease progression, may receive additional 28-day cycles for up to 1 year on Arm 1 or 2. Patients on Arm 1 who progress may elect to continue coenzyme Q10 treatment in combination with gemcitabine, 5-FU, or docetaxel at the treating physician's discretion. Once a dose level of coenzyme Q10 monotherapy is evaluated and the CRC determines it safe to escalate to the next dose level, Cohort 1 of Treatment Arm 2 of coenzyme Q10 in combination with chemotherapy opens to accrual. Cohort 1 of Arm 2 patients are enrolled onto one of 3 chemotherapies, gemcitabine, 5-FU, or docetaxel. Cycle 1 of combination therapy (Arm 2) is 6 weeks in duration for patients with coenzyme Q10 administered twice weekly on Tuesday and Friday for 6 weeks and chemotherapy administered on Mondays, Days 21, 28 and 35. Cycles 2-12 are 4 weeks in duration with coenzyme Q10 administered twice weekly on Tuesday and Friday, for 4 weeks and chemotherapy administered on Mondays, Days 7, 14 and 21 Dose limiting toxicities are assessed during Cycle 1. Response is assessed after Cycle 2 (10 weeks) and responders who continue onto Cycles 2-12 are assessed every 2 cycles (8 weeks). Patients who progress and crossover to Arm 2 are reconsented and must meet eligibility before restarting coenzyme Q10. Crossover patients are not evaluated for DLTs on Arm 2 and all cycles of combination therapy are 4 weeks in duration (Cycles 1-12). Coenzyme Q10 is administered twice weekly on Tuesdays and Fridays for 4 weeks and chemotherapy administered on Mondays, Days 7, 14 and 21 for all crossover patients on Arm 2. Patients continue coenzyme Q10 in combination with chemotherapy for a maximum of 12 cycles in the absence of intolerable toxicity and progression. Patients on Arm 2 who progress on one type of chemotherapy may not switch to one of the other chemotherapy agents in combination with coenzyme Q10. However, if the chemotherapy component (i.e., 5-FU, gemcitabine, or docetaxel) of combination therapy is discontinued due to chemotherapy-related toxicity, patients may continue to receive coenzyme Q10 as monotherapy.

Once the maximum tolerated doses (MTD) of coenzyme Q10 as monotherapy and in combination with chemotherapy are established, an expansion cohort is enrolled (a total of 12-15 patients for monotherapy and a total of 10 patients for each combination therapy).

PK/PD Assessments

Safety observations and measurements including study drug exposure, adverse events, laboratory data (hematology, coagulation, serum chemistry, urinalysis), vital signs, ECOG performance status, and concomitant medications are assessed.

Blood samples for pharmacokinetic (PK) and pharmacodynamics (PD) analyses are collected during coenzyme Q10 monotherapy and combination therapy. The Cycle 1 samples are analyzed for plasma concentrations and PK parameters of coenzyme Q10; samples collected in Cycles 2-12 are analyzed for evidence of coenzyme Q10 accumulation. Urine samples for analysis of renal clearance of coenzyme Q10 are collected during Cycle 1 of monotherapy and combination therapy A PET scan is performed within 2 weeks prior to starting treatment and after 2 weeks of coenzyme Q10 treatment, and 8 weeks of treatment on Arm 1 or 10 weeks of treatment on Arm 2 Core biopsies (5) are performed at the time of baseline and at the end of Week 2 for patients who opt-in to participate in these exploratory studies. Patients who progress on Arm 1 and crossover to Arm 2 have PET scans and, if they consented, 5 core biopsies, performed within 2 weeks of restarting coenzyme Q10 and at Week 3. Core biopsies are prohibited with patients who have tumors that are highly vascular, located near major blood vessels or are proximal to vital organs.

Plasma and urine samples are assayed for levels of markers of coenzyme Q10 activity including, but not limited to, genomic (e.g., microarray, SAGE, northern blotting, gene expression), proteomic (e.g., LC/MS based analysis, 2DE-MS, MALDI TOF, antibody array, ELISA, immunohistochemistry, tissue microarray, flow cytometry, western blotting), metabolomic (e.g., global analysis of metabolites in biological samples; identification of specific markers of energy metabolism e.g., pyruvate, lactate), and lipidomic (e.g., global analysis of lipid classes: identification of specific lipids e.g., derivatives of palmitate, linoleic acid, arachidonic acid) analyses. These exploratory data are correlated with additional exploratory endpoints including PFS and TTP. Lastly, myelosuppression in combination therapy is compared to historical data for each chemotherapy regimen to evaluate whether coenzyme Q10 reduces or prevents myelosuppression induced by chemotherapy.

Response is assessed by standard methods such as CT, PIT/CT or MRI at Screening/Baseline, and every 2 treatment cycles (8 weeks) for patients on treatment Arm 1 or who progress and crossover to Arm 2 in the absence of progression and intolerable toxicity. Patients on treatment Arm 2 are assessed after Cycle 2 (10 weeks) and responders continue to be assessed every 2 cycles (8 weeks) thereafter in the absence of progression and intolerable toxicity. Evidence of antitumor activity is evaluated using RECIST response criteria for solid tumors as described herein.

Assessment of tumor metabolic activity (FDG-PET/CT) is done within 2 weeks of starting treatment with coenzyme Q10 and repeated after 2 weeks of treatment, and Y weeks of treatment on Arm 1 or 10 weeks of treatment on Arm 2. Core biopsies are collected at the time of baseline and at the end of Week 2 in patients that choose to participate. Patients who progress on Arm 1 and crossover to Arm 2 will have PET scans and, if they consented, 5 core biopsies, performed within 2 weeks of restarting coenzyme Q10 and at Week 3. Core biopsies are prohibited with patients who have tumors that are highly vascular, located near major blood vessels or are proximal to vital organs.

Number of Patients.

Up to 45 patients are enrolled onto treatment Arm 1 (the single-agent coenzyme Q10 dose escalation and expansion portion of the study), and up to 120 patients onto treatment Arm 2 (coenzyme Q10 in combination with chemotherapy dose escalation and expansion). The exact number is determined by the number of dose escalations until the MTD is reached. Therefore, up to 165 patients may be enrolled Investigational Drug Product The investigational drug product for use in clinical trials is a 4% (w/v) sterile coenzyme Q10 aqueous nanosuspension. It is intended to deliver a high dose of the active drug, coenzyme Q10 (ubidecarenone: 800 mg [20 mL] to 4000 mg [100 mL]) undiluted when administered as a single, slow 72-hour IV infusion. The drug product is produced using a microfluidization process which results in a stable nanosuspension with a mean particle sire of 30 to 80 nm. The nanosuspension formulation consists of 40 mg/mL (36.0 to 44.0 mg/mL) coenzyme Q10.

Trial Drugs, Dose, and Mode of Administration.

Coenzyme Q10 Nanosuspension Injection (40 mg/mL) is administered intravenously over 144 hours at the starting dose of 66 mg/kg. Each patient receives 2 consecutive 72-hour infusions of coenzyme Q10 twice weekly on Tuesday and Friday (i.e., Days 1, 4, 8, 11, 15, 18, 22, and 25), essentially receiving coenzyme Q10 treatment for 144 hours per week of each 28-day cycle. The dose may be escalated 25% in subsequent cohorts until the MTD is reached.

Upon safe completion of a coenzyme Q10 dose level as monotherapy, treatment Arm 2 enrolls and patients are treated with coenzyme Q10 at the evaluated and confirmed safe dose in combination with one of 3 chemotherapies:

Gemcitabine IV once weekly at a starting dose of 600 $mg/m^2$,

5-Fluorouracil (5-FU) IV once weekly at a starting dose of 350 $mg/m^2$ with leucovorin (LV) 100 mg/m2

Docetaxel IV once weekly at a starting dose of 20 $mg/m^2$

Continuous Infusion Administration Methods and Devices

Chemotherapeutic agents are administered using routine methods well known in the art. Exemplary devices and methods for continuous infusion of coenzyme Q10 are provided above in Example 5 and Table 11 Other devices and methods can accomplish the same outcome as those provided in Table 11, and these exemplary devices are not limiting.

Duration of Therapy

The minimum duration of therapy is 8 weeks (2 cycles) for treatment Arm 1 and 10 weeks for treatment Arm 2.

For patients who do not progress on single agent coenzyme Q10 treatment after 2 cycles (8 weeks), treatment may continue for up to 12 cycles or until any of the discontinuation criteria are met. Patients who progressed after 2 cycles (8 weeks) and do not have unacceptable toxicity may continue to receive coenzyme Q10 in combination with gemcitabine, 5-FU, or docetaxel for up to 12 cycles in the absence of progressive disease and intolerable toxicities.

For patients treated with the combination of coenzyme Q10 plus chemotherapy, treatment may continue for up to 12 cycles in the absence of progressive disease, unacceptable toxicity, or until any, of the discontinuation criteria are met. At the discretion of the Cohort Review Committee (CRC), eligible subjects may continue to receive coenzyme Q10 treatment beyond 1 year, under a separate protocol. Dose-Limiting Toxicity Adverse events are graded according to CTCAE v4.02. A copy of this grading scale can be accessed at the URL ctep.cancer.gov.

A dose-limiting toxicity (DLT) is defined as a clinically significant adverse event or abnormal laboratory value that is at least possibly related to coenzyme Q10 occurring during Cycle 1 that meets any of the following criteria:

A treatment-related AE that, in the opinion of the CRC, is of potential clinical significance such that further dose escalation would expose patients in higher dose cohorts to risk of irreversible medical harm or require medical treatment to avoid irreversible medical harm.

Any≥grade 3 non-hematologic toxicities that are at least possibly related to study drug with the exception of alopecia and grade 3 diarrhea, nausea, and vomiting that resolves to grade 2 or less within 48 hours of institution of supportive care.

Grade 3 thrombocytopenia with clinically significant bleeding.

Any≥grade 4 hematologic toxicities including, but not limited to, death, grade 4 anemia of any kind, grade 4 thrombocytopenia, grade 4 neutropenia of >5 days duration, or grade 4 neutropenia of any duration with fever or documented infection will all be considered DLI.

Grade 2 INR/PTT elevation with clinically significant bleeding.

Grade 3 INR/PTT abnormalities (with or without bleeding)

Concomitant elevations of transaminases and bilirubin that meet Hy's Law criteria Grade 3 electrolyte abnormalities.

Any grade 3 hypokalemia or hypomagnesemia if standard measures have not reduced these to a grade 2 or better in 7 days or less Grade 4 (life threatening) hypokalemia or hypomagnesemia of any duration.

Grade 3 deterioration of kidney and liver function of any duration.

Use of colony stimulating factors will not be allowed during the DLT monitoring period so as not to affect the assessment of DLT.

A table of non-limiting, standard laboratory assessments is provided below:

TABLE 12

Laboratory Panels.

| | |
|---|---|
| Hematology | CBC with differential, platelets |
| Coagulation | PT/PTT/INR (Screening only: Vitamin K) |
| Serum Chemistry | Albumin, alkaline phosphatase, ALT, AST, blood urea nitrogen (BUN), calcium, carbon dioxide, chloride, creatinine, gamma-glutamyl transferase (GGT), glucose, lactate dehydrogenase, phosphorus, potassium, sodium, total bilirubin, total protein, serum magnesium, cholesterol, triglycerides |
| Urinalysis | Appearance, color, pH, specific gravity, ketones, protein, glucose, bilirubin, nitrite, urobilinogen, and occult blood (microscopic examination of sediment are performed only if the results of the urinalysis dipstick evaluation are positive) |
| Laboratory work-up for any ≥grade 2 INR | LFTs, levels of Vitamin-K dependent coagulation factors (II, VII, IX, X), Protein C, and Protein S. If ≥grade 2 INR is not corrected following administration of Vitamin K, cryoprecipitate or fresh frozen plasma, additional tests such as mixing studies, fibrinogen level, D-dimer and fibrin split products are performed. |

Determination of DLT

The patient population used for determination of DLT consists of patients who have met the minimum safety evaluation requirements of the trial. To be considered eligible for DLT assessment during Cycle 1 of treatment, patients must either have had a DLT (irrespective of the number of doses received) or have completed the first cycle and received at least 75% of the scheduled doses of coenzyme Q10 for Arm 1 and Arm 2.

Patients who discontinue treatment early due to disease progression or withdrawal are asked to have all End-of-Treatment safety evaluations performed. If a patient withdraws from treatment during Cycle 1 due to any reason other than a DLT and does not meet the minimum safety evaluation requirements described above, that patient is replaced. Patients who progress on Arm 1 may crossover to Arm 2, however they are not evaluated for DLTs.

Maximum Tolerated Dose

The MTD is the highest dose at which≤1 of 6 patients experience a DLT during Cycle 1 (28 days for Arm 1 or 6 weeks for Arm 2) of coenzyme Q10 therapy. If 2 or more patients in a dosing group experience a DLT, the MTD has been exceeded.

Expansion after Determination of the MTD

In the 1/b portion of the study, a total of 12 to 15 patients are evaluated at the MTD for coenzyme Q10 monotherapy and up to 10 patients are reevaluated at the MID for coenzyme Q10 in combination with one of each chemotherapy to confirm the safety and tolerability. PK and PD of coenzyme Q10 at that dose.

Initiation of Combination Chemotherapy Cohort

Once a dose level of coenzyme Q10 monotherapy is evaluated and the CRC determines it safe to escalate to the next dose level, treatment Arm 2 of coenzyme Q10 in combination with chemotherapy is open to accrual at a reduced dose level. Arm 2 patients are enrolled onto one of 3 chemotherapies, gemcitabine, 5-FU, or docetaxel according to the dose levels provided herein. Cycle 1 is 6 weeks in duration for Arm 2 patients with coenzyme Q10 administered twice weekly on Tuesdays and Fridays for 6 weeks and chemotherapy administered on Mondays. Days 21, 28 and 35. Cycles 2-12 are 4 weeks in duration with coenzyme Q10 administered twice weekly on Tuesdays and Fridays for 4 weeks and chemotherapy administered on Mondays, Days 7, 14 and 21 Dose limiting toxicities are assessed during Cycle 1. Response is assessed after Cycle 2 (10 weeks) and responders who continue onto Cycles 2-12 are assessed every 2 cycles (8 weeks). Patients continue coenzyme Q10 in combination with chemotherapy fix a maximum of 12 cycles in the absence of intolerable toxicity and progression.

Once the first Arm 2 dose level is evaluated, subjects on Arm 1 who progress may elect to continue coenzyme Q10 treatment in combination with gemcitabine, 5-FU, or docetaxel at the treating physician's discretion. Patients who progress and crossover to Arm 2 are reconsented and must meet eligibility before restarting coenzyme Q10. Crossover patients are not evaluated for DLTs on Arm 2 and all cycles of combination therapy are 4 weeks in duration (Cycles 1-12) coenzyme Q10 is administered twice weekly on Tuesday and Friday for 4 weeks and chemotherapy administered on Fridays. Days 7, 14 and 21 for all crossover patients on Arm 2. Response is assessed every 2 cycles (8 weeks). Patients continue coenzyme Q10 in combination with chemotherapy fix a maximum of 12 cycles in the absence of intolerable toxicity and progression.

Dose Cohorts

Single Agent Coenzyme Q10 (Treatment Arm 1)

The starting dose level of coenzyme Q10 is 66 mg/kg administered by IV infusion over 72 hours 2 times per week of each 28-day cycle (Table 2). The 2 doses are administered over 6 consecutive days. The study drug is administered undiluted via a central venous access device and the infusion rate is controlled by a programmable ambulatory infusion pump such as the CADD Prizm VIP (model 6101) ambulatory pump.

For the first dose of each week (i.e., on Days 1, 8, 15, and 22 of the cycle) a loading dose (approximately 8.2% of the total volume) is infused over 1 hour with the remainder of the dose volume infused over 71 hours as indicated in Table 13 below. At each dose level of Arm 1 and Arm 2, patients are treated for either 8 hours at minimum of outpatient monitoring or inpatient monitoring for the first 24-hrs of the first infusion of Cycle 1. Patients are monitored for dose-limiting toxicity (DLT) or an AE that requires prolonged hospitalization. If no reaction to coenzyme Q11) develops, the patient is discharged.

For the second dose of each week (i.e., on Days 4, 11, 18, and 25 of the cycle) the total dose volume is given over 72 hours with no loading dose. If the first dose of the week is missed or held, the second dose is still given over 72 hours with no loading dose.

Patients are dosed at their assigned dose cohort for the duration of their treatment. Intra-patient dose escalation is not allowed. If the starting dose of 66 mg/kg exceeds the MTD of coenzyme Q10, the dose is reduced to 50 mg/kg for Cohort−1. No more than 2 dose reductions are allowed during the study. The minimum dose is Dose Level −1.

TABLE 13A

Coenzyme Q10 Nanosuspension Infusion Dose Cohorts (Arm 1; Monotherapy)

| Cohort | Total Coenzyme Q10 Dose (2X per week) | Dose 1 (Tuesday) Loading Dose to be Infused over 1 hr. (8.2% of dose) | Dose 1 (Tuesday) Remainder to be Infused over 71 hrs. | Dose 2 (Friday) | Total Coenzyme Q10 Dose per week |
|---|---|---|---|---|---|
| −1 | 50 mg/kg | 4.1 mg/kg | 45.9 mg/kg | 50 mg/kg | 100 mg/kg |
| 1 | 66 mg/kg | 5.4 mg/kg | 60.6 mg/kg | 66 mg/kg | 132 mg/kg |
| 2 | 88 mg/kg | 7.2 mg/kg | 80.8 mg/kg | 88 mg/kg | 176 mg/kg |
| 3 | 110 mg/kg | 9.0 mg/kg | 101.0 mg/kg | 110 mg/kg | 220 mg/kg |
| 4 | 137 mg/kg | 11.2 mg/kg | 125.8 mg/kg | 137 mg/kg | 274 mg/kg |
| 5 | 171 mg/kg | 14.0 mg/kg | 157.0 mg/kg | 171 mg/kg | 342 mg/kg |
| 6 | 215 mg/kg | 17.6 mg/kg | 197.4 mg/kg | 215 mg/kg | 430 mg/kg |

TABLE 13B

Coenzyme Q10 Nanosuspension Infusion Dose Rates (Arm 1; Monotherapy)

| Cohort | Total Coenzyme Q10 Dose (2X per week) | Dose 1 (Tuesday) Loading Dose Rate (1 hr) | Dose 1 (Tuesday) Remainder Dose Rate (71 hrs.) | Dose 2 (Friday) Dose Rate (72 hrs.) | Total Coenzyme Q10 Dose per week |
|---|---|---|---|---|---|
| −1 | 50 mg/kg | 4.1 mg/kg/hr | 0.65 mg/kg/hr | 0.69 mg/kg/hr | 100 mg/kg |
| 1 | 66 mg/kg | 5.4 mg/kg/hr | 0.85 mg/kg/hr | 0.92 mg/kg/hr | 132 mg/kg |
| 2 | 88 mg/kg | 7.2 mg/kg/hr | 1.14 mg/kg/hr | 1.22 mg/kg/hr | 176 mg/kg |
| 3 | 110 mg/kg | 9.0 mg/kg/hr | 1.42 mg/kg/hr | 1.53 mg/kg/hr | 220 mg/kg |
| 4 | 137 mg/kg | 11.2 mg/kg/hr | 1.77 mg/kg/hr | 1.90 mg/kg/hr | 274 mg/kg |
| 5 | 171 mg/kg | 14.0 mg/kg/hr | 2.21 mg/kg/hr | 2.38 mg/kg/hr | 342 mg/kg |
| 6 | 215 mg/kg | 17.6 mg/kg/hr | 2.78 mg/kg/hr | 2.99 mg/kg/hr | 430 mg/kg |

TABLE 13C

Coenzyme Q10 Nanosuspension Infusion Dose Per Day (Arm 1; Monotherapy)

| Cohort | Total Coenzyme Q10 Dose (2X per week) | Dose per day (Tues.) | Dose per day (Wed./Thurs.) | Dose per day (Fri./Sat./Sun.) |
|---|---|---|---|---|
| −1 | 50 mg/kg | 19.05 mg/kg | 15.60 mg/kg | 16.67 mg/kg |
| 1 | 66 mg/kg | 24.95 mg/kg | 20.40 mg/kg | 22.00 mg/kg |
| 2 | 88 mg/kg | 33.42 mg/kg | 27.36 mg/kg | 29.33 mg/kg |
| 3 | 110 mg/kg | 41.66 mg/kg | 34.08 mg/kg | 36.67 mg/kg |
| 4 | 137 mg/kg | 51.91 mg/kg | 42.48 mg/kg | 45.67 mg/kg |
| 5 | 171 mg/kg | 64.83 mg/kg | 53.04 mg/kg | 57.00 mg/kg |
| 6 | 215 mg/kg | 81.54 mg/kg | 66.72 mg/kg | 71.67 mg/kg |

Treatment Arm 2 Combination Chemotherapy

Once a dose level of coenzyme Q10 monotherapy is evaluated and the CRC determines it safe to escalate to the next dose level, Arm 2 of coenzyme Q10 in combination with chemotherapy is open to accrual at a reduced dose level (see Table 14A below). A standard 3+3 design is used for Arm 2 of the study, and the definition of DU is the same as that used in Arm 1. Coenzyme Q10 is started at one dose level below the dose that has been studied and determined to be safe in the monotherapy portion of the trial. Arm 2 patients are enrolled onto one of 3 chemotherapies, gemcitabine, 5-FU, or docetaxel according to the dose levels below and the following schedule (see Tables 14-17).

Gemcitabine IV once weekly at a starting dose of 600 mg/m2;

5-Fluorouracil (5-FU) IV once weekly at a starting dose of 350 $mg/m^2$ with leucovorin (LV) 100 mg/m2, OR Docetaxel IV once weekly at a starting dose of 20 $mg/m^2$.

Note: Both coenzyme Q10 and the chemotherapy agent can escalate simultaneously in Cohorts 3 and 4 only if there are no DLTs observed in the previous cohorts. If one or more DLTs are observed, then intermediate dose levels are added where one agent is escalated.

Once assigned, patients may not switch to an alternative cohort. Arm 2 is expanded at the MTD dose to 10 patients for each chemotherapy combination to ensure safety and for additional PK modeling (a total of 30 additional patients). Note: Patients on Arm 2 who progress on one type of chemotherapy may not switch to one of the other chemotherapy agents in combination with coenzyme Q10. However, if the chemotherapy component (ie, 5-FU, gemcitabine, or docetaxel) of combination therapy is discontinued due to chemotherapy-related toxicity, patients may continue to receive coenzyme Q10 as monotherapy.

Cycle 1 is 6 weeks in duration for Arm 2 patients. Coenzyme Q10 is administered twice weekly on Tuesdays and Fridays for 6 weeks and chemotherapy administered on Mondays, Days 21, 28 and 35 Chemotherapy is administered by IV infusion over 30 minutes at the clinic. Dose limiting toxicities are assessed during Cycle 1. Response is assessed after Cycle 2 (10 weeks) and responders who continue onto Cycles 3-12 are assessed even 2 cycles (8 weeks). Cycles 2-12 are 4 weeks in duration with coenzyme Q10 administered twice weekly on Tuesdays and Fridays for 4 weeks and chemotherapy administered on Mondays. Days 7, 14 and 21. For subjects on an alternate dosing schedule, the chemotherapy treatment is given after the completion of the sixth infusion.

TABLE 14A

Coenzyme Q10 Nanosuspension Infusion Dose Cohorts (Arm 2; Combination Therapy)

| Cohort | Total Coenzyme Q10 Dose (2X per week) | Dose 1 (Monday) Loading Dose to be Infused over 1 Hour (8.2% of dose) | Dose 1 (Monday) Remainder to be Infused Over 71 hrs. | Dose 2 (Friday) | Total Coenzyme Q10 Dose per week |
|---|---|---|---|---|---|
| −1 | 38 mg/kg | 3.1 mg/kg | 34.9 mg/kg | 38 mg/kg | 76 mg/kg |
| 1 | 50 mg/kg | 4.1 mg/kg | 45.9 mg/kg | 50 mg/kg | 100 mg/kg |
| 2 | 66 mg/kg | 5.4 mg/kg | 60.6 mg/kg | 66 mg/kg | 132 mg/kg |
| 3 | 88 mg/kg | 7.2 mg/kg | 80.8 mg/kg | 88 mg/kg | 176 mg/kg |
| 4 | 110 mg/kg | 9.0 mg/kg | 101.0 mg/kg | 110 mg/kg | 220 mg/kg |
| 5 | 137 mg/kg | 11.2 mg/kg | 125.8 mg/kg | 137 mg/kg | 274 mg/kg |
| 6 | 171 mg/kg | 14.0 mg/kg | 157.0 mg/kg | 171 mg/kg | 342 mg/kg |

TABLE 14B

Coenzyme Q10 Nanosuspension Infusion Dose Rates (Arm 2; Combination Therapy)

| Cohort | Total Coenzyme Q10 Dose (2X per week) | Dose 1 (Monday) Loading Dose Rate (1 hr.) | Dose 1 (Monday) Remainder Dose Rate (71 hrs.) | Dose 2 (Friday) Dose Rate (72 hrs.) | Total Coenzyme Q10 Dose per week |
|---|---|---|---|---|---|
| −1 | 38 mg/kg | 3.1 mg/kg/hr | 0.49 mg/kg/hr | 0.53 mg/kg/hr | 76 mg/kg |
| 1 | 50 mg/kg | 4.1 mg/kg/hr | 0.65 mg/kg/hr | 0.69 mg/kg/hr | 100 mg/kg |
| 2 | 66 mg/kg | 5.4 mg/kg/hr | 0.85 mg/kg/hr | 0.92 mg/kg/hr | 132 mg/kg |
| 3 | 88 mg/kg | 7.2 mg/kg/hr | 1.14 mg/kg/hr | 1.22 mg/kg/hr | 176 mg/kg |
| 4 | 110 mg/kg | 9.0 mg/kg/hr | 1.42 mg/kg/hr | 1.53 mg/kg/hr | 220 mg/kg |
| 5 | 137 mg/kg | 11.2 mg/kg/hr | 1.77 mg/kg/hr | 1.90 mg/kg/hr | 274 mg/kg |
| 6 | 171 mg/kg | 14.0 mg/kg/hr | 2.21 mg/kg/hr | 2.38 mg/kg/hr | 342 mg/kg |

TABLE 14C

Coenzyme Q10 Nanosuspension Infusion Daily Doses (Arm 2; Combination Therapy)

| Cohort | Total Coenzyme Q10 Dose (2X per week) | Dose per day (Tues.) | Dose per day (Wed./Thurs.) | Dose per day (Fri./Sat./Sun.) |
|---|---|---|---|---|
| −1 | 38 mg/kg | 14.37 mg/kg | 11.76 mg/kg | 12.67 mg/kg |
| 1 | 50 mg/kg | 19.05 mg/kg | 15.60 mg/kg | 16.67 mg/kg |
| 2 | 66 mg/kg | 24.95 mg/kg | 20.40 mg/kg | 22.00 mg/kg |
| 3 | 88 mg/kg | 33.42 mg/kg | 27.36 mg/kg | 29.33 mg/kg |
| 4 | 110 mg/kg | 41.66 mg/kg | 34.08 mg/kg | 36.67 mg/kg |
| 5 | 137 mg/kg | 51.91 mg/kg | 42.48 mg/kg | 45.67 mg/kg |
| 6 | 171 mg/kg | 64.83 mg/kg | 53.04 mg/kg | 57.00 mg/kg |

For patients treated in combination % kith gemcitabine, the current dose levels are listed in Table 15 below as 600 mg/m$^2$, 800 mg/m$^2$, and 1000 mg/m$^2$. A patient receiving gemcitabine, may experience a platelet count decrease below 75,000/mm$^3$ as this is an expected toxicity. Gemcitabine must be held until platelet count improves to >75,000/mm upon which gemcitabine may continue at a dose reduction. Coenzyme Q10 may continue unless there is a grade 3 or 4 hematologic toxicity with the exception of INR, which must be normal. The CTCAE v4.0 defines grade 3 platelet count decrease as <30,000-25,000/mm$^3$. Therefore, patients with grade 1 or 2 platelet count decrease may continue coenzyme Q10, but should be monitored closely. Patients receiving 600 mg/m$^2$ experiencing a platelet count decrease may be dose reduced to 500 mg/m$^2$ and coenzyme Q10 dose continue without a dose reduction. If a patient's platelets decreases below 75,000/mm$^3$ at 500 mg/m$^2$, the patient will be discontinued from gemcitabine treatment. The patent may continue to receive coenzyme Q10 as monotherapy in the absence of intolerable toxicities and disease progression.

TABLE 15

Arm 2 Combination of Coenzyme Q10 and Gemcitabine Cohort

| | Gemcitabine Dose | Coenzyme Q10 Dose |
|---|---|---|
| −1 Gemcitabine | 500 mg/m$^2$ | 50 mg/kg |

TABLE 15-continued

Arm 2 Combination of Coenzyme Q10 and Gemcitabine Cohort

| | Gemcitabine Dose | Coenzyme Q10 Dose |
|---|---|---|
| −1 Coenzyme Q10 | 600 mg/m$^2$ | 38 mg/kg |
| 1 | 600 mg/m$^2$ | 50 mg/kg |
| 2 | 600 mg/m$^2$ | 66 mg/kg |
| 3 | 800 mg/m$^2$ | 88 mg/kg |
| 4 | 1000 mg/m$^2$ | 110 mg/kg |
| 5 | 1000 mg/m$^2$ | 137 mg/kg |
| 6 | 1000 mg/m$^2$ | 171 mg/kg |

TABLE 16

Arm 2 Combination of Coenzyme Q10 and 5-Fluorouracil

| Cohort | 5-FU + Leucovorin Dose [a] | Comzyme Q10 Dose |
|---|---|---|
| −1 | 350 $mg/m^2$/LV 100 $mg/m^2$ | 38 mg/kg |
| 1 | 350 $mg/m^2$/LV 100 $mg/m^2$ | 50 mg/kg |
| 2 | 350 $mg/m^2$/LV 100 $mg/m^2$ | 66 mg/kg |
| 3 | 450 $mg/m^2$/LV 100 $mg/m^2$ | 88 mg/kg |
| 4 | 500 $mg/m^2$/LV 100 $mg/m^2$ | 110 mg/kg |
| 5 | 500 $mg/m^2$/LV 100 $mg/m^2$ | 137 mg/kg |
| 6 | 500 $mg/m^2$/LV 100 $mg/m^2$ | 171 mg/kg |

[a] Leucovorin may be administered prior to 5-FU or both drugs may be given concurrently.

TABLE 17

Arm 2 Combination of Coenzyme Q10 and Docetaxel

| Cohort | Docetaxel Dose | Coenzyme Q10 Dose |
|---|---|---|
| −1 | 20 $mg/m^2$ | 38 mg/kg |
| 1 | 20 $mg/m^2$ | 50 mg/kg |
| 2 | 20 $mg/m^2$ | 66 mg/kg |
| 3 | 25 $mg/m^2$ | 88 mg/kg |
| 4 | 30 $mg/m^2$ | 110 mg/kg |
| 5 | 30 $mg/m^2$ | 137 mg/kg |
| 6 | 30 $mg/m^2$ | 171 mg/kg |

Dose Escalation of Coenzyme Q10 Monotherapy (Arm 1) & Combination Therapy (Arm 2)

The study is a standard 3+3 design with the dose of coenzyme Q10 escalated in successive dose cohorts of 3 patients each. Up to 3 to 6 patients are dosed at each dose level and in no case will cohorts contain more than 6 patients. If none of the 3 patients in a cohort experiences DLT during Cycle 1, then 3 new patients may be entered at the next higher dose level following CRC review of safety and PK data from lower cohorts.

A cohort may be expanded up to 6 patients from the normal 3 patient accrual with approval of the CRC or if 1 of 3 patients experiences DLT. If 1 of 3 patients experiences a DLT in Cycle 1, the cohort is expanded up to 6 patients. If no additional patient experiences a DLT at that dose, the next cohort will open to accrual and the dose escalated. If 2 or more patients in a cohort experience DLT during Cycle 1, no further patients are started at that dose The dose for subsequent cohorts is escalated only after the safety of the previous dose level has been established.

Dose escalation occurs in 25% increments from the immediate prior dose group in the absence of DLTs at the previous dose level.

Instructions Regarding Coagulation Assessments Prior to Each Coenzyme Q10 Dose

Prior to administering each dose of coenzyme Q10, the PT % PTT, INR and platelet count is assessed and any clinically significant abnormal result reported.

Prophylactic Vitamin K is given to all patients prior to the beginning of each week of therapy, unless contraindicated as determined by the Investigator.

Coenzyme Q10 may be administered if the INR. PT, and PTT are ≤1.5 times the upper limit of normal and the platelet count is ≥50,000 $mm^3$.

Any PIT or INR value grade 2 requires immediate treatment with Vitamin K (oral, IV, IM, or SC), cryoprecipitate or fresh frozen plasma as clinically indicated and coenzyme Q10 held until the abnormal lab returns to normal limits from previous elevations.

Patients who develop ≥grade 2 INR any time during the study should undergo laboratory testing to determine the underlying cause. The workup should include: LFTs, levels of Vitamin K-dependent coagulation factors (II, VII, IX, X), Protein C, and Protein S. If the ≥grade 2 INR is not corrected following administration of Vitamin K, cryoprecipitate or fresh frozen plasma, as noted above, additional tests such as mixing studies, fibrinogen level, D-dimer and fibrin split products should be performed.

Hematologic Toxicity

The Baseline Laboratory Requirements are ANC≥1500 mm3, platelets≥100,000 mm3, hemoglobin≥9 g/dL and INR<1.5×UNL. Hematology and chemistry is preferably assessed weekly and coagulation should be repeated within 24-72 hours prior to initiation of each dose. Coenzyme Q10 must be held for any grade 3 or 4 hematologic toxicity that is at least possibly drug-related. Any grade 3 or 4 hematologic toxicity must return to a grade 1 or resolved with the exception of INR which must be <1.5×UNL prior to administration of coenzyme Q10 in Cycles 2-12. Coenzyme Q10 may be resumed at a reduced dose (see guidelines in Section 7.4.1 and 7.4.2 and Tables 2-6.)

To monitor and mitigate coenzyme Q110-associated coagulopathies. PT, PIT, INR and platelet count must be assessed prior to administering each dose of coenzyme Q10 Prophylactic Vitamin K will be given to all patients prior to the beginning of every week of therapy, unless contraindicated as determined by the Investigator. An INR value of ≥grade 2 requires immediate treatment with Vitamin K, cryoprecipitate or fresh frozen plasma as clinically indicated. Any AE must decrease to ≤grade 1 and the INR must be <1.5×UNL before resuming coenzyme Q10 treatment.

If a second adverse event of ≥grade 3 INR elevation occurs, coenzyme Q10 is permanently discontinued.

Coenzyme Q10 is permanently discontinued in patients who experience clinically significant bleeding in conjunction with a ≥grade 2 elevation in INR.

Non-Hematologic Toxicity

A grade 3 or 4 non-hematologic toxicity that is at least possibly drug-related must return to grade 1 or resolve prior to administration of coenzyme Q10 in Cycles 2-12. Coenzyme Q10 may be resumed at a reduced dose. Grade 3 fasting lipid abnormalities are an exception in the absence of clinical signs or symptoms. Coenzyme Q10 causes a false positive fasting lipid elevation. Abnormal fasting lipid profiles should be monitored closely however coenzyme Q10 may continue in the absence of clinical signs or symptoms.

Patients with toxicities that are manageable with supportive therapy may not require dose reductions. Patients requiring greater than 2 dose reductions of coenzyme Q10 should be withdrawn from the study.

Coenzyme Q10 administered according to the above-described six day continuous infusion dosing regimen is shown to be safe and well tolerated in monotherapy and combination therapy. Clinical and/or radiographic responses are seen in monotherapy and combination therapy in at least some patients.

Example 8—a Phase 1a/b Study of Coenzyme Q10 Alone or in Combination with Fludarabine and Cytarabine in Patients with Relapsed or Refractory Acute Myelogenous Leukemia (AML) or Acute Lymphoblastic Leukemia (ALL)

Treatment options for patients with relapsed and refractory AML or ALL are limited. Re-treatment with the initial induction/consolidation regimen is considered standard for patients whose disease relapses after a long initial remission. For patients whose disease relapses after a shorter remission or with primary refractory disease, no true standard options exist and investigational therapy is considered appropriate.

The combination of fludarabine and cytarabine was shown to be superior to cytarabine alone in patients with relapsed acute myelogenous leukemia (AML) who had a relatively long first remission. The effectiveness of fludarabine and cytarabine may be due to the ability of fludarabine to modulate the pharmacologic behavior of cytarabine. Both drugs have efficacy against acute lymphoblastic leukemia (ALL).

In the treatment of AML, an induction regimen comprising of an anthracycline and cytarabine followed by high dose cytarabine (HDAC)-based consolidation is standard therapy for patients with newly diagnosed AML (excluding acute promyelocytic leukemia). Allogeneic stem cell transplantation (SCT) in first remission should be considered for patients with intermediate or high-risk cytogenetics or poor-risk molecular features. For patients relapsing after an initial remission of over a year, reinduction with the same regimen or with HDAC is usual practice. No standard therapy options exist for patients who relapse within the first year of remission. Similarly for patients over the age of 60 years who are not fit to receive intensive induction therapy, no standard options are available even though hypomethylating agents are being used with limited success in this setting. Fludarabine and cytarabine combinations with or without anthracycline and/or G-CSF, eg., FLAG+1da are often used as salvage therapy and to bridge patients with relapsed/refractory AML to SCT.

In the treatment of ALL, multiagent chemotherapy combination for induction and consolidation followed by prolonged low intensity maintenance is standard frontline therapy fix ALL. Reinduction with similar regimen as used in induction may be used as salvage therapy for patients with long remissions. For patients with short remissions, no standard salvage approach exists. In the recent times immunotoxins have shown promising activity but remissions are mostly short lasting. Stem cell transplant (SCT) in second remission is considered the most effective therapy but many adult patients are not candidates for SCT for various reasons. Fludarabine has activity in lymphoid diseases and cytarabine is used in induction/consolidation therapy of ALL.

This study aims to investigate the safety and tolerability of single-agent coenzyme Q10 and in combination with fludarabine and cytarabine in relapsed/refractory AML or ALL. Using a modified toxicity probability interval (TPI) dose-finding approach this Phase I study aims to also establish the MTD of coenzyme Q10 as monotherapy and as combination therapy with fludarabine and cytarabine in these patient populations.

A human clinical trial is performed to assess the efficacy of continuous infusion coenzyme Q10 alone, or in combination with a chemotherapeutic regimen, in the treatment of leukemia, particularly acute leukemias including relapsed or refractory leukemias.

The objective of the study is to evaluate the safety, toxicity, and pharmacokinetics to treatment with continuous infusion of coenzyme Q10 alone or in combination with fludarabine and cytarabine in patients with relapsed/refractory AML or ALL.

Primary objectives include determination of clinical responses of coenzyme Q10 alone or in combination with fludarabine and cytarabine in patients with relapsed/refractory AML or ALL Secondary objectives include analysis of pharmacodynamic effects of coenzyme Q10 alone or in combination with fludarabine and cytarabine in patients with relapsed/refractory AML or ALL.

Exploratory objectives include assessment of progression-free survival (PFS) and time to progression (TTP) are assessed for each treatment group. Myelosuppression is also recorded for the combination treatment arm is compared to historical data for treatment with fludarabine and cytarabine alone.

Trial Design

This is a Phase 1a/b single-center, open-label, non-randomized, dose-escalation study to examine the dose limiting toxicities of coenzyme Q10 when administered as monotherapy or as combination therapy (with fludarabine and cytarabine) in patients with AML or ALL. This study is conducted in the inpatient setting for the first 10 patients enrolled on monotherapy to closely monitor the coagulation profile, gain experience and collect safety data during the first full cycle of therapy (21 days) and at least 30 days of post-dosing follow-up Platelet count and coagulation parameters are obtained every day in the inpatient setting. Coagulation data and information regarding the use of Vitamin K, plasma or other interventions are summarized in a report to FDA. If coagulation abnormalities are seen but do not lead to clinically significant bleeding events such as major hemoptysis, epistaxis requiring packing or cauterization, etc. then this data are shared with FDA. If the data from the first 10 patients confirm the safety of coenzyme Q10, and with FDA approval, the treatment setting for cycle 1 are changed to preferably outpatient. Treatment may continue in either the inpatient and/or outpatient setting for subsequent patients enrolled on study. Platelet count and coagulation are monitored at least 3 times/week in the outpatient setting and daily in the inpatient setting.

All patients receive coenzyme Q10 monotherapy for 1 cycle (21 days) and are then assessed for response. Patients who respond and experience no DLT's in cycle 1 continue coenzyme Q10 monotherapy until progression for a maximum of 12 cycles in the absence of intolerable toxicities. Each cycle of monotherapy is 21 days in length. Patients who do not achieve a response and experience no DLTs during cycle 1 of monotherapy proceed to receive cycle 1 of combination therapy at the dose level that is open for enrollment. Each cycle of combination therapy is 28 days in length. Patients who achieve a response and do not experience a DLT in cycle 1 of combination therapy may continue combination therapy as consolidation for a maximum of 5 cycles in the absence of intolerable toxicities. Patients who experience a DLT during cycle 1 of monotherapy or cycle 1 of combination therapy are discontinued.

While patients on combination therapy are being assessed for DLT, accrual to monotherapy may continue based on the escalation decision rule for cycle 1 The dose of coenzyme Q10 (for monotherapy and combination therapy) escalates or de-escalates based on the DLT experience of patients at the current dose. DLTs experienced at a dose level of monotherapy are considered a DLT for combination therapy at the same coenzyme Q10 dose level. If the first dose level of 58.7 mg/kg per 24 hours exceeds the MTD of coenzyme Q10, the dose will be reduced to Dose Level −1 (44 mg/kg per 24 hours). No more than 2 dose reductions are allowed during the study. The minimum Dose Level is −2 (33 mg/kg per 24 hours).

TABLE 18

Cohort Dose Levels for Coenzyme Q10 Nanosuspension for Injection

| Dose Level | Dose of coenzyme Q10 based on weight | Total volume of coenzyme Q10 (rounded to nearest mL)[1] | 25% of Total Dose[1] (rounded to nearest mL) | Day 1 Accelerated rate over 1 hour[1], | 23 hr. volume | Infusion Rate for Hours 2-24 | Infusion Rate for Day 2-18 |
|---|---|---|---|---|---|---|---|
| −2 | 33 mg/kg | 59 mL | 15 mL | 0.25 mL/min | 44 mL | 0.03 mL/min | 0.04 mL/min |
| −1 | 44 mg/kg | 77 mL | 19 mL | 0.32 mL/min | 58 mL | 0.04 mL/min | 0.05 mL/min |
| 1 | 58.7 mg/kg | 104 mL | 26 mL | 0.43 mL/min | 78 mL | 0.06 mL/min | 0.07 mL/min |
| 2 | 73.4 mg/kg | 131 mL | 33 mL | 0.55 mL/min | 98 mL | 0.07 mL/min | 0.09 mL/min |
| 3 | 91.7 mg/kg | 162 mL | 41 mL | 0.68 mL/min | 121 mL | 0.09 mL/min | 0.11 mL/min |
| 4 | 114.6 mg/kg | 203 mL | 51 mL | 0.85 mL/min | 152 mL | 0.11 mL/min | 0.14 mL/min |
| 5 | 143.3 mg/kg | 252 mL | 63 mL | 1.05 mL/min | 189 mL | 0.14 mL/min | 0.18 mL/min |

[1]Assuming 70 kg subject.

Pharmacokinetic (PK) blood and urine samples are collected from all patients receiving coenzyme Q10 monotherapy or combination therapy during cycle 1 as well as in subsequent cycles. Blood and bone marrow samples collected throughout the trial are analyzed for markers of coenzyme Q10 activity and other exploratory PD parameters; PFS, TTP and myelosuppression.

Patients are monitored after every 2 patients to assess their DLT experience. Toxicity at each dose level is graded according to National Cancer Institute Common Terminology Criteria for Adverse Events (CTCAE v4.02). Safety oversight is provided by the Data Safety Monitoring Board (DSMB) comprised of independent advisors with expertise in hematology, leukemia, and coagulopathy. The DSMB reviews and confirms all DLTs and determine appropriate dose escalations, reductions, and modifications based on safety and PK data from previous dose cohorts.

A maximum of 60 patients are planned. Up to 40 patients may be enrolled in the dose escalation phase. Following determination of the recommended expansion phase dose, that cohort will be expanded to a total of 20 patients, including those treated with monotherapy or Combination Therapy.

Coenzyme Q10 nanosuspension for injection (40 mg % mL) is administered intravenously (IV) over 24 hours at the starting dose of 58.7 mg/kg. Each dose of coenzyme Q10 is 18 consecutive days of infusion. Exemplary devices and methods for continuous infusion are provide in the prior example.

Fludarabine 15 mg/$m^2$ administered IV over 15-30 minutes±15 minutes, every 12 hours±2 hours).

Cytarabine 0.5 g/$m^2$ in NS 250 mL administered IV over 2 hours±20 minutes, every 12 hours±2 hours).

For patients who have a response to coenzyme Q10 monotherapy in cycle 1: monotherapy may continue for up to 12 cycles (provided neutrophil/platelet count parameters are met prior to each cycle) or until any of the discontinuation criteria are met.

For patients treated with combination therapy, if a patient achieves CR or CRi, the patient can receive additional consolidations (a total of 5 additional cycles of consolidation) with combination therapy. For patients with response less than CR/CRi or with no response, the patient can receive another treatment cycle of combination therapy if considered to be in the patient's best interest by the primary investigator (PI), Medical Monitor, and Chair of the DSMB. If such a patient achieves CR/CRi the patient can receive additional consolidations (a total of 4 additional cycles of consolidation) with combination therapy.

Patient Criteria

Patients must meet the following criteria in order to be included in the clinical trial:

1. Dose Escalation Phase: Patients must have relapsed/refractory AML or ALL for which no standard therapies are anticipated to result in a durable remission.

Expansion Phase:

2 ECOG performance status of 0-3. ECOG assessment should be done prior to Cycle 1 of both monotherapy and combination therapy. Patients with ECOG performance status >3 after cycle 1 monotherapy will not be eligible to receive cycle 1 of combination therapy (see Enrollment to the Phase 1b part of study will be limited to patients with AML or ALL) and failing or relapsing after up to 2 prior therapies (Salvage 1 or 2). Based on response profile, the expansion cohort may be restricted to subgroups of patients among the above diagnosis groups.

3. The patient is at least 18 years old.
4. The patient has a life expectancy of >3 months.
5. Women of childbearing potential (i.e., pre-menopausal or not surgically sterile) must use acceptable contraceptive methods (abstinence, intrauterine device oral contraceptive or double barrier device), and must have a negative serum or urine pregnancy test within 1 week prior to beginning study treatment. Sexually active men who have partners with childbearing potential must also use acceptable contraceptive methods for the duration of time on study.
6. In the absence of rapidly progressing disease, the interval from prior treatment to time of study drug administration should be at least 2 weeks for chemotherapy or at least 5 half-lives for investigational agents.
7. Persistent toxicities from prior chemotherapy must not be >grade 1, with the exception of creatinine (see Inclusion Criterion 8).
8. The patient has serum electrolytes (including calcium, magnesium, phosphorous, sodium and potassium) within normal limits (supplementation to maintain normal electrolytes is allowed) and the following clinical laboratory values prior to enrollment:

Serum creatinine≤1.8 mg/dL or creatinine clearance>50 mL/min (Appendix G).

Total bilirubin≤1.5 mg/dL

Alanine aminotransferase (ALT) and aspartate aminotransferase (AST)≤2 times the upper limit of normal (ULN).

9. The patient has adequate coagulation: platelet threshold of 50,000/mcL prothrombin time (PT), partial thromboplastin time (PTT), and an International Normalized Ratio (INR) within normal limits.
10. Patients with known central nervous system (CNS) disease are allowed if there is no evidence of active CNS disease. Use of maintenance intrathecal chemotherapy is allowed if considered in the patients best interest.
11. Must be able and willing to give written informed consent.

Exclusion Criteria Include:

1. The patient has uncontrolled or severe coagulopathies or a history of clinically significant bleeding within the past 6 months, such as hemoptysis, epistaxis, hematochezia, hematuria, or gastrointestinal bleeding.
2. The patient has a known predisposition for bleeding such as von Willebrand's disease or other such condition.
3. The patient requires therapeutic doses of any anticoagulant, including low molecular weight heparin (LMWH). Concomitant use of warfarin, even at prophylactic doses, is prohibited.
4. Uncontrolled intercurrent illness including, but not limited to uncontrolled infection, symptomatic congestive heart failure (NYHA class III and IV), uncontrolled cardiac arrhythmia, or psychiatric illness/social situations that would limit compliance with study requirements.
5. Active heart disease including myocardial infarction within previous 3 months, symptomatic coronary artery disease, arrhythmias not controlled by medication, or uncontrolled congestive heart failure (NYHA class III and IV).
6. Patients receiving chemotherapy within past 2 weeks or within 5 half-lives for investigational agents.

7 The patient has not recovered to grade≤1 from adverse events (AEs) due to investigational drugs or other medications.

8 The patient is pregnant or lactating

9. The patient is known to be positive for the human immunodeficiency virus (HIV). The effect of coenzyme Q10 on HIV medications is unknown. Note: HIV testing is not required for eligibility, but if performed previously and was positive, the patient is ineligible for the study.
10. The patient has an inability or unwillingness to abide by the study protocol or cooperate fully with the investigator or designee
11. The patient is taking HMG-CoA reductase inhibitors (statin drugs).
12. The patient is receiving digoxin, digitoxin, lanatoside C, or any type of digitalis alkaloids.
13. The patient is receiving colony stimulating factors (CSFs) that cannot be held during the monitoring period for dose-limiting toxicities (DLT).

Statistical Methods

This phase lab trial will examine the dose limiting toxicities of coenzyme Q10 Monotherapy or Combination Therapy (with fludarabine and cytarabine) when given as potential therapy for patients with AML or ALL. All patients receive 1 cycle of coenzyme Q10 Monotherapy and be assessed for response. For patients who respond and do not experience a DLT in cycle 1, monotherapy continues until progression for a maximum of 12 cycles in the absence of intolerable toxicities. Patients who do not achieve a response and do not experience a DLT, may proceed to receive cycle 1 of combination therapy. Patients who achieve a response and do not experience a DLT in cycle 1 of combination Therapy may continue combination Therapy as consolidation for a maximum of 5 cycles in the absence of intolerable toxicities. Patients who experience a DLT during cycle 1 of monotherapy or cycle 1 of combination therapy are discontinued.

Data is summarized using descriptive statistics (number of patients, mean, median, standard deviation, minimum, and maximum) for continuous variables and using frequency and percentages for discrete variables.

The primary endpoint is the presence of any dose limiting toxicity (DLT), defined as a clinically significant adverse event or abnormal laboratory value that is at least possibly related to coenzyme Q10 and occurring during cycle 1 of monotherapy or cycle 1 of combination therapy that meets any of the following criteria:

CTCAE grade 3 AST (SGOT) or ALT (SGPT) for >7 days

CTCAE grade 4 AST (SGOT) or ALT (SGPT) of any duration

Any grade 3 or greater PT/PTT abnormality.

Grade 2 or greater PT PTT elevation with clinically significant bleeding. Clinically significant is defined as requiring factor replacement, hospitalization, or surgical intervention.

All other NCI CTCAE criteria that are CTCAE grade 3 or 4.

Inability of patient to complete cycle 1 due to treatment-emergent toxicity (regardless of attribution).

Prolonged myelosuppression, as defined by the NCI criteria specific for leukemia, i.e., marrow cellularity<5% on Day 42 or later (6 weeks) from start of therapy without evidence of leukemia.

Cytopenia associated with prolonged myelosuppression (i.e., >6 weeks) during either monotherapy or combination therapy.

Any SAE at least possibly related to coenzyme Q10 or its combination with fludarabine and cytarabine that occurs during cycle 1.

Nausea and vomiting<grade 3, alopecia, study drug-related fever, electrolyte abnormalities (including K, Na, CI, $HCO_3$, Mg, Ca, bilirubin) that are ≥grade 3 are not considered a DLT. Only prolonged myelosuppression, as defined by the NCI criteria specific for leukemia, i.e., marrow cellularity<5% on Day 42 or later (6 weeks) from start of therapy without evidence of leukemia, is considered in defining the DLT and establishing an MTD. Other cytopenias do not constitute DLT as defined herein.

Safety observations and measurements including study drug exposure, adverse events, laboratory data, vital signs, ECG, and ECOG performance status are summarized and presented in tables and listings. Toxicity at each dose level are graded according to National Cancer Institute Common Terminology Criteria for Adverse Events (CTCAE v4.02). The dose of coenzyme Q10 escalates or de-escalates based on the DLT experience of patients at the current dose. If a DLT occurs at a dose level of monotherapy, that dose level will not be open to enter patients on combination therapy.

Response, a secondary endpoint, is evaluated using routine methods of analysis. The plasma PK of coenzyme Q10 is calculated from plasma concentrations collected from all patients who receive coenzyme Q10 in cycle 1 of monotherapy or combination therapy as well as in subsequent cycles. PK parameters are calculated using noncompartmental models and PK parameters ($C_{ave}$, $C_{max}$, $T_{max}$, $AUG_{0-12}$, $AUC_{0-23.5}$, $t_{1/2}$, ke, Clp, Clr) are summarized and presented. Descriptive statistics (including number, mean, median, standard deviation, and range) for PK parameters are tabulated by dose level.

Exploratory objectives includes PD blood and bone marrow samples collected throughout the trial are analyzed for markers of coenzyme Q10 activity and other exploratory PD parameters.

Dosing Regimens

Cycle 1 Monotherapy

The starting dose level of coenzyme Q10 is 58.7 mg/kg given by continuous infusion over 24 hours and repeated every day for 18 consecutive days. On Day 1 of each cycle (i.e., Monday) the dose consists of an accelerated rate of infusion of 25% of the total dose volume over 1 hour with the remaining 75% of the dose volume infused over 23 hours. Subsequent daily doses (Days 2 through 18) are infused uniformly over 24 hours (no accelerated rate in the first hour). The dose for subsequent cohorts is escalated in approximately 25% increments as shown in Table 18 "Cohort Dose Levels for Coenzyme Q10 Nanosuspension for Injection" above. The principal investigator will consult with the Medical Monitor and the Chair of the DSMB to determine the appropriate dose level for each patient.

Subsequent Cycles of Monotherapy

If a patient a patient achieves CR or CRi after Cycle 1 of Monotherapy and does not have DLT, the patient can receive additional consolidations (a total of up to 12 cycles of Monotherapy) at the same dose levels shown in Table 18 "Cohort Dose Levels for Coenzyme Q10 Nanosuspension for Injection" above.

Cycle 1 Combination Therapy

The dose levels of coenzyme Q10 during Combination Therapy will be the same as for Monotherapy (see Table 18 "Cohort Dose Levels for Coenzyme Q10 Nanosuspension for Injection" above). The dose of fludarabine and cytarabine will be as follows.

- Fludarabine 15 mg/$m^2$ is administered IV over 15-30 minutes±15 minutes, every 12 hours±2 hours for 5 days (4 days in patient ≥65 years or ECOG of 3).
- Cytarabine 0.5 g/$m^2$ in NS 250 mL is administered IV over 2 hours±20 minutes, every 12 hours±2 hours for 5 days (4 days in patient ≥65 years or ECOG of 3).
- Coenzyme Q10 is administered as a continuous infusion on Day 1-18.

The dose of fludarabine and cytarabine is fixed except for dose adjustments based on organ function using methods known in the art.

Subsequent Cycles of Combination Therapy

If a patient achieves CR or CRi during combination therapy, the patient can receive additional consolidations (a total of 5 additional cycles of consolidation) with combination therapy. For patients with response less than CR/CRi or with no response, the patient can receive another treatment cycle of combination therapy if considered to be in the patient's best interest by the PI, Medical Monitor, and Chair of the DSMB. If such a patient achieves CR/CRi, the patient can receive additional consolidations (a total of 4 additional cycles of consolidation).

For patients with a response, post-remission cycles should begin once the neutrophil count has recovered to >1000×$10^9$/L and the platelet count to >100,000×$10^9$/L after the previous cycle. Patients who do not meet response criteria (CR or CRi) and these neutrophil/platelet parameters may not continue with post remission therapy until these parameters are met.

Patients who do not meet CR or PR criteria but received documented clinical benefit (i.e., stable disease, decreased need for transfusions, improved quality of life) may continue up to 4 more cycles of Combination Therapy after discussion with the Medical Monitor and the DSMB Chair. Patients are closely monitored and dosed following the standard protocol. No patient is allowed in this category until safety data is available in the first 10 inpatients and there is agreement with the FDA.

Duration of Therapy

For patients who have a response to coenzyme Q10 monotherapy: treatment may continue for up to 12 cycles or until any of the discontinuation criteria are met.

For patients treated with combination therapy, if the patient achieves CR or CRi, the patient can receive additional consolidations (a total of 5 additional cycles of consolidation) with coenzyme Q10 plus chemotherapy (fludarabine and cytarabine) if the neutrophil/platelet safety parameters have been met.

For patients with response less than CR/CRi or with no response: the patient can receive another cycle of coenzyme Q10 combination therapy if the investigator considers it to be in the patient's best interest (after discussion with the PI, the Medical Monitor and the Chair of the DSMB).

At the end of the study, patients are assessed for response by standard criteria to treatment with either coenzyme Q10 monotherapy or coenzyme Q10 combination therapy with chemotherapeutic agents. The frequency, duration, and extent of response is compared to a population or historical control to determine benefit of the subject to the treatment regimen. Subjects are demonstrated to achieve clinically relevant outcomes (e.g., decreased tumor burden) based on criteria described herein. Subjects are also assessed for adverse outcomes as compared to subjects treated with intravenously administered coenzyme Q10 delivered in a four hour infusion at a higher infusion rate than is used in this clinical trial. Increased infusion duration is found to decrease adverse events in subjects, thereby increasing the therapeutic range of coenzyme Q10, allowing subjects to receive higher doses and/or more doses of coenzyme Q10 without significant adverse events, e.g., adverse events that would require the subject to terminate treatment and/or withdraw from the study. Subjects are also assessed for myelosuppression, particularly in the combination therapy cohorts. Levels of myelosuppression in subjects in this study are compared to historical controls to identify decreases in myelosuppression in co-administration regimens with coenzyme Q10.

The invention claimed is:

1. A method of treating cancer in a subject, comprising administering to the subject a composition comprising a dose of coenzyme Q10 by continuous intravenous infusion for at least 48 hours, thereby treating the cancer in the subject.

2. The method of claim 1, wherein the coenzyme Q10 is administered by continuous intravenous infusion for at least 72 hours.

3. The method of claim 1, wherein the coenzyme Q10 is administered by continuous intravenous infusion for at least 96 hours.

4. The method of claim 1, wherein the coenzyme Q10 is administered by continuous intravenous infusion for at least 144 hours.

5. The method of claim 1, wherein the continuous intravenous infusion is administered once per week.

6. The method of claim 1, wherein the continuous infusion is administered twice per week.

7. A method of treating cancer in a subject, comprising (a) administering to the subject a composition comprising a dose of coenzyme Q10 by continuous intravenous infusion for at least 48 hours;

(b) monitoring the subject for decreased coagulation; and (c) discontinuing treatment with coenzyme Q10 in a subject identified as having decreased coagulation, thereby treating the cancer in the subject.

8. A method of treating cancer in a subject, comprising (a) administering to the subject a composition comprising a dose of coenzyme Q10 by continuous intravenous infusion for at least 48 hours;

(b) monitoring the subject for decreased coagulation;

(c) administering an agent to increase coagulation in a subject identified as having decreased coagulation;

(d) confirming the subject has normal coagulation; and (e) continuing treatment with coenzyme Q10, thereby treating the cancer in the subject.

9. A method of treating cancer in a subject, comprising (a) administering to the subject a composition comprising a dose of coenzyme Q10 by continuous intravenous infusion for at least 48 hours;

(b) monitoring the subject for decreased coagulation; and (c) continuing treatment with coenzyme Q10 in a subject identified as having normal coagulation, thereby treating the cancer in the subject.

10. The method of claim 1, further comprising administering to the subject an agent to increase coagulation in the subject.

11. The method of claim 10, wherein the agent to increase coagulation comprises vitamin K.

12. The method of claim 8, wherein the agent to increase coagulation comprises vitamin K.

* * * * *